US012527851B2

(12) United States Patent
Evgin et al.

(10) Patent No.: US 12,527,851 B2
(45) Date of Patent: Jan. 20, 2026

(54) METHODS AND MATERIALS FOR TREATING CANCER

(71) Applicant: Mayo Foundation for Medical Education and Research, Rochester, MN (US)

(72) Inventors: Laura Evgin, Rochester, MN (US); Richard G. Vile, Rochester, MN (US); Timothy J. Kottke, Oronoco, MN (US); Amanda L. Huff, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 1300 days.

(21) Appl. No.: 16/975,512

(22) PCT Filed: Mar. 29, 2019

(86) PCT No.: PCT/US2019/024994

§ 371 (c)(1),
(2) Date: Aug. 25, 2020

(87) PCT Pub. No.: WO2019/191681

PCT Pub. Date: Oct. 3, 2019

(65) Prior Publication Data

US 2021/0030858 A1 Feb. 4, 2021

Related U.S. Application Data

(60) Provisional application No. 62/751,334, filed on Oct. 26, 2018, provisional application No. 62/650,171, filed on Mar. 29, 2018.

(51) Int. Cl.

| | |
|---|---|
| ***A61K 39/00*** | (2006.01) |
| ***A61K 35/13*** | (2015.01) |
| ***A61K 39/395*** | (2006.01) |
| ***A61K 40/11*** | (2025.01) |
| ***A61K 40/19*** | (2025.01) |
| ***A61K 40/24*** | (2025.01) |
| ***A61K 40/42*** | (2025.01) |
| ***A61P 35/00*** | (2006.01) |
| ***C07K 16/28*** | (2006.01) |
| *A61K 35/15* | (2025.01) |

(52) U.S. Cl.

CPC ...... *A61K 39/001154* (2018.08); *A61K 40/11* (2025.01); *A61K 40/19* (2025.01); *A61K 40/24* (2025.01); *A61K 40/4244* (2025.01); *A61P 35/00* (2018.01); *A61K 2039/5152* (2013.01)

(58) Field of Classification Search

None

See application file for complete search history.

(56) References Cited

U.S. PATENT DOCUMENTS

| | | | |
|---|---|---|---|
| 2011/0129503 A1 | 6/2011 | Strober et al. | |
| 2016/0120962 A1* | 5/2016 | Langlade Demoyen .................... | C12Y 305/04014 514/44 R |
| 2020/0046671 A1 | 2/2020 | Harris | |

FOREIGN PATENT DOCUMENTS

| | | | |
|---|---|---|---|
| WO | WO-2014195331 A1 * | 12/2014 | ............. A61K 38/50 |
| WO | WO 2016/083791 | 6/2016 | |
| WO | WO 2016/149045 | 9/2016 | |
| WO | WO 2017/004165 | 1/2017 | |
| WO | WO 2017/004181 | 1/2017 | |
| WO | WO-2017004165 A1 * | 1/2017 | ............. A61K 31/23 |
| WO | WO 2018/165631 | 9/2018 | |

OTHER PUBLICATIONS

Kottke et al. ESGCT XXV Anniversary Congress in Collaboration with the German Society for Gene Therapy Oct. 17-20, 2017. Human Gene Therapy. 28: A2-A125 4537-4548; Published: Dec. 1, 2017 (Year: 2017).*

Glaser et al. APOBEC-mediated mutagenesis in urothelial carcinoma is associated with improved survival, mutations in DNA damage response genes, and immune response. Oncotarget. 9(4): 4537-4548; Published: Dec. 16, 2017 (Year: 2017).*

Richardson et al. APOBEC3A deaminates transiently exposed single-strand DNA during LINE-1 retrotransposition. Genetics and Genomic. 9(4): 4537-4548; Published: Apr. 29, 2014 (Year: 2014).*

Bogerd et al. APOBEC3A and APOBEC3B are potent inhibitors of LTR-retrotransposon function in human cells. Nucleic Acids Research. 34(1): 89-95; Published: Jan. 1, 2006 (Year: 2006).*

Akre et al. Mutation Processes in 293-Based Clones Overexpressing the DNA Cytosine Deaminase APOBEC3B. Plos One. 11(5): e0155391; Published: May 10, 2016 (Year: 2016).*

Stepanenko et al. HEK293 in cell biology and cancer research: phenotype, karyotype, tumorigenicity, and stress-induced genome-phenotype evolution. Gene. 569: 182-190; Published: May 27, 2015 (Year: 2015).*

Sieuwerts et al. Elevated APOBEC3B Correlates with Poor Outcomes for Estrogen-Receptor-Positive Breast Cancers. Hormones and Cancer. 5: 405-413; Published: Aug. 15, 2014 (Year: 2014).*

Miller et al. APOBEC3-mediated hypermutation of retroviral vectors produced from some retrovirus packaging cell lines. Gene Therapy. 18: 528-530; Published: Jan. 6, 2011 (Year: 2011).*

Shearer et al. Experimental design for stable genetic manipulation in mammalian cell lines: lentivirus and alternatives. Genes to Cells. 20(1): 1-10; Published: Oct. 13, 2014 (Year: 2014).*

(Continued)

*Primary Examiner* — Daniel E Kolker
*Assistant Examiner* — Katherine Ann Holtzman
(74) *Attorney, Agent, or Firm* — Fish & Richardson P.C.

(57) ABSTRACT

This document relates to methods and materials for treating a mammal having cancer. For example, compositions (e.g., vaccines) containing cells (e.g., tumor cells) expressing APOBEC3 which can be administered to a mammal (e.g., a human) having cancer to induce an immune response (e.g., an anti-tumor immune response) within the mammal are provided.

14 Claims, 56 Drawing Sheets

Specification includes a Sequence Listing.

(56) References Cited

OTHER PUBLICATIONS

Stenglein et al. APOBEC3 proteins mediate the clearance of foreign DNA from human cells. Nature Structural & Molecular Biology. 17: 222-229; Published: Jan. 20, 2010 (Year: 2010).*
Stavrou et al. APOBEC3 Proteins in Viral Immunity. Journal of Immunology. 195(10): 4565-4570; Published: Nov. 15, 2016 (Year: 2016).*
Seplyarskiy et al. APOBEC-induced mutations in human cancers are strongly enriched on the lagging DNA strand during replication. Genome Research. 26(2): 174-182; Published: Feb. 2016 (Year: 2016).*
Harris et al. Molecular mechanism and clinical impact of APOBEC3B-catalyzed mutagenesis in breast cancer. Breast Cancer Research. 17(8); Published: Jan. 21, 2015 (Year: 2015).*
Henderson et al. APOBEC-Mediated Cytosine Deamination Links PIK3CA Helical Domain Mutations to Human Papillomavirus-Driven Tumor Development. Cell Reports. 7(6): 1833-1841: Published: Jun. 5, 2014 (Year: 2014).*
Kanu et al. DNA replication stress mediates APOBEC3 family mutagenesis in breast cancer. Genome Biology. 17: 185; Published: Sep. 15, 2016 (Year: 2016).*
Chernova et al. Molecular profiling reveals primary mesothelioma cell lines recapitulate human disease. Cell Death and Differentiation. 23: 1152-1164; Published: Feb. 19, 2016 (Year: 2016).*
Hagemann et al. High efficiency transfection of glioma cell lines and primary cells for overexpression and RNAi experiments. Journal of Neuroscience Methods. 156 (1-2): 194-202; Published: Sep. 30, 2006 (Year: 2006).*
Swanton et al. APOBEC Enzymes: Mutagenic Fuel for Cancer Evolution and Heterogeneity. Cancer Discovery. 5(7): 704-712; Published: Jul. 6, 2015 (Year: 2015).*
Boichard et al. High expression of PD-1 ligands is associated with kataegis mutational signature and APOBEC3 alterations. Oncolmmunology. 6(3): e1284719; Published: Mar. 15, 2017 (Year: 2017).*
Rajani et al. Generation of Tumor Cells Resistant to Oncolysis Is Mediated Through Virus Induced APOBEC Expression. Molecular Therapy. 24: Supplement 1; Published: May 2016 (Year: 2016).*
Borzooee et al. Viral subversion of APOBECs: Lessons for anti-tumor immunity and tumor immunotherapy. International Reviews of Immunology. 37(3): 151-164; Published: Dec. 6, 2017 (Year: 2017).*
Chan et al. Nature Genetics. An APOBEC3A hypermutation signature is distinguishable from the signature of background mutagenesis of APOBEC3B in human cancers. 47: 1067-1072: Published; Aug. 10, 2015 (Year: 2015).*
Mullane et al. Correlation of Apobec Mrna Expression with overall Survival and pd-I1 Expression in Urothelial Carcinoma. Scientific Reports. 6: 27702; Published: Jun. 10, 2016 (Year: 2016).*
Covino et al., "Understanding the regulation of APOBEC3 expression: Current evidence and much to learn," J. Leukoc. Biol., Mar. 2018, 103(3):433-444.
Extended European Search Report in European Appln. No. 23176640.3, dated Sep. 29, 2023, 14 pages.
Yu et al., "Vaccination with tumor lysate-pulsed dendritic cells elicits antigen-specific, cytotoxic T-cells in patients with malignant glioma," Cancer Res., Jul. 2004, 64(14):4973-4979.
Akre et al., "Mutation Processes in 293-Based Clones Overexpressing the DNA Cytosine Deaminase APOBEC3B," PLoS ONE, May 10, 2016, 11(5):e0155391, 17 pages.
Alonso-Camino et al., "The Profile of Tumor Antigens Which Can be Targeted by Immunotherapy Depends Upon the Tumor's Anatomical Site," Mol, Therapy, Nov. 1, 2014, 22(22):1936-1948.
Anguille et al., "Clinical use of dendritic cells for cancer therapy," Lancet Oncology, Jun. 2014, 15(7):e257-267.
Annovazzi et al., "Chemotherapeutic Drugs: DNA Damage and Repair in Glioblastoma," Cancers, May 26, 2017, 9(6):57, 17 pages.
Becher et al., "Preclinical Evaluation of Radiation and Perifosine in a Genetically and Histologically Accurate Model of Brainstem Glioma," Cancer Research, Mar. 15, 2010, 70(6):2548-2557.
Boichard et al., "High expression of PD-1 ligands is associated with kataegis mutational signature and APOBEC3 alterations," Oncoimmunology, Jan. 31, 2017, 6(3):e1284719, 11 pages.
Brown et al., "Combining DNA damaging therapeutics with immunotherapy: more haste, less speed," Br. J. Cancer, Feb. 6, 2018, 118(3):312-324.
Buczkowicz et al., "Genomic analysis of diffuse intrinsic pontine gliomas identifies three molecular subgroups and recurrent activating ACVRI mutations," Nat Genetics, Apr. 6, 2014, 46(5):451-456.
Burns et al., "APOBEC3B is an enzymatic source of mutation in breast cancer," Nature, Feb. 21, 2013, 494(7437):366-370.
Burns et al., "Evidence for APOBEC3B mutagenesis in multiple human cancers," Nat Genetics, Sep. 2013, 45(9):977-983.
Caretti et al., "Monitoring of tumor growth and post-irradiation recurrence in a diffuse intrinsic pontine glioma mouse model," Brain Pathology, Jul. 2011, 21(4):441-451.
Carreno et al., "Cancer immunotherapy. A dendritic cell vaccine increases the breadth and diversity of melanoma neoantigen-specific T cells," Science, May 15, 2015, 348(6236):803-808.
Chan et al., "An APOBEC3A hypermutation signature is distinguishable from the signature of background mutagenesis by APOBEC3B in human cancers," Nat. Genetics, Aug. 10, 2015, 47(9):1067-1072.
Chan et al., "Correction: Genetic Basis for Clinical Response to CTLA-4 Blockade in Melanoma," N. Engl. J. Medicine, Nov. 12, 2015, 373(20):1984.
ClinicalTrials.gov [online], "Vaccine Therapy and Temozolomide in Treating Patients With Newly Diagnosed Glioblastoma," NCT01957956, Oct. 8, 2013, last updated Nov. 3, 2020, 19 pages.
Colli et al., "Burden of Nonsynonymous Mutations among TCGA Cancers and Candidate Immune Checkpoint Inhibitor Responses," Cancer Research, Jul. 1, 2016, 76(13):3767-3772.
Conticello et al., "Evolution of the AID/APOBEC family of polynucleotide (deoxy)cytidine deaminases," Mol. Biol. Evolution, Feb. 2005, 22(2):367-377.
Crespo-Diaz et al., "Platelet Lysate Consisting of a Natural Repair Proteome Supports Human Mesenchymal Stem Cell Proliferation and Chromosomal Stability," Cell Transplantation, Nov. 19, 2010, 20(6):797-811.
Dillman et al., "Randomized phase II trial of autologous dendritic cell vaccines versus autologous tumor cell vaccines in metastatic melanoma: 5-year follow up and additional analyses," J. Immunother; Cancer, Mar. 6, 2018, 6(1):19, 10 pages.
Driscoll et al., "APOBEC3B-mediated corruption of the tumor cell immunopeptidome induces heteroclitic neoepitopes for cancer immunotherapy," Nat. Communications, Feb. 7, 2020, 11:790, 14 pages.
Dyall et al., "Heteroclitic immunization induces tumor immunity," J. Exp. Medicine, Nov. 2, 1998, 188(9):1553-1561.
Engelhardt et al., "The movers and shapers in immune privilege of the CNS," Nat. Immunology, Feb. 2017, 18(2):123-131.
Fahmy et al., "Increased TCR Avidity after T Cell Activation: A Mechanism for Sensing Low-Density Antigen," Immunity, Feb. 1, 2001, 14(2):135-143.
Fortier et al., "The MHC class I peptide repertoire is molded by the transcriptome," J. Exp. Medicine, Feb. 25, 2008, 205(3):595-610.
Foster et al., "Characterization of Prostatic Epithelial Cell Lines Derived from Transgenic Adenocarcinoma of the Mouse Prostate (TRAMP) Model," Cancer Research, Aug. 1997, 57(16):3325-3330.
Fritsch et al., "HLA-Binding Properties of Tumor Neoepitopes in Humans," Cancer Immunol. Research, Jun. 2014, 2(6):522-529.
Garg et al., "Integrating Next-Generation Dendritic Cell Vaccines into the Current Cancer Immunotherapy Landscape," Trends Immunology, Aug. 2017, 38(8):577-593.
Genbank Accession No. NM_004900.4, "*Homo sapiens* apolipoprotein B mRNA editing enzyme catalytic subunit 3B (APOBEC3B), transcript variant 1, mRNA," Oct. 7, 2016, 3 pages.
Geukes Foppen et al., "Tumor-infiltrating lymphocytes for the treatment of metastatic cancer," Mol. Oncology, Dec. 2015, 9(10):1918-1935.
Gingrich et al., "Metastatic Prostate Cancer in a Transgenic Mouse," Cancer Research, Sep. 1996, 56(18):4096-4102.

(56) References Cited

OTHER PUBLICATIONS

Glaser et al., "APOBEC-mediated mutagenesis in urothelial carcinoma is associated with improved survival, mutations in DNA damage response genes, and immune response," Oncotarget, Dec. 16, 2017, 9(4):4537-4548.
Gold et al., "A Single Heteroclitic Epitope Determines Cancer Immunity After Xenogeneic DNA Immunization Against a Tumor Differentiation Antigen," J. Immunology, May 15, 2003, 170(10):5188-5194.
Gustafson et al., "Systemic immune suppression in glioblastoma: the interplay between CD14+HLA-DRlo/neg monocytes, tumor factors, and dexamethasone," Neuro-Oncology, Feb. 23, 2010, 12(7):631-644.
Hailemichael et al., "Cancer vaccine formulation dictates synergy with CTLA-4 and PD-LI checkpoint blockade therapy," J. Clin. Investigation, Feb. 26, 2018, 128(4):1338-1354.
Halvorson et al., "A High-Throughput In Vitro Drug Screen in a Genetically Engineered Mouse Model of Diffuse Intrinsic Pontine Glioma Identifies BMS-754807 as a Promising Therapeutic Agent," PLoS ONE, Mar. 6, 2015, 10(3):e0118926, 16 pages.
Hammerl et al., "Breast cancer genomics and immuno-oncological markers to guide immune therapies," Semin. Cancer Biology, Nov. 6, 2017, 52(Pt 2):178-188.
Harris et al., "Retroviral Restriction by APOBEC Proteins," Nat. Rev. Immunology, Nov. 2004, 4(11):868-877.
Hermans et al., "The VITAL assay: a versatile fluorometric technique for assessing CTL- and NKT-mediated cytotoxicity against multiple targets in vitro and in vivo," J. Immunol. Methods, Feb. 2004, 285(1):25-40.
Houghton et al., "Immune recognition of self in immunity against cancer," J. Clin. Investigation, Aug. 16, 2004, 114(4):468-471.
Huff et al., "APOBEC3 Mediates Resistance to Oncolytic Viral Therapy," Mol. Ther. Oncolytics, Aug. 29, 2018, 11:1-13.
Jarvis et al., "Mutation Signatures Including APOBEC in Cancer Cell Lines," JNCI Cancer Spectrum, Jan. 2018, 2(1):pky002, 7 pages.
Jones et al., "Pediatric high-grade glioma: biologically and clinically in need of new thinking," Neuro-Oncology, Jun. 9, 2016, 19(2):153-161.
Jones et al., "Unique genetic and epigenetic mechanisms driving paediatric diffuse high-grade glioma," Nat. Rev. Cancer, Sep. 18, 2014, 14:651-661.
Keenan et al., Whole Cell Vaccines—Past Progress and Future Strategies, Semin. Oncology, Jun. 2012, 39(3):276-286.
Kipnis et al., "The central nervous system; privileged by immune connections," Nat. Rev. Immunology, Feb. 2018, 18(2):83-84.
Kleponis et al., "Fueling the engine and releasing the break: combinational therapy of cancer vaccines and immune checkpoint inhibitors," Cancer Biol. Medicine, Sep. 2015, 12(3):201-208.
Kottke et al., "Broad antigenic coverage induced by vaccination with virus-based cDNA libraries cures established tumors," Nat. Medicine, Jun. 19, 2011, 17:854-859.
Kottke et al., "Immunogenicity of self tumor associated proteins is enhanced through protein truncation," Mol. Ther. Oncolytics, Dec. 2016, 3(C):16030, 8 pages.
Laborde et al., "Cancer vaccines in the world of immune suppressive monocytes (CD14+HLA-DRlo/neg cells): the gateway to improved responses," Front. Immunology, Apr. 4, 2014, 5:147, 5 pages.
Larkin et al., "Combined Nivolumab and Ipilimumab or Monotherapy in Untreated Melanoma," N. Engl. J. Medicine, Jul. 2, 2015, 373(1):23-34.
Law et al., "The DNA cytosine deaminase APOBEC3B promotes tamoxifen resistance in ER-positive breast cancer," Sci. Advances, Oct. 7, 2016, 2(10):e1601737, 10 pages.
Le et al., "Cellular vaccine approaches," Cancer Journal, Jul./Aug. 2010, 16(4):304-310.
Lee et al., "A post-transcriptional program coordinated by CSDE1 prevents intrinsic neural differentiation of human embryonic stem cells." Nat. Communications, Nov. 13, 2017, 8(1):1456, 19 pages.
Leonard et al., "APOBEC3B Upregulation and Genomic Mutation Patterns in Serous Ovarian Carcinoma," Cancer Research, Dec. 2013, 73(24):7222-7231.
Lipson et al., "Safety and immunologic correlates of Melanoma GVAX, a GM-CSF secreting allogeneic melanoma cell vaccine administered in the adjuvant setting," J. Transl. Medicine, Jul. 5, 2015, 13:214, 14 pages.
Louis et al., "The 2016 World Health Organization Classification of Tumors of the Central Nervous System: a summary," Acta Neuropathologica, May 9, 2016, 131(6):803-820.
Mackay et al., "Integrated Molecular Meta-Analysis of 1,000 Pediatric High-Grade and Diffuse Intrinsic Pontine Glioma," Cancer Cell, Oct. 9, 2017, 32(4):520-537.e5.
MacMillan et al., "APOBEC3 Inhibition of Mouse Mammary Tumor Virus Infection: the Role of Cytidine Deamination versus Inhibition of Reverse Transcription," J. Virology, May 2013, 87(9):4808-4817.
Mihailovich et al., "Eukaryotic cold shock domain proteins: highly versatile regulators of gene expression," Bioessays, Feb. 2010, 32(2):109-118.
Misuraca et al., "Pre-Clinical Models of Diffuse Intrinsic Pontine Glioma," Front. Oncology, Jul. 24, 2015, 5:172, 7 pages.
Mouw et al., "DNA Damage and Repair Biomarkers of Immunotherapy Response," Cancer Discovery, Jul. 2017, 7(7):675-693.
Muto et al., "Identification and analysis of host proteins that interact with the 3'-untranslated region of tick-borne encephalitis virus genomic RNA," Virus Research, Apr. 2, 2018, 249:52-56.
Olson et al., "APOBEC Enzymes as Targets for Virus and Cancer Therapy," Cell Chem. Biology, Jan. 18, 2018, 25(1):36-49.
Overwijk et al., "gp100/pmel 17 Is a Murine Tumor Rejection Antigen: Induction of "Self"-reactive, Tumoricidal T Cells Using High-affinity, Altered Peptide Ligand," J. Exp. Medicine, Jul. 20, 1998, 188(2):277-286.
Pak et al., "The Role of Amino-Terminal Sequences in Cellular Localization and Antiviral Activity of APOBEC3B," J. Virology, Sep. 2011, 85(17):8538-8547.
Parney et al., "ATIM-13. Allogeneic Tumor Lysate/Autologous Dendritic Cell Vaccines in Newly Diagnosed Glioblastoma: Results of Clinical Trial MC1272," Neuro-Oncology, Nov. 2017, 19(Suppl. 6):vi28-vi29.
Parney et al., "IT-24. Development of a Novel Autologous Dendritic Cell/Allogeneic Glioblastoma Lysate Vaccine Protocol," Neuro-Oncology, Nov. 2014, 16(Suppl. 5):v114-v115.
Paugh et al., "Novel oncogenic PDGFRA mutations in pediatric high-grade gliomas," Cancer Research, Oct. 15, 2013, 73(20):6219-6229.
Paul et al., "HLA class I alleles are associated with peptide-binding repertoires of different size, affinity, and immunogenicity," J. Immunology, Dec. 15, 2013, 191(12):5831-5839.
PCT International Preliminary Report on Patentability in International Appln. No. PCT/US2019/024994, dated Sep. 19, 2020 8 pages.
PCT International Search Report and Written Opinion in International Appln. No. PCT/US2019/024994, dated Jul. 30, 2019, 12 pages.
Prestwich et al., "Immune-Mediated Antitumor Activity of Reovirus Is Required for Therapy and Is Independent of Direct Viral Oncolysis and Replication," Clin, Cancer Research, Jul. 2009, 15(13):4374-4381.
Pulido et al., "Using virally expressed melanoma cDNA libraries to identify tumor-associated antigens that cure melanoma," Nat. Biotechnology, Mar. 18, 2012, 30(4):337-343.
Quail et al., "The Microenvironmental Landscape of Brain Tumors," Cancer Cell, Mar. 13, 2017, 31(3):326-341.
Rambow et al., "Identification of differentially expressed genes in spontaneously regressing melanoma using the MeLiM Swine Model," Pigment Cell Melanoma Research, Apr. 2008, 21(2):147-161.
Rizvi et al., "Mutational landscape determines sensitivity to PD-1 blockade in non-small cell lung cancer," Science, Apr. 3, 2015, 348(6230):124-128.
Roberts et al., "An APOBEC cytidine deaminase mutagenesis pattern is widespread in human cancers," Nat. Genetics, Jul. 14, 2013, 45(9):970-976.

(56) References Cited

OTHER PUBLICATIONS

Rommelfanger et al., "Systemic Combination Virotherapy for Melanoma with Tumor Antigen-Expressing Vesicular Stomatitis Virus and Adoptive T-cell Transfer," Cancer Research, Sep. 2012, 72(18):4753-4764.
Saini et al., "Novel tools to assist neoepitope targeting in personalized cancer immunotherapy," Ann. Oncology, Dec. 2017, 28(Suppl. 12):xii3-xii10.
Salter et al., "The APOBEC Protein Family: United by Structure, Divergent in Function," Trends Biochem. Sciences, Jul. 2016, 41(7):578-594.
Schubert et al., "Designing string-of-beads vaccines with optimal spacers," Genome Medicine, Jan. 26, 2016, 8(1):9, 10 pages.
Schumacher et al., "Neoantigens in cancer immunotherapy," Science, Apr. 3, 2015, 348(6230):69-74.
Schwartzentruber et al., "Driver mutations in histone H3.3 and chromatin remodelling genes in paediatric glioblastoma," Nature, Jan. 29, 2012, 482:226-231.
Sheehy et al., "Isolation of a human gene that inhibits HIV-I infection and is suppressed by the viral Vif protein," Nature, Aug. 8, 2002, 418(6898):646-650.
Shi et al., "Structural basis for targeted DNA cytosine deamination and mutagenesis by APOBEC3A and APOBEC3B," Nat. Struct. Mol. Biology, Feb. 2017, 24(2):131-139.
Shim et al., "Inhibitory Receptors Induced by VSV Viroimmunotherapy Are Not Necessarily Targets for Improving Treatment Efficacy," Mol. Therapy, Apr. 5, 2017, 25(4):962-975.
Smid et al., "Breast cancer genome and transcriptome integration implicates specific mutational signatures with immune cell infiltration," Nat. Communications, Sep. 26, 2016, 7:12910, 9 pages.
Snyder et al., "Genetic Basis for Clinical Response to CTLA-4 Blockade in Melanoma," N. Engl. J. Medicine, Dec. 4, 2014, 371(23):2189-2199.
Soares et al., "PD-1/PD-L1 Blockade Together With Vaccine Therapy Facilitates Effector T-Cell Infiltration Into Pancreatic Tumors," J. Immunotherapy, Jan. 2015, 38(1):1-11.
Solomos et al., "Get It through Your Thick Head: Emerging Principles in Neuroimmunology and Neurovirology Redefine Central Nervous System "Immune Privilege"," ACS Chem. Neuroscience, Apr. 20, 2016, 7(4):435-441.
Srinivasan et al., "PD-LI checkpoint inhibition and anti-CTLA-4 whole tumor cell vaccination counter adaptive immune resistance: A mouse neuroblastoma model that mimics human disease," PLoS Medicine, Jan. 29, 2018, 15(1):e 1002497, 21 pages.
Sturm et al., Hotspot Mutations in H3F3A and IDH1 Define Distinct Epigenetic and Biological Subgroups of Glioblastoma, Cancer Cell, Oct. 16, 2012, 22(4):425-437.
Swanton et al., "APOBEC Enzymes: Mutagenic Fuel for Cancer Evolution and Heterogeneity," Cancer Discovery, Jul. 2015, 5(7):704-712.
Taggart et al., "Anti-PD-1/anti-CTLA-4 efficacy in melanoma brain metastases depends on extracranial disease and augmentation of CD8+ T cell trafficking," Proc. Natl. Acad. Sci. USA, Jan. 3,1 2018, 115(7):E1540-E1549.
Tan et al., "Brainstem encephalitis: etiologies, treatment, and predictors of outcome," J. Neurology, Sep. 2013, 260(9):2312-2319.
Taylor et al., "Recurrent activating ACVR1 mutations in diffuse intrinsic pontine glioma," Nat. Genetics, May 2014, 46(5):457-461.
Van Allen et al., "Genomic correlates of response to CTLA-4 blockade in metastatic melanoma," Science, Oct. 9, 2015, 350(6257):207-211.
Van Nuffel et al., "Intravenous and intradermal TriMix-dendritic cell therapy results in a broad T-cell response and durable tumor response in a chemorefractory stage IV-M1c melanoma patient," Cancer Immunol. Immunotherapy, Jul. 2012, 61(7):1033-1043.
Varshavsky, "The N-end rule pathway and regulation by proteolysis," Protein Science, Aug. 2011, 20(8):1298-1345.
Velders et al., "Defined Flanking Spacers and Enhanced Proteolysis Is Essential for Eradication of Established Tumors by an Epitope String DNA Vaccine," J. Immunology, May 1, 2001, 166(9):5366-5373.
Venkatesan et al., "Perspective: APOBEC mutagenesis in drug resistance and immune escape in HIV and cancer evolution," Ann. Oncology, Mar. 1, 2018, 29(3):563-572.
Vile et al., "Generation of an anti-tumour immune response in a non-immunogenic tumour: HSVtk killing in vivo stimulates a mononuclear cell infiltrate and a Th1-like profile of intratumoural cytokine expression," Int. J. Cancer, Apr. 10, 1997, 71(2):267-274.
Wang et al., "APOBEC3B and APOBEC mutational signature as potential predictive markers for immunotherapy response in non-small cell lung cancer," Oncogene, Apr. 26, 2018, 37:3924-3936.
Wolchok et al., "Safety and Immunogenicity of Tyrosinase DNA Vaccines in Patients with Melanoma," Mol. Therapy, Nov. 1, 2007, 15(11):2044-2050.
Wongthida et al., "Activating Systemic T-Cell Immunity Against Self Tumor Antigens to Support. Oncolytic Virotherapy with Vesicular Stomatitis Virus," Hum. Gene Therapy, Mar. 2, 2011, 22(11):1343-1353.
Wu et al., "Somatic histone H3 alterations in pediatric diffuse intrinsic pontine gliomas and non-brainstem glioblastomas," Nat. Genetics, Jan. 29, 2012, 44(3):251-253.
Wu et al., "The genomic landscape of diffuse intrinsic pontine glioma and pediatric non-brainstem high-grade glioma," Nat. Genetics, Apr. 6, 2014, 46(5):444-450.
Wurth et al., "UNR/CSDE1 Drives a Post-transcriptional Program to Promote Melanoma Invasion and Metastasis," Cancer Cell, Nov. 14, 2016, 30(5):694-707.
Yarchoan et al., "Targeting neoantigens to augment antitumour immunity," Nat. Rev. Cancer, Feb. 24, 2017, 17(4):209-222.
Yarchoan et al., "Tumor Mutational Burden and Response Rate to PD-1 Inhibition," N. Engl. J. Medicine, Dec. 21, 2017, 377(25):2500-2501.
Yu et al., "Poor immunogenicity of a self/tumor antigen derives from peptide-MHC-I instability and is independent of tolerance," J. Clin. Investigation, Aug. 16, 2004, 114(4):551-559.
Zhou et al., "Persistence of Multiple Tumor-Specific T-Cell Clones Is Associated with Complete Tumor Regression in a Melanoma Patient Receiving Adoptive Cell Transfer Therapy," J. Immunotherarpy, Jan./Feb. 2005, 28(1):53-62.
Zirlik et al., "Cytotoxic T cells generated against heteroclitic peptides kill primary tumor cells independent of the binding affinity of the native tumor antigen peptide," Blood, Dec. 1, 2006, 108(12):3865-3870.
Zou et al., "APOBEC3B, a molecular driver of mutagenesis in human cancers," Cell Bioscience, May 30, 2017, 7:29, 7 pages.
Hollern et al., "Apobec3 induced mutagenesis sensitizes murine models of triple negative breast cancer to immunotherapy by activating B-cells and CD4+ T-cells," Cancer Research, Feb. 2019, 79(4 Suppl):GS1-05.
Kottke et al., "Immunotherapy for tumours through APOBEC3B-induced neo-epitope generation in combination with immune checkpoint blockade," Human Gene Therapy, 2017, 28(12):A16.
Vile et al., "Cancer immunotherapy with APOBEC3B-induced heteroclitic library tumor cell vaccines and immune checkpoint blockade," Cancer Immunol. Research, Feb. 2019, 7(2 Suppl):B138.
Evgin et al., "Cancer Immunotherapy with APOBEC3B-Induced Heteroclitic Library Tumor Cell Vaccines and Immune Checkpoint Blockade," Abstract, Presented at the Proceedings of the 22nd Annual ASGCT Meeting, Chicago, IL, May 16-19, 2018.

* cited by examiner

| CELL LINE ID | MUTATION STATUS | | | | |
|---|---|---|---|---|---|
| | H3F3A | HIST1H3B | ACVR1 | TP53 | PIK3CA |
| SF9427 | | | | X | |
| SF7761 | X | | | X | |
| MC-PED8 | X | | | X | |
| MC-PED17 | X | | | X | |
| SU-DIPG VI | X | | | X | |
| SU-DIPG XIII | X | | | X | |
| SU-DIPG XVII | X | | | X | |
| SU-DIPG 24 | X | | | X | |
| SU-DIPG XIX | | X | | X | X |
| SU-PCGBM2 | | X | X | X | X |
| SU-DIPG IV | | X | X | X | X |

Table 2. Amino acid changes induced by APOBEC3B. Mutations from Table 1 that resulted in a G to A or C to T transitions and an amino acid change.

| Chr | Pos | Ref | Alt | SNPEFF Effect | SNPEFF Gene | SNPEFF Feature type | SNPEFF Biotype | SNPEFF Amino Acid change |
|---|---|---|---|---|---|---|---|---|
| chr1 | 57406389 | G | A | missense_variant | Tyw5 | transcript | protein_coding | p.Pro25Ser |
| chr1 | 85577008 | G | A | missense_variant | G530012D18Rik | transcript | protein_coding | p.Val45Met |
| chr1 | 85609828 | G | A | missense_variant | Sp140 | transcript | protein_coding | p.Arg56Gln |
| chr1 | 85630513 | G | A | missense_variant | Sp140 | transcript | protein_coding | p.Val260Met |
| chr1 | 88212093 | G | A | missense_variant | Ugt1a1 | transcript | protein_coding | p.Arg31Lys |
| chr1 | 1.17E+08 | G | A | missense_variant | Gm19965 | transcript | protein_coding | p.Ala219Thr |
| chr1 | 1.28E+08 | G | A | missense_variant | Dars | transcript | protein_coding | p.Thr131Ile |
| chr1 | 1.71E+08 | G | A | missense_variant | Klhdc9 | transcript | protein_coding | p.Ala122Val |
| chr2 | 69948424 | G | A | missense_variant &splice_ region_ variant | Ubr3 | transcript | protein_coding | p.Glu594Lys |
| chr2 | 77075007 | G | A | missense_variant &splice_ region_ variant | Ccdc141 | transcript | protein_coding | p.Ser365Leu |
| chr2 | 85722196 | G | A | missense_variant | Olfr1009 | transcript | protein_coding | p.Ala264Thr |
| chr2 | 89144345 | G | A | missense_variant | Olfr1223 | transcript | protein_coding | p.Ser226Phe |
| chr2 | 1.19E+08 | G | A | missense_variant | Casc5 | transcript | protein_coding | p.Asp2Asn |
| chr2 | 1.75E+08 | G | A | missense_variant | Gm14444 | transcript | protein_coding | p.Arg207Gln |
| chr2 | 1.75E+08 | G | A | missense_variant | Gm14444 | transcript | protein_coding | p.Cys217Tyr |
| chr3 | 30965837 | G | A | missense_variant | Phc3 | transcript | protein_coding | p.Ser26Phe |
| chr3 | 55135642 | G | A | missense_variant | Spg20 | transcript | protein_coding | p.Glu660Lys |
| chr3 | 69027878 | G | A | missense_variant | Smc4 | transcript | protein_coding | p.Asp767Asn |
| chr3 | 82903198 | G | A | missense_variant | Lrat | transcript | protein_coding | p.Ser172Phe |
| chr3 | 88652163 | G | A | missense_variant | Rxfp4 | transcript | protein_coding | p.Ser327Phe |
| chr3 | 96527437 | G | A | missense_variant | Hfe2 | transcript | protein_coding | p.Gly164Glu |
| chr3 | 1.03E+08 | G | A | missense_variant | Csde1 | transcript | protein_coding | p.Ser2Asn |
| chr3 | 1.1E+08 | G | A | missense_variant | Vav3 | transcript | protein_coding | p.Arg321His |
| chr3 | 1.22E+08 | G | A | missense_variant | Abcd3 | transcript | protein_coding | p.His345Tyr |
| chr3 | 1.55E+08 | G | A | missense_variant | Lrriq3 | transcript | protein_coding | p.Ser263Asn |
| chr4 | 58069968 | G | A | missense_variant | Svep1 | transcript | protein_coding | p.Thr2606Ile |

FIG. 16

| Chr | Pos | Ref | Alt | SNPEFF Effect | SNPEFF Gene | SNPEFF Feature type | SNPEFF Biotype | SNPEFF Amino Acid change |
|---|---|---|---|---|---|---|---|---|
| chr4 | 94556660 | G | A | missense_variant | Gm10306 | transcript | protein_coding | p.Ala39Thr |
| chr4 | 1.13E+08 | G | A | missense_variant | Skint5 | transcript | protein_coding | p.Ser1310Phe |
| chr4 | 1.15E+08 | G | A | missense_variant | Cmpk1 | transcript | nonsense_ mediated_ decay | p.Ser58Phe |
| chr4 | 1.4E+08 | G | A | missense_variant | Iffo2 | transcript | protein_coding | p.Gly28Glu |
| chr4 | 1.46E+08 | G | A | missense_variant | Gm13242 | transcript | protein_coding | p.Gly516Ser |
| chr4 | 1.46E+08 | G | A | missense_variant | Gm13242 | transcript | protein_coding | p.Cys595Tyr |
| chr4 | 1.46E+08 | G | A | missense_variant | Gm13251 | transcript | protein_coding | p.Val64Ile |
| chr4 | 1.47E+08 | G | A | missense_variant | Gm13139 | transcript | protein_coding | p.Glu126Lys |
| chr5 | 9570035 | G | A | missense_variant | Grm3 | transcript | protein_coding | p.Ala403Val |
| chr5 | 32984015 | G | A | missense_variant | Depdc5 | transcript | protein_coding | p.Glu1442Lys |
| chr5 | 38228083 | G | A | missense_variant | Lyar | transcript | protein_coding | p.Asp127Asn |
| chr5 | 49285259 | G | A | missense_variant | Kcnip4 | transcript | protein_coding | p.His28Tyr |
| chr5 | 75183015 | G | A | missense_variant | Pdgfra | transcript | protein_coding | p.Met732Ile |
| chr5 | 90250399 | G | A | missense_variant | Ankrd17 | transcript | protein_coding | p.Thr1764Ile |
| chr5 | 1.07E+08 | G | A | missense_variant &splice_ region_ variant | Cdc7 | transcript | protein_coding | p.Gly107Glu |
| chr5 | 1.07E+08 | G | A | missense_variant | Cdc7 | transcript | protein_coding | p.Met112Ile |
| chr5 | 1.16E+08 | G | A | missense_variant | Cit | transcript | protein_coding | p.Met1630Ile |
| chr5 | 1.21E+08 | G | A | missense_variant | Plbd2 | transcript | protein_coding | p.Ala16Val |
| chr6 | 34839401 | G | A | missense_variant | Agbl3 | transcript | protein_coding | p.Glu754Lys |
| chr6 | 64320122 | G | A | missense_variant | Grid2 | transcript | protein_coding | p.Val490Ile |
| chr6 | 88222887 | G | A | missense_variant | Dnajb8 | transcript | protein_coding | p.Gly135Asp |
| chr6 | 1.21E+08 | G | A | missense_variant | Cecr2 | transcript | protein_coding | p.Arg119His |
| chr6 | 1.22E+08 | G | A | missense_variant | Mug2 | transcript | protein_coding | p.Val149Ile |
| chr6 | 1.22E+08 | G | A | missense_variant | Mug2 | transcript | protein_coding | p.Met151Ile |
| chr7 | 9097623 | G | A | missense_variant | Vmn2r38 | transcript | protein_coding | p.Ala48Val |
| chr7 | 23632941 | G | A | missense_variant | Vmn1r171 | transcript | protein_coding | p.Arg197His |
| chr7 | 26450788 | G | A | missense_variant | Nlrp4a | transcript | protein_coding | p.Val607Ile |
| chr7 | 36770946 | G | A | missense_variant | Tshz3 | transcript | protein_coding | p.Asp787Asn |

FIG. 16 (Cont.)

| Chr | Pos | Ref | Alt | SNPEFF Effect | SNPEFF Gene | SNPEFF Feature type | SNPEFF Biotype | SNPEFF Amino Acid change |
|---|---|---|---|---|---|---|---|---|
| chr7 | 63919293 | G | A | missense_variant | E030018B13Rik | transcript | protein_coding | p.Gly30Ser |
| chr7 | 1.07E+08 | G | A | missense_variant | Olfr705 | transcript | protein_coding | p.Ala156Val |
| chr7 | 1.08E+08 | G | A | missense_variant | Olfr480 | transcript | protein_coding | p.Ala245Val |
| chr7 | 1.08E+08 | G | A | missense_variant | Olfr491 | transcript | protein_coding | p.Arg229His |
| chr7 | 1.13E+08 | G | A | missense_variant | Tead1 | transcript | protein_coding | p.Asp405Asn |
| chr8 | 83997735 | G | A | missense_variant | Samd1 | transcript | protein_coding | p.Ala22Thr |
| chr8 | 1.06E+08 | G | A | missense_variant | 4933405L10Rik | transcript | protein_coding | p.Gly197Glu |
| chr8 | 1.07E+08 | G | A | missense_variant | Chtf8 | transcript | protein_coding | p.Ser183Phe |
| chr8 | 1.08E+08 | G | A | missense_variant | Wwp2 | transcript | protein_coding | p.Glu742Lys |
| chr8 | 1.14E+08 | G | A | missense_variant | Mon1b | transcript | protein_coding | p.Val118Met |
| chr8 | 1.21E+08 | G | A | missense_variant | Foxl1 | transcript | protein_coding | p.Glu271Lys |
| chr9 | 17030709 | G | A | missense_variant | Gm5611 | transcript | protein_coding | p.Gly210Glu |
| chr9 | 58033697 | G | A | missense_variant | Ccdc33 | transcript | protein_coding | p.Arg606Trp |
| chr9 | 76130366 | G | A | missense_variant | Hmgcll1 | transcript | protein_coding | p.Ala284Thr |
| chr9 | 86542459 | G | A | missense_variant | Dopey1 | transcript | nonsense_ mediated_ decay | p.Arg142Gln |
| chr9 | 94537706 | G | A | missense_variant | 1190002N15Rik | transcript | protein_coding | p.Ala57Val |
| chr9 | 1.07E+08 | G | A | missense_variant | Rbm15b | transcript | protein_coding | p.Ser9Phe |
| chr10 | 6789059 | G | A | missense_variant | Oprm1 | transcript | protein_coding | p.Ser62Asn |
| chr10 | 58223007 | G | A | missense_variant | AW822073 | transcript | protein_coding | p.Pro642Ser |
| chr10 | 58223810 | G | A | missense_variant | AW822073 | transcript | protein_coding | p.Ala374Val |
| chr10 | 84814685 | G | A | missense_variant | Rfx4 | transcript | protein_coding | p.Ala81Thr |
| chr10 | 1.3E+08 | G | A | missense_variant | Olfr815 | transcript | protein_coding | p.Ala129Val |
| chr11 | 23486872 | G | A | missense_variant | Usp34 | transcript | protein_coding | p.Glu3271Lys |
| chr11 | 29139233 | G | A | missense_variant | Pnpt1 | transcript | protein_coding | p.Met292Ile |
| chr11 | 69406836 | G | A | missense_variant | Kdm6b | transcript | protein_coding | p.Pro259Leu |
| chr11 | 77563672 | G | A | missense_variant | Taok1 | transcript | protein_coding | p.Leu275Phe |
| chr11 | 78291481 | G | A | missense_variant | BC030499 | transcript | protein_coding | p.Gly39Arg |
| chr11 | 87869936 | G | A | missense_variant | Epx | transcript | protein_coding | p.Thr390Met |
| chr11 | 95511448 | G | A | missense_variant | Nxph3 | transcript | protein_coding | p.Pro47Ser |

FIG. 16 (Cont.)

| Chr | Pos | Ref | Alt | SNPEFF Effect | SNPEFF Gene | SNPEFF Feature type | SNPEFF Biotype | SNPEFF Amino Acid change |
|---|---|---|---|---|---|---|---|---|
| chr11 | 1.01E+08 | G | A | missense_variant | Psme3 | transcript | protein_coding | p.Arg186Lys |
| chr12 | 4990907 | G | A | missense_variant | Atad2b | transcript | protein_coding | p.Arg770Gln |
| chr12 | 51891404 | G | A | missense_variant | Heatr5a | transcript | protein_coding | p.Ala1497Val |
| chr12 | 89260371 | G | A | missense_variant | Nrxn3 | transcript | nonsense_mediated_decay | p.Ala259Thr |
| chr13 | 11568551 | G | A | missense_variant | Ryr2 | transcript | protein_coding | p.Ala4739Val |
| chr13 | 17452500 | G | A | missense_variant | Sugct | transcript | protein_coding | p.Ala256Val |
| chr13 | 42157473 | G | A | missense_variant | Hivep1 | transcript | protein_coding | p.Ser1063Asn |
| chr13 | 44848393 | G | A | missense_variant | Jarid2 | transcript | protein_coding | p.Asp99Asn |
| chr13 | 58392402 | G | A | missense_variant | Hnrnpk | transcript | protein_coding | p.Ser390Phe |
| chr13 | 65296399 | G | A | missense_variant | Zfp369 | transcript | protein_coding | p.Gly452Asp |
| chr13 | 91564657 | G | A | missense_variant | Ssbp2 | transcript | protein_coding | p.Cys82Tyr |
| chr13 | 91884499 | G | A | missense_variant | Rasgrf2 | transcript | protein_coding | p.Ala566Val |
| chr13 | 92776945 | G | A | missense_variant | Thbs4 | transcript | protein_coding | p.Arg156Cys |
| chr14 | 43543686 | G | A | missense_variant | Gm5799 | transcript | protein_coding | p.Asp15Asn |
| chr14 | 68570141 | G | A | missense_variant | Adamdec1 | transcript | protein_coding | p.Leu357Phe |
| chr15 | 12592370 | G | A | missense_variant | Pdzd2 | transcript | protein_coding | p.Pro63Ser |
| chr15 | 66004749 | G | A | missense_variant | Kcnq3 | transcript | protein_coding | p.Thr515Ile |
| chr15 | 79648804 | G | A | missense_variant | Fam227a | transcript | protein_coding | p.Ser51Phe |
| chr15 | 81448488 | G | A | missense_variant | Xpnpep3 | transcript | protein_coding | p.Ala409Thr |
| chr15 | 1.01E+08 | G | A | missense_variant | Krt86 | transcript | protein_coding | p.Val401Ile |
| chr15 | 1.04E+08 | G | A | missense_variant | Spt1 | transcript | protein_coding | p.Thr107Met |
| chr16 | 33646589 | G | A | missense_variant | Slc12a8 | transcript | protein_coding | p.Glu489Lys |
| chr16 | 36042443 | G | A | missense_variant | Wdr5b | transcript | protein_coding | p.Ala311Thr |
| chr16 | 43662263 | G | A | missense_variant | Tigit | transcript | protein_coding | p.Ala36Val |
| chr17 | 8961981 | G | A | missense_variant | Pde10a | transcript | protein_coding | p.Arg467His |
| chr17 | 23401433 | G | A | missense_variant | Vmn2r116 | transcript | protein_coding | p.Val714Ile |
| chr17 | 23401515 | G | A | missense_variant | Vmn2r116 | transcript | protein_coding | p.Gly741Asp |
| chr17 | 23477456 | G | A | missense_variant | Vmn2r117 | transcript | protein_coding | p.His326Tyr |
| chr17 | 29138126 | G | A | missense_variant | Rab44 | transcript | protein_coding | p.Ala77Thr |

FIG. 16 (Cont.)

| Chr | Pos | Ref | Alt | SNPEFF Effect | SNPEFF Gene | SNPEFF Feature type | SNPEFF Biotype | SNPEFF Amino Acid change |
|---|---|---|---|---|---|---|---|---|
| chr17 | 29138126 | G | A | missense_variant | Rab44 | transcript | protein_coding | p.Ala77Thr |
| chr17 | 32135456 | G | A | missense_variant | Notch3 | transcript | protein_coding | p.Pro1765Leu |
| chr17 | 46302670 | G | A | missense_variant | Dlk2 | transcript | protein_coding | p.Gly241Ser |
| chr17 | 52905021 | G | A | missense_variant | Kcnh8 | transcript | protein_coding | p.Ala616Thr |
| chr17 | 64636606 | G | A | missense_variant | Man2a1 | transcript | protein_coding | p.Ala219Thr |
| chr17 | 68841609 | G | A | missense_variant | Tmem200c | transcript | protein_coding | p.Ala396Thr |
| chr18 | 25090624 | G | A | missense_variant | Fhod3 | transcript | protein_coding | p.Ser1009Asn |
| chr18 | 35978648 | G | A | missense_variant | Psd2 | transcript | protein_coding | p.Gly109Arg |
| chr18 | 37021463 | G | A | missense_variant | Pcdha12 | transcript | protein_coding | p.Ala412Thr |
| chr18 | 73791142 | G | A | missense_variant | Me2 | transcript | protein_coding | p.Ser333Leu |
| chr19 | 4001204 | G | A | missense_variant | Nudt8 | transcript | protein_coding | p.Gly68Asp |
| chr19 | 8064481 | G | A | missense_variant | Slc22a28 | transcript | protein_coding | p.Leu454Phe |
| chr19 | 13839077 | G | A | missense_variant | Olfr1501 | transcript | protein_coding | p.Ala32Val |
| chr19 | 42124953 | G | A | missense_variant | Avpi1 | transcript | protein_coding | p.Arg22Trp |
| chrX | 56968379 | G | A | missense_variant | Adgrg4 | transcript | protein_coding | p.Ala65Thr |
| chrX | 78126029 | G | A | missense_variant | Gm5938 | transcript | protein_coding | p.Ala29Thr |
| chrX | 79350311 | G | A | missense_variant | Gm7173 | transcript | protein_coding | p.Thr2390Ile |
| chrX | 79350318 | G | A | missense_variant | Gm7173 | transcript | protein_coding | p.Leu2388Phe |
| chrX | 1.4E+08 | G | A | missense_ variant&splice_ region_variant | Tbc1d8b | transcript | protein_coding | p.Gly956Asp |
| chrX | 1.41E+08 | G | A | missense_variant | Mid2 | transcript | protein_coding | p.Ala358Thr |
| chrX | 1.66E+08 | G | A | missense_variant | Gpm6b | transcript | nonsense_ media ted_decay | p.Gly72Ser |
| chr1 | 24085430 | C | T | missense_variant | Fam135a | transcript | protein_coding | p.Val20Met |
| chr1 | 85089537 | C | T | missense_variant | A530032D15Rik | transcript | protein_coding | p.Arg196Lys |
| chr1 | 1.72E+08 | C | T | missense_variant | Gm10521 | transcript | protein_coding | p.Leu43Phe |
| chr1 | 1.8E+08 | C | T | missense_variant | Ahctf1 | transcript | protein_coding | p.Ala578Thr |

FIG. 16 (Cont.)

| Chr | Pos | Ref | Alt | SNPEFF Effect | SNPEFF Gene | SNPEFF Feature type | SNPEFF Biotype | SNPEFF Amino Acid change |
|---|---|---|---|---|---|---|---|---|
| chr2 | 6872573 | C | T | missense_variant | Celf2 | transcript | nonsense_media ted_decay | p.Gly9Arg |
| chr2 | 6872594 | C | T | missense_variant | Celf2 | transcript | nonsense_media ted_decay | p.Ala2Thr |
| chr2 | 49257670 | C | T | missense_variant | Mbd5 | transcript | protein_coding | p.Leu631Phe |
| chr2 | 59289220 | C | T | missense_variant&splice_region_variant | Pkp4 | transcript | protein_coding | p.Ser83Leu |
| chr2 | 60458446 | C | T | missense_variant | Pla2r1 | transcript | protein_coding | p.Arg614His |
| chr2 | 77074987 | C | T | missense_variant | Ccdc141 | transcript | protein_coding | p.Val372Ile |
| chr2 | 77074993 | C | T | missense_variant | Ccdc141 | transcript | protein_coding | p.Gly370Arg |
| chr2 | 82976190 | C | T | missense_variant | Fsip2 | transcript | protein_coding | p.Pro951Leu |
| chr2 | 86046904 | C | T | missense_variant | Olfr1034 | transcript | protein_coding | p.Arg141Cys |
| chr2 | 1.25E+08 | C | T | missense_variant | Slc12a1 | transcript | protein_coding | p.Thr214Ile |
| chr2 | 1.26E+08 | C | T | missense_variant | Fgf7 | transcript | protein_coding | p.Thr179Met |
| chr3 | 15963594 | C | T | missense_variant | Gm5150 | transcript | protein_coding | p.Cys171Tyr |
| chr3 | 1.03E+08 | C | T | missense_variant | Csde1 | transcript | protein_coding | p.Pro5Ser |
| chr3 | 1.28E+08 | C | T | missense_variant&splice_region_variant | Ap1ar | transcript | protein_coding | p.Arg60Lys |
| chr3 | 1.52E+08 | C | T | missense_variant | Nexn | transcript | protein_coding | p.Gly165Glu |
| chr4 | 33031595 | C | T | missense_variant | Ube2j1 | transcript | protein_coding | p.Arg4Cys |
| chr4 | 93335173 | C | T | missense_variant | Tusc1 | transcript | protein_coding | p.Arg83His |
| chr4 | 1.27E+08 | C | T | missense_variant | Zmym4 | transcript | protein_coding | p.Asp929Asn |
| chr4 | 1.29E+08 | C | T | missense_variant | C77080 | transcript | protein_coding | p.Ala903Thr |
| chr4 | 1.48E+08 | C | T | missense_variant | Zfp534 | transcript | protein_coding | p.Glu213Lys |
| chr4 | 1.5E+08 | C | T | missense_variant | Pik3cd | transcript | protein_coding | p.Asp900Asn |
| chr4 | 1.56E+08 | C | T | missense_variant&splice_region_variant | Plekhn1 | transcript | protein_coding | p.Gly294Ser |

FIG. 16 (Cont.)

| Chr | Pos | Ref | Alt | SNPEFF Effect | SNPEFF Gene | SNPEFF Feature type | SNPEFF Biotype | SNPEFF Amino Acid change |
|---|---|---|---|---|---|---|---|---|
| chr5 | 15032826 | C | T | missense_variant | Gm17019 | transcript | protein_coding | p.Arg38Gln |
| chr5 | 90501551 | C | T | missense_variant | Afp | transcript | protein_coding | p.Pro326Ser |
| chr5 | 1.32E+08 | C | T | missense_variant | Auts2 | transcript | protein_coding | p.Met67Ile |
| chr6 | 55038135 | C | T | missense_variant | Gars | transcript | protein_coding | p.Arg32Trp |
| chr6 | 1.16E+08 | C | T | missense_variant | Zfand4 | transcript | protein_coding | p.Ala181Val |
| chr6 | 1.19E+08 | C | T | missense_variant | Cacna1c | transcript | protein_coding | p.Val1018Ile |
| chr6 | 1.33E+08 | C | T | missense_variant | Tas2r136 | transcript | protein_coding | p.Ser29Asn |
| chr6 | 1.37E+08 | C | T | missense_variant | Gucy2c | transcript | protein_coding | p.Arg887Gln |
| chr7 | 6717173 | C | T | missense_variant | Peg3 | transcript | protein_coding | p.Gly44Ser |
| chr7 | 7247210 | C | T | missense_variant | Vmn2r29 | transcript | protein_coding | p.Gly40Glu |
| chr7 | 14226036 | C | T | missense_variant | Sult2a6 | transcript | protein_coding | p.Ala191Thr |
| chr7 | 28090153 | C | T | missense_variant | Fcgbp | transcript | protein_coding | p.Leu715Phe |
| chr7 | 43466485 | C | T | missense_variant | Vsig10l | transcript | protein_coding | p.Pro519Ser |
| chr7 | 49848502 | C | T | missense_variant | Prmt3 | transcript | protein_coding | p.Ala449Val |
| chr7 | 58740379 | C | T | missense_variant | Atp10a | transcript | protein_coding | p.Arg217Cys |
| chr7 | 86756957 | C | T | missense_variant | Folh1 | transcript | protein_coding | p.Asp303Asn |
| chr7 | 1.09E+08 | C | T | missense_variant | Olfr503 | transcript | protein_coding | p.Pro162Ser |
| chr7 | 1.14E+08 | C | T | missense_variant | Pde3b | transcript | protein_coding | p.Ser323Phe |
| chr7 | 1.28E+08 | C | T | missense_variant | Stx1b | transcript | protein_coding | p.Glu7Lys |
| chr8 | 3439628 | C | T | missense_variant | Arhgef18 | transcript | protein_coding | p.Ser320Phe |
| chr8 | 13595352 | C | T | missense_variant | Rasa3 | transcript | protein_coding | p.Glu196Lys |
| chr8 | 19691613 | C | T | missense_variant | Gm6483 | transcript | protein_coding | p.Pro55Ser |
| chr8 | 41293499 | C | T | missense_variant | Pcm1 | transcript | protein_coding | p.Thr1206Ile |
| chr8 | 1.03E+08 | C | T | missense_variant | Cdh11 | transcript | protein_coding | p.Arg137Lys |
| chr8 | 1.11E+08 | C | T | missense_variant | Pdpr | transcript | protein_coding | p.Thr669Met |
| chr9 | 3028720 | C | T | missense_variant | Gm10717 | transcript | protein_coding | p.Leu225Phe |
| chr9 | 3030876 | C | T | missense_variant | Gm10717 | transcript | protein_coding | p.Pro179Leu |
| chr9 | 3030935 | C | T | missense_variant | Gm10717 | transcript | protein_coding | p.Arg122Cys |
| chr10 | 24281454 | C | T | missense_variant | Moxd1 | transcript | protein_coding | p.Thr328Ile |
| chr11 | 23284553 | C | T | missense_variant | Xpo1 | transcript | protein_coding | p.Leu464Phe |

FIG. 16 (Cont.)

| Chr | Pos | Ref | Alt | SNPEFF Effect | SNPEFF Gene | SNPEFF Feature type | SNPEFF Biotype | SNPEFF Amino Acid change |
|---|---|---|---|---|---|---|---|---|
| chr17 | 15522903 | C | T | missense_variant | Pdcd2 | transcript | protein_coding | p.Gly220Glu |
| chr17 | 20268154 | C | T | missense_variant | Vmn2r106 | transcript | protein_coding | p.Gly661Glu |
| chr17 | 23291037 | C | T | missense_variant | Vmn2r114 | transcript | protein_coding | p.Gly823Glu |
| chr17 | 23477505 | C | T | missense_variant | Vmn2r117 | transcript | protein_coding | p.Met309Ile |
| chr17 | 26926261 | C | T | missense_variant | Kifc5b | transcript | protein_coding | p.Ser647Phe |
| chr17 | 28991303 | C | T | missense_variant | Stk38 | transcript | protein_coding | p.Gly101Ser |
| chr17 | 32357901 | C | T | missense_variant | Wiz | transcript | protein_coding | p.Ala550Thr |
| chr17 | 33199924 | C | T | missense_variant | Olfr239 | transcript | protein_coding | p.Pro288Leu |
| chr17 | 33663242 | C | T | missense_variant | Hnrnpm | transcript | protein_coding | p.Arg253His |
| chr17 | 71725029 | C | T | missense_variant | Fam179a | transcript | protein_coding | p.Ala901Val |
| chr17 | 71749905 | C | T | missense_variant | BC027072 | transcript | protein_coding | p.Ala926Thr |
| chrX | 26028764 | C | T | missense_variant | Gm5168 | transcript | protein_coding | p.Glu170Lys |
| chrX | 41838184 | C | T | missense_variant | Thoc2 | transcript | protein_coding | p.Glu618Lys |
| chrX | 42229139 | C | T | missense_variant | Stag2 | transcript | protein_coding | p.Leu345Phe |
| chrX | 79332806 | C | T | missense_variant | Gm7173 | transcript | protein_coding | p.Gly2492Arg |
| chrX | 79445592 | C | T | missense_variant | Gm7173 | transcript | protein_coding | p.Val1266Ile |
| chrX | 1.08E+08 | C | T | missense_variant | Tbx22 | transcript | nonsense_mediated_decay | p.Ser81Leu |
| chrX | 1.12E+08 | C | T | missense_variant | 4933403O08Rik | transcript | protein_coding | p.Ser366Phe |
| chrX | 1.12E+08 | C | T | missense_variant | Satl1 | transcript | protein_coding | p.Glu711Lys |
| chrX | 1.13E+08 | C | T | missense_variant | Chm | transcript | protein_coding | p.Glu81Lys |
| chrX | 1.24E+08 | C | T | missense_variant | Vmn2r121 | transcript | protein_coding | p.Arg33Lys |
| chrX | 1.36E+08 | C | T | missense_variant | Gprasp2 | transcript | protein_coding | p.Pro797Ser |
| chrX | 1.36E+08 | C | T | missense_variant | Gprasp2 | transcript | protein_coding | p.Ala801Val |
| chrX | 1.36E+08 | C | T | missense_variant | Gprasp2 | transcript | protein_coding | p.His803Tyr |
| chrX | 1.5E+08 | C | T | missense_variant | Gm15097 | transcript | protein_coding | p.Ser396Phe |
| chrX | 1.53E+08 | C | T | missense_variant | Usp51 | transcript | protein_coding | p.Pro271Ser |
| chrX | 1.61E+08 | C | T | missense_variant | Cdkl5 | transcript | protein_coding | p.Gly7Asp |

FIG. 16 (Cont.)

| Chr | Pos | Ref | Alt | SNPEFF Effect | SNPEFF Gene | SNPEFF Feature type | SNPEFF Biotype | SNPEFF Amino Acid change |
|---|---|---|---|---|---|---|---|---|
| chr11 | 23343327 | C | T | missense_variant | Usp34 | transcript | protein_coding | p.Ser206Leu |
| chr11 | 56040871 | C | T | missense_variant | Nmur2 | transcript | protein_coding | p.Glu5Lys |
| chr11 | 68807275 | C | T | missense_variant | Myh10 | transcript | protein_coding | p.Arg1685Cys |
| chr11 | 77692999 | C | T | missense_variant | Nufip2 | transcript | protein_coding | p.Pro580Ser |
| chr11 | 84520304 | C | T | missense_variant | Lhx1 | transcript | protein_coding | p.Gly274Asp |
| chr11 | 91576642 | C | T | missense_variant | Kif2b | transcript | protein_coding | p.Asp272Asn |
| chr11 | 91576756 | C | T | missense_variant | Kif2b | transcript | protein_coding | p.Asp234Asn |
| chr12 | 32841038 | C | T | missense_variant | Nampt | transcript | protein_coding | p.Ala286Val |
| chr12 | 40079641 | C | T | missense_variant | Scin | transcript | protein_coding | p.Met384Ile |
| chr13 | 24756615 | C | T | missense_variant | Gmnn | transcript | protein_coding | p.Asp84Asn |
| chr13 | 33334326 | C | T | missense_variant | Serpinb9f | transcript | protein_coding | p.Leu270Phe |
| chr13 | 38210222 | C | T | missense_variant | Snrnp48 | transcript | protein_coding | p.Pro96Ser |
| chr13 | 38210223 | C | T | missense_variant | Snrnp48 | transcript | protein_coding | p.Pro96Leu |
| chr13 | 66431825 | C | T | missense_variant | 2410141K09Rik | transcript | protein_coding | p.Ala200Thr |
| chr13 | 69612954 | C | T | missense_variant | Nsun2 | transcript | protein_coding | p.Leu91Phe |
| chr14 | 4635370 | C | T | missense_variant | Gm8159 | transcript | protein_coding | p.Ala196Val |
| chr14 | 7549858 | C | T | missense_variant | Gm3558 | transcript | protein_coding | p.Gly181Arg |
| chr14 | 21686731 | C | T | missense_variant | Dupd1 | transcript | protein_coding | p.Arg101Gln |
| chr14 | 27438655 | C | T | missense_variant | Fam208a | transcript | protein_coding | p.Leu125Phe |
| chr14 | 54737632 | C | T | missense_variant | Slc7a8 | transcript | protein_coding | p.Arg180Gln |
| chr14 | 56584164 | C | T | missense_variant | Parp4 | transcript | protein_coding | p.Thr2Ile |
| chr14 | 73164783 | C | T | missense_variant | Rcbtb2 | transcript | protein_coding | p.Ser150Leu |
| chr15 | 9740528 | C | T | missense_variant | Spef2 | transcript | protein_coding | p.Glu49Lys |
| chr15 | 25701697 | C | T | missense_variant | Myo10 | transcript | protein_coding | p.Arg86Cys |
| chr15 | 77637945 | C | T | missense_variant | Apol11b | transcript | protein_coding | p.Glu51Lys |
| chr15 | 77967325 | C | T | missense_variant | Eif3d | transcript | protein_coding | p.Arg95Gln |
| chr15 | 1.03E+08 | C | T | missense_variant | Smug1 | transcript | protein_coding | p.Gly114Asp |
| chr16 | 10791892 | C | T | missense_variant | Prm2 | transcript | protein_coding | p.Arg36His |
| chr16 | 32755111 | C | T | missense_variant | Muc4 | transcript | protein_coding | p.Pro1662Ser |
| chr16 | 56687044 | C | T | missense_variant | Abi3bp | transcript | protein_coding | p.Thr1075Met |

FIG. 16 (Cont.)

Table 3. Generation of 21mer mutant and wild type peptides. Missense mutations from Table 2 were translated into peptided with the missense mutation flanked by 10 amino acids on each side, as well as corresponding peptides with the wild type amino acid sequence.

| SNPEFF | SNPEFF | SNPEFF | SNPEFF | | seq | | | | SEQ | | | SEQ | | | variant |
|---|---|---|---|---|---|---|---|---|---|---|---|---|---|---|---|
| Effect | Feature type | Biotype | AminoAcid change | aachange | position | wt | position | wt_pep | ID NO: | mt | mt_pep | ID NO: | HLA_D | HLA_K | no |
| missense_variant | transcript | protein_coding | p.Ala57Val | A57V | A | A | 57 | RRFLQLNKCPACFGTSWCRRF | 25 | V | RRFLQLNKCPVCFGTSWCRRF | 296 | H-2-Db | H-2-Kb | 0 |
| missense_variant | transcript | protein_coding | p.Ala200Thr | A200T | A | A | 200 | NQCGKAFARPANLQCHKRTHT | 26 | T | NQCGKAFARPTNLQCHKRTHT | 297 | H-2-Db | H-2-Kb | 1 |
| missense_variant | transcript | protein_coding | p.Ser3669Phe | S366F | S | S | 366 | SGRPSGHVVSSPLIELSKIGE | 27 | F | SGRPSGHVVSFPLIELSKIGE | 298 | H-2-Db | H-2-Kb | 2 |
| missense_variant | transcript | protein_coding | p.Ser3669Phe | S366F | S | S | 366 | SGRPSGHVVSSPLIELSKIGE | 27 | F | SGRPSGHVVSFPLIELSKIGE | 298 | H-2-Db | H-2-Kb | 3 |
| missense_variant | transcript | protein_coding | p.Gly197Glu | G197E | G | G | 197 | CNPELNQEEDGDREPEVEPEA | 28 | E | CNPELNQEEDEDREPEVEPEA | 299 | H-2-Db | H-2-Kb | 4 |
| missense_variant | transcript | protein_coding | p.Arg196Lys | R196K | R | R | 196 | PGGTFLQENPRSREEKRKATT | 29 | K | PGGTFLQENPKSREEKRKATT | 300 | H-2-Db | H-2-Kb | 5 |
| missense_variant | transcript | protein_coding | p.Arg196Lys | R196K | R | R | 196 | PGGTFLQENPRSRESWQVWSL | 30 | K | PGGTFLQENPKSREEKRKATT | 301 | H-2-Db | H-2-Kb | 6 |
| missense_variant | transcript | protein_coding | p.His345Tyr | H345Y | H | H | 345 | RPFLDLAHPRHLHSTHSELLE | 31 | Y | RPFLDLAHPRYLHSTHSELLE | 302 | H-2-Db | H-2-Kb | 7 |
| missense_variant | transcript | protein_coding | p.Thr1075Met | T1075M | T | T | 1075 | GQQLTSEQLPTKEGYFRAVRQ | 32 | M | GQQLTSEQLPMKEGYFRAVRQ | 303 | H-2-Db | H-2-Kb | 8 |
| missense_variant | transcript | protein_coding | p.Thr1075Met | T1075M | T | T | 1075 | ECKGKQYVKRTWYKKFVGVQL | 33 | M | ECKGKQYVKRMWYKKFVGVQL | 304 | H-2-Db | H-2-Kb | 9 |
| missense_variant | transcript | protein_coding | p.Leu357Phe | L357F | L | L | 357 | ALMSHELGHALGMKDVPYYTK | 34 | F | ALMSHELGHAFGMKDVPYYTK | 305 | H-2-Db | H-2-Kb | 10 |
| missense_variant | transcript | protein_coding | p.Ala55Thr | A65T | A | A | 65 | PVRIFFLYLFAICNTLQGFLI | 35 | T | PVRIFFLYLFTICNTLQGFLI | 306 | H-2-Db | H-2-Kb | 11 |
| missense_variant | transcript | protein_coding | p.Pro326Ser | P3268 | P | P | 326 | GVKPEGLSLNPSQFLGDRNFA | 36 | S | GVKPEGLSLNSSQFLGDRNFA | 307 | H-2-Db | H-2-Kb | 12 |
| missense_variant | transcript | protein_coding | p.Glu754Lys | E754K | E | E | 754 | ILETCKNPIQEVQSRGINIHE | 37 | K | ILETCKNPIQKVQSRGINIHE | 308 | H-2-Db | H-2-Kb | 13 |
| missense_variant | transcript | protein_coding | p.Ala578Thr | A578T | A | A | 578 | WIIEEQPNSAANLRFVLEWTW | 38 | T | WIIEEQPNSATNLRFVLEWTW | 309 | H-2-Db | H-2-Kb | 14 |
| missense_variant | transcript | protein_coding | p.Thr1764*e | T1764I | T | T | 1764 | HIDIDKQKDKTGDRIITIRGG | 39 | I | HIDIDKQKDKIGDRIITIRGG | 310 | H-2-Db | H-2-Kb | 15 |
| missense_variant &spice_region_ variant | transcript | protein_coding | p.Arg60Lys | R60K | R | R | 60 | DEGESPGSSHRPLTEDEIADL | 40 | K | DEGESPGSSHKPLTEDEIADL | 311 | H-2-Db | H-2-Kb | 16 |

FIG. 17

| | | | | | | | | | | | | | | | |
|---|---|---|---|---|---|---|---|---|---|---|---|---|---|---|---|
| missense_variant &spice_region_ variant | transcript | protein_coding | p.Arg60Lys | R60K | R | R | 60 | DEGESPGSSHRPLTEDEIADL | 40 | K | DEGESPGSSHKPLTEDEIADL | 311 | H-2-Db | H-2-Kb | 17 |
| missense_variant | transcript | protein_coding | p.Glu51Lys | E51K | E | E | 51 | GAWNGFVEAVELSSEEGEALR | 41 | K | GAWNGFVEAVKLSSEEGEALR | 312 | H-2-Db | H-2-Kb | 18 |
| missense_variant | transcript | protein_coding | p.Glu51Lys | E51K | E | E | 51 | GAWNGFVEAVELSSEEGEALR | 41 | K | GAWNGFVEAVKLSSEEGEALR | 312 | H-2-Db | H-2-Kb | 19 |
| missense_variant | transcript | protein_coding | p.Glu51Lys | E51K | E | E | 51 | GAWNGFVEAVELSSEEGEALR | 41 | K | GAWNGFVEAVKLSSEEGEALR | 312 | H-2-Db | H-2-Kb | 20 |
| missense_variant | transcript | protein_coding | p.Ser320Phe | S320F | S | S | 320 | EIAAKTDQKSSGKLKNGLTFR | 42 | F | EIAAKTDQKSFGKLKNGLTFR | 313 | H-2-Db | H-2-Kb | 21 |
| missense_variant | transcript | protein_coding | p.Arg770Gln | R770Q | R | R | 770 | MAFGPTSYRPRLLLSGERGSG | 43 | Q | MAFGPTSYRPQLLLSGERGSG | 314 | H-2-Db | H-2-Kb | 22 |
| missense_variant | transcript | protein_coding | p.Arg217Cys | R217C | R | R | 217 | ETNLKRRQVVRGFSELVSEFN | 44 | C | ETNLKRRQVVCGFSELVSEFN | 315 | H-2-Db | H-2-Kb | 23 |
| missense_variant | transcript | protein_coding | p.Met67Ile | M67I | M | M | 67 | LCQHLGKRKKMPKGLRQLKPG | 45 | I | LCQHLGKRKKIPKGLRQLKPG | 316 | H-2-Db | H-2-Kb | 24 |
| missense_variant | transcript | protein_coding | p.Arg22Trp | R22W | R | R | 22 | PLWQVSTPQTRGRKQASANIF | 46 | W | PLWQVSTPQTWGRKQASANIF | 317 | H-2-Db | H-2-Kb | 25 |
| missense_variant | transcript | protein_coding | p.Arg22Trp | R22W | R | R | 22 | PLWQVSTPQTRGRKQASANIF | 46 | W | PLWQVSTPQTWGRKQASANIF | 317 | H-2-Db | H-2-Kb | 26 |
| missense_variant | transcript | protein_coding | p.Ala374Val | A374V | A | A | 374 | QDSLLPLEEAANSGMDTSIPS | 47 | V | QDSLLPLEEAVNSGMDTSIPS | 318 | H-2-Db | H-2-Kb | 27 |
| missense_variant | transcript | protein_coding | p.Pro642Ser | P642S | P | P | 642 | MDTTPDLPLTPEEYQTLLDML | 48 | S | MDTTPDLPLTSEEYQTLLDML | 319 | H-2-Db | H-2-Kb | 28 |
| missense_variant | transcript | protein_coding | p.Ala925Thr | A926T | A | A | 926 | SKQTASPSSEAKSRAQIQARA | 49 | T | SKQTASPSSETKSRAQIQARA | 320 | H-2-Db | H-2-Kb | 29 |
| missense_variant | transcript | protein_coding | p.Gly39Arg | G39R | G | G | 39 | QGWKSLWCGMGTIRSGLEELW | 50 | R | QGWKSLWCGMRTIRSGLEELW | 321 | H-2-Db | H-2-Kb | 30 |
| missense_variant | transcript | protein_coding | p.Ala903Thr | A903T | A | A | 903 | PRSPQSPASKASFIFSKGTKK | 51 | T | PRSPQSPASKTSFIFSKGTKK | 322 | H-2-Db | H-2-Kb | 31 |
| missense_variant | transcript | protein_coding | p.Ala903Thr | A903T | A | A | 903 | ALSGRASPVTAPSSGLHAAVR | 52 | T | ALSGRASPVTTPSSGLHAAVR | 323 | H-2-Db | H-2-Kb | 32 |
| missense_variant | transcript | protein_coding | p.Val1018lie | V1018I | V | V | 1018 | AINRAKGLKHVVQCVFVAIRT | 53 | I | AINRAKGLKHIVQCVFVAIRT | 324 | H-2-Db | H-2-Kb | 33 |
| missense_variant | transcript | protein_coding | p.Val1018lie | V1018I | V | V | 1018 | AINRAKGLKHVVQCVFVAIRT | 53 | I | AINRAKGLKHIVQCVFVAIRT | 324 | H-2-Db | H-2-Kb | 34 |
| missense_variant | transcript | protein_coding | p.Val1018lie | V1018I | V | V | 1018 | AINRAKGLKHVVQCVFVAIRT | 53 | I | AINRAKGLKHIVQCVFVAIRT | 324 | H-2-Db | H-2-Kb | 35 |
| missense_variant | transcript | protein_coding | p.Val1018lie | V1018I | V | V | 1018 | AINRAKGLKHVVQCVFVAIRT | 53 | I | AINRAKGLKHIVQCVFVAIRT | 324 | H-2-Db | H-2-Kb | 36 |
| missense_variant | transcript | protein_coding | p.Val1018lie | V1018I | V | V | 1018 | AKGLKHVVQCVFVAIRTIGNI | 54 | I | AKGLKHVVQCIFVAIRTIGNI | 325 | H-2-Db | H-2-Kb | 37 |
| missense_variant | transcript | protein_coding | p.Val1018lie | V1018I | V | V | 1018 | SFGIQSSAINVVKILRVLRVL | 55 | I | SFGIQSSAINIVKILRVLRVL | 326 | H-2-Db | H-2-Kb | 38 |

FIG. 17 (Cont.)

| | | | | | | | | | | | | | | | |
|---|---|---|---|---|---|---|---|---|---|---|---|---|---|---|---|
| missense_variant | transcript | protein_coding | p.Val1018Ile | V1018I | V | V | 1018 | AINRAKGLKHVVQCVFVAIRT | 56 | I | AINRAKGLKHIVQCVFVAIRT | 327 | H-2-Db | H-2-Kb | 39 |
| missense_variant | transcript | protein_coding | p.Val1018Ile | V1018I | V | V | 1018 | AINRAKGLKHVVQCVFVAIRT | 56 | I | AINRAKGLKHIVQCVFVAIRT | 327 | H-2-Db | H-2-Kb | 40 |
| missense_variant | transcript | protein_coding | p.Val1018Ile | V1018I | V | V | 1018 | SFGIQSSAINVVKILRVLRVL | 57 | I | SFGIQSSAINIVKILRVLRVL | 328 | H-2-Db | H-2-Kb | 41 |
| missense_variant | transcript | protein_coding | p.Val1018Ile | V1018I | V | V | 1018 | AINRAKGLKHVVQCVFVAIRT | 58 | I | AINRAKGLKHIVQCVFVAIRT | 329 | H-2-Db | H-2-Kb | 42 |
| missense_variant | transcript | protein_coding | p.Val1018Ile | V1018I | V | V | 1018 | SFGIQSSAINVVKILRVLRVL | 59 | I | SFGIQSSAINIVKILRVLRVL | 330 | H-2-Db | H-2-Kb | 43 |
| missense_variant | transcript | protein_coding | p.Asp2Asn | D2N | D | D | 2 | MDGVYSEANEEN | 60 | N | MNGVYSEANEEN | 331 | H-2-Db | H-2-Kb | 44 |
| missense_variant | transcript | protein_coding | p.Asp2Asn | D2N | D | D | 2 | MDGVYSEANEEN | 60 | N | MNGVYSEANEEN | 331 | H-2-Db | H-2-Kb | 45 |
| missense_variant | transcript | protein_coding | p.Asp2Asn | D2N | D | D | 2 | MDGVYSEANEEN | 60 | N | MNGVYSEANEEN | 331 | H-2-Db | H-2-Kb | 46 |
| missense_variant | transcript | protein_coding | p.Asp2Asn | D2N | D | D | 2 | MDGVYSEANEEN | 60 | N | MNGVYSEANEEN | 331 | H-2-Db | H-2-Kb | 47 |
| missense_variant | transcript | protein_coding | p.Asp2Asn | D2N | D | D | 2 | MDGVYSEANEEN | 60 | N | MNGVYSEANEEN | 331 | H-2-Db | H-2-Kb | 48 |
| missense_variant | transcript | protein_coding | p.Val372Ile | V372I | V | V | 372 | ANKSFDVLGKVEAYLKLLKSE | 61 | I | ANKSFDVLGKIEAYLKLLKSE | 332 | H-2-Db | H-2-Kb | 49 |
| missense_variant | transcript | protein_coding | p.Val372Ile | V372I | V | V | 372 | ANKSFDVLGKVEAYLKLLKSE | 61 | I | ANKSFDVLGKIEAYLKLLKSE | 332 | H-2-Db | H-2-Kb | 50 |
| missense_variant &spice_region_variant | transcript | protein_coding | p.Ser365Leu | S365L | S | S | 365 | ANDFFTSANKSFDVLGKVEAY | 62 | L | ANDFFTSANKLFDVLGKVEAY | 333 | H-2-Db | H-2-Kb | 51 |
| missense_variant &spice_region_variant | transcript | protein_coding | p.Ser365Leu | S365L | S | S | 365 | ANDFFTSANKSFDVLGKVEAY | 62 | L | ANDFFTSANKLFDVLGKVEAY | 333 | H-2-Db | H-2-Kb | 52 |
| missense_variant | transcript | protein_coding | p.Gly370Arg | G370R | G | G | 370 | TSANKSFDVLGKVEAYLKLLK | 63 | R | TSANKSFDVLRKVEAYLKLLK | 334 | H-2-Db | H-2-Kb | 53 |
| missense_variant | transcript | protein_coding | p.Gly370Arg | G370R | G | G | 370 | TSANKSFDVLGKVEAYLKLLK | 63 | R | TSANKSFDVLRKVEAYLKLLK | 334 | H-2-Db | H-2-Kb | 54 |
| missense_variant | transcript | protein_coding | p.Arg606Trp | R606W | R | R | 606 | PRDVEMNNYRRAMQKMAEDIL | 64 | W | PRDVEMNNYRWAMQKMAEDIL | 335 | H-2-Db | H-2-Kb | 55 |
| missense_variant | transcript | protein_coding | p.Met112Ile | M112I | M | M | 112 | LTVAGGQDNVMGLKYCFRKND | 65 | I | LTVAGGQDNVIGLKYCFRKND | 336 | H-2-Db | H-2-Kb | 56 |
| missense_variant | transcript | protein_coding | p.Met112Ile | M112I | M | M | 112 | LTVAGGQDNVMGLKYCFRKND | 65 | I | LTVAGGQDNVIGLKYCFRKND | 336 | H-2-Db | H-2-Kb | 57 |
| missense_variant | transcript | protein_coding | p.Met112Ile | M112I | M | M | 112 | LTVAGGQDNVMGLKYCFRKND | 65 | I | LTVAGGQDNVIGLKYCFRKND | 336 | H-2-Db | H-2-Kb | 58 |

FIG. 17 (Cont.)

| | | | | | | | | | | | | | | | |
|---|---|---|---|---|---|---|---|---|---|---|---|---|---|---|---|
| missense_variant | transcript | protein_coding | p.Met112lie | M112I | M | M | 112 | LTVAGGQDNVMGLKYCFRKND | 65 | I | LTVAGGQDNVIGLKYCFRKND | 336 | H-2-Db | H-2-Kb | 59 |
| missense_variant | transcript | protein_coding | p.Met112lie | M112I | M | M | 112 | LTVAGGQDNVMGLKYCFRKND | 65 | I | LTVAGGQDNVIGLKYCFRKND | 336 | H-2-Db | H-2-Kb | 60 |
| missense_variant &spice_region_ variant | transcript | protein_coding | p.Gly107Glu | G107E | G | G | 107 | AELQCLTVAGGQDNVMGLKYC | 66 | E | AELQCLTVAGEQDNVMGLKYC | 337 | H-2-Db | H-2-Kb | 61 |
| missense_variant &spice_region_ variant | transcript | protein_coding | p.Gly107Glu | G107E | G | G | 107 | AELQCLTVAGGQDNVMGLKYC | 66 | E | AELQCLTVAGEQDNVMGLKYC | 337 | H-2-Db | H-2-Kb | 62 |
| missense_variant &spice_region_ variant | transcript | protein_coding | p.Gly107Glu | G107E | G | G | 107 | AELQCLTVAGGQDNVMGLKYC | 66 | E | AELQCLTVAGEQDNVMGLKYC | 337 | H-2-Db | H-2-Kb | 63 |
| missense_variant &spice_region_ variant | transcript | protein_coding | p.Gly107Glu | G107E | G | G | 107 | AELQCLTVAGGQDNVMGLKYC | 66 | E | AELQCLTVAGEQDNVMGLKYC | 337 | H-2-Db | H-2-Kb | 64 |
| missense_variant &spice_region_ variant | transcript | protein_coding | p.Gly107Glu | G107E | G | G | 107 | AELQCLTVAGGQDNVMGLKYC | 66 | E | AELQCLTVAGEQDNVMGLKYC | 337 | H-2-Db | H-2-Kb | 65 |
| missense_variant | transcript | protein_coding | p.Arg137Lys | R137K | R | R | 137 | MAQAVDRDTNRPLEPPSEFIV | 67 | K | MAQAVDRDTNKPLEPPSEFIV | 338 | H-2-Db | H-2-Kb | 66 |
| missense_variant | transcript | protein_coding | p.Gly7Asp | G7D | G | G | 7 | MKIPNIGNVMNKFEILG | 68 | D | MKIPNDNVMNKFEILG | 339 | H-2-Db | H-2-Kb | 67 |
| missense_variant | transcript | protein_coding | p.Gly7Asp | G7D | G | G | 7 | MKIPNIGNVMNKFEILG | 68 | D | MKIPNDNVMNKFEILG | 339 | H-2-Db | H-2-Kb | 68 |
| missense_variant | transcript | protein_coding | p.Gly7Asp | G7D | G | G | 7 | MKIPNIGNVMNKFEILG | 68 | D | MKIPNDNVMNKFEILG | 339 | H-2-Db | H-2-Kb | 69 |
| missense_variant | transcript | protein_coding | p.Gly7Asp | G7D | G | G | 7 | MKIPNIGNVMNKFEILG | 68 | D | MKIPNDNVMNKFEILG | 339 | H-2-Db | H-2-Kb | 70 |
| missense_variant | transcript | protein_coding | p.Arg119His | R119H | R | R | 119 | PLRTRVEILHRLCDYRLDADD | 69 | H | PLTRVEILHHLCDYRLDADD | 340 | H-2-Db | H-2-Kb | 71 |
| missense_variant | transcript | protein_coding | p.Arg119His | R119H | R | R | 119 | PLRTRVEILHRLCDYRLDADD | 69 | H | PLTRVEILHHLCDYRLDADD | 340 | H-2-Db | H-2-Kb | 72 |
| missense_variant | transcript | nonsense_mediate | p.Gly9Arg | G9R | G | G | 9 | SARFGGRPGRPRAPVPACL | 70 | R | SARFGGRPRRPRAPVPACL | 341 | H-2-Db | H-2-Kb | 73 |
| missense_variant | transcript | nonsense_mediate | p.Ala2Thr | A2T | A | A | 2 | SARFGGRPGRR | 71 | T | STRFGGRPGRPR | 342 | H-2-Db | H-2-Kb | 74 |

FIG. 17 (Cont.)

| | | | | | | | | | | | | | | | | |
|---|---|---|---|---|---|---|---|---|---|---|---|---|---|---|---|---|
| missense_variant | transcript | protein_coding | p.Glu81Lys | E81K | E | E | 81 | ENSMWQEQILENEEAILLSSK | 72 | K | ENSMWQEQILKNEEAILLSSK | 343 | H-2-Db | H-2-Kb | 75 |
| missense_variant | transcript | protein_coding | p.Glu81Lys | E81K | E | E | 81 | ENSMWQEQILENEEAILLSSK | 72 | K | ENSMWQEQILKNEEAILLSSK | 343 | H-2-Db | H-2-Kb | 76 |
| missense_variant | transcript | protein_coding | p.Ser183Phe | S183F | S | S | 183 | CGPNMRAGVLSSGTGPPNPRP | 73 | F | CGPNMRAGVLFSGTGPPNPRP | 344 | H-2-Db | H-2-Kb | 77 |
| missense_variant | transcript | protein_coding | p.Met1630Ile | M1630I | M | M | 1630 | YIIKDLEKLLMIAGEERALCL | 74 | I | YIIKDLEKLLIIAGEERALCL | 345 | H-2-Db | H-2-Kb | 78 |
| missense_variant | transcript | nonsense_mediate | p.Ser58Phe | S58F | S | S | 58 | GTQCARIVESSAPAS | 75 | F | GTQCARIVESFAPAS | 346 | H-2-Db | H-2-Kb | 79 |
| missense_variant | transcript | protein_coding | p.Ser2Asn | S2N | S | S | 2 | MSFDPNLLHNNG | 76 | N | MNFDPNLLHNNG | 347 | H-2-Db | H-2-Kb | 80 |
| missense_variant | transcript | protein_coding | p.Ser2Asn | S2N | S | S | 2 | MSFDPNLLHNNG | 76 | N | MNFDPNLLHNNG | 347 | H-2-Db | H-2-Kb | 81 |
| missense_variant | transcript | protein_coding | p.Ser2Asn | S2N | S | S | 2 | MSFDPNLLHNNG | 76 | N | MNFDPNLLHNNG | 347 | H-2-Db | H-2-Kb | 82 |
| missense_variant | transcript | protein_coding | p.Ser2Asn | S2N | S | S | 2 | MSFDPNLLHNNG | 76 | N | MNFDPNLLHNNG | 347 | H-2-Db | H-2-Kb | 83 |
| missense_variant | transcript | protein_coding | p.Ser2Asn | S2N | S | S | 2 | MSFDPNLLHNNG | 76 | N | MNFDPNLLHNNG | 347 | H-2-Db | H-2-Kb | 84 |
| missense_variant | transcript | protein_coding | p.Ser2Asn | S2N | S | S | 2 | MSFDPNLLHNNG | 76 | N | MNFDPNLLHNNG | 347 | H-2-Db | H-2-Kb | 85 |
| missense_variant | transcript | protein_coding | p.Pro5Ser | P5S | P | P | 5 | MSFDPNLLHNNGHNG | 77 | S | MSFDSNLLHNNGHNG | 348 | H-2-Db | H-2-Kb | 86 |
| missense_variant | transcript | protein_coding | p.Pro5Ser | P5S | P | P | 5 | MSFDPNLLHNNGHNG | 77 | S | MSFDSNLLHNNGHNG | 348 | H-2-Db | H-2-Kb | 87 |
| missense_variant | transcript | protein_coding | p.Pro5Ser | P5S | P | P | 5 | MSFDPNLLHNNGHNG | 77 | S | MSFDSNLLHNNGHNG | 348 | H-2-Db | H-2-Kb | 88 |
| missense_variant | transcript | protein_coding | p.Pro5Ser | P5S | P | P | 5 | MSFDPNLLHNNGHNG | 77 | S | MSFDSNLLHNNGHNG | 348 | H-2-Db | H-2-Kb | 89 |
| missense_variant | transcript | protein_coding | p.Pro5Ser | P5S | P | P | 5 | MSFDPNLLHNNGHNG | 77 | S | MSFDSNLLHNNGHNG | 348 | H-2-Db | H-2-Kb | 90 |
| missense_variant | transcript | protein_coding | p.Pro5Ser | P5S | P | P | 5 | MSFDPNLLHNNGHNG | 77 | S | MSFDSNLLHNNGHNG | 348 | H-2-Db | H-2-Kb | 91 |
| missense_variant | transcript | protein_coding | p.Thr131Ile | T131I | T | T | 131 | RKVNQKIGSCTQQDVELHVQK | 78 | I | RKVNQKIGSCIQQDVELHVQK | 349 | H-2-Db | H-2-Kb | 92 |
| missense_variant | transcript | protein_coding | p.Glu1442Lys | E1442K | E | E | 1442 | NLSCLLKEGSEHLFDSFEPET | 79 | K | NLSCLLKEGSKHLFDSFEPET | 350 | H-2-Db | H-2-Kb | 93 |
| missense_variant | transcript | protein_coding | p.Gly241Ser | G241S | G | G | 241 | VHDFDCLCPSGYGGKTCELVL | 80 | S | VHDFDCLCPSSYGGKTCELVL | 351 | H-2-Db | H-2-Kb | 94 |
| missense_variant | transcript | protein_coding | p.Gly241Ser | G241S | G | G | 241 | VHDFDCLCPSGYGGKTCELVL | 80 | S | VHDFDCLCPSSYGGKTCELVL | 351 | H-2-Db | H-2-Kb | 95 |
| missense_variant | transcript | protein_coding | p.Gly135Asp | G135D | G | G | 135 | PHGLHRVFPSGFGEFPAFMEA | 81 | D | PHGLHRVFPSDFGEFPAFMEA | 352 | H-2-Db | H-2-Kb | 96 |
| missense_variant | transcript | nonsense_mediate | p.Arg142Gln | R142Q | R | R | 142 | NIMHYWPYLRNHSAHNAPSY | 82 | Q | NIMHYWPYLQNHSAHNAPSY | 353 | H-2-Db | H-2-Kb | 97 |

FIG. 17 (Cont.)

| | | | | | | | | | | | | | | | |
|---|---|---|---|---|---|---|---|---|---|---|---|---|---|---|---|
| missense_variant | transcript | protein_coding | p.Arg101Gln | R101Q | R | R | 101 | WNVDTGPDYYRDMAIEYHGVE | 83 | Q | WNVDTGPDYYQDMAIEYHGVE | 354 | H-2-Db | H-2-Kb | 98 |
| missense_variant | transcript | protein_coding | p.Gly30Ser | G30S | G | G | 30 | SVFSTHAGCAGAHEAEGYPAE | 84 | S | SVFSTHAGCASAHEAGGYPAE | 355 | H-2-Db | H-2-Kb | 99 |
| missense_variant | transcript | protein_coding | p.Arg95Gln | R95Q | R | R | 95 | TARTQKTAYQRNRMRFAQRNL | 85 | Q | TARTQKTAYQQNRMRFAQRNL | 356 | H-2-Db | H-2-Kb | 100 |
| missense_variant | transcript | protein_coding | p.Thr390Met | T390M | T | T | 390 | SETPKLTALHTLFVREHNRLA | 86 | M | SETPKLTALHMLFVREHNRLA | 357 | H-2-Db | H-2-Kb | 101 |
| missense_variant | transcript | nonsense_mediate | p.Val20Met | V20M | V | V | 20 | FSVELNKFYNVDLFQRGFYQI | 87 | M | FSVELNKFYNMDLFQRGFYQI | 358 | H-2-Db | H-2-Kb | 102 |
| missense_variant | transcript | protein_coding | p.Val20Met | V20M | V | V | 20 | FSVELNKFYNVDLFQRGFYQI | 87 | M | FSVELNKFYNMDLFQRGFYQI | 358 | H-2-Db | H-2-Kb | 103 |
| missense_variant | transcript | protein_coding | p.Val20Met | V20M | V | V | 20 | FSVELNKFYNVDLFQRGKTFQ | 88 | M | FSVELNKFYNMDLFQRGKTFQ | 359 | H-2-Db | H-2-Kb | 104 |
| missense_variant | transcript | protein_coding | p.Val20Met | V20M | V | V | 20 | FSVELNKFYNVDLFQRGFYQI | 87 | M | FSVELNKFYNMDLFQRGFYQI | 360 | H-2-Db | H-2-Kb | 105 |
| missense_variant | transcript | protein_coding | p.Val20Met | V20M | V | V | 20 | FSVELNKFYNVDLFQRGFYQI | 87 | M | FSVELNKFYNMDLFQRGFYQI | 360 | H-2-Db | H-2-Kb | 106 |
| missense_variant | transcript | protein_coding | p.Ala901Val | A901V | A | A | 901 | AGRVRFLTGPAVLDITDRLSV | 89 | V | AGRVRFLTGPWLDITDRLSV | 361 | H-2-Db | H-2-Kb | 107 |
| missense_variant | transcript | protein_coding | p.Leu125Phe | L125F | L | L | 125 | SREFEDVLNILHSSYLEPSSV | 90 | F | SREFEDVLNIFHSSYLEPSSV | 362 | H-2-Db | H-2-Kb | 108 |
| missense_variant | transcript | protein_coding | p.Ser51Phe | S51F | S | S | 51 | PICLSACIIGSMSQVNQRIME | 91 | F | PICLSACIIGFMSQVNQRIME | 363 | H-2-Db | H-2-Kb | 109 |
| missense_variant | transcript | protein_coding | p.Ser51Phe | S51F | S | S | 51 | PICLSACIIGSMSQVNQRIME | 91 | F | PICLSACIIGFMSQVNQRIME | 363 | H-2-Db | H-2-Kb | 110 |
| missense_variant | transcript | protein_coding | p.Leu715Phe | L715F | L | L | 715 | GTVHPWRSEELCPLTCPPNSH | 92 | F | GTVHPWRSEEFCPLTCPPNSH | 364 | H-2-Db | H-2-Kb | 111 |
| missense_variant | transcript | protein_coding | p.Leu715Phe | L715F | L | L | 715 | GTVHPWRSEELCPLTCPPNSH | 92 | F | GTVHPWRSEEFCPLTCPPNSH | 364 | H-2-Db | H-2-Kb | 112 |
| missense_variant | transcript | protein_coding | p.Thr179Met | T179M | T | T | 179 | QKGIPVKGKKTKKEQKTAHFL | 93 | M | QKGIPVKGKKMKKEQKTAHFL | 365 | H-2-Db | H-2-Kb | 113 |
| missense_variant | transcript | protein_coding | p.Thr179Met | T179M | T | T | 179 | QKGIPVKGKKTKKEQKTAHFL | 93 | M | QKGIPVKGKKMKKEQKTAHFL | 365 | H-2-Db | H-2-Kb | 114 |
| missense_variant | transcript | protein_coding | p.Ser1009Asn | S1009N | S | S | 1009 | PPPPPPPLLDSVPPPPVPGNL | 94 | N | PPPPPPPLLDNVPPPPVPGNL | 366 | H-2-Db | H-2-Kb | 115 |
| missense_variant | transcript | protein_coding | p.Asp303Asn | D303N | D | D | 303 | SIPVHPIGYDDAQKLLEKVKM | 95 | N | SIPVHPIGYDNAQKLLEKVKM | 367 | H-2-Db | H-2-Kb | 116 |
| missense_variant | transcript | protein_coding | p.Asp303Asn | D303N | D | D | 303 | SIPVHPIGYDDAQKLLEKVKM | 96 | N | SIPVHPIGYDNAQKLLEHMGG | 368 | H-2-Db | H-2-Kb | 117 |

FIG. 17 (Cont.)

| | | | | | | | | | | | | | | |
|---|---|---|---|---|---|---|---|---|---|---|---|---|---|---|
| missense_variant | transcript | Protein_coding | p.Glu271Lys | E271K | E | E | 271 | AVRPTPASGAEAPGIPKPVPG | 97 | K | AVRPTPASGAKAPGIPKPVPG | 369 | H-2-Db | H-2-Kb | 118 |
| missense_variant | transcript | Protein_coding | p.Pro951Leu | P951L | P | P | 951 | QQPVKAGVKKPRRPRVRNLSD | 98 | L | QQPVKAGVKKKRRPRVRNLSD | 370 | H-2-Db | H-2-Kb | 119 |
| missense_variant | transcript | Protein_coding | p.Val45Met | V45M | V | V | 45 | IHALCHCKSAVNKDIVSVYHS | 99 | M | IHALCHCKSAMNKDIVSVYHS | 371 | H-2-Db | H-2-Kb | 120 |
| missense_variant | transcript | Protein_coding | p.Arg32Trp | R32W | R | R | 32 | PRWAASASQRLLSAPAQPAA | 100 | W | PRWAASASQWLLSAPAQPAA | 372 | H-2-Db | H-2-Kb | 121 |
| missense_variant | transcript | Protein_coding | p.Ala39Thr | A39T | A | A | 39 | GCERRGCLLPAPLAPLFSGRL | 101 | T | GECRRGCLLPTPLAPLFSGRL | 373 | H-2-Db | H-2-Kb | 122 |
| missense_variant | transcript | Protein_coding | p.Leu43Phe | L43F | L | L | 43 | LSLSLSLSLSLSLSLSLSPSLSL | 102 | F | LSLSLSLSLSFSLSLSPSLSLS | 374 | H-2-Db | H-2-Kb | 123 |
| missense_variant | transcript | Protein_coding | p.Leu225Phe | L225F | L | L | 225 | WMFLIFHDFQLSC | 103 | F | WMFLIFHDFQFSC | 375 | H-2-Db | H-2-Kb | 124 |
| missense_variant | transcript | Protein_coding | p.Leu225Phe | L225F | L | L | 225 | WKFLIFHDFQLSS | 104 | F | WKFLIFHDFQFSS | 376 | H-2-Db | H-2-Kb | 125 |
| missense_variant | transcript | Protein_coding | p.Pro179Leu | P179L | P | P | 179 | HVLQWTFLNFPPFSVSPYSRS | 105 | L | HVLQWTFLNFLPFSVSPYSRS | 377 | H-2-Db | H-2-Kb | 126 |
| missense_variant | transcript | Protein_coding | p.Arg122Cys | R122C | R | R | 122 | HVLKCVFLIFRDFQVSRHIPG | 106 | C | HVLKCVFLIFCDFQVSRHIPG | 378 | H-2-Db | H-2-Kb | 127 |
| missense_variant | transcript | Protein_coding | p.Arg122Cys | R122C | R | R | 122 | HVLKCVFLIFRDFQVSRHIPG | 106 | C | HVLKCVFLIFCDFQVSRHIPG | 378 | H-2-Db | H-2-Kb | 128 |
| missense_variant | transcript | Protein_coding | p.Arg122Cys | R122C | R | R | 122 | HVLKCVFLIFRDFQFSCYIPS | 107 | C | HVLKCVFLIFCDFQFSCYIPS | 379 | H-2-Db | H-2-Kb | 129 |
| missense_variant | transcript | Protein_coding | p.Arg122Cys | R122C | R | R | 122 | HVLKCVFLIFRVFQFPRHIPG | 108 | C | HVLKCVFLIFRVFQFPRHIPG | 380 | H-2-Db | H-2-Kb | 130 |
| missense_variant | transcript | Protein_coding | p.Glu126Lys | E126K | E | E | 126 | QKRLKPRNTKEVCKYNDSVNS | 109 | K | QKRLKPRNTKKVCKYNDSVNS | 381 | H-2-Db | H-2-Kb | 131 |
| missense_variant | transcript | Protein_coding | p.Cys595Tyr | C595Y | C | C | 595 | KPYKCSECDKCFTEKNGLRRH | 110 | Y | KPYKCSECDKYFTEKNGLRRH | 382 | H-2-Db | H-2-Kb | 132 |
| missense_variant | transcript | Protein_coding | p.Gly516Ser | G516S | G | G | 516 | SECDKCFTDKGSLAVHHRIHA | 111 | S | SECDKCFTDKSSLRVHHRIHA | 383 | H-2-Db | H-2-Kb | 133 |
| missense_variant | transcript | Protein_coding | p.Va541e | V541 | V | V | 64 | NHCICGKYEKVLDQDQYIVH | 112 | I | NHCICGKYEKILDQDSQYIVH | 384 | H-2-Db | H-2-Kb | 134 |
| missense_variant | transcript | Protein_coding | p.Cys217Tyr | C217Y | C | C | 217 | RTHTREKPYECKQCGKAFSQS | 113 | Y | RTHTREKPYEYKQCGKAFSQS | 385 | H-2-Db | H-2-Kb | 134 |
| missense_variant | transcript | Protein_coding | p.Arg207G** | R207Q | R | R | 207 | AHSSHLHIHERTHTREKPYEC | 114 | Q | AHSSHLHIHEQTHTREKPYEC | 386 | H-2-Db | H-2-Kb | 136 |
| missense_variant | transcript | Protein_coding | p.Ser396Phe | S396F | S | S | 396 | PGSEPEIDRSSAIRERTDYLW | 115 | F | PGSEPEIDRSFAIRERTDYLW | 387 | H-2-Db | H-2-Kb | 137 |
| missense_variant | transcript | Protein_coding | p.Ser396Phe | S396F | S | S | 396 | PGSEPEIDRSSAIRERTDYLW | 115 | F | PGSEPEIDRSFAIRERTDYLW | 387 | H-2-Db | H-2-Kb | 138 |
| missense_variant | transcript | Protein_coding | p.Arg38** | R38Q | R | R | 38 | ADLPSERNEGRRRWTWRMWM | 116 | Q | ADLPSERNEGQRRWTWRMWM | 388 | H-2-Db | H-2-Kb | 139 |
| missense_variant | transcript | Protein_coding | p.Ala219Thr | A219T | A | A | 219 | DISHNMRLSRASVLYEQMREC | 117 | T | DISHNMRLSRTSVLYEQMREC | 389 | H-2-Db | H-2-Kb | 140 |
| missense_variant | transcript | Protein_coding | p.Gly181Arg | G1B1R | G | G | 181 | VEQAGHKCPVGKKRGSLRRPA | 118 | R | VEQAGHKCPVRKKRGSLRRPA | 390 | H-2-Db | H-2-Kb | 141 |

FIG. 17 (Cont.)

| | | | | | | | | | | | | | | |
|---|---|---|---|---|---|---|---|---|---|---|---|---|---|---|
| missense_variant | transcript | Protein_coding | p.Cys171Tyr | C171Y | C | C | 171 | VRAGGLATLNCTVTSLIPVGP | 119 | Y | VRAGGLATLNYTVTSLIPVGP | 391 | H-2-Db | H-2-Kb | 142 |
| missense_variant | transcript | Protein_coding | p.Cys171Tyr | C171Y | C | C | 171 | VRAGGLATLNCTVTSLIPVGP | 119 | Y | VRAGGLATLNYTVTSLIPVGP | 391 | H-2-Db | H-2-Kb | 143 |
| missense_variant | transcript | Protein_coding | p.Glu170Lys | E170K | E | E | 170 | QKEQEALKLSECSQRQTLEAI | 120 | K | QKEQEALKLSKCSQRQTLEAI | 392 | H-2-Db | H-2-Kb | 144 |
| missense_variant | transcript | Protein_coding | p.Glu170Lys | E170K | E | E | 170 | QKEQEALKLSECSQRQTLEAI | 120 | K | QKEQEALKLSKCSQRQTLEAI | 392 | H-2-Db | H-2-Kb | 145 |
| missense_variant | transcript | Protein_coding | p.Gly210Glu | G210E | G | G | 210 | SKGQESFKKQGKIPKIPKGPS | 121 | E | SKGQESFKKQEKIPKIPKGPS | 393 | H-2-Db | H-2-Kb | 146 |
| missense_variant | transcript | Protein_coding | p.Asp15Asn | D15N | D | D | 15 | LCRLFHRENGDQGETRPRQKE | 122 | N | LCRLFHRENGNQGETRPRQKE | 394 | H-2-Db | H-2-Kb | 147 |
| missense_variant | transcript | Protein_coding | p.Ala29Thr | A29T | A | A | 29 | EGPWKTVAIAADRVDKIERGG | 123 | T | EGPWKTVAIATDRVDKIERGG | 395 | H-2-Db | H-2-Kb | 148 |
| missense_variant | transcript | Protein_coding | p.Pro55Ser | P55S | P | P | 55 | KLVYSILEGQPYFSVEQTGI | 124 | S | KLVYSILEGQSYFSVEAQTGI | 396 | H-2-Db | H-2-Kb | 149 |
| missense_variant | transcript | Protein_coding | p.Val1266Ile | VI266I | V | V | 1266 | TPVPLDVTTGVDIRILPQNYF | 125 | I | TPVPLDVTTGIDIRILPQNYF | 397 | H-2-Db | H-2-Kb | 150 |
| missense_variant | transcript | Protein_coding | p.Leu2388Phe | L2388F | L | L | 2388 | SIIVPNYTKSLLTFKVTSDLS | 126 | F | SIIVPNYTKSFLTFKVTSDLS | 398 | H-2-Db | H-2-Kb | 151 |
| missense_variant | transcript | Protein_coding | p.Gly2495Arg | G2492R | G | G | 2492 | WYHLEIRSSPGPPVDIIELHC | 127 | R | WYHLEIRSSPRPPVDIIELHC | 399 | H-2-Db | H-2-Kb | 152 |
| missense_variant | transcript | Protein_coding | p.Thr2390** | T2390I | T | T | 2390 | IVPNYTKSLLTFKVTSDLSIV | 128 | I | IVPNYTKSLLIFKVTSDLSIV | 400 | H-2-Db | H-2-Kb | 153 |
| missense_variant | transcript | Protein_coding | p.Ala196Val | A196V | A | A | 196 | FCEEASKNICASSAKEQQSEI | 129 | V | FCEEASKNICVSSAKEQQSEI | 401 | H-2-Db | H-2-Kb | 154 |
| missense_variant | transcript | Protein_coding | p.Ala195Val | A196V | A | A | 196 | FCEEASKNICASSAKEQQV$^+$ | 130 | V | FCEEASKNICVSSAKEQQV$^+$ | 402 | H-2-Db | H-2-Kb | 155 |
| missense_variant | transcript | Protein_coding | p.Ala196Val | A196V | A | A | 196 | FCEEASKNICASSAKEQQVG$^+$ | 131 | V | FCEEASKNICVSSAKEQQVG$^+$ | 403 | H-2-Db | H-2-Kb | 156 |
| missense_variant | transcript | Protein_coding | p.Asp84Asn | D84N | D | D | 84 | DVGDLTQEAFDLISKENPSSQ | 132 | N | DVGDLTQEAFNLISKENIPSSQ | 404 | H-2-Db | H-2-Kb | 157 |
| missense_variant | transcript | Protein_coding | p.Asp84Asn | D84N | D | D | 84 | DVGDLTQEAFDLISKENPSSQ | 132 | N | DVGDLTQEAFNLISKENIPSSQ | 404 | H-2-Db | H-2-Kb | 158 |
| missense_variant | transcript | Protein_coding | p.Asp84Asn | D84N | D | D | 84 | DVGDLTQEAFDLISKENPSSQ | 132 | N | DVGDLTQEAFNLISKENIPSSQ | 404 | H-2-Db | H-2-Kb | 159 |
| missense_variant | transcript | nonsense_med | p.Asp84Asn | D84N | D | D | 84 | DVGDLTQEAFDLISKENPSSQ | 132 | N | DVGDLTQEAFNLISKENIPSSQ | 404 | H-2-Db | H-2-Kb | 160 |
| missense_variant | transcript | nonsense_med | p.Gly72Ser | G72S | G | G | 72 | CFECCIKCLGSVPYASLVATI | 133 | S | CFECCIKCLGSVPYASLVATI | 405 | H-2-Db | H-2-Kb | 161 |
| missense_variant | transcript | nonsense_med | p.Gly72Ser | G72S | G | G | 72 | CFECCIKCLGSVPYASLVATI | 133 | S | CFECCIKCLGSVPYASLVATI | 405 | H-2-Db | H-2-Kb | 162 |
| missense_variant | transcript | nonsense_med | p.Gly72Ser | G72S | G | G | 72 | SKNAKHLAKAGIANRFRMPHL | 134 | S | SKNAKHLAKASIANRFRMPHL | 406 | H-2-Db | H-2-Kb | 163 |
| missense_variant | transcript | Protein_coding | p.Gly72Ser | G72S | G | G | 72 | CFECCIKCLGGVPYASLVATI | 135 | S | CFECCIKCLGSVPYASLVATI | 407 | H-2-Db | H-2-Kb | 164 |
| missense_variant | transcript | Protein_coding | p.Pro797Ser | P797S | P | P | 797 | SLLDDDFSLEPLVSAFHEFEE | 136 | S | SLLDDDFSLESLVSAFHEFEE | 408 | H-2-Db | H-2-Kb | 165 |

FIG. 17 (Cont.)

| | | | | | | | | | | | | | | | |
|---|---|---|---|---|---|---|---|---|---|---|---|---|---|---|---|
| missense_variant | transcript | Protein_coding | p.Pro797Ser | P797S | P | P | 797 | SLLDDDFSLEPLVSAFHEFEE | 136 | S | SLLDDDFSLESLVSAFHEFEE | 408 | H-2-Db | H-2-Kb | 166 |
| missense_variant | transcript | Protein_coding | p.Ala801Val | A801V | A | A | 801 | DDFSLEPLVSAFHEFEELAKQ | 137 | V | DDFSLEPLVSVFHEFEELAKQ | 409 | H-2-Db | H-2-Kb | 167 |
| missense_variant | transcript | Protein_coding | p.Ala801Val | A801V | A | A | 801 | DDFSLEPLVSAFHEFEELAKQ | 137 | V | DDFSLEPLVSVFHEFEELAKQ | 409 | H-2-Db | H-2-Kb | 168 |
| missense_variant | transcript | Protein_coding | p.His803Tyr | H803Y | H | H | 803 | FSLEPLVSAFHEFEELAKQLQ | 138 | Y | FSLEPLVSAFYEFEELAKQLQ | 410 | H-2-Db | H-2-Kb | 169 |
| missense_variant | transcript | Protein_coding | p.His803Tyr | H803Y | H | H | 803 | FSLEPLVSAFHEFEELAKQLQ | 138 | Y | FSLEPLVSAFYEFEELAKQLQ | 410 | H-2-Db | H-2-Kb | 170 |
| missense_variant | transcript | Protein_coding | p.Val490Ie | V4901 | V | V | 490 | NYLGFNYEIYVAPDHKYGSPQ | 139 | I | NYLGFNYEIYIAPDHKYGSPQ | 411 | H-2-Db | H-2-Kb | 171 |
| missense_variant | transcript | Protein_coding | p.Ala403Val | A403V | A | A | 403 | WNAVYAMAHALHKMQRTLCP | 140 | V | WNAVYAMAHVLHKMQRTLCP | 412 | H-2-Db | H-2-Kb | 172 |
| missense_variant | transcript | Protein_coding | p.Arg887Gln | R887Q | R | R | 887 | ASGLPMRNGNRHAVDISKMAL | 141 | Q | ASGLPMRNGNQHAVDISKMAL | 413 | H-2-Db | H-2-Kb | 173 |
| missense_variant | transcript | Protein_coding | p.Ala1497Val | A1497V | A | A | 1497 | SAKLHYHDSWALILHAALWL | 142 | V | SAKLHYHDSWVLILHAAALWL | 414 | H-2-Db | H-2-Kb | 174 |
| missense_variant | transcript | Protein_coding | p.Gly164Glu | G164E | G | G | 164 | APGFLHCASFGDPHVRSFHNQ | 143 | E | APGFLHCASFEDPHVRSFHNQ | 415 | H-2-Db | H-2-Kb | 175 |
| missense_variant | transcript | Protein_coding | p.Ser1063Asn | S1063N | S | S | 1063 | QLQPVPGAAPSPSKHTSATAA | 144 | N | QLQPVPGAAPNPSKHTSATAA | 416 | H-2-Db | H-2-Kb | 176 |
| missense_variant | transcript | Protein_coding | p.Ala284Thr | A284T | A | A | 284 | AVSGLGGCPYAKGASGNVATE | 145 | T | AVSGLGGCPYTKGASGNVATE | 417 | H-2-Db | H-2-Kb | 177 |

FIG. 17 (Cont.)

| | | | | | | | | | | | | | | | | |
|---|---|---|---|---|---|---|---|---|---|---|---|---|---|---|---|---|
| missense_variant | transcript | protein_coding | p.Ser390Phe | S390F | S | S | 390 | YLLQNSVKQYSGKFF* | 146 | F | YLLQNSVKQYSGKFF* | 418 | H-2-Db | H-2-Kb | 178 |
| missense_variant | transcript | protein_coding | p.Arg253His | R253H | R | R | 253 | LPKGDFFPPERPQQLPHGLGG | 147 | H | LPKGDFFPPEHPQQLPHGLGG | 419 | H-2-Db | H-2-Kb | 179 |
| missense_variant | transcript | protein_coding | p.Arg253His | R253H | R | R | 253 | LPKGDFFPPERPQQLPHGLGG | 148 | H | LPKGDFFPPEHPQQLPHGLGG | 419 | H-2-Db | H-2-Kb | 180 |
| missense_variant | transcript | protein_coding | p.Gly28GlU | G28E | G | G | 28 | PGGGGCAGGGGGGGAGPGPSP | 149 | E | PGGGGCAGGGEGGGAGPGPSP | 420 | H-2-Db | H-2-Kb | 181 |
| missense_variant | transcript | protein_coding | p.Asp99Asn | D99N | D | D | 99 | SSTSNDVSSSDFEEGPSRKRP | 150 | N | SSTSNDVSSSNFEEGPSRKRP | 421 | H-2-Db | H-2-Kb | 182 |
| missense_variant | transcript | protein_coding | p.Asp99Asn | D99N | D | D | 99 | SSTSNDVSSSDFEEGPSRKRP | 150 | N | SSTSNDVSSSNFEEGPSRKRP | 421 | H-2-Db | H-2-Kb | 183 |
| missense_variant | transcript | protein_coding | p.Asp99Asn | D99N | D | D | 99 | SSTSNDVSSSDFEEGPSRKRP | 150 | N | SSTSNDVSSSNFEEGPSRKRP | 421 | H-2-Db | H-2-Kb | 184 |
| missense_variant | transcript | protein_coding | p.Ala616Thr | A616T | A | A | 616 | AILGKGDLIGANLSIKDQVIK | 151 | T | AILGKGDLIGTNLSIKDQVIK | 422 | H-2-Db | H-2-Kb | 185 |
| missense_variant | transcript | protein_coding | p.His28Tyr | H28Y | H | H | 28 | VIICASLKLLHLLGLIDFSED | 152 | Y | VIICASLKLLYLLGLIDFSED | 423 | H-2-Db | H-2-Kb | 186 |
| missense_variant | transcript | protein_coding | p.His28Tyr | H28Y | H | H | 28 | YLLRLLTGSLHTDSVEDELEM | 153 | Y | YLLRLLTGSLYTDSVEDELEM | 424 | H-2-Db | H-2-Kb | 187 |
| missense_variant | transcript | protein_coding | p.Thr515IIS | T5151 | T | T | 515 | NDFLIEDMIPLKAAIRAVRI | 154 | I | NDFLIEDMIPLKAAIRAVRI | 425 | H-2-Db | H-2-Kb | 188 |
| missense_variant | transcript | protein_coding | p.Pro259Leu | P259L | P | P | 259 | PPPPPPPPPPPPPPPPPPLPG | 155 | L | PPPPPPPPPPLPPPPPPPLPG | 426 | H-2-Db | H-2-Kb | 189 |
| missense_variant | transcript | protein_coding | p.Asp234Asn | D234N | D | D | 234 | NQRETTMKDLDIITIPSHNVV | 156 | N | NQRETTMKDLNIITIPSHNVV | 427 | H-2-Db | H-2-Kb | 190 |
| missense_variant | transcript | protein_coding | p.Asp272Asn | D272N | D | D | 272 | QTFCFDHAFDDKASNELVYQF | 157 | N | QTFCFDHAFDNKASNELVYQF | 428 | H-2-Db | H-2-Kb | 191 |
| missense_variant | transcript | protein_coding | p.Ser647Phe | S647F | S | S | 647 | VNISPLEENVSESLNSLRFAS | 158 | F | VNISPLEENVFESLNSLRFAS | 429 | H-2-Db | H-2-Kb | 192 |
| missense_variant | transcript | protein_coding | p.Ala122Val | A122V | A | A | 122 | TEREVWEAWAANPGNCPPAGL | 159 | V | TEREVWEAWAVNPGNCPPAGL | 430 | H-2-Db | H-2-Kb | 193 |
| missense_variant | transcript | protein_coding | p.Val401Ile | V4011 | V | V | 401 | EVMNSKLGLDVETTYRRLLE | 160 | I | EVMNSKLGLDIETTYRRLLE | 431 | H-2-Db | H-2-Kb | 194 |
| missense_variant | transcript | protein_coding | p.Gly274Asp | G274D | G | G | 274 | RLEPGELIPNGPFSFYGDYQS | 161 | D | RLEPGELIPNDPFSFYGDYQS | 432 | H-2-Db | H-2-Kb | 195 |
| missense_variant | transcript | protein_coding | p.Ser172Phe | S172F | S | S | 172 | EHFVTYCRYGSRISPQAEKFY | 162 | F | EHFVTYCRYGFRISPQAEKFY | 433 | H-2-Db | H-2-Kb | 196 |
| missense_variant | transcript | protein_coding | p.Ser263Asn | S263N | S | S | 263 | LETKLICIGRSDEDKYLEDFF | 163 | N | LETKLICIGRNDEDKYLEDFF | 434 | H-2-Db | H-2-Kb | 197 |
| missense_variant | transcript | protein_coding | p.Ser263Asn | S263N | S | S | 263 | LETKLICIGRSDEDKYLEDFF | 163 | N | LETKLICIGRNDEDKYLEDFF | 434 | H-2-Db | H-2-Kb | 198 |
| missense_variant | transcript | protein_coding | p.Ser263Asn | S263N | S | S | 263 | LETKLICIGRSDEDKYLEDFF | 163 | N | LETKLICIGRNDEDKYLEDFF | 434 | H-2-Db | H-2-Kb | 199 |
| missense_variant | transcript | protein_coding | p.Asp127Asn | S127F | D | D | 127 | WMKNSLKVHSDSVLEQVWDIF | 164 | N | WMKNSLKVHSNSVLEQVWDIF | 435 | H-2-Db | H-2-Kb | 200 |

FIG. 17 (Cont.)

| | | | | | | | | | | | | | | | |
|---|---|---|---|---|---|---|---|---|---|---|---|---|---|---|---|
| missense_variant | transcript | protein_coding | p.Asp127Asn | D127N | D | D | 127 | WMKNSLKVHSDSVLEQVWDIF | 164 | N | WMKNSLKVHSNSVLEQVWDIF | 435 | H-2-Db | H-2-Kb | 201 |
| missense_variant | transcript | protein_coding | p.Asp127Asn | D127N | D | D | 127 | WMKNSLKVHSDSVLEQVWDIF | 164 | N | WMKNSLKVHSNSVLEQVWDIF | 435 | H-2-Db | H-2-Kb | 202 |
| missense_variant | transcript | protein_coding | p.Asp127Asn | D127N | D | D | 127 | WMKNSLKVHSDSVLE | 165 | N | WMKNSLKVHSNSVLE | 436 | H-2-Db | H-2-Kb | 203 |
| missense_variant | transcript | protein_coding | p.Asp127Asn | D127N | D | D | 127 | WMKNSLKVHSDSVLEQVWDIF | 164 | N | WMKNSLKVHSNSVLEQVWDIF | 436 | H-2-Db | H-2-Kb | 204 |
| missense_variant | transcript | protein_coding | Ala219Thr | A219T | A | A | 219 | KFMVVSEISYLAKWWDIIDIPK | 165 | T | KFMVVSEISYLTKWWDIIDIPK | 437 | H-2-Db | H-2-Kb | 205 |
| missense_variant | transcript | protein_coding | p.Leu631Phe | L631F | L | L | 631 | NTMFPPTANMLLPTGEGQSGR | 166 | F | NTMFPPTANMFLPTGEGQSGR | 438 | H-2-Db | H-2-Kb | 206 |
| missense_variant | transcript | protein_coding | p.Leu631Phe | L631F | L | L | 631 | NTMFPPTANMLLPTGEGQSGR | 166 | F | NTMFPPTANMFLPTGEGQSGR | 438 | H-2-Db | H-2-Kb | 207 |
| missense_variant | transcript | protein_coding | p.Leu631Phe | L631F | L | L | 631 | NTMFPPTANMLLPTGEGQSGR | 166 | F | NTMFPPTANMFLPTGEGQSGR | 438 | H-2-Db | H-2-Kb | 208 |
| missense_variant | transcript | protein_coding | p.Ser333Leu | S333L | S | S | 333 | IVLSMVESGLSEEEAQRKIWM | 167 | L | IVLSMVESGLLEEEAQRKIWM | 439 | H-2-Db | H-2-Kb | 209 |
| missense_variant | transcript | protein_coding | p.Ala358Thr | A358T | A | A | 358 | VLIPDINFNDAFENFALDFSR | 168 | T | VLIPDINFNDTFENFALDFSR | 440 | H-2-Db | H-2-Kb | 210 |
| missense_variant | transcript | protein_coding | p.Ala358Thr | A358T | A | A | 358 | VLIPDINFNDAFENFALDFSR | 168 | T | VLIPDINFNDTFENFALDFSR | 440 | H-2-Db | H-2-Kb | 211 |
| missense_variant | transcript | protein_coding | p.Ala358Thr | A358T | A | A | 358 | VLIPDINFNDAFENFALDFSR | 168 | T | VLIPDINFNDTFENFALDFSR | 440 | H-2-Db | H-2-Kb | 212 |
| missense_variant | transcript | protein_coding | p.Val118Met | V118M | V | V | 118 | DEDWRSQRKHVFVLSEAGKPI | 169 | M | DEDWRSQRKHMFVLSEAGKPI | 441 | H-2-Db | H-2-Kb | 213 |
| missense_variant | transcript | protein_coding | p.Val118Met | V118M | V | V | 118 | DEDWRSQRKHVFVLSEAGKPI | 169 | M | DEDWRSQRKHMFVLSEAGKPI | 441 | H-2-Db | H-2-Kb | 214 |
| missense_variant | transcript | protein_coding | p.Thr328Ile | T3281 | T | T | 328 | IDSSGLRVFHTTDIRRYDAGV | 170 | I | IDSSGLRVFHITDIRRYDAGV | 442 | H-2-Db | H-2-Kb | 215 |
| missense_variant | transcript | protein_coding | p.Pro1662Ser | P1662S | P | P | 1662 | ITSIQMLSTLPQSQHTESKST | 171 | S | ITSIQMLSTLSQSQHTESKST | 443 | H-2-Db | H-2-Kb | 216 |
| missense_variant | transcript | protein_coding | p.Val149Ile | V149I | V | V | 149 | KPGQSVKFRVVSMDKTLRPLN | 172 | I | KPGQSVKFRVISMDKTLRPLN | 444 | H-2-Db | H-2-Kb | 217 |
| missense_variant | transcript | protein_coding | p.Met151Is | M151I | M | M | 151 | GQSVKFRVVSMCKTLRPLNEL | 173 | I | GQSVKFRVVSIDKTLRPLNEL | 445 | H-2-Db | H-2-Kb | 218 |
| missense_variant | transcript | protein_coding | p.Arg1685Cys | R1685C | R | R | 1685 | KARDEVIKQLRKLQAQMKDYQ | 174 | C | KARDEVIKQLCKLQAQMKDYQ | 446 | H-2-Db | H-2-Kb | 219 |
| missense_variant | transcript | protein_coding | p.Arg86Cys | R86C | R | R | 86 | GGSIMYNLFQRYKRNQIYTYI | 175 | C | GGSIMYNLFQCYKRNQIYTYI | 447 | H-2-Db | H-2-Kb | 220 |
| missense_variant | transcript | protein_coding | p.Ala286Val | A286V | A | A | 286 | VVSDSYDIYNACEKIVVGEDLR | 176 | V | VVSDSYDIYNVCEKIVVGEDLR | 448 | H-2-Db | H-2-Kb | 221 |
| missense_variant | transcript | protein_coding | p.Gly165Glu | G165E | G | G | 165 | NTGTESASEEGDDSLLITVVP | 177 | E | NTGTESASEEEDDSLLITVVP | 449 | H-2-Db | H-2-Kb | 222 |
| missense_variant | transcript | protein_coding | p.Val6071le | V607I | V | V | 607 | LKKLSFSTQNVLSGAQEHSYM | 178 | I | LKKLSFSTQNILSGAQEHSYM | 450 | H-2-Db | H-2-Kb | 223 |

FIG. 17 (Cont.)

| | | | | | | | | | | | | | | | |
|---|---|---|---|---|---|---|---|---|---|---|---|---|---|---|---|
| missense_variant | transcript | protein_coding | p.Val607Ile | V607I | V | V | 607 | LKKLSFSTQNVLSGAQEHSYM | 178 | I | LKKLSFSTQNILSGAQEHSYM | 450 | H-2-Db | H-2-Kb | 224 |
| missense_variant | transcript | protein_coding | p.Val607Ile | V607I | V | V | 607 | LKKLSFSTQNVLSGAQEHSYM | 178 | I | LKKLSFSTQNILSGAQEHSYM | 450 | H-2-Db | H-2-Kb | 225 |
| missense_variant | transcript | protein_coding | p.Glu5Lys | E5K | E | E | 5 | MGKLENASVVIHQSLM | 179 | K | MGKLKNASVVIHQSLM | 451 | H-2-Db | H-2-Kb | 226 |
| missense_variant | transcript | protein_coding | p.Pro1765Leu | P1765L | P | P | 1765 | HLVAADIRVAPATALTPPQGD | 180 | L | HLVAADIRVALATALTPPQGD | 452 | H-2-Db | H-2-Kb | 227 |
| missense_variant | transcript | protein_coding | p.Ala259Thr | A259T | A | A | 259 | NIRQLAEMQNAAGVKSSCSRM | 181 | T | NIRQLAEMQNTAGVKSSCSRM | 453 | H-2-Db | H-2-Kb | 228 |
| missense_variant | transcript | nonsense_mediate | p.Ala259Thr | A259T | A | A | 259 | NIRQLAEMQNAAGVKSSCSRM | 181 | T | NIRQLAEMQNTAGVKSSCSRM | 453 | H-2-Db | H-2-Kb | 229 |
| missense_variant | transcript | nonsense_mediate | p.Ala259Thr | A259T | A | A | 259 | MSEQAREENVATFRGSEYLCY | 182 | T | MSEQAREENVTTFRGSEYLCY | 454 | H-2-Db | H-2-Kb | 230 |
| missense_variant | transcript | nonsense_mediate | p.Ala259Thr | A259T | A | A | 259 | MSEQAREENVATFRGSEYLCY | 182 | T | MSEQAREENVTTFRGSEYLCY | 454 | H-2-Db | H-2-Kb | 231 |
| missense_variant | transcript | nonsense_mediate | p.Ala259Thr | A259T | A | A | 259 | NIRQLAEMQNAAGVKSSCSRM | 183 | T | NIRQLAEMQNTAGVKSSCSRM | 455 | H-2-Db | H-2-Kb | 232 |
| missense_variant | transcript | nonsense_mediate | p.Leu91Phe | L91F | L | L | 91 | TGYKSHAKEILHCLKNKYFKE | 184 | F | TGYKSHAKEIFHCLKNKYFKE | 456 | H-2-Db | H-2-Kb | 233 |
| missense_variant | transcript | protein_coding | p.Gly68Asp | G68D | G | G | 68 | GRHKGEVSFPGGKCDPDDQDV | 185 | D | GRHKGEVSFPDGKCDPDDQDV | 457 | H-2-Db | H-2-Kb | 234 |
| missense_variant | transcript | protein_coding | p.Gly68Asp | G68D | G | G | 68 | GRHKGEVSFPGGKCDPDDQDV | 185 | D | GRHKGEVSFPDGKCDPDDQDV | 457 | H-2-Db | H-2-Kb | 235 |
| missense_variant | transcript | protein_coding | p.Pro580Ser | P580S | P | P | 580 | SPQVLGHILKPGTTESGALSL | 186 | S | SPQVLGHILKSGTTESGALSL | 458 | H-2-Db | H-2-Kb | 236 |
| missense_variant | transcript | protein_coding | p.Pro580Ser | P580S | P | P | 580 | SPQVLGHILKPGTTESGALSL | 186 | S | SPQVLGHILKSGTTESGALSL | 458 | H-2-Db | H-2-Kb | 237 |
| missense_variant | transcript | protein_coding | p.Pro47Ser | P47S | P | P | 47 | DHEGQPRPRVPRKRGHISPKS | 187 | S | DHEGQPRPRVSRKRGHIS | 459 | H-2-Db | H-2-Kb | 238 |
| missense_variant | transcript | protein_coding | p.Ala264Thr | A264T | A | A | 264 | TLFFIYVRPSAISSLDLNKVV | 188 | T | TLFFIYVRPSTISSLDLNKW | 460 | H-2-Db | H-2-Kb | 239 |
| missense_variant | transcript | protein_coding | p.Arg141Cys | R141C | R | R | 141 | SSKMSRVVCIRLISVPYVYGF | 189 | C | SSKMSRWCICLISVPYVYGF | 461 | H-2-Db | H-2-Kb | 240 |
| missense_variant | transcript | protein_coding | p.Ser226Phe | S226F | S | S | 226 | SYGVILFSLRSHSSEGRSKAL | 190 | F | SYGVILFSLRFHSSEGRSKAL | 462 | H-2-Db | H-2-Kb | 241 |
| missense_variant | transcript | protein_coding | p.Ala32Val | A32V | A | A | 32 | LQLCLFFIFLAFYLITIVGNL | 191 | V | LQLCLFFIFLVFYLITIVGNL | 463 | H-2-Db | H-2-Kb | 242 |
| missense_variant | transcript | protein_coding | p.Ala32Val | A32V | A | A | 32 | LQLCLFFIFLAFYLITIVGNL | 191 | V | LQLCLFFIFLVFYLITIVGNL | 463 | H-2-Db | H-2-Kb | 243 |
| missense_variant | transcript | protein_coding | p.Pro288Leu | P288L | P | P | 288 | TYTVLTPFLSPIIFSLRNIKEL | 192 | L | TYTVLTPFLSLIIFSLRNKEL | 464 | H-2-Db | H-2-Kb | 244 |
| missense_variant | transcript | protein_coding | p.Ala245Val | A245V | A | A | 245 | SIIVVTVFIIALSYVYILVSI | 193 | V | SIIVVTVFIIVLSYVYILVSI | 465 | H-2-Db | H-2-Kb | 245 |
| missense_variant | transcript | protein_coding | p.Arg229His | R229H | R | R | 229 | IYILITILKMRSTEGRHKAFS | 194 | H | IYILITILKMHSTEGRHKAFS | 466 | H-2-Db | H-2-Kb | 246 |

FIG. 17 (Cont.)

| | | | | | | | | | | | | | | | |
|---|---|---|---|---|---|---|---|---|---|---|---|---|---|---|---|
| missense_variant | transcript | protein_coding | p.Arg229His | R229H | R | R | 229 | IYILITILKMRSTEGRHKAFS | 194 | H | IYILITILKMHSTEGRHKAFS | 466 | H-2-Db | H-2-Kb | 247 |
| missense_variant | transcript | protein_coding | p.Pro162Ser | P162S | P | P | 162 | TFLRGVLLIIPFIFLSKCLPY | 195 | S | TFLRGVLLIISFIFLSKCLPY | 467 | H-2-Db | H-2-Kb | 248 |
| missense_variant | transcript | protein_coding | p.Ala156Val | A156V | A | A | 156 | ATSWILASLSALGYSMYTMQY | 196 | V | ATSWILASLSVLGYSMYTMQY | 468 | H-2-Db | H-2-Kb | 249 |
| missense_variant | transcript | protein_coding | p.Ala129Val | A129V | A | A | 129 | LATMSYDRYIAICKPLHYASI | 197 | V | LATMSYDRYIVICKPLHYASI | 469 | H-2-Db | H-2-Kb | 250 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 251 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 252 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 253 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 254 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 255 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 256 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 257 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 258 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 259 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 260 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 261 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 262 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 263 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 264 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 265 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 266 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 267 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 268 |
| missense_variant | transcript | protein_coding | p.Ser62Asn | S62N | S | S | 62 | GSHSLCPQTGSPSMVTAITIM | 198 | N | GSHSLCPQGNPSMVTAITIM | 470 | H-2-Db | H-2-Kb | 269 |

FIG. 17 (Cont.)

| | | | | | | | | | | | | | | | | |
|---|---|---|---|---|---|---|---|---|---|---|---|---|---|---|---|---|
| missense_variant | transcript | protein_coding | p.Ser62Asn | S62N | S | S | 62 | GSHSLCPQGNPSMVTAITIM | 198 | N | GSHSLCPQGNPSMVTAITIM | 470 | H-2-Db | H-2-Kb | 270 |
| missense_variant | transcript | protein_coding | p.Thr2Ile | T2I | T | T | 2 | MTLGIFANCIFC | 199 | H | MILGIFANCIFC | 471 | H-2-Db | H-2-Kb | 271 |
| missense_variant | transcript | protein_coding | p.Ala412Thr | A412T | A | A | 412 | KNYYSLVLDSALDRETTADYK | 200 | H | KNYYSLVLDSTLDRETTADYK | 472 | H-2-Db | H-2-Kb | 272 |
| missense_variant | transcript | protein_coding | p.Thr1206Ile | T1206I | T | T | 1206 | QPEEEAENTKTPWLYDQEGGV | 201 | H | QPEEEAENTKIPWLYDQEGGV | 473 | H-2-Db | H-2-Kb | 273 |
| missense_variant | transcript | protein_coding | p.Gly220Glu | G220E | G | G | 220 | DYSEVTGSMGGIPEEELDSMA | 202 | H | DYSEVTGSMGEIPEEELDSMA | 474 | H-2-Db | H-2-Kb | 274 |
| missense_variant | transcript | protein_coding | p.Gly220Glu | G220E | G | G | 220 | DYSEVTGSMGGIPEEELDSMA | 202 | H | DYSEVTGSMGEIPEEELDSMA | 474 | H-2-Db | H-2-Kb | 275 |
| missense_variant | transcript | protein_coding | p.Arg467His | R467H | R | R | 467 | QGLMRFNLPARICRDIELFHF | 203 | H | QGLMRFNLPAHICRDIELFHF | 475 | H-2-Db | H-2-Kb | 276 |
| missense_variant | transcript | protein_coding | p.Ser323Phe | S323F | S | S | 323 | KQWCKPHYQNSGGGNGVDLS | 204 | H | KQWCKPHYQNFGGGNGVDLSV | 476 | H-2-Db | H-2-Kb | 277 |
| missense_variant | transcript | protein_coding | p.Met732Ile | M7321 | M | M | 732 | ILSFENNGDYMDMKQADTTQY | 205 | H | ILSFENNGDYIDMKQADTTQY | 477 | H-2-Db | H-2-Kb | 278 |
| missense_variant | transcript | protein_coding | p.Met732Ile | M7321 | M | M | 732 | ILSFENNGDYMDMKQADTTQY | 205 | H | ILSFENNGDYIDMKQADTTQY | 477 | H-2-Db | H-2-Kb | 279 |
| missense_variant | transcript | protein_coding | p.Met732Ile | M7321 | M | M | 732 | ILSFENNGDYMDMKQADTTQY | 205 | H | ILSFENNGDYIDMKQADTTQY | 477 | H-2-Db | H-2-Kb | 280 |
| missense_variant | transcript | protein_coding | p.Met732Ile | M7321 | M | M | 732 | ILSFENNGDYMDMKQADTTQY | 205 | H | ILSFENNGDYIDMKQADTTQY | 477 | H-2-Db | H-2-Kb | 281 |
| missense_variant | transcript | protein_coding | p.Thr669Met | T669M | T | T | 669 | YANGIRVMSMTHTGEPGFMLY | 206 | H | YANGIRVMSMMHTGEPGFMLY | 478 | H-2-Db | H-2-Kb | 282 |
| missense_variant | transcript | protein_coding | p.Pro63Ser | P63S | P | P | 63 | EENTVPPEHSPPEMEICTVYL | 207 | H | EENTVPPEHSSPEMEICTVYL | 479 | H-2-Db | H-2-Kb | 283 |
| missense_variant | transcript | protein_coding | p.Gly44Ser | G44S | G | G | 44 | FGSERDLERRGRSRDVEPRDR | 208 | H | FGSERDLERRSRSRDVEPRDR | 480 | H-2-Db | H-2-Kb | 284 |
| missense_variant | transcript | protein_coding | p.Gly44Ser | G44S | G | G | 44 | FGSERDLERRGRSRDVEPRDR | 208 | H | FGSERDLERRSRSRDVEPRDR | 480 | H-2-Db | H-2-Kb | 285 |
| missense_variant | transcript | protein_coding | p.Gly44Ser | G44S | G | G | 44 | FGSERDLERRGRSRDVEPRDR | 208 | H | FGSERDLERRSRSRDVEPRDR | 480 | H-2-Db | H-2-Kb | 286 |
| missense_variant | transcript | protein_coding | p.Ser26Phe | S26F | S | S | 26 | SSTTTTTITTSSSRMQQPQIS | 209 | H | SSTTTTTITTFSSRMQQPQIS | 481 | H-2-Db | H-2-Kb | 287 |
| missense_variant | transcript | protein_coding | p.Ser26Phe | S26F | S | S | 26 | SSTTTTTITTSSSRMQQPQIS | 209 | H | SSTTTTTITTFSSRMQQPQIS | 481 | H-2-Db | H-2-Kb | 288 |
| missense_variant | transcript | protein_coding | p.Ser26Phe | S26F | S | S | 26 | SSTTTTTITTSSSRMQQPQIS | 209 | H | SSTTTTTITTFSSRMQQPQIS | 481 | H-2-Db | H-2-Kb | 289 |
| missense_variant | transcript | protein_coding | p.Ser26Phe | S26F | S | S | 26 | SSTTTTTITTSSSRMQQPQIS | 209 | H | SSTTTTTITTFSSRMQQPQIS | 481 | H-2-Db | H-2-Kb | 290 |
| missense_variant | transcript | protein_coding | p.Asp900Asn | D900N | D | D | 900 | YVLGIGDRHSDNIMRESGQL | 210 | H | YVLGIGDRHSNNIMIRESGQL | 482 | H-2-Db | H-2-Kb | 291 |
| missense_variant | transcript | protein_coding | p.Asp900Asn | D900N | D | D | 900 | YVLGIGDRHSDNIMRESGQL | 210 | H | YVLGIGDRHSNNIMIRESGQL | 482 | H-2-Db | H-2-Kb | 292 |

FIG. 17 (Cont.)

| | | | | | | | | | | | | | | | |
|---|---|---|---|---|---|---|---|---|---|---|---|---|---|---|---|
| missense_variant &spice_region_ varient | transcript | protein_coding | p.Ser83Leu | S83L | S | S | 83 | AESPSIASTSSTEKSFPWRST | 211 | L | AESPSIASTSLTEKSFPWRST | 470 | H-2-Db | H-2-Kb | 293 |
| missense_variant &spice_region_ varient | transcript | protein_coding | p.Ser83Leu | S83L | S | S | 83 | AESPSIASTSSTEKSFPWRST | 211 | L | AESPSIASTSLTEKSFPWRST | 470 | H-2-Db | H-2-Kb | 294 |
| missense_variant &spice_region_ varient | transcript | protein_coding | p.Ser83Leu | S83L | S | S | 83 | AESPSIASTSSTEKSFPWRST | 211 | L | AESPSIASTSLTEKSFPWRST | 470 | H-2-Db | H-2-Kb | 295 |
| missense_variant &spice_region_ varient | transcript | protein_coding | p.Ser83Leu | S83L | S | S | 83 | AESPSIASTSSTEKSFPWRST | 211 | L | AESPSIASTSLTEKSFPWRST | 470 | H-2-Db | H-2-Kb | 296 |
| missense_variant &spice_region_ varient | transcript | protein_coding | p.Ser83Leu | S83L | S | S | 83 | AESPSIASTSSTEKSFPWRST | 211 | L | AESPSIASTSLTEKSFPWRST | 470 | H-2-Db | H-2-Kb | 297 |

FIG. 17 (Cont.)

| | | | | | | | | | | | | | | | |
|---|---|---|---|---|---|---|---|---|---|---|---|---|---|---|---|
| missense_variant | transcript | Protein_coding | p.Arg6146His | R614H | R | R | 614 | TYWNTRQPSNRGGCWVRGGS | 212 | H | TYWNTRQPSNHGGCWVRGGS | 484 | H-2-Db | H-2-Kb | 298 |
| missense_variant | transcript | Protein_coding | p.Ala16Val | A16V | A | A | 16 | DGSSGGWAARALRRALALTSL | 213 | V | DGSSGGWAARLRRALALTSL | 485 | H-2-Db | H-2-Kb | 299 |
| missense_variant &spice_region_ variant | transcript | Protein_coding | p.Gly294Ser | G294S | G | G | 294 | EKEIRSFLIEGHLINTIRWC | 214 | S | EKEIRSFLIESHLINTIRWC | 486 | H-2-Db | H-2-Kb | 300 |
| missense_variant | transcript | Protein_coding | p.Met292Ie | M292I | M | M | 292 | EIVKYTKIIAMEKLYAVFTDY | 215 | I | EIVKYTKIIAIEKLYAVFTDY | 487 | H-2-Db | H-2-Kb | 301 |
| missense_variant | transcript | Protein_coding | p.Arg36His | R36H | R | R | 36 | QGQGQGLSPERVEDYGRTHRG | 216 | H | QGQGQGLSPEHVEDYGRTHRG | 488 | H-2-Db | H-2-Kb | 302 |
| missense_variant | transcript | Protein_coding | p.Arg36His | R36H | R | R | 36 | QGQGQGLSPERVEDYGRTHRG | 216 | H | QGQGQGLSPEHVEDYGRTHRG | 488 | H-2-Db | H-2-Kb | 303 |
| missense_variant | transcript | Protein_coding | p.Ala449Val | A449V | A | A | 449 | TTKTAMCTAVAGYFDIYFEKN | 217 | V | TTKTAMCTAWGYFDIYFEKN | 489 | H-2-Db | H-2-Kb | 304 |
| missense_variant | transcript | Protein_coding | p.Gly109Arg | G109R | G | G | 109 | SGPAEEEDVPGSPCPDAGDPQ | 218 | R | SGPAEEEDVPRSPCPDAGDPQ | 490 | H-2-Db | H-2-Kb | 305 |
| missense_variant | transcript | Protein_coding | p.Gly109Arg | G109R | G | G | 109 | SGPAEEEDVPGSPCPDAGDPQ | 218 | R | SGPAEEEDVPRSPCPDAGDPQ | 490 | H-2-Db | H-2-Kb | 306 |
| missense_variant | transcript | Protein_coding | p.Gly109Arg | G109R | G | G | 109 | SGPAEEEDVPGSPCPDAGDPQ | 218 | R | SGPAEEEDVPRSPCPDAGDPQ | 490 | H-2-Db | H-2-Kb | 307 |
| missense_variant | transcript | Protein_coding | p.Gly109Arg | G109R | G | G | 109 | SGPAEEEDVPGSPCPDAGDPQ | 218 | R | SGPAEEEDVPRSPCPDAGDPQ | 490 | H-2-Db | H-2-Kb | 308 |
| missense_variant | transcript | Protein_coding | p.Gly109Arg | G109R | G | G | 109 | SGPAEEEDVPGSPCPDAGDPQ | 218 | R | SGPAEEEDVPRSPCPDAGDPQ | 490 | H-2-Db | H-2-Kb | 309 |
| missense_variant | transcript | Protein_coding | p.Arg186Lys | R186K | R | R | 186 | LDQISRYYITRAKLVSKIAKY | 219 | K | LDQISRYYITKAKLVSKIAKY | 491 | H-2-Db | H-2-Kb | 310 |
| missense_variant | transcript | Protein_coding | p.Ala77Thr | A77T | A | A | 77 | LQVTRGHLDTARTRGKVSWQI | 220 | T | LQVTRGHLDTTRTRGKVSWQI | 492 | H-2-Db | H-2-Kb | 311 |
| missense_variant | transcript | Protein_coding | p.Glu196Lys | E196K | E | E | 196 | KKKTNNPQFDEVFYFEVTRPC | 221 | K | KKKTNNPQFDKVFYFEVTRPC | 493 | H-2-Db | H-2-Kb | 312 |
| missense_variant | transcript | Protein_coding | p.Ser9Phe | S9F | S | S | 9 | MKRQSERDSSPSGRGSSSS | 222 | F | MKRQSERDFSPSGRSSSS | 494 | H-2-Db | H-2-Kb | 313 |
| missense_variant | transcript | Protein_coding | p.Ser150Leu | S150L | S | S | 150 | LVPCHISTNLSNKQVIEVACG | 223 | L | LVPCHISTNLLNKQVIEVACG | 495 | H-2-Db | H-2-Kb | 314 |
| missense_variant | transcript | Protein_coding | p.Ser150Leu | S150L | S | S | 150 | LVPCHISTNLSNKQVIEVACG | 223 | L | LVPCHISTNLLNKQVIEVACG | 496 | H-2-Db | H-2-Kb | 315 |
| missense_variant | transcript | Protein_coding | p.Ser150Leu | S150L | S | S | 150 | LVPCHISTNLSNKQVIEVACG | 223 | L | LVPCHISTNLLNKQVIEVACG | 495 | H-2-Db | H-2-Kb | 316 |
| missense_variant | transcript | Protein_coding | p.Ser150Leu | S150L | S | S | 150 | LVPCHISTNLS | 224 | L | LVPCHISTNLL | 496 | H-2-Db | H-2-Kb | 317 |
| missense_variant | transcript | Protein_coding | p.Ser150Leu | S150L | S | S | 150 | VIEVACGSYHSLVLTSDGEVF | 225 | L | VIEVACGSYHLLVLTSDGEVF | 497 | H-2-Db | H-2-Kb | 318 |
| missense_variant | transcript | Protein_coding | p.Ser150Leu | S150L | S | S | 150 | LVPCHISTNLSNKQVIEVACG | 226 | L | LVPCHISTNLLNKQVIEVACG | 498 | H-2-Db | H-2-Kb | 319 |

FIG. 17 (Cont.)

| | | | | | | | | | | | | | | | |
|---|---|---|---|---|---|---|---|---|---|---|---|---|---|---|---|
| missense_variant | transcript | Protein_coding | p.Ser150Leu | S150L | S | S | 150 | LVPCHISTNLSNKQVIEVACG | 226 | L | LVPCHISTNLLNKQVIEVACG | 498 | H-2-Db | H-2-Kb | 320 |
| missense_variant | transcript | Protein_coding | p.Ser150Leu | S150L | S | S | 150 | LVPCHISTNLSNKQVIEVACG | 226 | L | LVPCHISTNLLNKQVIEVACG | 498 | H-2-Db | H-2-Kb | 321 |
| missense_variant | transcript | Protein_coding | p.ALA81Thr | A81T | A | A | 81 | IAEGVCIPRSALYMHYLDFCE | 227 | T | IAEGVCIPRSTLYMHYLDFCE | 499 | H-2-Db | H-2-Kb | 322 |
| missense_variant | transcript | Protein_coding | p.Ser327Phe | S327F | S | S | 327 | RREPQQLVSSFRALWSRLWP | 228 | F | RREPQQVLVSFFRALWSRLWP | 500 | H-2-Db | H-2-Kb | 323 |
| missense_variant | transcript | Protein_coding | p.Ala4739Val | A4739V | A | A | 4739 | VLGHYNNFFFAAHLLDIAMGF | 229 | V | VLGHYNNFFFVAHLLDIAMGF | 501 | H-2-Db | H-2-Kb | 324 |
| missense_variant | transcript | Protein_coding | p.Ala4739Val | A4739V | A | A | 4739 | VLGHYNNFFFAAHLLDIAMGF | 229 | V | VLGHYNNFFFVAHLLDIAMGF | 501 | H-2-Db | H-2-Kb | 325 |
| missense_variant | transcript | Protein_coding | p.Ala22Thr | A22T | A | A | 22 | TAAAATTAAAASSSAASPHYQ | 230 | T | TAAAATTAAATSSSAASPHYQ | 502 | H-2-Db | H-2-Kb | 326 |
| missense_variant | transcript | Protein_coding | p.Glu711Lys | E711K | E | E | 711 | LVIIWNQDSVEYYTRLGALDL | 231 | K | LVIIWNQDSVKYYTRLGALDL | 503 | H-2-Db | H-2-Kb | 327 |
| missense_variant | transcript | Protein_coding | p.Met384Ile | M384I | M | M | 384 | DASKLHSSPQMAAQHNMVDDG | 232 | I | DASKLHSSPQIAAQHNMVDDG | 504 | H-2-Db | H-2-Kb | 328 |
| missense_variant | transcript | Protein_coding | p.Met384Ile | M384I | M | M | 384 | DASKLHSSPQMAAQHNMVDDG | 232 | I | DASKLHSSPQIAAQHNMVDDG | 504 | H-2-Db | H-2-Kb | 329 |
| missense_variant | transcript | Protein_coding | p.Leu270Phe | L270F | L | L | 270 | FMNRTEFHVYLPKFQLQEDYD | 234 | F | FMNRTEFHVYFPKFQLQEDYD | 505 | H-2-Db | H-2-Kb | 330 |
| missense_variant | transcript | Protein_coding | p.Ser1310Phe | S1310F | S | S | 1310 | ILKSSSVQKESCNKRNPFWKK | 235 | F | ILKSSSVQKEFCNKRNPFWKK | 506 | H-2-Db | H-2-Kb | 331 |
| missense_variant | transcript | Protein_coding | p.Thr214Ile | T214I | T | T | 214 | VLIILLSTMVTSIGLSTSAI | 236 | I | VILKKLLSTMVISITGLSTSAI | 507 | H-2-Db | H-2-Kb | 332 |
| missense_variant | transcript | Protein_coding | p.Thr214Ile | T214I | T | T | 214 | VIIIGLAVTVTAITGLSTSAI | 237 | I | VIIIGLAVTVIAITGLSTSAI | 508 | H-2-Db | H-2-Kb | 333 |
| missense_variant | transcript | Protein_coding | p.Thr214Ile | T214I | T | T | 214 | VIIIGLASVVVTTLTGISMSAI | 238 | I | VIIIGLSVVVITLTGISMSAI | 509 | H-2-Db | H-2-Kb | 334 |
| missense_variant | transcript | Protein_coding | p.Glu489Lys | E489K | E | E | 489 | EDFFLKCRLQEQEIQRRPSVF | 239 | K | EDFFLKCRLQKQEIRRPSVF | 510 | H-2-Db | H-2-Kb | 335 |
| missense_variant | transcript | Protein_coding | p.Lew454Phe | L454F | L | L | 454 | LSSLCMCVSNLHINELLPTTL | 240 | F | LSSLCMCVSNFHINELLPTTL | 511 | H-2-Db | H-2-Kb | 336 |
| missense_variant | transcript | Protein_coding | p.Arg180Gh | R180Q | R | R | 180 | LLTWVNCSSVRWATRVQDIFT | 241 | Q | LLTWVNCSSVQWATRVQDIFT | 512 | H-2-Db | H-2-Kb | 337 |
| missense_variant | transcript | Protein_coding | p.Asp767Asn | D767N | D | D | 767 | MRGRMGSSVIDEISVEEVNKM | 242 | N | MRGRMGSSVINEISVEEVNKM | 513 | H-2-Db | H-2-Kb | 338 |
| missense_variant | transcript | Protein_coding | p.Gly114Asp | G114D | G | G | 114 | NVVRDWLGVGGPVLTPPQEHP | 243 | D | NVVRDWLGVGDPVLTPPQEHP | 514 | H-2-Db | H-2-Kb | 339 |
| missense_variant | transcript | Protein_coding | p.Pro96Ser | P96S | P | P | 96 | TKEEENEMYNPTFFYENLKIP | 244 | S | TKEEENEMYNSTFFYENLKIP | 515 | H-2-Db | H-2-Kb | 340 |
| missense_variant | transcript | Protein_coding | p.Pro96Ser | P96S | P | P | 96 | TKEEENEMYNPTFFYENLKIP | 244 | S | TKEEENEMYNSTFFYENLKIP | 515 | H-2-Db | H-2-Kb | 341 |
| missense_variant | transcript | Protein_coding | p.Pro96Leu | P96L | P | P | 96 | TKEEENEMYNPTFFYENLKIP | 244 | L | TKEEENEMYNSTFFYENLKIP | 515 | H-2-Db | H-2-Kb | 342 |

FIG. 17 (Cont.)

| | | | | | | | | | | | | | | | | |
|---|---|---|---|---|---|---|---|---|---|---|---|---|---|---|---|---|
| missense_variant | transcript | Protein_coding | p.Pro96Leu | P96L | P | P | 96 | TKEEENEMYNPTFFYENLKIP | 244 | L | TKEEENEMYNSTFFYENLKIP | 515 | H-2-Db | H-2-Kb | 343 |
| missense_variant | transcript | Protein_coding | p.Arg56Gh | R56Q | R | R | 56 | PFPFLMSLRDRDFISEQKFQE | 245 | Q | PFPFLMSLRDQDFISEQKFQE | 516 | H-2-Db | H-2-Kb | 344 |
| missense_variant | transcript | Protein_coding | p.Val260Met | V260M | V | V | 260 | NANFSAELLPVTCGNLKGVLH | 246 | M | NANFSAELLPMTCGNLKGVLH | 517 | H-2-Db | H-2-Kb | 345 |
| missense_variant | transcript | Protein_coding | p.Glu49Lysl | E49K | E | E | 49 | FKFELQSDFAEFSESRGSTAK | 247 | K | FKFELQSDFAKFSESRGSTAK | 518 | H-2-Db | H-2-Kb | 346 |
| missense_variant | transcript | Protein_coding | p.Glu49Lys | E49K | E | E | 49 | FKFELQSDFAEFSESRGSTAK | 247 | K | FKFELQSDFAKFSESRGSTAK | 518 | H-2-Db | H-2-Kb | 347 |
| missense_variant | transcript | Protein_coding | p.Glu49Lys | E49K | E | E | 49 | FKFELQSDFAEFSESRGSTAK | 247 | K | FKFELQSDFAKFSESRGSTAK | 518 | H-2-Db | H-2-Kb | 348 |
| missense_variant | transcript | Protein_coding | p.Glu49Lys | E49K | E | E | 49 | FKFELQSDFAEFSESRGSTAK | 247 | K | FKFELQSDFAKFSESRGSTAK | 518 | H-2-Db | H-2-Kb | 349 |
| missense_variant | transcript | Protein_coding | p.Glu49Lys | E49K | E | E | 49 | FKFELQSDFAEFSESRGSTAK | 247 | K | FKFELQSDFAKFSESRGSTAK | 518 | H-2-Db | H-2-Kb | 350 |
| missense_variant | transcript | Protein_coding | p.Glu49Lys | E49K | E | E | 49 | FKFELQSDFAEFSESRGSTAK | 247 | K | FKFELQSDFAKFSESRGSTAK | 518 | H-2-Db | H-2-Kb | 351 |
| missense_variant | transcript | Protein_coding | p.Glu660Lys | E660K | E | E | 660 | EGRRDIGKQVEEEKPGAGKKD | 248 | K | EGRRDIGKQVKEEKPGAGKKD | 519 | H-2-Db | H-2-Kb | 352 |
| missense_variant | transcript | Protein_coding | p.Glu660Lys | E660K | E | E | 660 | EGRRDIGKQVEEEKPGAGKKD | 248 | K | EGRRDIGKQVKEEKPGAGKKD | 519 | H-2-Db | H-2-Kb | 353 |
| missense_variant | transcript | Protein_coding | p.Cys82Tyr | C82Y | C | C | 82 | YCAAPERRETCEHSSEAKAFH | 249 | Y | YCAAPERRETYEHSSEAKAFH | 520 | H-2-Db | H-2-Kb | 354 |
| missense_variant | transcript | Protein_coding | p.Cys82Tyr | C82Y | C | C | 82 | YCAAPERRETCEHSSEAKAFH | 249 | Y | YCAAPERRETYEHSSEAKAFH | 520 | H-2-Db | H-2-Kb | 355 |
| missense_variant | transcript | Protein_coding | p.Leu345Phe | L345F | L | L | 345 | TMHDKQGEVRLKCLTALQGLY | 250 | F | TMHDKQGEVRLKCLTALQGLY | 521 | H-2-Db | H-2-Kb | 356 |
| missense_variant | transcript | Protein_coding | p.Leu345Phe | L345F | L | L | 345 | TMHDKQGEVRLKCLTALQGLY | 250 | F | TMHDKQGEVRLKCLTALQGLY | 521 | H-2-Db | H-2-Kb | 357 |

FIG. 17 (Cont.)

| | | | | | | | | | | | | | | |
|---|---|---|---|---|---|---|---|---|---|---|---|---|---|---|
| missense_variant | transcript | Protein_coding | p.Leu345Phe | L345F | L | L | 345 | TMHDKQGEVRLKCLTALQGLY | 250 | F | TMHDKQGEVRFKCLTALQGLY | 521 | H-2-Db | H-2-Kb | 358 |
| missense_variant | transcript | Protein_coding | p.Gly101Ser | G101S | G | G | 101 | SLKVIGRGAFGEVRLVQKKDT | 251 | S | SLKVIGRGAFSEVRLVQKKDT | 522 | H-2-Db | H-2-Kb | 359 |
| missense_variant | transcript | Protein_coding | p.Gly101Ser | G101S | G | G | 101 | SLKVIGRGAFSEVRLVQKKDT | 251 | S | SLKVIGRGAFSEVRLVQKKDT | 522 | H-2-Db | H-2-Kb | 360 |
| missense_variant | transcript | Protein_coding | p.Glu7Lys | E7K | E | E | 7 | MKDRTQELRSAKDSDDE | 252 | K | MKDRTQKLRSAKDSDDE | 523 | H-2-Db | H-2-Kb | 361 |
| missense_variant | transcript | Protein_coding | p.Glu7Lys | E7K | E | E | 7 | RIQRQLEITGRTTTNEE | 253 | K | RIQRQLKITGRTTTNEE | 524 | H-2-Db | H-2-Kb | 362 |
| missense_variant | transcript | Protein_coding | p.Ala256Val | A256V | A | A | 256 | AANYLIGAQKEAKRWGTAHGSI | 254 | V | AANYLIGQKEVKRWGTAHGSI | 525 | H-2-Db | H-2-Kb | 363 |
| missense_variant | transcript | Protein_coding | p.Ala191Thr | A191T | A | A | 191 | VLYYEDMKKDAKGTIKKICDF | 255 | T | VLYYEDMKKDTKGTKKICDF | 526 | H-2-Db | H-2-Kb | 364 |
| missense_variant | transcript | Protein_coding | p.Thr2606Ile | T2602I | T | T | 2606 | EESGWSSSSPTCVPIDCGLPP | 256 | I | EESGWSSSSPICVPIDCGLPP | 527 | H-2-Db | H-2-Kb | 365 |
| missense_variant | transcript | Protein_coding | p.Leu275Phe | L275F | L | L | 275 | IPQDRPTSEELLKHMFVLRER | 257 | F | IPQDRPTSEEFLKHMFVLRER | 528 | H-2-Db | H-2-Kb | 366 |
| missense_variant | transcript | Protein_coding | p.Leu275Phe | L275F | L | L | 275 | IPQDRPTSEELLKHMFVLRER | 257 | F | IPQDRPTSEEFLKHMFVLRER | 528 | H-2-Db | H-2-Kb | 367 |
| missense_variant | transcript | Protein_coding | p.Set29Asn | S29N | S | S | 29 | TCSDMMSFLVSIASIAMLVKI | 258 | N | TCSDMMSFLVNIASIAMLVKI | 529 | H-2-Db | H-2-Kb | 368 |
| missense_variant &spice_region_ variant | transcript | Protein_coding | p.Gly956Asp | G956D | G | G | 956 | TESGRNSPEKGKGKIDIQAYL | 259 | D | TESGRNSPEKDKGKIDIQAYL | 530 | H-2-Db | H-2-Kb | 369 |
| missense_variant | transcript | Protein_coding | p.Ser81Leu | S81L | S | S | 81 | QPDVCFLLFGSR | 260 | L | QPDVCFLLFGLR | 531 | H-2-Db | H-2-Kb | 370 |
| missense_variant | transcript | Protein_coding | p.Ser81Leu | S81L | S | S | 81 | QPEKRLKAESSKTVFSCSDES | 261 | L | QPEKRLKAESLKTVFSCSDES | 532 | H-2-Db | H-2-Kb | 371 |
| missense_variant | transcript | Protein_coding | p.Asp405Asn | D405N | D | D | 405 | FTILLWTNRDTQETLLCMAC | 262 | N | FTILLWTNRNTQETLLCMAC | 533 | H-2-Db | H-2-Kb | 372 |
| missense_variant | transcript | Protein_coding | p.Asp405Asn | D405N | D | D | 405 | FTILLWTNRDTQETLLCMAC | 262 | N | FTILLWTNRNTQETLLCMAC | 533 | H-2-Db | H-2-Kb | 373 |
| missense_variant | transcript | Protein_coding | p.Arg156Cys | R156C | R | R | 156 | YLDCAQADSVRNLPRAFSGLT | 263 | C | YLDCAQADSVCNLPRAFSGLT | 534 | H-2-Db | H-2-Kb | 374 |
| missense_variant | transcript | Protein_coding | p.Glu618Lys | E618K | E | E | 618 | NYDVLAYCIIEALANPEKERM | 264 | K | NYDVLAYCIIKALANPEKERM | 535 | H-2-Db | H-2-Kb | 375 |
| missense_variant | transcript | Protein_coding | p.Ala36Val | A36V | A | A | 36 | GTIDTKRNISAEEGGSVILQC | 265 | V | GTIDTKRNISVEEGGSVILQC | 536 | H-2-Db | H-2-Kb | 376 |
| missense_variant | transcript | Protein_coding | p.Ala396Thr | A396T | A | A | 396 | SLVGSSLSAFALLPLQGDRDR | 266 | T | SLVGSSLSAFTLLPLQGDRDR | 537 | H-2-Db | H-2-Kb | 377 |
| missense_variant | transcript | Protein_coding | p.Asp787Asn | D787N | D | D | 787 | LDRYFHVNNDQPIDLTKGKS | 267 | N | LDRYFYHVNNNQPIDLTKGKS | 538 | H-2-Db | H-2-Kb | 378 |
| missense_variant | transcript | Protein_coding | p.Arg83His | R83H | R | R | 83 | DERDRQNARLREENARLRLEN | 268 | H | DERDRQNARLHEENARLRLEN | 539 | H-2-Db | H-2-Kb | 379 |

FIG. 17(Cont.)

| | | | | | | | | | | | | | | | |
|---|---|---|---|---|---|---|---|---|---|---|---|---|---|---|---|
| missense_variant | transcript | Protein_coding | p.Pro25Ser | P25S | P | P | 25 | SREQFMEHLYPQRKPLVLEGH | 269 | S | SREQFMEHLYSQRKPLVLEGL | 540 | H-2-Db | H-2-Kb | 380 |
| missense_variant | transcript | Protein_coding | p.Pro25Ser | P25S | P | P | 25 | SREQFMEHLYPQRKPLVLEGH | 269 | S | SREQFMEHLYSQRKPLVLEGL | 540 | H-2-Db | H-2-Kb | 381 |
| missense_variant | transcript | Protein_coding | p.Pro25Ser | P25S | P | P | 25 | SREQFMEHLYPQRKPLVLEGH | 269 | S | SREQFMEHLYSQRKPLVLEGL | 540 | H-2-Db | H-2-Kb | 382 |
| missense_variant | transcript | Protein_coding | p.Arg4Cys | R4C | R | R | 4 | METRYNLKSPAVKR | 270 | C | METCYNLKSPAVKR | 541 | H-2-Db | H-2-Kb | 383 |
| missense_variant &spice_region_ variant | transcript | Protein_coding | p.Glu594Lys | E594K | E | E | 594 | WGLLSHCKVRETQEYTRNWR | 271 | K | WGLLSHCKVPRKTQEYTRNWR | 542 | H-2-Db | H-2-Kb | 384 |
| missense_variant | transcript | Protein_coding | p.Arg31Lys | R31K | R | R | 31 | VFGPSASHAGRLLVFPMDGSH | 272 | K | VFGPSASHAGKLLVFPMDGSH | 543 | H-2-Db | H-2-Kb | 385 |
| missense_variant | transcript | Protein_coding | p.Ser205Leu | S206L | S | S | 205 | ARQAVFTAKYSEDMKHKTTLL | 273 | L | ARQAVFTAKYLEDMKHKTTLL | 544 | H-2-Db | H-2-Kb | 386 |
| missense_variant | transcript | Protein_coding | p.Pro271Ser | P271S | P | P | 271 | KEKILGLLSSPTGDASYQQLM | 274 | S | KEKILGLLSSSTGDASYQQLM | 545 | H-2-Db | H-2-Kb | 387 |
| missense_variant | transcript | Protein_coding | p.Arg321His | R321H | R | R | 321 | KRANNGKFTLRDLLVVPMQRV | 275 | H | KRANNGKFTLHDLLWPMQRV | 546 | H-2-Db | H-2-Kb | 388 |
| missense_variant | transcript | Protein_coding | p.Arg197His | R197H | R | R | 197 | CSTTGFSIGMRILSFAHDAVF | 276 | H | CSTTGFSIGMHILSFAHDAVF | 547 | H-2-Db | H-2-Kb | 389 |
| missense_variant | transcript | Protein_coding | p.Gly661Glu | G661E | G | G | 661 | TTCILQQTTFGVAFTMALATV | 277 | E | TTCILQQTTFEVAFTMALATV | 548 | H-2-Db | H-2-Kb | 390 |
| missense_variant | transcript | Protein_coding | p.Gly823Glu | G823E | G | G | 823 | SILASSAGMLGCIFVPKCYTI | 278 | E | SILASSAGMLECIFPKCYTI | 549 | H-2-Db | H-2-Kb | 391 |
| missense_variant | transcript | Protein_coding | p.Val714Ile | V714I | V | V | 714 | CILIQVIVCAVWLRASPPSVD | 279 | I | CILIQVIVCAIWLRASPPSVD | 550 | H-2-Db | H-2-Kb | 392 |
| missense_variant | transcript | Protein_coding | p.Gly741Asp | G741D | G | G | 741 | HGQIIIVCHKGSVNAFYCVLG | 280 | D | HGQIIIVCHKDSVNAFYCVLG | 551 | H-2-Db | H-2-Kb | 393 |
| missense_variant | transcript | Protein_coding | p.Met309Ile | M309I | M | M | 309 | TTSQWDVSPSMKDFTFGNEYG | 281 | I | TTSQWDVSPSIKDFTFGNEYG | 552 | H-2-Db | H-2-Kb | 394 |
| missense_variant | transcript | Protein_coding | p.His326Tyr | H326Y | H | H | 326 | NEYGTFAFGQHHSEISGFKHF | 282 | Y | NEYGTFAFGQYHSEISGFKHF | 553 | H-2-Db | H-2-Kb | 395 |
| missense_variant | transcript | Protein_coding | p.Arg33Lys | R33K | R | R | 33 | LSEPSCFWRIRNSEDSDGDLQ | 283 | K | LSEPSCFWRIKNSEDSDGDLQ | 554 | H-2-Db | H-2-Kb | 396 |
| missense_variant | transcript | Protein_coding | p.Glu40Glu | G40E | G | G | 40 | NLNEIQDEYLGLTCAFILAAV | 284 | E | NLNEIQDEYLELTCAFILAAV | 555 | H-2-Db | H-2-Kb | 397 |
| missense_variant | transcript | Protein_coding | p.Ala48Val | A48V | A | A | 48 | YLGLTCAFILAAVQKPIEKDY | 285 | V | YLGLTCAFILVAVQKPIEKDY | 556 | H-2-Db | H-2-Kb | 398 |
| missense_variant | transcript | Protein_coding | p.Pro519Ser | P519S | P | P | 519 | PAASLQFQGLPEGVRAGPVPS | 286 | S | PAASLQFQGLSEGVRAGPVPS | 557 | H-2-Db | H-2-Kb | 399 |
| missense_variant | transcript | Protein_coding | p.Ala311Thr | A311T | A | A | 311 | AACHPTKNIIASAALENDKTI | 287 | T | AACHPTKNIITSAALENDKTI | 558 | H-2-Db | H-2-Kb | 400 |
| missense_variant | transcript | Protein_coding | p.Ala550Thr | A550T | A | A | 550 | FENRKGLSSHARSHLRQMGVT | 288 | T | FENRKGLSSHTRSHLRQMGVT | 559 | H-2-Db | H-2-Kb | 401 |

FIG. 17(Cont.)

| | | | | | | | | | | | | | | | |
|---|---|---|---|---|---|---|---|---|---|---|---|---|---|---|---|
| missense_variant | transcript | Protein_coding | p.Glu742Lys | E742K | E | E | 742 | APLEWLRYFDEKELELMLCGM | 289 | K | APLEWLRYFDKKELELMLCGM | 560 | H-2-Db | H-2-Kb | 402 |
| missense_variant | transcript | Protein_coding | p.Ala409Thr | A409T | A | A | 409 | LGITKTSKESAFKAARKYCPH | 290 | T | LGITKTSKESTFKAARKYCPH | 561 | H-2-Db | H-2-Kb | 403 |
| missense_variant | transcript | Protein_coding | p.Leu464Phe | L464F | L | L | 464 | YKNMRETLVYLTHLDYVDTEI | 291 | F | YKNMRETLVYFTHLDYVDTEI | 562 | H-2-Db | H-2-Kb | 404 |
| missense_variant | transcript | Protein_coding | p.Leu464Phe | L464F | L | L | 464 | YKNMRETLVYLTHLDYVDTEI | 291 | F | YKNMRETLVYFTHLDYVDTEI | 562 | H-2-Db | H-2-Kb | 405 |
| missense_variant | transcript | Protein_coding | p.Leu464Phe | L464F | L | L | 464 | YKNMRETLVYLTHLDYVDTEI | 291 | F | YKNMRETLVYFTHLDYVDTEI | 562 | H-2-Db | H-2-Kb | 406 |
| missense_variant | transcript | Protein_coding | p.Leu464Phe | L464F | L | L | 464 | YKNMRETLVYLTHLDYVDTEI | 291 | F | YKNMRETLVYFTHLDYVDTEI | 562 | H-2-Db | H-2-Kb | 407 |
| missense_variant | transcript | Protein_coding | p.Ala181Val | A181V | A | A | 181 | ETSRNAGPSPAAQAPADRPVS | 292 | V | ETSRNAGPSPVAQAPADRPVS | 563 | H-2-Db | H-2-Kb | 408 |
| missense_variant | transcript | Protein_coding | p.Gly452Asp | G452D | G | G | 452 | VKQKGTGKGKGRTNTISMTGG | 293 | D | VKQKGTGKGKDRTNTISMTGG | 564 | H-2-Db | H-2-Kb | 409 |
| missense_variant | transcript | Protein_coding | p.Glu213Lys | E213K | E | E | 213 | QRIYHGKKPYESSKSDKCFTH | 294 | K | QRIYHGKKPYKSSKSDKCFTH | 565 | H-2-Db | H-2-Kb | 410 |
| missense_variant | transcript | Protein_coding | p.Asp929Asn | D929N | D | D | 929 | KIIGDASTQTDALKLPPSQPP | 295 | N | KIIGDASTQTNALKLPPSQPP | 566 | H-2-Db | H-2-Kb | 411 |

FIG. 17(Cont.)

Apobec Deaminase Assay
5'ATTATTATTATTCAAATGGATTTATTTATTTATTTATTTATTT-Fluorescein3'
↓ In the presence of APOBEC3B
5'ATTATTATTATTTAAATGGATTTATTTATTTATTTATTTATTT-Fluorescein3'
FIG. 20A
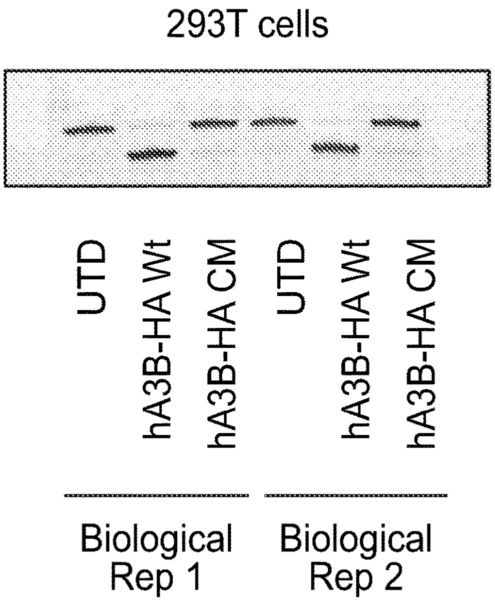
FIG. 20B
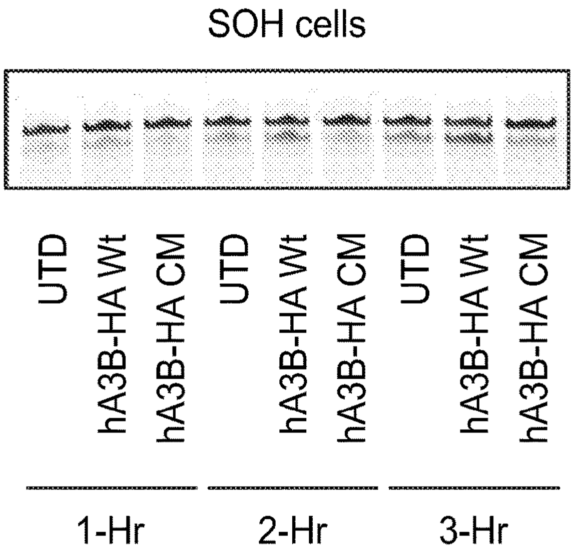
FIG. 20C ATGAACCCTCAAATTCGCAATCCGATGGAACGGATGTACAGGGACACATTTT
ACGACAATTTTGAGAACGAGCCCATACTCTACGGTAGGAGCTATACGTGGCT
TTGTTATGAAGTGAAAATCAAGCGCGGGCGCAGTAATCTCCTGTGGGACACC
GGAGTATTTCGAGGGCAGGTCTATTTCAAACCGCAATACCATGCTGAGATGT
GCTTTCTGTCCTGGTTCTGTGGAAATCAGCTGCCCGCGTACAAATGCTTTCA
GATAACATGGTTCGTCTCCTGGACCCCATGCCCCGACTGTGTCGCCAAATTG
GCTGAATTTCTTTCTGAACATCCGAACGTGACGCTCACAATCAGCGCAGCTC
GGCTGTATTACTACTGGGAGCGGGATTACAGGCGGGCTCTTTGTAGATTGTC
TCAGGCCGGAGCTAGGGTCAAGATCATGGACTATGAGGAGTTCGCATACTGT
TGGGAGAACTTTGTGTATAACGAAGGGCAGCAGTTTATGCCGTGGTATAAGT
TTGACGAGAACTATGCCTTCCTGCATCGGACTTTGAAAGAGATACTTCGATA
TTTGATGGATCCTGACACCTTTACTTTTAATTTCAATAATGACCCCCTTGTC
CTGCGGCGCAGACAGACATATCTGTGCTATGAAGTAGAGCGCCTTGACAATG
GGACGTGGGTGCTGATGGACCAGCACATGGGTTTCCTTTGCAATGAAGCAAA
AAACCTGCTTTGCGGTTTCTACGGTAGACATGCGGAACTGCGGTTCTTGGAT
CTCGTGCCCAGTCTCCAGCTGGATCCCGCGCAAATCTATAGGGTAACTTGGT
TCATCAGCTGGAGTCCATGTTTCTCATGGGGCTGTGCCGGAGAGGTCAGGGC
TTTTCTCCAAGAGAATACTCATGTTAGGCTCCGCATTTTCGCCGCCAGAATC
TATGACTATGACCCTCTCTATAAAGAAGCGCTCCAAATGCTTCGAGACGCCG
GCGCCCAGGTCTCCATTATGACCTACGACGAATTCGAGTATTGCTGGGACAC
CTTTGTTTATAGGCAGGGCTGCCCCTTTCAGCCATGGGATGGGCTGGAGGAG
CACTCACAAGCACTGAGCGGCAGACTTAGAGCTATACTTCAAAATCAGGGTA
ACTACCCATACGATGTTCCAGATTACGCTTGA

FIG. 22

ATGAACCCTCAAATTCGCAATCCGATGGAACGGATGTACAGGGACACATTTTACG
ACAATTTTGAGAACGAGCCCATACTCTACGGTAGGAGCTATACGTGGCTTTGTTA
TGAAGTGAAAATCAAGCGCGGGCGCAGTAATCTCCTGTGGGACACCGGAGTATTT
CGAGGGCAGGTCTATTTCAAACCGCAATACCATGCTGCGATGTGCTTTCTGTCCT
GGTTCTGTGGAAATCAGCTGCCCGCGTACAAATGCTTTCAGATAACATGGTTCGT
CTCCTGGACCCCATGCCCCGACTGTGTCGCCAAATTGGCTGAATTTCTTTCTGAA
CATCCGAACGTGACGCTCACAATCAGCGCAGCTCGGCTGTATTACTACTGGGAGC
GGGATTACAGGCGGGCTCTTTGTAGATTGTCTCAGGCCGGAGCTAGGGTCAAGAT
CATGGACTATGAGGAGTTCGCATACTGTTGGGAGAACTTTGTGTATAACGAAGGG
CAGCAGTTTATGCCGTGGTATAAGTTTGACGAGAACTATGCCTTCCTGCATCGGA
CTTTGAAAGAGATACTTCGATATTTGATGGATCCTGACACCTTTACTTTTAATTT
CAATAATGACCCCCTTGTCCTGCGGCGCAGACAGACATATCTGTGCTATGAAGTA
GAGCGCCTTGACAATGGGACGTGGGTGCTGATGGACCAGCACATGGGTTTCCTTT
GCAATGAAGCAAAAAACCTGCTTTGCGGTTTCTACGGTAGACATGCGGCGCTGCG
GTTCTTGGATCTCGTGCCCAGTCTCCAGCTGGATCCCGCGCAAATCTATAGGGTA
ACTTGGTTCATCAGCTGGAGTCCATGTTTCTCATGGGGCTGTGCCGGAGAGGTCA
GGGCTTTTCTCCAAGAGAATACTCATGTTAGGCTCCGCATTTTCGCCGCCAGAAT
CTATGACTATGACCCTCTCTATAAAGAAGCGCTCCAAATGCTTCGAGACGCCGGC
GCCCAGGTCTCCATTATGACCTACGACGAATTCGAGTATTGCTGGGACACCTTTG
TTTATAGGCAGGGCTGCCCCTTTCAGCCATGGGATGGGCTGGAGGAGCACTCACA
AGCACTGAGCGGCAGACTTAGAGCTATACTTCAAAATCAGGGTAACTACCCATAC
GATGTTCCAGATTACGCTTGA

FIG. 23

SEQUENCE LISTING

```
<160> NUMBER OF SEQ ID NOS: 575

<210> SEQ ID NO 1
<211> LENGTH: 15
<212> TYPE: DNA
<213> ORGANISM: Homo sapiens

<400> SEQUENCE: 1

atgagctttg atcca                                                    15


<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2

atgagctttg attca                                                    15


<210> SEQ ID NO 3
<211> LENGTH: 9
<212> TYPE: PRT
<213> ORGANISM: Homo sapiens

<400> SEQUENCE: 3

Asn Ser Ala Ala Asn Leu Arg Phe Val
1               5


<210> SEQ ID NO 4
<211> LENGTH: 9
<212> TYPE: PRT
<213> ORGANISM: Artificial Sequence
```

<220> FEATURE:
<223> OTHER INFORMATION: Description of Artificial Sequence: Synthetic
peptide

<400> SEQUENCE: 4

Asn Ser Ala Thr Asn Leu Arg Phe Val
1 5

<210> SEQ ID NO 5
<211> LENGTH: 8
<212> TYPE: PRT
<213> ORGANISM: Homo sapiens

<400> SEQUENCE: 5

Ala Ser Phe Ile Phe Ser Lys Gly
1 5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 6

Thr Ser Phe Ile Phe Ser Lys Gly
1 5

<210> SEQ ID NO 7
<211> LENGTH: 8
<212> TYPE: PRT
<213> ORGANISM: Homo sapiens

<400> SEQUENCE: 7

Met Ser Phe Asp Pro Asn Leu Leu
1 5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Met Ser Phe Asp Ser Asn Leu Leu
1 5

<210> SEQ ID NO 9
<211> LENGTH: 8
<212> TYPE: PRT
<213> ORGANISM: Homo sapiens

<400> SEQUENCE: 9

Arg Ser Glu Glu Leu Cys Pro Leu
1 5

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Arg Ser Glu Glu Phe Cys Pro Leu
1 5

<210> SEQ ID NO 11
<211> LENGTH: 9
<212> TYPE: PRT
<213> ORGANISM: Homo sapiens

<400> SEQUENCE: 11

Ser Ser Gly Gly Trp Ala Ala Arg Ala
1 5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Ser Ser Gly Gly Trp Ala Ala Arg Val
1 5

<210> SEQ ID NO 13
<211> LENGTH: 9
<212> TYPE: PRT
<213> ORGANISM: Homo sapiens

<400> SEQUENCE: 13

Ser Ser Val Ile Asp Glu Ile Ser Val
1 5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Ser Ser Val Ile Asn Glu Ile Ser Val
1 5

<210> SEQ ID NO 15
<211> LENGTH: 9
<212> TYPE: PRT
<213> ORGANISM: Homo sapiens

<400> SEQUENCE: 15

Val Arg Leu Lys Cys Leu Thr Ala Leu
1 5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 16

Val Arg Phe Lys Cys Leu Thr Ala Leu
1 5

<210> SEQ ID NO 17
<211> LENGTH: 8
<212> TYPE: PRT
<213> ORGANISM: Homo sapiens

<400> SEQUENCE: 17

Thr Leu Val Tyr Leu Thr His Leu
1 5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Thr Leu Val Tyr Phe Thr His Leu
1 5

<210> SEQ ID NO 19
<211> LENGTH: 9
<212> TYPE: PRT
<213> ORGANISM: Homo sapiens

<400> SEQUENCE: 19

Val Tyr Leu Thr His Leu Asp Tyr Val
1 5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Val Tyr Phe Thr His Leu Asp Tyr Val
1 5

<210> SEQ ID NO 21
<211> LENGTH: 10
<212> TYPE: PRT
<213> ORGANISM: Homo sapiens

<400> SEQUENCE: 21

Arg Glu Thr Leu Val Tyr Leu Thr His Leu
1 5 10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Arg Glu Thr Leu Val Tyr Phe Thr His Leu
1 5 10

<210> SEQ ID NO 23
<211> LENGTH: 5

<212> TYPE: PRT
<213> ORGANISM: Homo sapiens

<400> SEQUENCE: 23

Met Ser Phe Asp Pro
1 5

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 24

Met Ser Phe Asp Ser
1 5

<210> SEQ ID NO 25
<211> LENGTH: 21
<212> TYPE: PRT
<213> ORGANISM: Homo sapiens

<400> SEQUENCE: 25

Arg Arg Phe Leu Gln Leu Asn Lys Cys Pro Ala Cys Phe Gly Thr Ser
1 5 10 15

Trp Cys Arg Arg Phe
20

<210> SEQ ID NO 26
<211> LENGTH: 21
<212> TYPE: PRT
<213> ORGANISM: Homo sapiens

<400> SEQUENCE: 26

Asn Gln Cys Gly Lys Ala Phe Ala Arg Pro Ala Asn Leu Gln Cys His
1 5 10 15

Lys Arg Thr His Thr
20

<210> SEQ ID NO 27
<211> LENGTH: 21
<212> TYPE: PRT
<213> ORGANISM: Homo sapiens

<400> SEQUENCE: 27

Ser Gly Arg Pro Ser Gly His Val Val Ser Ser Pro Leu Ile Glu Leu
1 5 10 15

Ser Lys Ile Gly Glu
20

<210> SEQ ID NO 28
<211> LENGTH: 21
<212> TYPE: PRT
<213> ORGANISM: Homo sapiens

<400> SEQUENCE: 28

Cys Asn Pro Glu Leu Asn Gln Glu Glu Asp Gly Asp Arg Glu Pro Glu
1 5 10 15

Val Glu Pro Glu Ala
20

<210> SEQ ID NO 29
<211> LENGTH: 21
<212> TYPE: PRT
<213> ORGANISM: Homo sapiens

<400> SEQUENCE: 29

Pro Gly Gly Thr Phe Leu Gln Glu Asn Pro Arg Ser Arg Glu Glu Lys
1 5 10 15

Arg Lys Ala Thr Thr
20

<210> SEQ ID NO 30
<211> LENGTH: 21
<212> TYPE: PRT
<213> ORGANISM: Homo sapiens

<400> SEQUENCE: 30

Pro Gly Gly Thr Phe Leu Gln Glu Asn Pro Arg Ser Arg Glu Ser Trp
1 5 10 15

Gln Val Trp Ser Leu
20

<210> SEQ ID NO 31
<211> LENGTH: 21
<212> TYPE: PRT
<213> ORGANISM: Homo sapiens

<400> SEQUENCE: 31

Arg Pro Phe Leu Asp Leu Ala His Pro Arg His Leu His Ser Thr His
1 5 10 15

Ser Glu Leu Leu Glu
20

<210> SEQ ID NO 32
<211> LENGTH: 21
<212> TYPE: PRT
<213> ORGANISM: Homo sapiens

<400> SEQUENCE: 32

Gly Gln Gln Leu Thr Ser Glu Gln Leu Pro Thr Lys Glu Gly Tyr Phe
1 5 10 15

Arg Ala Val Arg Gln
20

<210> SEQ ID NO 33
<211> LENGTH: 21
<212> TYPE: PRT
<213> ORGANISM: Homo sapiens

<400> SEQUENCE: 33

Glu Cys Lys Gly Lys Gln Tyr Val Lys Arg Thr Trp Tyr Lys Lys Phe
1 5 10 15

Val Gly Val Gln Leu
20

<210> SEQ ID NO 34
<211> LENGTH: 21
<212> TYPE: PRT
<213> ORGANISM: Homo sapiens

<400> SEQUENCE: 34

Ala Leu Met Ser His Glu Leu Gly His Ala Leu Gly Met Lys Asp Val
1 5 10 15

Pro Tyr Tyr Thr Lys
20

<210> SEQ ID NO 35
<211> LENGTH: 21
<212> TYPE: PRT
<213> ORGANISM: Homo sapiens

<400> SEQUENCE: 35

Pro Val Arg Ile Phe Phe Leu Tyr Leu Phe Ala Ile Cys Asn Thr Leu
1 5 10 15

Gln Gly Phe Leu Ile
20

<210> SEQ ID NO 36
<211> LENGTH: 21
<212> TYPE: PRT
<213> ORGANISM: Homo sapiens

<400> SEQUENCE: 36

Gly Val Lys Pro Glu Gly Leu Ser Leu Asn Pro Ser Gln Phe Leu Gly
1 5 10 15

Asp Arg Asn Phe Ala
20

<210> SEQ ID NO 37
<211> LENGTH: 21
<212> TYPE: PRT
<213> ORGANISM: Homo sapiens

<400> SEQUENCE: 37

Ile Leu Glu Thr Cys Lys Asn Pro Ile Gln Glu Val Gln Ser Arg Gly
1 5 10 15

Ile Asn Ile His Glu
20

<210> SEQ ID NO 38
<211> LENGTH: 21
<212> TYPE: PRT
<213> ORGANISM: Homo sapiens

<400> SEQUENCE: 38

Trp Ile Ile Glu Glu Gln Pro Asn Ser Ala Ala Asn Leu Arg Phe Val
1 5 10 15

Leu Glu Trp Thr Trp
20

<210> SEQ ID NO 39
<211> LENGTH: 21
<212> TYPE: PRT
<213> ORGANISM: Homo sapiens

<400> SEQUENCE: 39

His Ile Asp Ile Asp Lys Gln Lys Asp Lys Thr Gly Asp Arg Ile Ile
1 5 10 15

Thr Ile Arg Gly Gly
20

<210> SEQ ID NO 40
<211> LENGTH: 21
<212> TYPE: PRT
<213> ORGANISM: Homo sapiens

```
<400> SEQUENCE: 40

Asp Glu Gly Glu Ser Pro Gly Ser Ser His Arg Pro Leu Thr Glu Asp
1               5                   10                  15

Glu Ile Ala Asp Leu
            20


<210> SEQ ID NO 41
<211> LENGTH: 21
<212> TYPE: PRT
<213> ORGANISM: Homo sapiens

<400> SEQUENCE: 41

Gly Ala Trp Asn Gly Phe Val Glu Ala Val Glu Leu Ser Ser Glu Glu
1               5                   10                  15

Gly Glu Ala Leu Arg
            20


<210> SEQ ID NO 42
<211> LENGTH: 21
<212> TYPE: PRT
<213> ORGANISM: Homo sapiens

<400> SEQUENCE: 42

Glu Ile Ala Ala Lys Thr Asp Gln Lys Ser Ser Gly Lys Leu Lys Asn
1               5                   10                  15

Gly Leu Thr Phe Arg
            20


<210> SEQ ID NO 43
<211> LENGTH: 21
<212> TYPE: PRT
<213> ORGANISM: Homo sapiens

<400> SEQUENCE: 43

Met Ala Phe Gly Pro Thr Ser Tyr Arg Pro Arg Leu Leu Leu Ser Gly
1               5                   10                  15

Glu Arg Gly Ser Gly
            20


<210> SEQ ID NO 44
<211> LENGTH: 21
<212> TYPE: PRT
<213> ORGANISM: Homo sapiens

<400> SEQUENCE: 44

Glu Thr Asn Leu Lys Arg Arg Gln Val Val Arg Gly Phe Ser Glu Leu
1               5                   10                  15

Val Ser Glu Phe Asn
            20


<210> SEQ ID NO 45
<211> LENGTH: 21
<212> TYPE: PRT
<213> ORGANISM: Homo sapiens

<400> SEQUENCE: 45

Leu Cys Gln His Leu Gly Lys Arg Lys Lys Met Pro Lys Gly Leu Arg
1               5                   10                  15

Gln Leu Lys Pro Gly
            20
```

<210> SEQ ID NO 46
<211> LENGTH: 21
<212> TYPE: PRT
<213> ORGANISM: Homo sapiens

<400> SEQUENCE: 46

Pro Leu Trp Gln Val Ser Thr Pro Gln Thr Arg Gly Arg Lys Gln Ala
1 5 10 15

Ser Ala Asn Ile Phe
20

<210> SEQ ID NO 47
<211> LENGTH: 21
<212> TYPE: PRT
<213> ORGANISM: Homo sapiens

<400> SEQUENCE: 47

Gln Asp Ser Leu Leu Pro Leu Glu Glu Ala Ala Asn Ser Gly Met Asp
1 5 10 15

Thr Ser Ile Pro Ser
20

<210> SEQ ID NO 48
<211> LENGTH: 21
<212> TYPE: PRT
<213> ORGANISM: Homo sapiens

<400> SEQUENCE: 48

Met Asp Thr Thr Pro Asp Leu Pro Leu Thr Pro Glu Glu Tyr Gln Thr
1 5 10 15

Leu Leu Asp Met Leu
20

<210> SEQ ID NO 49
<211> LENGTH: 21
<212> TYPE: PRT
<213> ORGANISM: Homo sapiens

<400> SEQUENCE: 49

Ser Lys Gln Thr Ala Ser Pro Ser Ser Glu Ala Lys Ser Arg Ala Gln
1 5 10 15

Ile Gln Ala Arg Ala
20

<210> SEQ ID NO 50
<211> LENGTH: 21
<212> TYPE: PRT
<213> ORGANISM: Homo sapiens

<400> SEQUENCE: 50

Gln Gly Trp Lys Ser Leu Trp Cys Gly Met Gly Thr Ile Arg Ser Gly
1 5 10 15

Leu Glu Glu Leu Trp
20

<210> SEQ ID NO 51
<211> LENGTH: 21
<212> TYPE: PRT
<213> ORGANISM: Homo sapiens

<400> SEQUENCE: 51

Pro Arg Ser Pro Gln Ser Pro Ala Ser Lys Ala Ser Phe Ile Phe Ser

```
1               5                   10                  15

Lys Gly Thr Lys Lys
            20


<210> SEQ ID NO 52
<211> LENGTH: 21
<212> TYPE: PRT
<213> ORGANISM: Homo sapiens

<400> SEQUENCE: 52

Ala Leu Ser Gly Arg Ala Ser Pro Val Thr Ala Pro Ser Ser Gly Leu
1               5                   10                  15

His Ala Ala Val Arg
            20


<210> SEQ ID NO 53
<211> LENGTH: 21
<212> TYPE: PRT
<213> ORGANISM: Homo sapiens

<400> SEQUENCE: 53

Ala Ile Asn Arg Ala Lys Gly Leu Lys His Val Val Gln Cys Val Phe
1               5                   10                  15

Val Ala Ile Arg Thr
            20


<210> SEQ ID NO 54
<211> LENGTH: 21
<212> TYPE: PRT
<213> ORGANISM: Homo sapiens

<400> SEQUENCE: 54

Ala Lys Gly Leu Lys His Val Val Gln Cys Val Phe Val Ala Ile Arg
1               5                   10                  15

Thr Ile Gly Asn Ile
            20


<210> SEQ ID NO 55
<211> LENGTH: 21
<212> TYPE: PRT
<213> ORGANISM: Homo sapiens

<400> SEQUENCE: 55

Ser Phe Gly Ile Gln Ser Ser Ala Ile Asn Val Val Lys Ile Leu Arg
1               5                   10                  15

Val Leu Arg Val Leu
            20


<210> SEQ ID NO 56
<211> LENGTH: 21
<212> TYPE: PRT
<213> ORGANISM: Homo sapiens

<400> SEQUENCE: 56

Ala Ile Asn Arg Ala Lys Gly Leu Lys His Val Val Gln Cys Val Phe
1               5                   10                  15

Val Ala Ile Arg Thr
            20


<210> SEQ ID NO 57
<211> LENGTH: 21
<212> TYPE: PRT
```

<213> ORGANISM: Homo sapiens

<400> SEQUENCE: 57

Ser Phe Gly Ile Gln Ser Ser Ala Ile Asn Val Val Lys Ile Leu Arg
1 5 10 15

Val Leu Arg Val Leu
20

<210> SEQ ID NO 58
<211> LENGTH: 21
<212> TYPE: PRT
<213> ORGANISM: Homo sapiens

<400> SEQUENCE: 58

Ala Ile Asn Arg Ala Lys Gly Leu Lys His Val Val Gln Cys Val Phe
1 5 10 15

Val Ala Ile Arg Thr
20

<210> SEQ ID NO 59
<211> LENGTH: 21
<212> TYPE: PRT
<213> ORGANISM: Homo sapiens

<400> SEQUENCE: 59

Ser Phe Gly Ile Gln Ser Ser Ala Ile Asn Val Val Lys Ile Leu Arg
1 5 10 15

Val Leu Arg Val Leu
20

<210> SEQ ID NO 60
<211> LENGTH: 12
<212> TYPE: PRT
<213> ORGANISM: Homo sapiens

<400> SEQUENCE: 60

Met Asp Gly Val Tyr Ser Glu Ala Asn Glu Glu Asn
1 5 10

<210> SEQ ID NO 61
<211> LENGTH: 21
<212> TYPE: PRT
<213> ORGANISM: Homo sapiens

<400> SEQUENCE: 61

Ala Asn Lys Ser Phe Asp Val Leu Gly Lys Val Glu Ala Tyr Leu Lys
1 5 10 15

Leu Leu Lys Ser Glu
20

<210> SEQ ID NO 62
<211> LENGTH: 21
<212> TYPE: PRT
<213> ORGANISM: Homo sapiens

<400> SEQUENCE: 62

Ala Asn Asp Phe Phe Thr Ser Ala Asn Lys Ser Phe Asp Val Leu Gly
1 5 10 15

Lys Val Glu Ala Tyr
20

<210> SEQ ID NO 63

<211> LENGTH: 21
<212> TYPE: PRT
<213> ORGANISM: Homo sapiens

<400> SEQUENCE: 63

Thr Ser Ala Asn Lys Ser Phe Asp Val Leu Gly Lys Val Glu Ala Tyr
1 5 10 15

Leu Lys Leu Leu Lys
20

<210> SEQ ID NO 64
<211> LENGTH: 21
<212> TYPE: PRT
<213> ORGANISM: Homo sapiens

<400> SEQUENCE: 64

Pro Arg Asp Val Glu Met Asn Asn Tyr Arg Arg Ala Met Gln Lys Met
1 5 10 15

Ala Glu Asp Ile Leu
20

<210> SEQ ID NO 65
<211> LENGTH: 21
<212> TYPE: PRT
<213> ORGANISM: Homo sapiens

<400> SEQUENCE: 65

Leu Thr Val Ala Gly Gly Gln Asp Asn Val Met Gly Leu Lys Tyr Cys
1 5 10 15

Phe Arg Lys Asn Asp
20

<210> SEQ ID NO 66
<211> LENGTH: 21
<212> TYPE: PRT
<213> ORGANISM: Homo sapiens

<400> SEQUENCE: 66

Ala Glu Leu Gln Cys Leu Thr Val Ala Gly Gly Gln Asp Asn Val Met
1 5 10 15

Gly Leu Lys Tyr Cys
20

<210> SEQ ID NO 67
<211> LENGTH: 21
<212> TYPE: PRT
<213> ORGANISM: Homo sapiens

<400> SEQUENCE: 67

Met Ala Gln Ala Val Asp Arg Asp Thr Asn Arg Pro Leu Glu Pro Pro
1 5 10 15

Ser Glu Phe Ile Val
20

<210> SEQ ID NO 68
<211> LENGTH: 17
<212> TYPE: PRT
<213> ORGANISM: Homo sapiens

<400> SEQUENCE: 68

Met Lys Ile Pro Asn Ile Gly Asn Val Met Asn Lys Phe Glu Ile Leu
1 5 10 15

Gly

<210> SEQ ID NO 69
<211> LENGTH: 21
<212> TYPE: PRT
<213> ORGANISM: Homo sapiens

<400> SEQUENCE: 69

Pro Leu Arg Thr Arg Val Glu Ile Leu His Arg Leu Cys Asp Tyr Arg
1 5 10 15

Leu Asp Ala Asp Asp
20

<210> SEQ ID NO 70
<211> LENGTH: 19
<212> TYPE: PRT
<213> ORGANISM: Homo sapiens

<400> SEQUENCE: 70

Ser Ala Arg Phe Gly Gly Arg Pro Gly Arg Pro Arg Ala Pro Val Pro
1 5 10 15

Ala Cys Leu

<210> SEQ ID NO 71
<211> LENGTH: 12
<212> TYPE: PRT
<213> ORGANISM: Homo sapiens

<400> SEQUENCE: 71

Ser Ala Arg Phe Gly Gly Arg Pro Gly Arg Pro Arg
1 5 10

<210> SEQ ID NO 72
<211> LENGTH: 21
<212> TYPE: PRT
<213> ORGANISM: Homo sapiens

<400> SEQUENCE: 72

Glu Asn Ser Met Trp Gln Glu Gln Ile Leu Glu Asn Glu Glu Ala Ile
1 5 10 15

Leu Leu Ser Ser Lys
20

<210> SEQ ID NO 73
<211> LENGTH: 21
<212> TYPE: PRT
<213> ORGANISM: Homo sapiens

<400> SEQUENCE: 73

Cys Gly Pro Asn Met Arg Ala Gly Val Leu Ser Ser Gly Thr Gly Pro
1 5 10 15

Pro Asn Pro Arg Pro
20

<210> SEQ ID NO 74
<211> LENGTH: 21
<212> TYPE: PRT
<213> ORGANISM: Homo sapiens

<400> SEQUENCE: 74

Tyr Ile Ile Lys Asp Leu Glu Lys Leu Leu Met Ile Ala Gly Glu Glu
1 5 10 15

Arg Ala Leu Cys Leu
            20

<210> SEQ ID NO 75
<211> LENGTH: 15
<212> TYPE: PRT
<213> ORGANISM: Homo sapiens

<400> SEQUENCE: 75

Gly Thr Gln Cys Ala Arg Ile Val Glu Ser Ser Ala Pro Ala Ser
1               5                   10                  15

<210> SEQ ID NO 76
<211> LENGTH: 12
<212> TYPE: PRT
<213> ORGANISM: Homo sapiens

<400> SEQUENCE: 76

Met Ser Phe Asp Pro Asn Leu Leu His Asn Asn Gly
1               5                   10

<210> SEQ ID NO 77
<211> LENGTH: 15
<212> TYPE: PRT
<213> ORGANISM: Homo sapiens

<400> SEQUENCE: 77

Met Ser Phe Asp Pro Asn Leu Leu His Asn Asn Gly His Asn Gly
1               5                   10                  15

<210> SEQ ID NO 78
<211> LENGTH: 21
<212> TYPE: PRT
<213> ORGANISM: Homo sapiens

<400> SEQUENCE: 78

Arg Lys Val Asn Gln Lys Ile Gly Ser Cys Thr Gln Gln Asp Val Glu
1               5                   10                  15

Leu His Val Gln Lys
            20

<210> SEQ ID NO 79
<211> LENGTH: 21
<212> TYPE: PRT
<213> ORGANISM: Homo sapiens

<400> SEQUENCE: 79

Asn Leu Ser Cys Leu Leu Lys Glu Gly Ser Glu His Leu Phe Asp Ser
1               5                   10                  15

Phe Glu Pro Glu Thr
            20

<210> SEQ ID NO 80
<211> LENGTH: 21
<212> TYPE: PRT
<213> ORGANISM: Homo sapiens

<400> SEQUENCE: 80

Val His Asp Phe Asp Cys Leu Cys Pro Ser Gly Tyr Gly Gly Lys Thr
1               5                   10                  15

Cys Glu Leu Val Leu
            20

<210> SEQ ID NO 81
<211> LENGTH: 21
<212> TYPE: PRT
<213> ORGANISM: Homo sapiens

<400> SEQUENCE: 81

Pro His Gly Leu His Arg Val Phe Pro Ser Gly Phe Gly Glu Phe Pro
1 5 10 15

Ala Phe Met Glu Ala
20

<210> SEQ ID NO 82
<211> LENGTH: 21
<212> TYPE: PRT
<213> ORGANISM: Homo sapiens

<400> SEQUENCE: 82

Asn Ile Met His Tyr Val Val Pro Tyr Leu Arg Asn His Ser Ala His
1 5 10 15

Asn Ala Pro Ser Tyr
20

<210> SEQ ID NO 83
<211> LENGTH: 21
<212> TYPE: PRT
<213> ORGANISM: Homo sapiens

<400> SEQUENCE: 83

Trp Asn Val Asp Thr Gly Pro Asp Tyr Tyr Arg Asp Met Ala Ile Glu
1 5 10 15

Tyr His Gly Val Glu
20

<210> SEQ ID NO 84
<211> LENGTH: 21
<212> TYPE: PRT
<213> ORGANISM: Homo sapiens

<400> SEQUENCE: 84

Ser Val Phe Ser Thr His Ala Gly Cys Ala Gly Ala His Glu Ala Glu
1 5 10 15

Gly Tyr Pro Ala Glu
20

<210> SEQ ID NO 85
<211> LENGTH: 21
<212> TYPE: PRT
<213> ORGANISM: Homo sapiens

<400> SEQUENCE: 85

Thr Ala Arg Thr Gln Lys Thr Ala Tyr Gln Arg Asn Arg Met Arg Phe
1 5 10 15

Ala Gln Arg Asn Leu
20

<210> SEQ ID NO 86
<211> LENGTH: 21
<212> TYPE: PRT
<213> ORGANISM: Homo sapiens

<400> SEQUENCE: 86

Ser Glu Thr Pro Lys Leu Thr Ala Leu His Thr Leu Phe Val Arg Glu
1 5 10 15

```
His Asn Arg Leu Ala
            20


<210> SEQ ID NO 87
<211> LENGTH: 21
<212> TYPE: PRT
<213> ORGANISM: Homo sapiens

<400> SEQUENCE: 87

Phe Ser Val Glu Leu Asn Lys Phe Tyr Asn Val Asp Leu Phe Gln Arg
1               5                   10                  15

Gly Phe Tyr Gln Ile
            20


<210> SEQ ID NO 88
<211> LENGTH: 21
<212> TYPE: PRT
<213> ORGANISM: Homo sapiens

<400> SEQUENCE: 88

Phe Ser Val Glu Leu Asn Lys Phe Tyr Asn Val Asp Leu Phe Gln Arg
1               5                   10                  15

Gly Lys Thr Phe Gln
            20


<210> SEQ ID NO 89
<211> LENGTH: 21
<212> TYPE: PRT
<213> ORGANISM: Homo sapiens

<400> SEQUENCE: 89

Ala Gly Arg Val Arg Phe Leu Thr Gly Pro Ala Val Leu Asp Ile Thr
1               5                   10                  15

Asp Arg Leu Ser Val
            20


<210> SEQ ID NO 90
<211> LENGTH: 21
<212> TYPE: PRT
<213> ORGANISM: Homo sapiens

<400> SEQUENCE: 90

Ser Arg Glu Phe Glu Asp Val Leu Asn Ile Leu His Ser Ser Tyr Leu
1               5                   10                  15

Glu Pro Ser Ser Val
            20


<210> SEQ ID NO 91
<211> LENGTH: 21
<212> TYPE: PRT
<213> ORGANISM: Homo sapiens

<400> SEQUENCE: 91

Pro Ile Cys Leu Ser Ala Cys Ile Ile Gly Ser Met Ser Gln Val Asn
1               5                   10                  15

Gln Arg Ile Met Glu
            20


<210> SEQ ID NO 92
<211> LENGTH: 21
<212> TYPE: PRT
<213> ORGANISM: Homo sapiens
```

<400> SEQUENCE: 92

Gly Thr Val His Pro Trp Arg Ser Glu Glu Leu Cys Pro Leu Thr Cys
1               5                   10                  15

Pro Pro Asn Ser His
            20

<210> SEQ ID NO 93
<211> LENGTH: 21
<212> TYPE: PRT
<213> ORGANISM: Homo sapiens

<400> SEQUENCE: 93

Gln Lys Gly Ile Pro Val Lys Gly Lys Lys Thr Lys Lys Glu Gln Lys
1               5                   10                  15

Thr Ala His Phe Leu
            20

<210> SEQ ID NO 94
<211> LENGTH: 21
<212> TYPE: PRT
<213> ORGANISM: Homo sapiens

<400> SEQUENCE: 94

Pro Pro Pro Pro Pro Pro Pro Leu Leu Asp Ser Val Pro Pro Pro Pro
1               5                   10                  15

Val Pro Gly Asn Leu
            20

<210> SEQ ID NO 95
<211> LENGTH: 21
<212> TYPE: PRT
<213> ORGANISM: Homo sapiens

<400> SEQUENCE: 95

Ser Ile Pro Val His Pro Ile Gly Tyr Asp Asp Ala Gln Lys Leu Leu
1               5                   10                  15

Glu Lys Val Lys Met
            20

<210> SEQ ID NO 96
<211> LENGTH: 21
<212> TYPE: PRT
<213> ORGANISM: Homo sapiens

<400> SEQUENCE: 96

Ser Ile Pro Val His Pro Ile Gly Tyr Asp Asp Ala Gln Lys Leu Leu
1               5                   10                  15

Glu His Met Gly Gly
            20

<210> SEQ ID NO 97
<211> LENGTH: 21
<212> TYPE: PRT
<213> ORGANISM: Homo sapiens

<400> SEQUENCE: 97

Ala Val Arg Pro Thr Pro Ala Ser Gly Ala Glu Ala Pro Gly Ile Pro
1               5                   10                  15

Lys Pro Val Pro Gly
            20

<210> SEQ ID NO 98
<211> LENGTH: 21
<212> TYPE: PRT
<213> ORGANISM: Homo sapiens

<400> SEQUENCE: 98

Gln Gln Pro Val Lys Ala Gly Val Lys Lys Pro Arg Arg Pro Arg Val
1 5 10 15

Arg Asn Leu Ser Asp
20

<210> SEQ ID NO 99
<211> LENGTH: 21
<212> TYPE: PRT
<213> ORGANISM: Homo sapiens

<400> SEQUENCE: 99

Ile His Ala Leu Cys His Cys Lys Ser Ala Val Asn Lys Asp Ile Val
1 5 10 15

Ser Val Tyr His Ser
20

<210> SEQ ID NO 100
<211> LENGTH: 21
<212> TYPE: PRT
<213> ORGANISM: Homo sapiens

<400> SEQUENCE: 100

Pro Arg Val Val Ala Ala Ser Ala Ser Gln Arg Leu Leu Ser Ala Pro
1 5 10 15

Ala Gln Pro Ala Ala
20

<210> SEQ ID NO 101
<211> LENGTH: 21
<212> TYPE: PRT
<213> ORGANISM: Homo sapiens

<400> SEQUENCE: 101

Gly Cys Glu Arg Arg Gly Cys Leu Leu Pro Ala Pro Leu Ala Pro Leu
1 5 10 15

Phe Ser Gly Arg Leu
20

<210> SEQ ID NO 102
<211> LENGTH: 21
<212> TYPE: PRT
<213> ORGANISM: Homo sapiens

<400> SEQUENCE: 102

Leu Ser Leu Ser Leu Ser Leu Ser Leu Ser Leu Ser Leu Ser Leu Ser
1 5 10 15

Pro Ser Leu Ser Leu
20

<210> SEQ ID NO 103
<211> LENGTH: 13
<212> TYPE: PRT
<213> ORGANISM: Homo sapiens

<400> SEQUENCE: 103

Trp Met Phe Leu Ile Phe His Asp Phe Gln Leu Ser Cys 1 5 10

<210> SEQ ID NO 104
<211> LENGTH: 13
<212> TYPE: PRT
<213> ORGANISM: Homo sapiens

<400> SEQUENCE: 104

Trp Lys Phe Leu Ile Phe His Asp Phe Gln Leu Ser Ser
1 5 10

<210> SEQ ID NO 105
<211> LENGTH: 21
<212> TYPE: PRT
<213> ORGANISM: Homo sapiens

<400> SEQUENCE: 105

His Val Leu Gln Trp Thr Phe Leu Asn Phe Pro Pro Phe Ser Val Ser
1 5 10 15

Pro Tyr Ser Arg Ser
20

<210> SEQ ID NO 106
<211> LENGTH: 21
<212> TYPE: PRT
<213> ORGANISM: Homo sapiens

<400> SEQUENCE: 106

His Val Leu Lys Cys Val Phe Leu Ile Phe Arg Asp Phe Gln Val Ser
1 5 10 15

Arg His Ile Pro Gly
20

<210> SEQ ID NO 107
<211> LENGTH: 21
<212> TYPE: PRT
<213> ORGANISM: Homo sapiens

<400> SEQUENCE: 107

His Val Leu Lys Cys Val Phe Leu Ile Phe Arg Asp Phe Gln Phe Ser
1 5 10 15

Cys Tyr Ile Pro Ser
20

<210> SEQ ID NO 108
<211> LENGTH: 21
<212> TYPE: PRT
<213> ORGANISM: Homo sapiens

<400> SEQUENCE: 108

His Val Leu Lys Cys Val Phe Leu Ile Phe Arg Val Phe Gln Phe Pro
1 5 10 15

Arg His Ile Pro Gly
20

<210> SEQ ID NO 109
<211> LENGTH: 21
<212> TYPE: PRT
<213> ORGANISM: Homo sapiens

<400> SEQUENCE: 109

Gln Lys Arg Leu Lys Pro Arg Asn Thr Lys Glu Val Cys Lys Tyr Asn
1 5 10 15

Asp Ser Val Asn Ser
20

<210> SEQ ID NO 110
<211> LENGTH: 21
<212> TYPE: PRT
<213> ORGANISM: Homo sapiens

<400> SEQUENCE: 110

Lys Pro Tyr Lys Cys Ser Glu Cys Asp Lys Cys Phe Thr Glu Lys Asn
1 5 10 15

Gly Leu Arg Arg His
20

<210> SEQ ID NO 111
<211> LENGTH: 21
<212> TYPE: PRT
<213> ORGANISM: Homo sapiens

<400> SEQUENCE: 111

Ser Glu Cys Asp Lys Cys Phe Thr Asp Lys Gly Ser Leu Arg Val His
1 5 10 15

His Arg Ile His Ala
20

<210> SEQ ID NO 112
<211> LENGTH: 21
<212> TYPE: PRT
<213> ORGANISM: Homo sapiens

<400> SEQUENCE: 112

Asn His Cys Ile Cys Gly Lys Tyr Glu Lys Val Leu Asp Gln Asp Ser
1 5 10 15

Gln Tyr Ile Val His
20

<210> SEQ ID NO 113
<211> LENGTH: 21
<212> TYPE: PRT
<213> ORGANISM: Homo sapiens

<400> SEQUENCE: 113

Arg Thr His Thr Arg Glu Lys Pro Tyr Glu Cys Lys Gln Cys Gly Lys
1 5 10 15

Ala Phe Ser Gln Ser
20

<210> SEQ ID NO 114
<211> LENGTH: 21
<212> TYPE: PRT
<213> ORGANISM: Homo sapiens

<400> SEQUENCE: 114

Ala His Ser Ser His Leu His Ile His Glu Arg Thr His Thr Arg Glu
1 5 10 15

Lys Pro Tyr Glu Cys
20

<210> SEQ ID NO 115
<211> LENGTH: 21
<212> TYPE: PRT
<213> ORGANISM: Homo sapiens

<400> SEQUENCE: 115

Pro Gly Ser Glu Pro Glu Ile Asp Arg Ser Ser Ala Ile Arg Glu Arg
1 5 10 15

Thr Asp Tyr Leu Trp
20

<210> SEQ ID NO 116
<211> LENGTH: 21
<212> TYPE: PRT
<213> ORGANISM: Homo sapiens

<400> SEQUENCE: 116

Ala Asp Leu Pro Ser Glu Arg Asn Glu Gly Arg Arg Arg Trp Thr Trp
1 5 10 15

Arg Met Trp Met Ala
20

<210> SEQ ID NO 117
<211> LENGTH: 21
<212> TYPE: PRT
<213> ORGANISM: Homo sapiens

<400> SEQUENCE: 117

Asp Ile Ser His Asn Met Arg Leu Ser Arg Ala Ser Val Leu Tyr Glu
1 5 10 15

Gln Met Arg Glu Cys
20

<210> SEQ ID NO 118
<211> LENGTH: 21
<212> TYPE: PRT
<213> ORGANISM: Homo sapiens

<400> SEQUENCE: 118

Val Glu Gln Ala Gly His Lys Cys Pro Val Gly Lys Lys Arg Gly Ser
1 5 10 15

Leu Arg Arg Pro Ala
20

<210> SEQ ID NO 119
<211> LENGTH: 21
<212> TYPE: PRT
<213> ORGANISM: Homo sapiens

<400> SEQUENCE: 119

Val Arg Ala Gly Gly Leu Ala Thr Leu Asn Cys Thr Val Thr Ser Leu
1 5 10 15

Ile Pro Val Gly Pro
20

<210> SEQ ID NO 120
<211> LENGTH: 21
<212> TYPE: PRT
<213> ORGANISM: Homo sapiens

<400> SEQUENCE: 120

Gln Lys Glu Gln Glu Ala Leu Lys Leu Ser Glu Cys Ser Gln Arg Gln
1 5 10 15

Thr Leu Glu Ala Ile
20

<210> SEQ ID NO 121
<211> LENGTH: 21
<212> TYPE: PRT
<213> ORGANISM: Homo sapiens

<400> SEQUENCE: 121

Ser Lys Gly Gln Glu Ser Phe Lys Lys Gln Gly Lys Ile Pro Lys Ile
1 5 10 15

Pro Lys Gly Pro Ser
20

<210> SEQ ID NO 122
<211> LENGTH: 21
<212> TYPE: PRT
<213> ORGANISM: Homo sapiens

<400> SEQUENCE: 122

Leu Cys Arg Leu Phe His Arg Glu Asn Gly Asp Gln Gly Glu Thr Arg
1 5 10 15

Pro Arg Gln Lys Glu
20

<210> SEQ ID NO 123
<211> LENGTH: 21
<212> TYPE: PRT
<213> ORGANISM: Homo sapiens

<400> SEQUENCE: 123

Glu Gly Pro Trp Lys Thr Val Ala Ile Ala Ala Asp Arg Val Asp Lys
1 5 10 15

Ile Glu Arg Gly Gly
20

<210> SEQ ID NO 124
<211> LENGTH: 21
<212> TYPE: PRT
<213> ORGANISM: Homo sapiens

<400> SEQUENCE: 124

Lys Leu Val Tyr Ser Ile Leu Glu Gly Gln Pro Tyr Phe Ser Val Glu
1 5 10 15

Ala Gln Thr Gly Ile
20

<210> SEQ ID NO 125
<211> LENGTH: 21
<212> TYPE: PRT
<213> ORGANISM: Homo sapiens

<400> SEQUENCE: 125

Thr Pro Val Pro Leu Asp Val Thr Thr Gly Val Asp Ile Arg Ile Leu
1 5 10 15

Pro Gln Asn Tyr Phe
20

<210> SEQ ID NO 126
<211> LENGTH: 21
<212> TYPE: PRT
<213> ORGANISM: Homo sapiens

<400> SEQUENCE: 126

Ser Ile Ile Val Pro Asn Tyr Thr Lys Ser Leu Leu Thr Phe Lys Val

```
1               5                   10                  15

Thr Ser Asp Leu Ser
            20


<210> SEQ ID NO 127
<211> LENGTH: 21
<212> TYPE: PRT
<213> ORGANISM: Homo sapiens

<400> SEQUENCE: 127

Trp Tyr His Leu Glu Ile Arg Ser Ser Pro Gly Pro Pro Val Asp Ile
1               5                   10                  15

Ile Glu Leu His Cys
            20


<210> SEQ ID NO 128
<211> LENGTH: 21
<212> TYPE: PRT
<213> ORGANISM: Homo sapiens

<400> SEQUENCE: 128

Ile Val Pro Asn Tyr Thr Lys Ser Leu Leu Thr Phe Lys Val Thr Ser
1               5                   10                  15

Asp Leu Ser Ile Val
            20


<210> SEQ ID NO 129
<211> LENGTH: 21
<212> TYPE: PRT
<213> ORGANISM: Homo sapiens

<400> SEQUENCE: 129

Phe Cys Glu Glu Ala Ser Lys Asn Ile Cys Ala Ser Ser Ala Lys Glu
1               5                   10                  15

Gln Gln Ser Glu Ile
            20


<210> SEQ ID NO 130
<211> LENGTH: 19
<212> TYPE: PRT
<213> ORGANISM: Homo sapiens

<400> SEQUENCE: 130

Phe Cys Glu Glu Ala Ser Lys Asn Ile Cys Ala Ser Ser Ala Lys Glu
1               5                   10                  15

Gln Gln Val


<210> SEQ ID NO 131
<211> LENGTH: 20
<212> TYPE: PRT
<213> ORGANISM: Homo sapiens

<400> SEQUENCE: 131

Phe Cys Glu Glu Ala Ser Lys Asn Ile Cys Ala Ser Ser Ala Lys Glu
1               5                   10                  15

Gln Gln Val Gly
            20


<210> SEQ ID NO 132
<211> LENGTH: 21
<212> TYPE: PRT
<213> ORGANISM: Homo sapiens
```

<400> SEQUENCE: 132

Asp Val Gly Asp Leu Thr Gln Glu Ala Phe Asp Leu Ile Ser Lys Glu
1 5 10 15

Asn Pro Ser Ser Gln
20

<210> SEQ ID NO 133
<211> LENGTH: 21
<212> TYPE: PRT
<213> ORGANISM: Homo sapiens

<400> SEQUENCE: 133

Cys Phe Glu Cys Cys Ile Lys Cys Leu Gly Gly Val Pro Tyr Ala Ser
1 5 10 15

Leu Val Ala Thr Ile
20

<210> SEQ ID NO 134
<211> LENGTH: 21
<212> TYPE: PRT
<213> ORGANISM: Homo sapiens

<400> SEQUENCE: 134

Ser Lys Asn Ala Lys His Leu Ala Lys Ala Gly Ile Ala Asn Arg Phe
1 5 10 15

Arg Met Pro His Leu
20

<210> SEQ ID NO 135
<211> LENGTH: 21
<212> TYPE: PRT
<213> ORGANISM: Homo sapiens

<400> SEQUENCE: 135

Cys Phe Glu Cys Cys Ile Lys Cys Leu Gly Gly Val Pro Tyr Ala Ser
1 5 10 15

Leu Val Ala Thr Ile
20

<210> SEQ ID NO 136
<211> LENGTH: 21
<212> TYPE: PRT
<213> ORGANISM: Homo sapiens

<400> SEQUENCE: 136

Ser Leu Leu Asp Asp Asp Phe Ser Leu Glu Pro Leu Val Ser Ala Phe
1 5 10 15

His Glu Phe Glu Glu
20

<210> SEQ ID NO 137
<211> LENGTH: 21
<212> TYPE: PRT
<213> ORGANISM: Homo sapiens

<400> SEQUENCE: 137

Asp Asp Phe Ser Leu Glu Pro Leu Val Ser Ala Phe His Glu Phe Glu
1 5 10 15

Glu Leu Ala Lys Gln
20

<210> SEQ ID NO 138
<211> LENGTH: 21
<212> TYPE: PRT
<213> ORGANISM: Homo sapiens

<400> SEQUENCE: 138

Phe Ser Leu Glu Pro Leu Val Ser Ala Phe His Glu Phe Glu Glu Leu
1 5 10 15

Ala Lys Gln Leu Gln
20

<210> SEQ ID NO 139
<211> LENGTH: 21
<212> TYPE: PRT
<213> ORGANISM: Homo sapiens

<400> SEQUENCE: 139

Asn Tyr Leu Gly Phe Asn Tyr Glu Ile Tyr Val Ala Pro Asp His Lys
1 5 10 15

Tyr Gly Ser Pro Gln
20

<210> SEQ ID NO 140
<211> LENGTH: 21
<212> TYPE: PRT
<213> ORGANISM: Homo sapiens

<400> SEQUENCE: 140

Val Val Asn Ala Val Tyr Ala Met Ala His Ala Leu His Lys Met Gln
1 5 10 15

Arg Thr Leu Cys Pro
20

<210> SEQ ID NO 141
<211> LENGTH: 21
<212> TYPE: PRT
<213> ORGANISM: Homo sapiens

<400> SEQUENCE: 141

Ala Ser Gly Leu Pro Met Arg Asn Gly Asn Arg His Ala Val Asp Ile
1 5 10 15

Ser Lys Met Ala Leu
20

<210> SEQ ID NO 142
<211> LENGTH: 21
<212> TYPE: PRT
<213> ORGANISM: Homo sapiens

<400> SEQUENCE: 142

Ser Ala Lys Leu His Tyr His Asp Ser Trp Ala Leu Ile Leu His Ala
1 5 10 15

Ala Ala Leu Trp Leu
20

<210> SEQ ID NO 143
<211> LENGTH: 21
<212> TYPE: PRT
<213> ORGANISM: Homo sapiens

<400> SEQUENCE: 143

Ala Pro Gly Phe Leu His Cys Ala Ser Phe Gly Asp Pro His Val Arg

```
1               5                   10                  15

Ser Phe His Asn Gln
            20


<210> SEQ ID NO 144
<211> LENGTH: 21
<212> TYPE: PRT
<213> ORGANISM: Homo sapiens

<400> SEQUENCE: 144

Gln Leu Gln Pro Val Pro Gly Ala Ala Pro Ser Pro Ser Lys His Thr
1               5                   10                  15

Ser Ala Thr Ala Ala
            20


<210> SEQ ID NO 145
<211> LENGTH: 21
<212> TYPE: PRT
<213> ORGANISM: Homo sapiens

<400> SEQUENCE: 145

Ala Val Ser Gly Leu Gly Gly Cys Pro Tyr Ala Lys Gly Ala Ser Gly
1               5                   10                  15

Asn Val Ala Thr Glu
            20


<210> SEQ ID NO 146
<211> LENGTH: 15
<212> TYPE: PRT
<213> ORGANISM: Homo sapiens

<400> SEQUENCE: 146

Tyr Leu Leu Gln Asn Ser Val Lys Gln Tyr Ser Gly Lys Phe Phe
1               5                   10                  15


<210> SEQ ID NO 147
<211> LENGTH: 21
<212> TYPE: PRT
<213> ORGANISM: Homo sapiens

<400> SEQUENCE: 147

Leu Pro Lys Gly Asp Phe Phe Pro Pro Glu Arg Pro Gln Gln Leu Pro
1               5                   10                  15

His Gly Leu Gly Gly
            20


<210> SEQ ID NO 148
<211> LENGTH: 21
<212> TYPE: PRT
<213> ORGANISM: Homo sapiens

<400> SEQUENCE: 148

Leu Pro Lys Gly Asp Phe Phe Pro Pro Glu Arg Pro Gln Gln Leu Pro
1               5                   10                  15

His Gly Leu Gly Gly
            20


<210> SEQ ID NO 149
<211> LENGTH: 21
<212> TYPE: PRT
<213> ORGANISM: Homo sapiens

<400> SEQUENCE: 149
```

Pro Gly Gly Gly Gly Cys Ala Gly Gly Gly Gly Gly Gly Gly Ala Gly
1 5 10 15

Pro Gly Pro Ser Pro
20

<210> SEQ ID NO 150
<211> LENGTH: 21
<212> TYPE: PRT
<213> ORGANISM: Homo sapiens

<400> SEQUENCE: 150

Ser Ser Thr Ser Asn Asp Val Ser Ser Ser Asp Phe Glu Glu Gly Pro
1 5 10 15

Ser Arg Lys Arg Pro
20

<210> SEQ ID NO 151
<211> LENGTH: 21
<212> TYPE: PRT
<213> ORGANISM: Homo sapiens

<400> SEQUENCE: 151

Ala Ile Leu Gly Lys Gly Asp Leu Ile Gly Ala Asn Leu Ser Ile Lys
1 5 10 15

Asp Gln Val Ile Lys
20

<210> SEQ ID NO 152
<211> LENGTH: 21
<212> TYPE: PRT
<213> ORGANISM: Homo sapiens

<400> SEQUENCE: 152

Val Ile Ile Cys Ala Ser Leu Lys Leu Leu His Leu Leu Gly Leu Ile
1 5 10 15

Asp Phe Ser Glu Asp
20

<210> SEQ ID NO 153
<211> LENGTH: 21
<212> TYPE: PRT
<213> ORGANISM: Homo sapiens

<400> SEQUENCE: 153

Tyr Leu Leu Arg Leu Leu Thr Gly Ser Leu His Thr Asp Ser Val Glu
1 5 10 15

Asp Glu Leu Glu Met
20

<210> SEQ ID NO 154
<211> LENGTH: 21
<212> TYPE: PRT
<213> ORGANISM: Homo sapiens

<400> SEQUENCE: 154

Asn Asp Phe Leu Ile Glu Asp Met Ile Pro Thr Leu Lys Ala Ala Ile
1 5 10 15

Arg Ala Val Arg Ile
20

<210> SEQ ID NO 155

<211> LENGTH: 21
<212> TYPE: PRT
<213> ORGANISM: Homo sapiens

<400> SEQUENCE: 155

Pro Pro Pro Pro Pro Pro Pro Pro Pro Pro Pro Pro Pro Pro Pro Pro
1 5 10 15

Pro Pro Leu Pro Gly
20

<210> SEQ ID NO 156
<211> LENGTH: 21
<212> TYPE: PRT
<213> ORGANISM: Homo sapiens

<400> SEQUENCE: 156

Asn Gln Arg Glu Thr Thr Met Lys Asp Leu Asp Ile Ile Thr Ile Pro
1 5 10 15

Ser His Asn Val Val
20

<210> SEQ ID NO 157
<211> LENGTH: 21
<212> TYPE: PRT
<213> ORGANISM: Homo sapiens

<400> SEQUENCE: 157

Gln Thr Phe Cys Phe Asp His Ala Phe Asp Asp Lys Ala Ser Asn Glu
1 5 10 15

Leu Val Tyr Gln Phe
20

<210> SEQ ID NO 158
<211> LENGTH: 21
<212> TYPE: PRT
<213> ORGANISM: Homo sapiens

<400> SEQUENCE: 158

Val Asn Ile Ser Pro Leu Glu Glu Asn Val Ser Glu Ser Leu Asn Ser
1 5 10 15

Leu Arg Phe Ala Ser
20

<210> SEQ ID NO 159
<211> LENGTH: 21
<212> TYPE: PRT
<213> ORGANISM: Homo sapiens

<400> SEQUENCE: 159

Thr Glu Arg Glu Val Trp Glu Ala Trp Ala Ala Asn Pro Gly Asn Cys
1 5 10 15

Pro Pro Ala Gly Leu
20

<210> SEQ ID NO 160
<211> LENGTH: 21
<212> TYPE: PRT
<213> ORGANISM: Homo sapiens

<400> SEQUENCE: 160

Glu Val Met Asn Ser Lys Leu Gly Leu Asp Val Glu Ile Thr Thr Tyr
1 5 10 15

```
Arg Arg Leu Leu Glu
            20


<210> SEQ ID NO 161
<211> LENGTH: 21
<212> TYPE: PRT
<213> ORGANISM: Homo sapiens

<400> SEQUENCE: 161

Arg Leu Glu Pro Gly Glu Leu Ile Pro Asn Gly Pro Phe Ser Phe Tyr
1               5                   10                  15

Gly Asp Tyr Gln Ser
            20


<210> SEQ ID NO 162
<211> LENGTH: 21
<212> TYPE: PRT
<213> ORGANISM: Homo sapiens

<400> SEQUENCE: 162

Glu His Phe Val Thr Tyr Cys Arg Tyr Gly Ser Arg Ile Ser Pro Gln
1               5                   10                  15

Ala Glu Lys Phe Tyr
            20


<210> SEQ ID NO 163
<211> LENGTH: 21
<212> TYPE: PRT
<213> ORGANISM: Homo sapiens

<400> SEQUENCE: 163

Leu Glu Thr Lys Leu Ile Cys Ile Gly Arg Ser Asp Glu Asp Lys Tyr
1               5                   10                  15

Leu Glu Asp Phe Phe
            20


<210> SEQ ID NO 164
<211> LENGTH: 21
<212> TYPE: PRT
<213> ORGANISM: Homo sapiens

<400> SEQUENCE: 164

Trp Met Lys Asn Ser Leu Lys Val His Ser Asp Ser Val Leu Glu Gln
1               5                   10                  15

Val Trp Asp Ile Phe
            20


<210> SEQ ID NO 165
<211> LENGTH: 15
<212> TYPE: PRT
<213> ORGANISM: Homo sapiens

<400> SEQUENCE: 165

Trp Met Lys Asn Ser Leu Lys Val His Ser Asp Ser Val Leu Glu
1               5                   10                  15


<210> SEQ ID NO 166
<211> LENGTH: 21
<212> TYPE: PRT
<213> ORGANISM: Homo sapiens

<400> SEQUENCE: 166

Asn Thr Met Phe Pro Pro Thr Ala Asn Met Leu Leu Pro Thr Gly Glu
```

1 5 10 15

Gly Gln Ser Gly Arg
20

<210> SEQ ID NO 167
<211> LENGTH: 21
<212> TYPE: PRT
<213> ORGANISM: Homo sapiens

<400> SEQUENCE: 167

Ile Val Leu Ser Met Val Glu Ser Gly Leu Ser Glu Glu Glu Ala Gln
1 5 10 15

Arg Lys Ile Trp Met
20

<210> SEQ ID NO 168
<211> LENGTH: 21
<212> TYPE: PRT
<213> ORGANISM: Homo sapiens

<400> SEQUENCE: 168

Val Leu Ile Pro Asp Ile Asn Phe Asn Asp Ala Phe Glu Asn Phe Ala
1 5 10 15

Leu Asp Phe Ser Arg
20

<210> SEQ ID NO 169
<211> LENGTH: 21
<212> TYPE: PRT
<213> ORGANISM: Homo sapiens

<400> SEQUENCE: 169

Asp Glu Asp Trp Arg Ser Gln Arg Lys His Val Phe Val Leu Ser Glu
1 5 10 15

Ala Gly Lys Pro Ile
20

<210> SEQ ID NO 170
<211> LENGTH: 21
<212> TYPE: PRT
<213> ORGANISM: Homo sapiens

<400> SEQUENCE: 170

Ile Asp Ser Ser Gly Leu Arg Val Phe His Thr Thr Asp Ile Arg Arg
1 5 10 15

Tyr Asp Ala Gly Val
20

<210> SEQ ID NO 171
<211> LENGTH: 21
<212> TYPE: PRT
<213> ORGANISM: Homo sapiens

<400> SEQUENCE: 171

Ile Thr Ser Ile Gln Met Leu Ser Thr Leu Pro Gln Ser Gln His Thr
1 5 10 15

Glu Ser Lys Ser Thr
20

<210> SEQ ID NO 172
<211> LENGTH: 21
<212> TYPE: PRT

<213> ORGANISM: Homo sapiens

<400> SEQUENCE: 172

Lys Pro Gly Gln Ser Val Lys Phe Arg Val Val Ser Met Asp Lys Thr
1 5 10 15

Leu Arg Pro Leu Asn
20

<210> SEQ ID NO 173
<211> LENGTH: 21
<212> TYPE: PRT
<213> ORGANISM: Homo sapiens

<400> SEQUENCE: 173

Gly Gln Ser Val Lys Phe Arg Val Val Ser Met Asp Lys Thr Leu Arg
1 5 10 15

Pro Leu Asn Glu Leu
20

<210> SEQ ID NO 174
<211> LENGTH: 21
<212> TYPE: PRT
<213> ORGANISM: Homo sapiens

<400> SEQUENCE: 174

Lys Ala Arg Asp Glu Val Ile Lys Gln Leu Arg Lys Leu Gln Ala Gln
1 5 10 15

Met Lys Asp Tyr Gln
20

<210> SEQ ID NO 175
<211> LENGTH: 21
<212> TYPE: PRT
<213> ORGANISM: Homo sapiens

<400> SEQUENCE: 175

Gly Gly Ser Ile Met Tyr Asn Leu Phe Gln Arg Tyr Lys Arg Asn Gln
1 5 10 15

Ile Tyr Thr Tyr Ile
20

<210> SEQ ID NO 176
<211> LENGTH: 21
<212> TYPE: PRT
<213> ORGANISM: Homo sapiens

<400> SEQUENCE: 176

Val Val Ser Asp Ser Tyr Asp Ile Tyr Asn Ala Cys Glu Lys Ile Trp
1 5 10 15

Gly Glu Asp Leu Arg
20

<210> SEQ ID NO 177
<211> LENGTH: 21
<212> TYPE: PRT
<213> ORGANISM: Homo sapiens

<400> SEQUENCE: 177

Asn Thr Gly Thr Glu Ser Ala Ser Glu Glu Gly Asp Asp Ser Leu Leu
1 5 10 15

Ile Thr Val Val Pro
20

<210> SEQ ID NO 178
<211> LENGTH: 21
<212> TYPE: PRT
<213> ORGANISM: Homo sapiens

<400> SEQUENCE: 178

Leu Lys Lys Leu Ser Phe Ser Thr Gln Asn Val Leu Ser Gly Ala Gln
1 5 10 15

Glu His Ser Tyr Met
20

<210> SEQ ID NO 179
<211> LENGTH: 15
<212> TYPE: PRT
<213> ORGANISM: Homo sapiens

<400> SEQUENCE: 179

Met Gly Lys Leu Glu Asn Ala Ser Trp Ile His Asp Ser Leu Met
1 5 10 15

<210> SEQ ID NO 180
<211> LENGTH: 21
<212> TYPE: PRT
<213> ORGANISM: Homo sapiens

<400> SEQUENCE: 180

His Leu Val Ala Ala Asp Ile Arg Val Ala Pro Ala Thr Ala Leu Thr
1 5 10 15

Pro Pro Gln Gly Asp
20

<210> SEQ ID NO 181
<211> LENGTH: 21
<212> TYPE: PRT
<213> ORGANISM: Homo sapiens

<400> SEQUENCE: 181

Asn Ile Arg Gln Leu Ala Glu Met Gln Asn Ala Ala Gly Val Lys Ser
1 5 10 15

Ser Cys Ser Arg Met
20

<210> SEQ ID NO 182
<211> LENGTH: 21
<212> TYPE: PRT
<213> ORGANISM: Homo sapiens

<400> SEQUENCE: 182

Met Ser Glu Gln Ala Arg Glu Glu Asn Val Ala Thr Phe Arg Gly Ser
1 5 10 15

Glu Tyr Leu Cys Tyr
20

<210> SEQ ID NO 183
<211> LENGTH: 21
<212> TYPE: PRT
<213> ORGANISM: Homo sapiens

<400> SEQUENCE: 183

Asn Ile Arg Gln Leu Ala Glu Met Gln Asn Ala Ala Gly Val Lys Ser
1 5 10 15

Ser Cys Ser Arg Met
20

<210> SEQ ID NO 184
<211> LENGTH: 21
<212> TYPE: PRT
<213> ORGANISM: Homo sapiens

<400> SEQUENCE: 184

Thr Gly Tyr Lys Ser His Ala Lys Glu Ile Leu His Cys Leu Lys Asn
1 5 10 15

Lys Tyr Phe Lys Glu
20

<210> SEQ ID NO 185
<211> LENGTH: 21
<212> TYPE: PRT
<213> ORGANISM: Homo sapiens

<400> SEQUENCE: 185

Gly Arg His Lys Gly Glu Val Ser Phe Pro Gly Gly Lys Cys Asp Pro
1 5 10 15

Asp Asp Gln Asp Val
20

<210> SEQ ID NO 186
<211> LENGTH: 21
<212> TYPE: PRT
<213> ORGANISM: Homo sapiens

<400> SEQUENCE: 186

Ser Pro Gln Val Leu Gly His Ile Leu Lys Pro Gly Thr Thr Glu Ser
1 5 10 15

Gly Ala Leu Ser Leu
20

<210> SEQ ID NO 187
<211> LENGTH: 21
<212> TYPE: PRT
<213> ORGANISM: Homo sapiens

<400> SEQUENCE: 187

Asp His Glu Gly Gln Pro Arg Pro Arg Val Pro Arg Lys Arg Gly His
1 5 10 15

Ile Ser Pro Lys Ser
20

<210> SEQ ID NO 188
<211> LENGTH: 21
<212> TYPE: PRT
<213> ORGANISM: Homo sapiens

<400> SEQUENCE: 188

Thr Leu Phe Phe Ile Tyr Val Arg Pro Ser Ala Ile Ser Ser Leu Asp
1 5 10 15

Leu Asn Lys Val Val
20

<210> SEQ ID NO 189
<211> LENGTH: 21
<212> TYPE: PRT
<213> ORGANISM: Homo sapiens

<400> SEQUENCE: 189

Ser Ser Lys Met Ser Arg Val Val Cys Ile Arg Leu Ile Ser Val Pro
1 5 10 15

Tyr Val Tyr Gly Phe
20

<210> SEQ ID NO 190
<211> LENGTH: 21
<212> TYPE: PRT
<213> ORGANISM: Homo sapiens

<400> SEQUENCE: 190

Ser Tyr Gly Val Ile Leu Phe Ser Leu Arg Ser His Ser Ser Glu Gly
1 5 10 15

Arg Ser Lys Ala Leu
20

<210> SEQ ID NO 191
<211> LENGTH: 21
<212> TYPE: PRT
<213> ORGANISM: Homo sapiens

<400> SEQUENCE: 191

Leu Gln Leu Cys Leu Phe Phe Ile Phe Leu Ala Phe Tyr Leu Ile Thr
1 5 10 15

Ile Val Gly Asn Leu
20

<210> SEQ ID NO 192
<211> LENGTH: 21
<212> TYPE: PRT
<213> ORGANISM: Homo sapiens

<400> SEQUENCE: 192

Thr Tyr Thr Val Leu Thr Pro Phe Leu Ser Pro Ile Ile Phe Ser Leu
1 5 10 15

Arg Asn Lys Glu Leu
20

<210> SEQ ID NO 193
<211> LENGTH: 21
<212> TYPE: PRT
<213> ORGANISM: Homo sapiens

<400> SEQUENCE: 193

Ser Ile Ile Val Val Thr Val Phe Ile Ile Ala Leu Ser Tyr Val Tyr
1 5 10 15

Ile Leu Val Ser Ile
20

<210> SEQ ID NO 194
<211> LENGTH: 21
<212> TYPE: PRT
<213> ORGANISM: Homo sapiens

<400> SEQUENCE: 194

Ile Tyr Ile Leu Ile Thr Ile Leu Lys Met Arg Ser Thr Glu Gly Arg
1 5 10 15

His Lys Ala Phe Ser
20

<210> SEQ ID NO 195
<211> LENGTH: 21
<212> TYPE: PRT
<213> ORGANISM: Homo sapiens

<400> SEQUENCE: 195

Thr Phe Leu Arg Gly Val Leu Leu Ile Ile Pro Phe Ile Phe Leu Ser
1               5                   10                  15

Lys Cys Leu Pro Tyr
            20

<210> SEQ ID NO 196
<211> LENGTH: 21
<212> TYPE: PRT
<213> ORGANISM: Homo sapiens

<400> SEQUENCE: 196

Ala Thr Ser Trp Ile Leu Ala Ser Leu Ser Ala Leu Gly Tyr Ser Met
1               5                   10                  15

Tyr Thr Met Gln Tyr
            20

<210> SEQ ID NO 197
<211> LENGTH: 21
<212> TYPE: PRT
<213> ORGANISM: Homo sapiens

<400> SEQUENCE: 197

Leu Ala Thr Met Ser Tyr Asp Arg Tyr Ile Ala Ile Cys Lys Pro Leu
1               5                   10                  15

His Tyr Ala Ser Ile
            20

<210> SEQ ID NO 198
<211> LENGTH: 21
<212> TYPE: PRT
<213> ORGANISM: Homo sapiens

<400> SEQUENCE: 198

Gly Ser His Ser Leu Cys Pro Gln Thr Gly Ser Pro Ser Met Val Thr
1               5                   10                  15

Ala Ile Thr Ile Met
            20

<210> SEQ ID NO 199
<211> LENGTH: 12
<212> TYPE: PRT
<213> ORGANISM: Homo sapiens

<400> SEQUENCE: 199

Met Thr Leu Gly Ile Phe Ala Asn Cys Ile Phe Cys
1               5                   10

<210> SEQ ID NO 200
<211> LENGTH: 21
<212> TYPE: PRT
<213> ORGANISM: Homo sapiens

<400> SEQUENCE: 200

Lys Asn Tyr Tyr Ser Leu Val Leu Asp Ser Ala Leu Asp Arg Glu Thr
1               5                   10                  15

Thr Ala Asp Tyr Lys
            20

<210> SEQ ID NO 201
<211> LENGTH: 21
<212> TYPE: PRT
<213> ORGANISM: Homo sapiens

<400> SEQUENCE: 201

```
Gln Pro Glu Glu Glu Ala Glu Asn Thr Lys Thr Pro Trp Leu Tyr Asp
1               5                   10                  15

Gln Glu Gly Gly Val
            20
```

<210> SEQ ID NO 202
<211> LENGTH: 21
<212> TYPE: PRT
<213> ORGANISM: Homo sapiens

<400> SEQUENCE: 202

```
Asp Tyr Ser Glu Val Thr Gly Ser Met Gly Gly Ile Pro Glu Glu Glu
1               5                   10                  15

Leu Asp Ser Met Ala
            20
```

<210> SEQ ID NO 203
<211> LENGTH: 21
<212> TYPE: PRT
<213> ORGANISM: Homo sapiens

<400> SEQUENCE: 203

```
Gln Gly Leu Met Arg Phe Asn Leu Pro Ala Arg Ile Cys Arg Asp Ile
1               5                   10                  15

Glu Leu Phe His Phe
            20
```

<210> SEQ ID NO 204
<211> LENGTH: 21
<212> TYPE: PRT
<213> ORGANISM: Homo sapiens

<400> SEQUENCE: 204

```
Lys Gln Trp Cys Lys Pro His Tyr Gln Asn Ser Gly Gly Gly Asn Gly
1               5                   10                  15

Val Asp Leu Ser Val
            20
```

<210> SEQ ID NO 205
<211> LENGTH: 21
<212> TYPE: PRT
<213> ORGANISM: Homo sapiens

<400> SEQUENCE: 205

```
Ile Leu Ser Phe Glu Asn Asn Gly Asp Tyr Met Asp Met Lys Gln Ala
1               5                   10                  15

Asp Thr Thr Gln Tyr
            20
```

<210> SEQ ID NO 206
<211> LENGTH: 21
<212> TYPE: PRT
<213> ORGANISM: Homo sapiens

<400> SEQUENCE: 206

```
Tyr Ala Asn Gly Ile Arg Val Met Ser Met Thr His Thr Gly Glu Pro
1               5                   10                  15

Gly Phe Met Leu Tyr
            20


<210> SEQ ID NO 207
<211> LENGTH: 21
<212> TYPE: PRT
<213> ORGANISM: Homo sapiens

<400> SEQUENCE: 207

Glu Glu Asn Thr Val Pro Pro Glu His Ser Pro Pro Glu Met Glu Ile
1               5                   10                  15

Cys Thr Val Tyr Leu
            20


<210> SEQ ID NO 208
<211> LENGTH: 21
<212> TYPE: PRT
<213> ORGANISM: Homo sapiens

<400> SEQUENCE: 208

Phe Gly Ser Glu Arg Asp Leu Glu Arg Arg Gly Arg Ser Arg Asp Val
1               5                   10                  15

Glu Pro Arg Asp Arg
            20


<210> SEQ ID NO 209
<211> LENGTH: 21
<212> TYPE: PRT
<213> ORGANISM: Homo sapiens

<400> SEQUENCE: 209

Ser Ser Thr Thr Thr Thr Thr Ile Thr Thr Ser Ser Ser Arg Met Gln
1               5                   10                  15

Gln Pro Gln Ile Ser
            20


<210> SEQ ID NO 210
<211> LENGTH: 21
<212> TYPE: PRT
<213> ORGANISM: Homo sapiens

<400> SEQUENCE: 210

Tyr Val Leu Gly Ile Gly Asp Arg His Ser Asp Asn Ile Met Ile Arg
1               5                   10                  15

Glu Ser Gly Gln Leu
            20


<210> SEQ ID NO 211
<211> LENGTH: 21
<212> TYPE: PRT
<213> ORGANISM: Homo sapiens

<400> SEQUENCE: 211

Ala Glu Ser Pro Ser Ile Ala Ser Thr Ser Ser Thr Glu Lys Ser Phe
1               5                   10                  15

Pro Trp Arg Ser Thr
            20


<210> SEQ ID NO 212
<211> LENGTH: 21
```

<212> TYPE: PRT
<213> ORGANISM: Homo sapiens

<400> SEQUENCE: 212

Thr Tyr Trp Asn Thr Arg Gln Pro Ser Asn Arg Gly Gly Cys Val Val
1               5                   10                  15

Val Arg Gly Gly Ser
            20

<210> SEQ ID NO 213
<211> LENGTH: 21
<212> TYPE: PRT
<213> ORGANISM: Homo sapiens

<400> SEQUENCE: 213

Asp Gly Ser Ser Gly Gly Trp Ala Ala Arg Ala Leu Arg Arg Ala Leu
1               5                   10                  15

Ala Leu Thr Ser Leu
            20

<210> SEQ ID NO 214
<211> LENGTH: 21
<212> TYPE: PRT
<213> ORGANISM: Homo sapiens

<400> SEQUENCE: 214

Glu Lys Glu Ile Arg Ser Phe Leu Ile Glu Gly His Leu Ile Asn Thr
1               5                   10                  15

Ile Arg Val Val Cys
            20

<210> SEQ ID NO 215
<211> LENGTH: 21
<212> TYPE: PRT
<213> ORGANISM: Homo sapiens

<400> SEQUENCE: 215

Glu Ile Val Lys Tyr Thr Lys Ile Ile Ala Met Glu Lys Leu Tyr Ala
1               5                   10                  15

Val Phe Thr Asp Tyr
            20

<210> SEQ ID NO 216
<211> LENGTH: 21
<212> TYPE: PRT
<213> ORGANISM: Homo sapiens

<400> SEQUENCE: 216

Gln Gly Gln Gly Gln Gly Leu Ser Pro Glu Arg Val Glu Asp Tyr Gly
1               5                   10                  15

Arg Thr His Arg Gly
            20

<210> SEQ ID NO 217
<211> LENGTH: 21
<212> TYPE: PRT
<213> ORGANISM: Homo sapiens

<400> SEQUENCE: 217

Thr Thr Lys Thr Ala Met Cys Thr Ala Val Ala Gly Tyr Phe Asp Ile
1               5                   10                  15

Tyr Phe Glu Lys Asn

20

<210> SEQ ID NO 218
<211> LENGTH: 21
<212> TYPE: PRT
<213> ORGANISM: Homo sapiens

<400> SEQUENCE: 218

Ser Gly Pro Ala Glu Glu Glu Asp Val Pro Gly Ser Pro Cys Pro Asp
1 5 10 15

Ala Gly Asp Pro Gln
20

<210> SEQ ID NO 219
<211> LENGTH: 21
<212> TYPE: PRT
<213> ORGANISM: Homo sapiens

<400> SEQUENCE: 219

Leu Asp Gln Ile Ser Arg Tyr Tyr Ile Thr Arg Ala Lys Leu Val Ser
1 5 10 15

Lys Ile Ala Lys Tyr
20

<210> SEQ ID NO 220
<211> LENGTH: 21
<212> TYPE: PRT
<213> ORGANISM: Homo sapiens

<400> SEQUENCE: 220

Leu Gln Val Thr Arg Gly His Leu Asp Thr Ala Arg Thr Arg Gly Lys
1 5 10 15

Val Ser Trp Gln Ile
20

<210> SEQ ID NO 221
<211> LENGTH: 21
<212> TYPE: PRT
<213> ORGANISM: Homo sapiens

<400> SEQUENCE: 221

Lys Lys Lys Thr Asn Asn Pro Gln Phe Asp Glu Val Phe Tyr Phe Glu
1 5 10 15

Val Thr Arg Pro Cys
20

<210> SEQ ID NO 222
<211> LENGTH: 19
<212> TYPE: PRT
<213> ORGANISM: Homo sapiens

<400> SEQUENCE: 222

Met Lys Arg Gln Ser Glu Arg Asp Ser Ser Pro Ser Gly Arg Gly Ser
1 5 10 15

Ser Ser Ser

<210> SEQ ID NO 223
<211> LENGTH: 21
<212> TYPE: PRT
<213> ORGANISM: Homo sapiens

<400> SEQUENCE: 223

Leu Val Pro Cys His Ile Ser Thr Asn Leu Ser Asn Lys Gln Val Ile
1 5 10 15

Glu Val Ala Cys Gly
20

<210> SEQ ID NO 224
<211> LENGTH: 11
<212> TYPE: PRT
<213> ORGANISM: Homo sapiens

<400> SEQUENCE: 224

Leu Val Pro Cys His Ile Ser Thr Asn Leu Ser
1 5 10

<210> SEQ ID NO 225
<211> LENGTH: 21
<212> TYPE: PRT
<213> ORGANISM: Homo sapiens

<400> SEQUENCE: 225

Val Ile Glu Val Ala Cys Gly Ser Tyr His Ser Leu Val Leu Thr Ser
1 5 10 15

Asp Gly Glu Val Phe
20

<210> SEQ ID NO 226
<211> LENGTH: 21
<212> TYPE: PRT
<213> ORGANISM: Homo sapiens

<400> SEQUENCE: 226

Leu Val Pro Cys His Ile Ser Thr Asn Leu Ser Asn Lys Gln Val Ile
1 5 10 15

Glu Val Ala Cys Gly
20

<210> SEQ ID NO 227
<211> LENGTH: 21
<212> TYPE: PRT
<213> ORGANISM: Homo sapiens

<400> SEQUENCE: 227

Ile Ala Glu Gly Val Cys Ile Pro Arg Ser Ala Leu Tyr Met His Tyr
1 5 10 15

Leu Asp Phe Cys Glu
20

<210> SEQ ID NO 228
<211> LENGTH: 21
<212> TYPE: PRT
<213> ORGANISM: Homo sapiens

<400> SEQUENCE: 228

Arg Arg Glu Pro Gln Gln Val Leu Val Ser Ser Phe Arg Ala Leu Trp
1 5 10 15

Ser Arg Leu Trp Pro
20

<210> SEQ ID NO 229
<211> LENGTH: 21
<212> TYPE: PRT
<213> ORGANISM: Homo sapiens

<400> SEQUENCE: 229

Val Leu Gly His Tyr Asn Asn Phe Phe Phe Ala Ala His Leu Leu Asp
1 5 10 15

Ile Ala Met Gly Phe
20

<210> SEQ ID NO 230
<211> LENGTH: 21
<212> TYPE: PRT
<213> ORGANISM: Homo sapiens

<400> SEQUENCE: 230

Thr Ala Ala Ala Ala Thr Thr Ala Ala Ala Ala Ser Ser Ser Ala Ala
1 5 10 15

Ser Pro His Tyr Gln
20

<210> SEQ ID NO 231
<211> LENGTH: 21
<212> TYPE: PRT
<213> ORGANISM: Homo sapiens

<400> SEQUENCE: 231

Leu Val Ile Ile Trp Asn Gln Asp Ser Val Glu Tyr Tyr Thr Arg Leu
1 5 10 15

Gly Ala Leu Asp Leu
20

<210> SEQ ID NO 232
<211> LENGTH: 21
<212> TYPE: PRT
<213> ORGANISM: Homo sapiens

<400> SEQUENCE: 232

Asp Ala Ser Lys Leu His Ser Ser Pro Gln Met Ala Ala Gln His Asn
1 5 10 15

Met Val Asp Asp Gly
20

<210> SEQ ID NO 233

<400> SEQUENCE: 233

000

<210> SEQ ID NO 234
<211> LENGTH: 21
<212> TYPE: PRT
<213> ORGANISM: Homo sapiens

<400> SEQUENCE: 234

Phe Met Asn Arg Thr Glu Phe His Val Tyr Leu Pro Lys Phe Gln Leu
1 5 10 15

Gln Glu Asp Tyr Asp
20

<210> SEQ ID NO 235
<211> LENGTH: 21
<212> TYPE: PRT
<213> ORGANISM: Homo sapiens

<400> SEQUENCE: 235

```
Ile Leu Lys Ser Ser Ser Val Gln Lys Glu Ser Cys Asn Lys Arg Asn
1               5                   10                  15

Pro Phe Trp Lys Lys
            20


<210> SEQ ID NO 236
<211> LENGTH: 21
<212> TYPE: PRT
<213> ORGANISM: Homo sapiens

<400> SEQUENCE: 236

Val Leu Ile Ile Leu Leu Ser Thr Met Val Thr Ser Ile Thr Gly Leu
1               5                   10                  15

Ser Thr Ser Ala Ile
            20


<210> SEQ ID NO 237
<211> LENGTH: 21
<212> TYPE: PRT
<213> ORGANISM: Homo sapiens

<400> SEQUENCE: 237

Val Ile Ile Ile Gly Leu Ala Val Thr Val Thr Ala Ile Thr Gly Leu
1               5                   10                  15

Ser Thr Ser Ala Ile
            20


<210> SEQ ID NO 238
<211> LENGTH: 21
<212> TYPE: PRT
<213> ORGANISM: Homo sapiens

<400> SEQUENCE: 238

Val Ile Ile Ile Gly Leu Ser Val Val Val Thr Thr Leu Thr Gly Ile
1               5                   10                  15

Ser Met Ser Ala Ile
            20


<210> SEQ ID NO 239
<211> LENGTH: 21
<212> TYPE: PRT
<213> ORGANISM: Homo sapiens

<400> SEQUENCE: 239

Glu Asp Phe Phe Leu Lys Cys Arg Leu Gln Glu Gln Glu Ile Gln Arg
1               5                   10                  15

Arg Pro Ser Val Phe
            20


<210> SEQ ID NO 240
<211> LENGTH: 21
<212> TYPE: PRT
<213> ORGANISM: Homo sapiens

<400> SEQUENCE: 240

Leu Ser Ser Leu Cys Met Cys Val Ser Asn Leu His Ile Asn Glu Leu
1               5                   10                  15

Leu Pro Thr Thr Leu
            20


<210> SEQ ID NO 241
<211> LENGTH: 21
```

<212> TYPE: PRT
<213> ORGANISM: Homo sapiens

<400> SEQUENCE: 241

Leu Leu Thr Trp Val Asn Cys Ser Ser Val Arg Trp Ala Thr Arg Val
1 5 10 15

Gln Asp Ile Phe Thr
20

<210> SEQ ID NO 242
<211> LENGTH: 21
<212> TYPE: PRT
<213> ORGANISM: Homo sapiens

<400> SEQUENCE: 242

Met Arg Gly Arg Met Gly Ser Ser Val Ile Asp Glu Ile Ser Val Glu
1 5 10 15

Glu Val Asn Lys Met
20

<210> SEQ ID NO 243
<211> LENGTH: 21
<212> TYPE: PRT
<213> ORGANISM: Homo sapiens

<400> SEQUENCE: 243

Asn Val Val Arg Asp Trp Leu Gly Val Gly Gly Pro Val Leu Thr Pro
1 5 10 15

Pro Gln Glu His Pro
20

<210> SEQ ID NO 244
<211> LENGTH: 21
<212> TYPE: PRT
<213> ORGANISM: Homo sapiens

<400> SEQUENCE: 244

Thr Lys Glu Glu Glu Asn Glu Met Tyr Asn Pro Thr Phe Phe Tyr Glu
1 5 10 15

Asn Leu Lys Ile Pro
20

<210> SEQ ID NO 245
<211> LENGTH: 21
<212> TYPE: PRT
<213> ORGANISM: Homo sapiens

<400> SEQUENCE: 245

Pro Phe Pro Phe Leu Met Ser Leu Arg Asp Arg Asp Phe Ile Ser Glu
1 5 10 15

Gln Lys Phe Gln Glu
20

<210> SEQ ID NO 246
<211> LENGTH: 21
<212> TYPE: PRT
<213> ORGANISM: Homo sapiens

<400> SEQUENCE: 246

Asn Ala Asn Phe Ser Ala Glu Leu Leu Pro Val Thr Cys Gly Asn Leu
1 5 10 15

Lys Gly Val Leu His

20

<210> SEQ ID NO 247
<211> LENGTH: 21
<212> TYPE: PRT
<213> ORGANISM: Homo sapiens

<400> SEQUENCE: 247

Phe Lys Phe Glu Leu Gln Ser Asp Phe Ala Glu Phe Ser Glu Ser Arg
1 5 10 15

Gly Ser Thr Ala Lys
20

<210> SEQ ID NO 248
<211> LENGTH: 21
<212> TYPE: PRT
<213> ORGANISM: Homo sapiens

<400> SEQUENCE: 248

Glu Gly Arg Arg Asp Ile Gly Lys Gln Val Glu Glu Glu Lys Pro Gly
1 5 10 15

Ala Gly Lys Lys Asp
20

<210> SEQ ID NO 249
<211> LENGTH: 21
<212> TYPE: PRT
<213> ORGANISM: Homo sapiens

<400> SEQUENCE: 249

Tyr Cys Ala Ala Pro Glu Arg Arg Glu Thr Cys Glu His Ser Ser Glu
1 5 10 15

Ala Lys Ala Phe His
20

<210> SEQ ID NO 250
<211> LENGTH: 21
<212> TYPE: PRT
<213> ORGANISM: Homo sapiens

<400> SEQUENCE: 250

Thr Met His Asp Lys Gln Gly Glu Val Arg Leu Lys Cys Leu Thr Ala
1 5 10 15

Leu Gln Gly Leu Tyr
20

<210> SEQ ID NO 251
<211> LENGTH: 21
<212> TYPE: PRT
<213> ORGANISM: Homo sapiens

<400> SEQUENCE: 251

Ser Leu Lys Val Ile Gly Arg Gly Ala Phe Gly Glu Val Arg Leu Val
1 5 10 15

Gln Lys Lys Asp Thr
20

<210> SEQ ID NO 252
<211> LENGTH: 17
<212> TYPE: PRT
<213> ORGANISM: Homo sapiens

<400> SEQUENCE: 252

Met Lys Asp Arg Thr Gln Glu Leu Arg Ser Ala Lys Asp Ser Asp Asp
1 5 10 15

Glu

<210> SEQ ID NO 253
<211> LENGTH: 17
<212> TYPE: PRT
<213> ORGANISM: Homo sapiens

<400> SEQUENCE: 253

Arg Ile Gln Arg Gln Leu Glu Ile Thr Gly Arg Thr Thr Thr Asn Glu
1 5 10 15

Glu

<210> SEQ ID NO 254
<211> LENGTH: 21
<212> TYPE: PRT
<213> ORGANISM: Homo sapiens

<400> SEQUENCE: 254

Ala Ala Asn Tyr Leu Ile Gly Gln Lys Glu Ala Lys Arg Trp Gly Thr
1 5 10 15

Ala His Gly Ser Ile
20

<210> SEQ ID NO 255
<211> LENGTH: 21
<212> TYPE: PRT
<213> ORGANISM: Homo sapiens

<400> SEQUENCE: 255

Val Leu Tyr Tyr Glu Asp Met Lys Lys Asp Ala Lys Gly Thr Ile Lys
1 5 10 15

Lys Ile Cys Asp Phe
20

<210> SEQ ID NO 256
<211> LENGTH: 21
<212> TYPE: PRT
<213> ORGANISM: Homo sapiens

<400> SEQUENCE: 256

Glu Glu Ser Gly Trp Ser Ser Ser Ser Pro Thr Cys Val Pro Ile Asp
1 5 10 15

Cys Gly Leu Pro Pro
20

<210> SEQ ID NO 257
<211> LENGTH: 21
<212> TYPE: PRT
<213> ORGANISM: Homo sapiens

<400> SEQUENCE: 257

Ile Pro Gln Asp Arg Pro Thr Ser Glu Glu Leu Leu Lys His Met Phe
1 5 10 15

Val Leu Arg Glu Arg
20

<210> SEQ ID NO 258
<211> LENGTH: 21
<212> TYPE: PRT

<213> ORGANISM: Homo sapiens

<400> SEQUENCE: 258

Thr Cys Ser Asp Met Met Ser Phe Leu Val Ser Ile Ala Ser Ile Ala
1 5 10 15

Met Leu Val Lys Ile
20

<210> SEQ ID NO 259
<211> LENGTH: 21
<212> TYPE: PRT
<213> ORGANISM: Homo sapiens

<400> SEQUENCE: 259

Thr Glu Ser Gly Arg Asn Ser Pro Glu Lys Gly Lys Gly Lys Ile Asp
1 5 10 15

Ile Gln Ala Tyr Leu
20

<210> SEQ ID NO 260
<211> LENGTH: 12
<212> TYPE: PRT
<213> ORGANISM: Homo sapiens

<400> SEQUENCE: 260

Gln Pro Asp Val Cys Phe Leu Leu Phe Gly Ser Arg
1 5 10

<210> SEQ ID NO 261
<211> LENGTH: 21
<212> TYPE: PRT
<213> ORGANISM: Homo sapiens

<400> SEQUENCE: 261

Gln Pro Glu Lys Arg Leu Lys Ala Glu Ser Ser Lys Thr Val Phe Ser
1 5 10 15

Cys Ser Asp Glu Ser
20

<210> SEQ ID NO 262
<211> LENGTH: 21
<212> TYPE: PRT
<213> ORGANISM: Homo sapiens

<400> SEQUENCE: 262

Phe Thr Ile Leu Leu Val Val Thr Asn Arg Asp Thr Gln Glu Thr Leu
1 5 10 15

Leu Cys Met Ala Cys
20

<210> SEQ ID NO 263
<211> LENGTH: 21
<212> TYPE: PRT
<213> ORGANISM: Homo sapiens

<400> SEQUENCE: 263

Tyr Leu Asp Cys Ala Gln Ala Asp Ser Val Arg Asn Leu Pro Arg Ala
1 5 10 15

Phe Ser Gly Leu Thr
20

<210> SEQ ID NO 264

<211> LENGTH: 21
<212> TYPE: PRT
<213> ORGANISM: Homo sapiens

<400> SEQUENCE: 264

Asn Tyr Asp Val Leu Ala Tyr Cys Ile Ile Glu Ala Leu Ala Asn Pro
1 5 10 15

Glu Lys Glu Arg Met
20

<210> SEQ ID NO 265
<211> LENGTH: 21
<212> TYPE: PRT
<213> ORGANISM: Homo sapiens

<400> SEQUENCE: 265

Gly Thr Ile Asp Thr Lys Arg Asn Ile Ser Ala Glu Glu Gly Gly Ser
1 5 10 15

Val Ile Leu Gln Cys
20

<210> SEQ ID NO 266
<211> LENGTH: 21
<212> TYPE: PRT
<213> ORGANISM: Homo sapiens

<400> SEQUENCE: 266

Ser Leu Val Gly Ser Ser Leu Ser Ala Phe Ala Leu Leu Pro Leu Gln
1 5 10 15

Gly Asp Arg Asp Arg
20

<210> SEQ ID NO 267
<211> LENGTH: 21
<212> TYPE: PRT
<213> ORGANISM: Homo sapiens

<400> SEQUENCE: 267

Leu Asp Arg Tyr Phe Tyr His Val Asn Asn Asp Gln Pro Ile Asp Leu
1 5 10 15

Thr Lys Gly Lys Ser
20

<210> SEQ ID NO 268
<211> LENGTH: 21
<212> TYPE: PRT
<213> ORGANISM: Homo sapiens

<400> SEQUENCE: 268

Asp Glu Arg Asp Arg Gln Asn Ala Arg Leu Arg Glu Glu Asn Ala Arg
1 5 10 15

Leu Arg Leu Glu Asn
20

<210> SEQ ID NO 269
<211> LENGTH: 21
<212> TYPE: PRT
<213> ORGANISM: Homo sapiens

<400> SEQUENCE: 269

Ser Arg Glu Gln Phe Met Glu His Leu Tyr Pro Gln Arg Lys Pro Leu
1 5 10 15

Val Leu Glu Gly Leu
20

<210> SEQ ID NO 270
<211> LENGTH: 14
<212> TYPE: PRT
<213> ORGANISM: Homo sapiens

<400> SEQUENCE: 270

Met Glu Thr Arg Tyr Asn Leu Lys Ser Pro Ala Val Lys Arg
1 5 10

<210> SEQ ID NO 271
<211> LENGTH: 21
<212> TYPE: PRT
<213> ORGANISM: Homo sapiens

<400> SEQUENCE: 271

Trp Gly Leu Leu Ser His Cys Lys Val Arg Glu Thr Gln Glu Tyr Thr
1 5 10 15

Arg Asn Val Val Arg
20

<210> SEQ ID NO 272
<211> LENGTH: 21
<212> TYPE: PRT
<213> ORGANISM: Homo sapiens

<400> SEQUENCE: 272

Val Phe Gly Pro Ser Ala Ser His Ala Gly Arg Leu Leu Val Phe Pro
1 5 10 15

Met Asp Gly Ser His
20

<210> SEQ ID NO 273
<211> LENGTH: 21
<212> TYPE: PRT
<213> ORGANISM: Homo sapiens

<400> SEQUENCE: 273

Ala Arg Gln Ala Val Phe Thr Ala Lys Tyr Ser Glu Asp Met Lys His
1 5 10 15

Lys Thr Thr Leu Leu
20

<210> SEQ ID NO 274
<211> LENGTH: 21
<212> TYPE: PRT
<213> ORGANISM: Homo sapiens

<400> SEQUENCE: 274

Lys Glu Lys Ile Leu Gly Leu Leu Ser Ser Pro Thr Gly Asp Ala Ser
1 5 10 15

Tyr Gln Gln Leu Met
20

<210> SEQ ID NO 275
<211> LENGTH: 21
<212> TYPE: PRT
<213> ORGANISM: Homo sapiens

<400> SEQUENCE: 275

Lys Arg Ala Asn Asn Gly Lys Phe Thr Leu Arg Asp Leu Leu Val Val

```
1               5                   10                  15

Pro Met Gln Arg Val
            20


<210> SEQ ID NO 276
<211> LENGTH: 21
<212> TYPE: PRT
<213> ORGANISM: Homo sapiens

<400> SEQUENCE: 276

Cys Ser Thr Thr Gly Phe Ser Ile Gly Met Arg Ile Leu Ser Phe Ala
1               5                   10                  15

His Asp Ala Val Phe
            20


<210> SEQ ID NO 277
<211> LENGTH: 21
<212> TYPE: PRT
<213> ORGANISM: Homo sapiens

<400> SEQUENCE: 277

Thr Thr Cys Ile Leu Gln Gln Thr Thr Phe Gly Val Ala Phe Thr Met
1               5                   10                  15

Ala Leu Ala Thr Val
            20


<210> SEQ ID NO 278
<211> LENGTH: 21
<212> TYPE: PRT
<213> ORGANISM: Homo sapiens

<400> SEQUENCE: 278

Ser Ile Leu Ala Ser Ser Ala Gly Met Leu Gly Cys Ile Phe Val Pro
1               5                   10                  15

Lys Cys Tyr Thr Ile
            20


<210> SEQ ID NO 279
<211> LENGTH: 21
<212> TYPE: PRT
<213> ORGANISM: Homo sapiens

<400> SEQUENCE: 279

Cys Ile Leu Ile Gln Val Ile Val Cys Ala Val Trp Leu Arg Ala Ser
1               5                   10                  15

Pro Pro Ser Val Asp
            20


<210> SEQ ID NO 280
<211> LENGTH: 21
<212> TYPE: PRT
<213> ORGANISM: Homo sapiens

<400> SEQUENCE: 280

His Gly Gln Ile Ile Ile Val Cys His Lys Gly Ser Val Asn Ala Phe
1               5                   10                  15

Tyr Cys Val Leu Gly
            20


<210> SEQ ID NO 281
<211> LENGTH: 21
<212> TYPE: PRT
```

<213> ORGANISM: Homo sapiens

<400> SEQUENCE: 281

Thr Thr Ser Gln Trp Asp Val Ser Pro Ser Met Lys Asp Phe Thr Phe
1 5 10 15

Gly Asn Glu Tyr Gly
20

<210> SEQ ID NO 282
<211> LENGTH: 21
<212> TYPE: PRT
<213> ORGANISM: Homo sapiens

<400> SEQUENCE: 282

Asn Glu Tyr Gly Thr Phe Ala Phe Gly Gln His His Ser Glu Ile Ser
1 5 10 15

Gly Phe Lys His Phe
20

<210> SEQ ID NO 283
<211> LENGTH: 21
<212> TYPE: PRT
<213> ORGANISM: Homo sapiens

<400> SEQUENCE: 283

Leu Ser Glu Pro Ser Cys Phe Trp Arg Ile Arg Asn Ser Glu Asp Ser
1 5 10 15

Asp Gly Asp Leu Gln
20

<210> SEQ ID NO 284
<211> LENGTH: 21
<212> TYPE: PRT
<213> ORGANISM: Homo sapiens

<400> SEQUENCE: 284

Asn Leu Asn Glu Ile Gln Asp Glu Tyr Leu Gly Leu Thr Cys Ala Phe
1 5 10 15

Ile Leu Ala Ala Val
20

<210> SEQ ID NO 285
<211> LENGTH: 21
<212> TYPE: PRT
<213> ORGANISM: Homo sapiens

<400> SEQUENCE: 285

Tyr Leu Gly Leu Thr Cys Ala Phe Ile Leu Ala Ala Val Gln Lys Pro
1 5 10 15

Ile Glu Lys Asp Tyr
20

<210> SEQ ID NO 286
<211> LENGTH: 21
<212> TYPE: PRT
<213> ORGANISM: Homo sapiens

<400> SEQUENCE: 286

Pro Ala Ala Ser Leu Gln Phe Gln Gly Leu Pro Glu Gly Val Arg Ala
1 5 10 15

Gly Pro Val Pro Ser
20

<210> SEQ ID NO 287
<211> LENGTH: 21
<212> TYPE: PRT
<213> ORGANISM: Homo sapiens

<400> SEQUENCE: 287

Ala Ala Cys His Pro Thr Lys Asn Ile Ile Ala Ser Ala Ala Leu Glu
1 5 10 15

Asn Asp Lys Thr Ile
20

<210> SEQ ID NO 288
<211> LENGTH: 21
<212> TYPE: PRT
<213> ORGANISM: Homo sapiens

<400> SEQUENCE: 288

Phe Glu Asn Arg Lys Gly Leu Ser Ser His Ala Arg Ser His Leu Arg
1 5 10 15

Gln Met Gly Val Thr
20

<210> SEQ ID NO 289
<211> LENGTH: 21
<212> TYPE: PRT
<213> ORGANISM: Homo sapiens

<400> SEQUENCE: 289

Ala Pro Leu Glu Trp Leu Arg Tyr Phe Asp Glu Lys Glu Leu Glu Leu
1 5 10 15

Met Leu Cys Gly Met
20

<210> SEQ ID NO 290
<211> LENGTH: 21
<212> TYPE: PRT
<213> ORGANISM: Homo sapiens

<400> SEQUENCE: 290

Leu Gly Ile Thr Lys Thr Ser Lys Glu Ser Ala Phe Lys Ala Ala Arg
1 5 10 15

Lys Tyr Cys Pro His
20

<210> SEQ ID NO 291
<211> LENGTH: 21
<212> TYPE: PRT
<213> ORGANISM: Homo sapiens

<400> SEQUENCE: 291

Tyr Lys Asn Met Arg Glu Thr Leu Val Tyr Leu Thr His Leu Asp Tyr
1 5 10 15

Val Asp Thr Glu Ile
20

<210> SEQ ID NO 292
<211> LENGTH: 21
<212> TYPE: PRT
<213> ORGANISM: Homo sapiens

<400> SEQUENCE: 292

```
Glu Thr Ser Arg Asn Ala Gly Pro Ser Pro Ala Ala Gln Ala Pro Ala
1               5                   10                  15

Asp Arg Pro Val Ser
            20


<210> SEQ ID NO 293
<211> LENGTH: 21
<212> TYPE: PRT
<213> ORGANISM: Homo sapiens

<400> SEQUENCE: 293

Val Lys Gln Lys Gly Thr Gly Lys Gly Lys Gly Arg Thr Asn Thr Ile
1               5                   10                  15

Ser Met Thr Gly Gly
            20


<210> SEQ ID NO 294
<211> LENGTH: 21
<212> TYPE: PRT
<213> ORGANISM: Homo sapiens

<400> SEQUENCE: 294

Gln Arg Ile Tyr His Gly Lys Lys Pro Tyr Glu Ser Ser Lys Ser Asp
1               5                   10                  15

Lys Cys Phe Thr His
            20


<210> SEQ ID NO 295
<211> LENGTH: 21
<212> TYPE: PRT
<213> ORGANISM: Homo sapiens

<400> SEQUENCE: 295

Lys Ile Ile Gly Asp Ala Ser Thr Gln Thr Asp Ala Leu Lys Leu Pro
1               5                   10                  15

Pro Ser Gln Pro Pro
            20


<210> SEQ ID NO 296
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 296

Arg Arg Phe Leu Gln Leu Asn Lys Cys Pro Val Cys Phe Gly Thr Ser
1               5                   10                  15

Trp Cys Arg Arg Phe
            20


<210> SEQ ID NO 297
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Asn Gln Cys Gly Lys Ala Phe Ala Arg Pro Thr Asn Leu Gln Cys His
1               5                   10                  15
```

Lys Arg Thr His Thr
20

<210> SEQ ID NO 298
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 298

Ser Gly Arg Pro Ser Gly His Val Val Ser Phe Pro Leu Ile Glu Leu
1 5 10 15

Ser Lys Ile Gly Glu
20

<210> SEQ ID NO 299
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 299

Cys Asn Pro Glu Leu Asn Gln Glu Glu Asp Glu Asp Arg Glu Pro Glu
1 5 10 15

Val Glu Pro Glu Ala
20

<210> SEQ ID NO 300
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 300

Pro Gly Gly Thr Phe Leu Gln Glu Asn Pro Lys Ser Arg Glu Glu Lys
1 5 10 15

Arg Lys Ala Thr Thr
20

<210> SEQ ID NO 301
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 301

Pro Gly Gly Thr Phe Leu Gln Glu Asn Pro Lys Ser Arg Glu Ser Trp
1 5 10 15

Gln Val Trp Ser Leu
20

<210> SEQ ID NO 302
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 302

Arg Pro Phe Leu Asp Leu Ala His Pro Arg Tyr Leu His Ser Thr His
1 5 10 15

Ser Glu Leu Leu Glu
20

<210> SEQ ID NO 303
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 303

Gly Gln Gln Leu Thr Ser Glu Gln Leu Pro Met Lys Glu Gly Tyr Phe
1 5 10 15

Arg Ala Val Arg Gln
20

<210> SEQ ID NO 304
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 304

Glu Cys Lys Gly Lys Gln Tyr Val Lys Arg Met Trp Tyr Lys Lys Phe
1 5 10 15

Val Gly Val Gln Leu
20

<210> SEQ ID NO 305
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 305

Ala Leu Met Ser His Glu Leu Gly His Ala Phe Gly Met Lys Asp Val
1 5 10 15

Pro Tyr Tyr Thr Lys
20

<210> SEQ ID NO 306
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 306

Pro Val Arg Ile Phe Phe Leu Tyr Leu Phe Thr Ile Cys Asn Thr Leu
1 5 10 15

Gln Gly Phe Leu Ile
20

<210> SEQ ID NO 307

<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 307

Gly Val Lys Pro Glu Gly Leu Ser Leu Asn Ser Ser Gln Phe Leu Gly
1 5 10 15

Asp Arg Asn Phe Ala
20

<210> SEQ ID NO 308
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 308

Ile Leu Glu Thr Cys Lys Asn Pro Ile Gln Lys Val Gln Ser Arg Gly
1 5 10 15

Ile Asn Ile His Glu
20

<210> SEQ ID NO 309
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 309

Trp Ile Ile Glu Glu Gln Pro Asn Ser Ala Thr Asn Leu Arg Phe Val
1 5 10 15

Leu Glu Trp Thr Trp
20

<210> SEQ ID NO 310
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 310

His Ile Asp Ile Asp Lys Gln Lys Asp Lys Ile Gly Asp Arg Ile Ile
1 5 10 15

Thr Ile Arg Gly Gly
20

<210> SEQ ID NO 311
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 311

Asp Glu Gly Glu Ser Pro Gly Ser Ser His Lys Pro Leu Thr Glu Asp
1 5 10 15

Glu Ile Ala Asp Leu
20

<210> SEQ ID NO 312
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 312

Gly Ala Trp Asn Gly Phe Val Glu Ala Val Lys Leu Ser Ser Glu Glu
1 5 10 15

Gly Glu Ala Leu Arg
20

<210> SEQ ID NO 313
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 313

Glu Ile Ala Ala Lys Thr Asp Gln Lys Ser Phe Gly Lys Leu Lys Asn
1 5 10 15

Gly Leu Thr Phe Arg
20

<210> SEQ ID NO 314
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 314

Met Ala Phe Gly Pro Thr Ser Tyr Arg Pro Gln Leu Leu Leu Ser Gly
1 5 10 15

Glu Arg Gly Ser Gly
20

<210> SEQ ID NO 315
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 315

Glu Thr Asn Leu Lys Arg Arg Gln Val Val Cys Gly Phe Ser Glu Leu
1 5 10 15

Val Ser Glu Phe Asn
20

<210> SEQ ID NO 316
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 316

Leu Cys Gln His Leu Gly Lys Arg Lys Lys Ile Pro Lys Gly Leu Arg
1 5 10 15

Gln Leu Lys Pro Gly
20

<210> SEQ ID NO 317
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 317

Pro Leu Trp Gln Val Ser Thr Pro Gln Thr Trp Gly Arg Lys Gln Ala
1 5 10 15

Ser Ala Asn Ile Phe
20

<210> SEQ ID NO 318
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 318

Gln Asp Ser Leu Leu Pro Leu Glu Glu Ala Val Asn Ser Gly Met Asp
1 5 10 15

Thr Ser Ile Pro Ser
20

<210> SEQ ID NO 319
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 319

Met Asp Thr Thr Pro Asp Leu Pro Leu Thr Ser Glu Glu Tyr Gln Thr
1 5 10 15

Leu Leu Asp Met Leu
20

<210> SEQ ID NO 320
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 320

Ser Lys Gln Thr Ala Ser Pro Ser Ser Glu Thr Lys Ser Arg Ala Gln
1 5 10 15

Ile Gln Ala Arg Ala
20

<210> SEQ ID NO 321
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 321

Gln Gly Trp Lys Ser Leu Trp Cys Gly Met Arg Thr Ile Arg Ser Gly
1 5 10 15

Leu Glu Glu Leu Trp
20

<210> SEQ ID NO 322
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 322

Pro Arg Ser Pro Gln Ser Pro Ala Ser Lys Thr Ser Phe Ile Phe Ser
1 5 10 15

Lys Gly Thr Lys Lys
20

<210> SEQ ID NO 323
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 323

Ala Leu Ser Gly Arg Ala Ser Pro Val Thr Thr Pro Ser Ser Gly Leu
1 5 10 15

His Ala Ala Val Arg
20

<210> SEQ ID NO 324
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 324

Ala Ile Asn Arg Ala Lys Gly Leu Lys His Ile Val Gln Cys Val Phe
1 5 10 15

Val Ala Ile Arg Thr
20

<210> SEQ ID NO 325
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 325

Ala Lys Gly Leu Lys His Val Val Gln Cys Ile Phe Val Ala Ile Arg

```
1               5                   10                  15

Thr Ile Gly Asn Ile
            20


<210> SEQ ID NO 326
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Ser Phe Gly Ile Gln Ser Ser Ala Ile Asn Ile Val Lys Ile Leu Arg
1               5                   10                  15

Val Leu Arg Val Leu
            20


<210> SEQ ID NO 327
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Ala Ile Asn Arg Ala Lys Gly Leu Lys His Ile Val Gln Cys Val Phe
1               5                   10                  15

Val Ala Ile Arg Thr
            20


<210> SEQ ID NO 328
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 328

Ser Phe Gly Ile Gln Ser Ser Ala Ile Asn Ile Val Lys Ile Leu Arg
1               5                   10                  15

Val Leu Arg Val Leu
            20


<210> SEQ ID NO 329
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Ala Ile Asn Arg Ala Lys Gly Leu Lys His Ile Val Gln Cys Val Phe
1               5                   10                  15

Val Ala Ile Arg Thr
            20


<210> SEQ ID NO 330
<211> LENGTH: 21
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 330

Ser Phe Gly Ile Gln Ser Ser Ala Ile Asn Ile Val Lys Ile Leu Arg
1               5                   10                  15

Val Leu Arg Val Leu
            20

<210> SEQ ID NO 331
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Met Asn Gly Val Tyr Ser Glu Ala Asn Glu Glu Asn
1               5                   10

<210> SEQ ID NO 332
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Ala Asn Lys Ser Phe Asp Val Leu Gly Lys Ile Glu Ala Tyr Leu Lys
1               5                   10                  15

Leu Leu Lys Ser Glu
            20

<210> SEQ ID NO 333
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Ala Asn Asp Phe Phe Thr Ser Ala Asn Lys Leu Phe Asp Val Leu Gly
1               5                   10                  15

Lys Val Glu Ala Tyr
            20

<210> SEQ ID NO 334
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Thr Ser Ala Asn Lys Ser Phe Asp Val Leu Arg Lys Val Glu Ala Tyr
1               5                   10                  15

Leu Lys Leu Leu Lys
            20

<210> SEQ ID NO 335
<211> LENGTH: 21

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 335

Pro Arg Asp Val Glu Met Asn Asn Tyr Arg Trp Ala Met Gln Lys Met
1 5 10 15

Ala Glu Asp Ile Leu
20

<210> SEQ ID NO 336
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 336

Leu Thr Val Ala Gly Gly Gln Asp Asn Val Ile Gly Leu Lys Tyr Cys
1 5 10 15

Phe Arg Lys Asn Asp
20

<210> SEQ ID NO 337
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 337

Ala Glu Leu Gln Cys Leu Thr Val Ala Gly Glu Gln Asp Asn Val Met
1 5 10 15

Gly Leu Lys Tyr Cys
20

<210> SEQ ID NO 338
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 338

Met Ala Gln Ala Val Asp Arg Asp Thr Asn Lys Pro Leu Glu Pro Pro
1 5 10 15

Ser Glu Phe Ile Val
20

<210> SEQ ID NO 339
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 339

Met Lys Ile Pro Asn Ile Asp Asn Val Met Asn Lys Phe Glu Ile Leu
1 5 10 15

Gly

<210> SEQ ID NO 340
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 340

Pro Leu Arg Thr Arg Val Glu Ile Leu His His Leu Cys Asp Tyr Arg
1 5 10 15

Leu Asp Ala Asp Asp
20

<210> SEQ ID NO 341
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 341

Ser Ala Arg Phe Gly Gly Arg Pro Arg Arg Pro Arg Ala Pro Val Pro
1 5 10 15

Ala Cys Leu

<210> SEQ ID NO 342
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 342

Ser Thr Arg Phe Gly Gly Arg Pro Gly Arg Pro Arg
1 5 10

<210> SEQ ID NO 343
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 343

Glu Asn Ser Met Trp Gln Glu Gln Ile Leu Lys Asn Glu Glu Ala Ile
1 5 10 15

Leu Leu Ser Ser Lys
20

<210> SEQ ID NO 344
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 344

Cys Gly Pro Asn Met Arg Ala Gly Val Leu Phe Ser Gly Thr Gly Pro
1 5 10 15

Pro Asn Pro Arg Pro
20

<210> SEQ ID NO 345
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 345

Tyr Ile Ile Lys Asp Leu Glu Lys Leu Leu Ile Ile Ala Gly Glu Glu
1 5 10 15

Arg Ala Leu Cys Leu
20

<210> SEQ ID NO 346
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 346

Gly Thr Gln Cys Ala Arg Ile Val Glu Ser Phe Ala Pro Ala Ser
1 5 10 15

<210> SEQ ID NO 347
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 347

Met Asn Phe Asp Pro Asn Leu Leu His Asn Asn Gly
1 5 10

<210> SEQ ID NO 348
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 348

Met Ser Phe Asp Ser Asn Leu Leu His Asn Asn Gly His Asn Gly
1 5 10 15

<210> SEQ ID NO 349
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 349

Arg Lys Val Asn Gln Lys Ile Gly Ser Cys Ile Gln Gln Asp Val Glu
1 5 10 15

Leu His Val Gln Lys
20

<210> SEQ ID NO 350
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 350

Asn Leu Ser Cys Leu Leu Lys Glu Gly Ser Lys His Leu Phe Asp Ser
1 5 10 15

Phe Glu Pro Glu Thr
20

<210> SEQ ID NO 351
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 351

Val His Asp Phe Asp Cys Leu Cys Pro Ser Ser Tyr Gly Gly Lys Thr
1 5 10 15

Cys Glu Leu Val Leu
20

<210> SEQ ID NO 352
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 352

Pro His Gly Leu His Arg Val Phe Pro Ser Asp Phe Gly Glu Phe Pro
1 5 10 15

Ala Phe Met Glu Ala
20

<210> SEQ ID NO 353
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 353

Asn Ile Met His Tyr Val Val Pro Tyr Leu Gln Asn His Ser Ala His
1 5 10 15

Asn Ala Pro Ser Tyr
20

<210> SEQ ID NO 354
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 354

Trp Asn Val Asp Thr Gly Pro Asp Tyr Tyr Gln Asp Met Ala Ile Glu
1 5 10 15

Tyr His Gly Val Glu
20

<210> SEQ ID NO 355
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 355

Ser Val Phe Ser Thr His Ala Gly Cys Ala Ser Ala His Glu Ala Glu
1 5 10 15

Gly Tyr Pro Ala Glu
20

<210> SEQ ID NO 356
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 356

Thr Ala Arg Thr Gln Lys Thr Ala Tyr Gln Gln Asn Arg Met Arg Phe
1 5 10 15

Ala Gln Arg Asn Leu
20

<210> SEQ ID NO 357
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 357

Ser Glu Thr Pro Lys Leu Thr Ala Leu His Met Leu Phe Val Arg Glu
1 5 10 15

His Asn Arg Leu Ala
20

<210> SEQ ID NO 358
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 358

Phe Ser Val Glu Leu Asn Lys Phe Tyr Asn Met Asp Leu Phe Gln Arg
1 5 10 15

Gly Phe Tyr Gln Ile
20

<210> SEQ ID NO 359
<211> LENGTH: 21
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 359

Phe Ser Val Glu Leu Asn Lys Phe Tyr Asn Met Asp Leu Phe Gln Arg
1 5 10 15

Gly Lys Thr Phe Gln
20

<210> SEQ ID NO 360
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 360

Phe Ser Val Glu Leu Asn Lys Phe Tyr Asn Met Asp Leu Phe Gln Arg
1 5 10 15

Gly Phe Tyr Gln Ile
20

<210> SEQ ID NO 361
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 361

Ala Gly Arg Val Arg Phe Leu Thr Gly Pro Val Val Leu Asp Ile Thr
1 5 10 15

Asp Arg Leu Ser Val
20

<210> SEQ ID NO 362
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 362

Ser Arg Glu Phe Glu Asp Val Leu Asn Ile Phe His Ser Ser Tyr Leu
1 5 10 15

Glu Pro Ser Ser Val
20

<210> SEQ ID NO 363
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 363

Pro Ile Cys Leu Ser Ala Cys Ile Ile Gly Phe Met Ser Gln Val Asn
1 5 10 15

Gln Arg Ile Met Glu

20

<210> SEQ ID NO 364
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 364

Gly Thr Val His Pro Trp Arg Ser Glu Glu Phe Cys Pro Leu Thr Cys
1 5 10 15

Pro Pro Asn Ser His
20

<210> SEQ ID NO 365
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 365

Gln Lys Gly Ile Pro Val Lys Gly Lys Lys Met Lys Lys Glu Gln Lys
1 5 10 15

Thr Ala His Phe Leu
20

<210> SEQ ID NO 366
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 366

Pro Pro Pro Pro Pro Pro Pro Leu Leu Asp Asn Val Pro Pro Pro Pro
1 5 10 15

Val Pro Gly Asn Leu
20

<210> SEQ ID NO 367
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 367

Ser Ile Pro Val His Pro Ile Gly Tyr Asp Asn Ala Gln Lys Leu Leu
1 5 10 15

Glu Lys Val Lys Met
20

<210> SEQ ID NO 368
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 368

Ser Ile Pro Val His Pro Ile Gly Tyr Asp Asn Ala Gln Lys Leu Leu
1               5                   10                  15

Glu His Met Gly Gly
            20

<210> SEQ ID NO 369
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 369

Ala Val Arg Pro Thr Pro Ala Ser Gly Ala Lys Ala Pro Gly Ile Pro
1               5                   10                  15

Lys Pro Val Pro Gly
            20

<210> SEQ ID NO 370
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 370

Gln Gln Pro Val Lys Ala Gly Val Lys Lys Leu Arg Arg Pro Arg Val
1               5                   10                  15

Arg Asn Leu Ser Asp
            20

<210> SEQ ID NO 371
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 371

Ile His Ala Leu Cys His Cys Lys Ser Ala Met Asn Lys Asp Ile Val
1               5                   10                  15

Ser Val Tyr His Ser
            20

<210> SEQ ID NO 372
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 372

Pro Arg Val Val Ala Ala Ser Ala Ser Gln Trp Leu Leu Ser Ala Pro
1               5                   10                  15

Ala Gln Pro Ala Ala
            20

<210> SEQ ID NO 373
<211> LENGTH: 21

<212> TYPE: PRT
<213> ORGANISM: Artificial Sequence
<220> FEATURE:
<223> OTHER INFORMATION: Description of Artificial Sequence: Synthetic peptide

<400> SEQUENCE: 373

Gly Cys Glu Arg Arg Gly Cys Leu Leu Pro Thr Pro Leu Ala Pro Leu
1 5 10 15

Phe Ser Gly Arg Leu
20

<210> SEQ ID NO 374
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 374

Leu Ser Leu Ser Leu Ser Leu Ser Leu Ser Phe Ser Leu Ser Leu Ser
1 5 10 15

Pro Ser Leu Ser Leu
20

<210> SEQ ID NO 375
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 375

Trp Met Phe Leu Ile Phe His Asp Phe Gln Phe Ser Cys
1 5 10

<210> SEQ ID NO 376
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 376

Trp Lys Phe Leu Ile Phe His Asp Phe Gln Phe Ser Ser
1 5 10

<210> SEQ ID NO 377
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 377

His Val Leu Gln Trp Thr Phe Leu Asn Phe Leu Pro Phe Ser Val Ser
1 5 10 15

Pro Tyr Ser Arg Ser
20

<210> SEQ ID NO 378
<211> LENGTH: 21

<212> TYPE: PRT
<213> ORGANISM: Artificial Sequence
<220> FEATURE:
<223> OTHER INFORMATION: Description of Artificial Sequence: Synthetic
peptide

<400> SEQUENCE: 378

His Val Leu Lys Cys Val Phe Leu Ile Phe Cys Asp Phe Gln Val Ser
1 5 10 15

Arg His Ile Pro Gly
20

<210> SEQ ID NO 379
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 379

His Val Leu Lys Cys Val Phe Leu Ile Phe Cys Asp Phe Gln Phe Ser
1 5 10 15

Cys Tyr Ile Pro Ser
20

<210> SEQ ID NO 380
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 380

His Val Leu Lys Cys Val Phe Leu Ile Phe Cys Val Phe Gln Phe Pro
1 5 10 15

Arg His Ile Pro Gly
20

<210> SEQ ID NO 381
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 381

Gln Lys Arg Leu Lys Pro Arg Asn Thr Lys Lys Val Cys Lys Tyr Asn
1 5 10 15

Asp Ser Val Asn Ser
20

<210> SEQ ID NO 382
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 382

Lys Pro Tyr Lys Cys Ser Glu Cys Asp Lys Tyr Phe Thr Glu Lys Asn
1 5 10 15

Gly Leu Arg Arg His
20

<210> SEQ ID NO 383
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 383

Ser Glu Cys Asp Lys Cys Phe Thr Asp Lys Ser Ser Leu Arg Val His
1 5 10 15

His Arg Ile His Ala
20

<210> SEQ ID NO 384
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 384

Asn His Cys Ile Cys Gly Lys Tyr Glu Lys Ile Leu Asp Gln Asp Ser
1 5 10 15

Gln Tyr Ile Val His
20

<210> SEQ ID NO 385
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 385

Arg Thr His Thr Arg Glu Lys Pro Tyr Glu Tyr Lys Gln Cys Gly Lys
1 5 10 15

Ala Phe Ser Gln Ser
20

<210> SEQ ID NO 386
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 386

Ala His Ser Ser His Leu His Ile His Glu Gln Thr His Thr Arg Glu
1 5 10 15

Lys Pro Tyr Glu Cys
20

<210> SEQ ID NO 387
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 387

Pro Gly Ser Glu Pro Glu Ile Asp Arg Ser Phe Ala Ile Arg Glu Arg
1 5 10 15

Thr Asp Tyr Leu Trp
20

<210> SEQ ID NO 388
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 388

Ala Asp Leu Pro Ser Glu Arg Asn Glu Gly Gln Arg Arg Trp Thr Trp
1 5 10 15

Arg Met Trp Met Ala
20

<210> SEQ ID NO 389
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 389

Asp Ile Ser His Asn Met Arg Leu Ser Arg Thr Ser Val Leu Tyr Glu
1 5 10 15

Gln Met Arg Glu Cys
20

<210> SEQ ID NO 390
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 390

Val Glu Gln Ala Gly His Lys Cys Pro Val Arg Lys Lys Arg Gly Ser
1 5 10 15

Leu Arg Arg Pro Ala
20

<210> SEQ ID NO 391
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 391

Val Arg Ala Gly Gly Leu Ala Thr Leu Asn Tyr Thr Val Thr Ser Leu
1 5 10 15

Ile Pro Val Gly Pro
20

<210> SEQ ID NO 392

<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 392

Gln Lys Glu Gln Glu Ala Leu Lys Leu Ser Lys Cys Ser Gln Arg Gln
1               5                   10                  15

Thr Leu Glu Ala Ile
            20

<210> SEQ ID NO 393
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 393

Ser Lys Gly Gln Glu Ser Phe Lys Lys Gln Glu Lys Ile Pro Lys Ile
1               5                   10                  15

Pro Lys Gly Pro Ser
            20

<210> SEQ ID NO 394
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 394

Leu Cys Arg Leu Phe His Arg Glu Asn Gly Asn Gln Gly Glu Thr Arg
1               5                   10                  15

Pro Arg Gln Lys Glu
            20

<210> SEQ ID NO 395
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 395

Glu Gly Pro Trp Lys Thr Val Ala Ile Ala Thr Asp Arg Val Asp Lys
1               5                   10                  15

Ile Glu Arg Gly Gly
            20

<210> SEQ ID NO 396
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 396

Lys Leu Val Tyr Ser Ile Leu Glu Gly Gln Ser Tyr Phe Ser Val Glu
1               5                   10                  15

Ala Gln Thr Gly Ile
20

<210> SEQ ID NO 397
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 397

Thr Pro Val Pro Leu Asp Val Thr Thr Gly Ile Asp Ile Arg Ile Leu
1 5 10 15

Pro Gln Asn Tyr Phe
20

<210> SEQ ID NO 398
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 398

Ser Ile Ile Val Pro Asn Tyr Thr Lys Ser Phe Leu Thr Phe Lys Val
1 5 10 15

Thr Ser Asp Leu Ser
20

<210> SEQ ID NO 399
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 399

Trp Tyr His Leu Glu Ile Arg Ser Ser Pro Arg Pro Pro Val Asp Ile
1 5 10 15

Ile Glu Leu His Cys
20

<210> SEQ ID NO 400
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 400

Ile Val Pro Asn Tyr Thr Lys Ser Leu Leu Ile Phe Lys Val Thr Ser
1 5 10 15

Asp Leu Ser Ile Val
20

<210> SEQ ID NO 401
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 401

Phe Cys Glu Glu Ala Ser Lys Asn Ile Cys Val Ser Ser Ala Lys Glu
1 5 10 15

Gln Gln Ser Glu Ile
20

<210> SEQ ID NO 402
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 402

Phe Cys Glu Glu Ala Ser Lys Asn Ile Cys Val Ser Ser Ala Lys Glu
1 5 10 15

Gln Gln Val

<210> SEQ ID NO 403
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 403

Phe Cys Glu Glu Ala Ser Lys Asn Ile Cys Val Ser Ser Ala Lys Glu
1 5 10 15

Gln Gln Val Gly
20

<210> SEQ ID NO 404
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 404

Asp Val Gly Asp Leu Thr Gln Glu Ala Phe Asn Leu Ile Ser Lys Glu
1 5 10 15

Asn Pro Ser Ser Gln
20

<210> SEQ ID NO 405
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 405

Cys Phe Glu Cys Cys Ile Lys Cys Leu Gly Ser Val Pro Tyr Ala Ser
1 5 10 15

Leu Val Ala Thr Ile
20

<210> SEQ ID NO 406

<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 406

Ser Lys Asn Ala Lys His Leu Ala Lys Ala Ser Ile Ala Asn Arg Phe
1               5                   10                  15

Arg Met Pro His Leu
            20

<210> SEQ ID NO 407
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 407

Cys Phe Glu Cys Cys Ile Lys Cys Leu Gly Ser Val Pro Tyr Ala Ser
1               5                   10                  15

Leu Val Ala Thr Ile
            20

<210> SEQ ID NO 408
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 408

Ser Leu Leu Asp Asp Asp Phe Ser Leu Glu Ser Leu Val Ser Ala Phe
1               5                   10                  15

His Glu Phe Glu Glu
            20

<210> SEQ ID NO 409
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 409

Asp Asp Phe Ser Leu Glu Pro Leu Val Ser Val Phe His Glu Phe Glu
1               5                   10                  15

Glu Leu Ala Lys Gln
            20

<210> SEQ ID NO 410
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 410

Phe Ser Leu Glu Pro Leu Val Ser Ala Phe Tyr Glu Phe Glu Glu Leu
1               5                   10                  15

Ala Lys Gln Leu Gln
20

<210> SEQ ID NO 411
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 411

Asn Tyr Leu Gly Phe Asn Tyr Glu Ile Tyr Ile Ala Pro Asp His Lys
1 5 10 15

Tyr Gly Ser Pro Gln
20

<210> SEQ ID NO 412
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 412

Val Val Asn Ala Val Tyr Ala Met Ala His Val Leu His Lys Met Gln
1 5 10 15

Arg Thr Leu Cys Pro
20

<210> SEQ ID NO 413
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 413

Ala Ser Gly Leu Pro Met Arg Asn Gly Asn Gln His Ala Val Asp Ile
1 5 10 15

Ser Lys Met Ala Leu
20

<210> SEQ ID NO 414
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 414

Ser Ala Lys Leu His Tyr His Asp Ser Trp Val Leu Ile Leu His Ala
1 5 10 15

Ala Ala Leu Trp Leu
20

<210> SEQ ID NO 415
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 415

Ala Pro Gly Phe Leu His Cys Ala Ser Phe Glu Asp Pro His Val Arg
1 5 10 15

Ser Phe His Asn Gln
20

<210> SEQ ID NO 416
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 416

Gln Leu Gln Pro Val Pro Gly Ala Ala Pro Asn Pro Ser Lys His Thr
1 5 10 15

Ser Ala Thr Ala Ala
20

<210> SEQ ID NO 417
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 417

Ala Val Ser Gly Leu Gly Gly Cys Pro Tyr Thr Lys Gly Ala Ser Gly
1 5 10 15

Asn Val Ala Thr Glu
20

<210> SEQ ID NO 418
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 418

Tyr Leu Leu Gln Asn Ser Val Lys Gln Tyr Phe Gly Lys Phe Phe
1 5 10 15

<210> SEQ ID NO 419
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 419

Leu Pro Lys Gly Asp Phe Phe Pro Pro Glu His Pro Gln Gln Leu Pro
1 5 10 15

His Gly Leu Gly Gly
20

<210> SEQ ID NO 420
<211> LENGTH: 21
<212> TYPE: PRT

<213> ORGANISM: Artificial Sequence
<220> FEATURE:
<223> OTHER INFORMATION: Description of Artificial Sequence: Synthetic peptide

<400> SEQUENCE: 420

Pro Gly Gly Gly Gly Cys Ala Gly Gly Gly Glu Gly Gly Gly Ala Gly
1 5 10 15

Pro Gly Pro Ser Pro
20

<210> SEQ ID NO 421
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 421

Ser Ser Thr Ser Asn Asp Val Ser Ser Ser Asn Phe Glu Glu Gly Pro
1 5 10 15

Ser Arg Lys Arg Pro
20

<210> SEQ ID NO 422
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 422

Ala Ile Leu Gly Lys Gly Asp Leu Ile Gly Thr Asn Leu Ser Ile Lys
1 5 10 15

Asp Gln Val Ile Lys
20

<210> SEQ ID NO 423
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 423

Val Ile Ile Cys Ala Ser Leu Lys Leu Leu Tyr Leu Leu Gly Leu Ile
1 5 10 15

Asp Phe Ser Glu Asp
20

<210> SEQ ID NO 424
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 424

Tyr Leu Leu Arg Leu Leu Thr Gly Ser Leu Tyr Thr Asp Ser Val Glu
1 5 10 15

Asp Glu Leu Glu Met

20

<210> SEQ ID NO 425
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 425

Asn Asp Phe Leu Ile Glu Asp Met Ile Pro Ile Leu Lys Ala Ala Ile
1 5 10 15

Arg Ala Val Arg Ile
20

<210> SEQ ID NO 426
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 426

Pro Pro Pro Pro Pro Pro Pro Pro Pro Pro Leu Pro Pro Pro Pro Pro
1 5 10 15

Pro Pro Leu Pro Gly
20

<210> SEQ ID NO 427
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 427

Asn Gln Arg Glu Thr Thr Met Lys Asp Leu Asn Ile Ile Thr Ile Pro
1 5 10 15

Ser His Asn Val Val
20

<210> SEQ ID NO 428
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 428

Gln Thr Phe Cys Phe Asp His Ala Phe Asp Asn Lys Ala Ser Asn Glu
1 5 10 15

Leu Val Tyr Gln Phe
20

<210> SEQ ID NO 429
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 429

Val Asn Ile Ser Pro Leu Glu Glu Asn Val Phe Glu Ser Leu Asn Ser
1 5 10 15

Leu Arg Phe Ala Ser
20

<210> SEQ ID NO 430
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 430

Thr Glu Arg Glu Val Trp Glu Ala Trp Ala Val Asn Pro Gly Asn Cys
1 5 10 15

Pro Pro Ala Gly Leu
20

<210> SEQ ID NO 431
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 431

Glu Val Met Asn Ser Lys Leu Gly Leu Asp Ile Glu Ile Thr Thr Tyr
1 5 10 15

Arg Arg Leu Leu Glu
20

<210> SEQ ID NO 432
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 432

Arg Leu Glu Pro Gly Glu Leu Ile Pro Asn Asp Pro Phe Ser Phe Tyr
1 5 10 15

Gly Asp Tyr Gln Ser
20

<210> SEQ ID NO 433
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 433

Glu His Phe Val Thr Tyr Cys Arg Tyr Gly Phe Arg Ile Ser Pro Gln
1 5 10 15

Ala Glu Lys Phe Tyr
20

<210> SEQ ID NO 434
<211> LENGTH: 21

<212> TYPE: PRT
<213> ORGANISM: Artificial Sequence
<220> FEATURE:
<223> OTHER INFORMATION: Description of Artificial Sequence: Synthetic peptide

<400> SEQUENCE: 434

Leu Glu Thr Lys Leu Ile Cys Ile Gly Arg Asn Asp Glu Asp Lys Tyr
1 5 10 15

Leu Glu Asp Phe Phe
20

<210> SEQ ID NO 435
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 435

Trp Met Lys Asn Ser Leu Lys Val His Ser Asn Ser Val Leu Glu Gln
1 5 10 15

Val Trp Asp Ile Phe
20

<210> SEQ ID NO 436
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 436

Trp Met Lys Asn Ser Leu Lys Val His Ser Asn Ser Val Leu Glu
1 5 10 15

<210> SEQ ID NO 437
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 437

Lys Phe Met Trp Ser Glu Ile Ser Tyr Leu Thr Lys Trp Trp Asp Ile
1 5 10 15

Ile Asp Ile Pro Lys
20

<210> SEQ ID NO 438
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 438

Asn Thr Met Phe Pro Pro Thr Ala Asn Met Phe Leu Pro Thr Gly Glu
1 5 10 15

Gly Gln Ser Gly Arg
20

<210> SEQ ID NO 439
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 439

```
Ile Val Leu Ser Met Val Glu Ser Gly Leu Leu Glu Glu Glu Ala Gln
1               5                   10                  15

Arg Lys Ile Trp Met
            20
```

<210> SEQ ID NO 440
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 440

```
Val Leu Ile Pro Asp Ile Asn Phe Asn Asp Thr Phe Glu Asn Phe Ala
1               5                   10                  15

Leu Asp Phe Ser Arg
            20
```

<210> SEQ ID NO 441
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 441

```
Asp Glu Asp Trp Arg Ser Gln Arg Lys His Met Phe Val Leu Ser Glu
1               5                   10                  15

Ala Gly Lys Pro Ile
            20
```

<210> SEQ ID NO 442
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 442

```
Ile Asp Ser Ser Gly Leu Arg Val Phe His Ile Thr Asp Ile Arg Arg
1               5                   10                  15

Tyr Asp Ala Gly Val
            20
```

<210> SEQ ID NO 443
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 443

Ile Thr Ser Ile Gln Met Leu Ser Thr Leu Ser Gln Ser Gln His Thr
1 5 10 15

Glu Ser Lys Ser Thr
20

<210> SEQ ID NO 444
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 444

Lys Pro Gly Gln Ser Val Lys Phe Arg Val Ile Ser Met Asp Lys Thr
1 5 10 15

Leu Arg Pro Leu Asn
20

<210> SEQ ID NO 445
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 445

Gly Gln Ser Val Lys Phe Arg Val Val Ser Ile Asp Lys Thr Leu Arg
1 5 10 15

Pro Leu Asn Glu Leu
20

<210> SEQ ID NO 446
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 446

Lys Ala Arg Asp Glu Val Ile Lys Gln Leu Cys Lys Leu Gln Ala Gln
1 5 10 15

Met Lys Asp Tyr Gln
20

<210> SEQ ID NO 447
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 447

Gly Gly Ser Ile Met Tyr Asn Leu Phe Gln Cys Tyr Lys Arg Asn Gln
1 5 10 15

Ile Tyr Thr Tyr Ile
20

<210> SEQ ID NO 448
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 448

Val Val Ser Asp Ser Tyr Asp Ile Tyr Asn Val Cys Glu Lys Ile Trp
1 5 10 15

Gly Glu Asp Leu Arg
20

<210> SEQ ID NO 449
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 449

Asn Thr Gly Thr Glu Ser Ala Ser Glu Glu Glu Asp Asp Ser Leu Leu
1 5 10 15

Ile Thr Val Val Pro
20

<210> SEQ ID NO 450
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 450

Leu Lys Lys Leu Ser Phe Ser Thr Gln Asn Ile Leu Ser Gly Ala Gln
1 5 10 15

Glu His Ser Tyr Met
20

<210> SEQ ID NO 451
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 451

Met Gly Lys Leu Lys Asn Ala Ser Trp Ile His Asp Ser Leu Met
1 5 10 15

<210> SEQ ID NO 452
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 452

His Leu Val Ala Ala Asp Ile Arg Val Ala Leu Ala Thr Ala Leu Thr
1 5 10 15

Pro Pro Gln Gly Asp
20

<210> SEQ ID NO 453

<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 453

Asn Ile Arg Gln Leu Ala Glu Met Gln Asn Thr Ala Gly Val Lys Ser
1 5 10 15

Ser Cys Ser Arg Met
20

<210> SEQ ID NO 454
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 454

Met Ser Glu Gln Ala Arg Glu Glu Asn Val Thr Thr Phe Arg Gly Ser
1 5 10 15

Glu Tyr Leu Cys Tyr
20

<210> SEQ ID NO 455
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 455

Asn Ile Arg Gln Leu Ala Glu Met Gln Asn Thr Ala Gly Val Lys Ser
1 5 10 15

Ser Cys Ser Arg Met
20

<210> SEQ ID NO 456
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 456

Thr Gly Tyr Lys Ser His Ala Lys Glu Ile Phe His Cys Leu Lys Asn
1 5 10 15

Lys Tyr Phe Lys Glu
20

<210> SEQ ID NO 457
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 457

Gly Arg His Lys Gly Glu Val Ser Phe Pro Asp Gly Lys Cys Asp Pro
1 5 10 15

Asp Asp Gln Asp Val
20

<210> SEQ ID NO 458
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 458

Ser Pro Gln Val Leu Gly His Ile Leu Lys Ser Gly Thr Thr Glu Ser
1 5 10 15

Gly Ala Leu Ser Leu
20

<210> SEQ ID NO 459
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 459

Asp His Glu Gly Gln Pro Arg Pro Arg Val Ser Arg Lys Arg Gly His
1 5 10 15

Ile Ser Pro Lys Ser
20

<210> SEQ ID NO 460
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 460

Thr Leu Phe Phe Ile Tyr Val Arg Pro Ser Thr Ile Ser Ser Leu Asp
1 5 10 15

Leu Asn Lys Val Val
20

<210> SEQ ID NO 461
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 461

Ser Ser Lys Met Ser Arg Val Val Cys Ile Cys Leu Ile Ser Val Pro
1 5 10 15

Tyr Val Tyr Gly Phe
20

<210> SEQ ID NO 462
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 462

Ser Tyr Gly Val Ile Leu Phe Ser Leu Arg Phe His Ser Ser Glu Gly
1 5 10 15

Arg Ser Lys Ala Leu
20

<210> SEQ ID NO 463
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 463

Leu Gln Leu Cys Leu Phe Phe Ile Phe Leu Val Phe Tyr Leu Ile Thr
1 5 10 15

Ile Val Gly Asn Leu
20

<210> SEQ ID NO 464
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 464

Thr Tyr Thr Val Leu Thr Pro Phe Leu Ser Leu Ile Ile Phe Ser Leu
1 5 10 15

Arg Asn Lys Glu Leu
20

<210> SEQ ID NO 465
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 465

Ser Ile Ile Val Val Thr Val Phe Ile Ile Val Leu Ser Tyr Val Tyr
1 5 10 15

Ile Leu Val Ser Ile
20

<210> SEQ ID NO 466
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 466

Ile Tyr Ile Leu Ile Thr Ile Leu Lys Met His Ser Thr Glu Gly Arg
1 5 10 15

His Lys Ala Phe Ser
20

<210> SEQ ID NO 467
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 467

Thr Phe Leu Arg Gly Val Leu Leu Ile Ile Ser Phe Ile Phe Leu Ser
1 5 10 15

Lys Cys Leu Pro Tyr
20

<210> SEQ ID NO 468
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 468

Ala Thr Ser Trp Ile Leu Ala Ser Leu Ser Val Leu Gly Tyr Ser Met
1 5 10 15

Tyr Thr Met Gln Tyr
20

<210> SEQ ID NO 469
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 469

Leu Ala Thr Met Ser Tyr Asp Arg Tyr Ile Val Ile Cys Lys Pro Leu
1 5 10 15

His Tyr Ala Ser Ile
20

<210> SEQ ID NO 470
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 470

Gly Ser His Ser Leu Cys Pro Gln Thr Gly Asn Pro Ser Met Val Thr
1 5 10 15

Ala Ile Thr Ile Met
20

<210> SEQ ID NO 471
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 471

Met Ile Leu Gly Ile Phe Ala Asn Cys Ile Phe Cys 1 5 10

<210> SEQ ID NO 472
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 472

Lys Asn Tyr Tyr Ser Leu Val Leu Asp Ser Thr Leu Asp Arg Glu Thr
1 5 10 15

Thr Ala Asp Tyr Lys
20

<210> SEQ ID NO 473
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 473

Gln Pro Glu Glu Glu Ala Glu Asn Thr Lys Ile Pro Trp Leu Tyr Asp
1 5 10 15

Gln Glu Gly Gly Val
20

<210> SEQ ID NO 474
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 474

Asp Tyr Ser Glu Val Thr Gly Ser Met Gly Glu Ile Pro Glu Glu Glu
1 5 10 15

Leu Asp Ser Met Ala
20

<210> SEQ ID NO 475
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 475

Gln Gly Leu Met Arg Phe Asn Leu Pro Ala His Ile Cys Arg Asp Ile
1 5 10 15

Glu Leu Phe His Phe
20

<210> SEQ ID NO 476
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 476

Lys Gln Trp Cys Lys Pro His Tyr Gln Asn Phe Gly Gly Gly Asn Gly
1 5 10 15

Val Asp Leu Ser Val
20

<210> SEQ ID NO 477
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 477

Ile Leu Ser Phe Glu Asn Asn Gly Asp Tyr Ile Asp Met Lys Gln Ala
1 5 10 15

Asp Thr Thr Gln Tyr
20

<210> SEQ ID NO 478
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 478

Tyr Ala Asn Gly Ile Arg Val Met Ser Met Met His Thr Gly Glu Pro
1 5 10 15

Gly Phe Met Leu Tyr
20

<210> SEQ ID NO 479
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 479

Glu Glu Asn Thr Val Pro Pro Glu His Ser Ser Pro Glu Met Glu Ile
1 5 10 15

Cys Thr Val Tyr Leu
20

<210> SEQ ID NO 480
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 480

Phe Gly Ser Glu Arg Asp Leu Glu Arg Arg Ser Arg Ser Arg Asp Val
1 5 10 15

Glu Pro Arg Asp Arg
20

<210> SEQ ID NO 481
<211> LENGTH: 21

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 481

Ser Ser Thr Thr Thr Thr Thr Ile Thr Thr Phe Ser Ser Arg Met Gln
1               5                   10                  15

Gln Pro Gln Ile Ser
            20

<210> SEQ ID NO 482
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 482

Tyr Val Leu Gly Ile Gly Asp Arg His Ser Asn Asn Ile Met Ile Arg
1               5                   10                  15

Glu Ser Gly Gln Leu
            20

<210> SEQ ID NO 483
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 483

Ala Glu Ser Pro Ser Ile Ala Ser Thr Ser Leu Thr Glu Lys Ser Phe
1               5                   10                  15

Pro Trp Arg Ser Thr
            20

<210> SEQ ID NO 484
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 484

Thr Tyr Trp Asn Thr Arg Gln Pro Ser Asn His Gly Gly Cys Val Val
1               5                   10                  15

Val Arg Gly Gly Ser
            20

<210> SEQ ID NO 485
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 485

Asp Gly Ser Ser Gly Gly Trp Ala Ala Arg Val Leu Arg Arg Ala Leu
1               5                   10                  15

Ala Leu Thr Ser Leu
20

<210> SEQ ID NO 486
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 486

Glu Lys Glu Ile Arg Ser Phe Leu Ile Glu Ser His Leu Ile Asn Thr
1 5 10 15

Ile Arg Val Val Cys
20

<210> SEQ ID NO 487
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 487

Glu Ile Val Lys Tyr Thr Lys Ile Ile Ala Ile Glu Lys Leu Tyr Ala
1 5 10 15

Val Phe Thr Asp Tyr
20

<210> SEQ ID NO 488
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 488

Gln Gly Gln Gly Gln Gly Leu Ser Pro Glu His Val Glu Asp Tyr Gly
1 5 10 15

Arg Thr His Arg Gly
20

<210> SEQ ID NO 489
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 489

Thr Thr Lys Thr Ala Met Cys Thr Ala Val Val Gly Tyr Phe Asp Ile
1 5 10 15

Tyr Phe Glu Lys Asn
20

<210> SEQ ID NO 490
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 490

```
Ser Gly Pro Ala Glu Glu Glu Asp Val Pro Arg Ser Pro Cys Pro Asp
1               5                   10                  15

Ala Gly Asp Pro Gln
            20
```

<210> SEQ ID NO 491
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 491

```
Leu Asp Gln Ile Ser Arg Tyr Tyr Ile Thr Lys Ala Lys Leu Val Ser
1               5                   10                  15

Lys Ile Ala Lys Tyr
            20
```

<210> SEQ ID NO 492
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 492

```
Leu Gln Val Thr Arg Gly His Leu Asp Thr Thr Arg Thr Arg Gly Lys
1               5                   10                  15

Val Ser Trp Gln Ile
            20
```

<210> SEQ ID NO 493
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 493

```
Lys Lys Lys Thr Asn Asn Pro Gln Phe Asp Lys Val Phe Tyr Phe Glu
1               5                   10                  15

Val Thr Arg Pro Cys
            20
```

<210> SEQ ID NO 494
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 494

```
Met Lys Arg Gln Ser Glu Arg Asp Phe Ser Pro Ser Gly Arg Gly Ser
1               5                   10                  15

Ser Ser Ser
```

<210> SEQ ID NO 495
<211> LENGTH: 21

<212> TYPE: PRT
<213> ORGANISM: Artificial Sequence
<220> FEATURE:
<223> OTHER INFORMATION: Description of Artificial Sequence: Synthetic peptide

<400> SEQUENCE: 495

Leu Val Pro Cys His Ile Ser Thr Asn Leu Leu Asn Lys Gln Val Ile
1 5 10 15

Glu Val Ala Cys Gly
20

<210> SEQ ID NO 496
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 496

Leu Val Pro Cys His Ile Ser Thr Asn Leu Leu
1 5 10

<210> SEQ ID NO 497
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 497

Val Ile Glu Val Ala Cys Gly Ser Tyr His Leu Leu Val Leu Thr Ser
1 5 10 15

Asp Gly Glu Val Phe
20

<210> SEQ ID NO 498
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 498

Leu Val Pro Cys His Ile Ser Thr Asn Leu Leu Asn Lys Gln Val Ile
1 5 10 15

Glu Val Ala Cys Gly
20

<210> SEQ ID NO 499
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 499

Ile Ala Glu Gly Val Cys Ile Pro Arg Ser Thr Leu Tyr Met His Tyr
1 5 10 15

Leu Asp Phe Cys Glu
20

<210> SEQ ID NO 500
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 500

Arg Arg Glu Pro Gln Gln Val Leu Val Ser Phe Phe Arg Ala Leu Trp
1 5 10 15

Ser Arg Leu Trp Pro
20

<210> SEQ ID NO 501
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 501

Val Leu Gly His Tyr Asn Asn Phe Phe Phe Val Ala His Leu Leu Asp
1 5 10 15

Ile Ala Met Gly Phe
20

<210> SEQ ID NO 502
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 502

Thr Ala Ala Ala Ala Thr Thr Ala Ala Ala Thr Ser Ser Ser Ala Ala
1 5 10 15

Ser Pro His Tyr Gln
20

<210> SEQ ID NO 503
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 503

Leu Val Ile Ile Trp Asn Gln Asp Ser Val Lys Tyr Tyr Thr Arg Leu
1 5 10 15

Gly Ala Leu Asp Leu
20

<210> SEQ ID NO 504
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 504

```
Asp Ala Ser Lys Leu His Ser Ser Pro Gln Ile Ala Ala Gln His Asn
1               5                   10                  15

Met Val Asp Asp Gly
            20


<210> SEQ ID NO 505
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 505

Phe Met Asn Arg Thr Glu Phe His Val Tyr Phe Pro Lys Phe Gln Leu
1               5                   10                  15

Gln Glu Asp Tyr Asp
            20


<210> SEQ ID NO 506
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 506

Ile Leu Lys Ser Ser Ser Val Gln Lys Glu Phe Cys Asn Lys Arg Asn
1               5                   10                  15

Pro Phe Trp Lys Lys
            20


<210> SEQ ID NO 507
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 507

Val Leu Ile Ile Leu Leu Ser Thr Met Val Ile Ser Ile Thr Gly Leu
1               5                   10                  15

Ser Thr Ser Ala Ile
            20


<210> SEQ ID NO 508
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 508

Val Ile Ile Ile Gly Leu Ala Val Thr Val Ile Ala Ile Thr Gly Leu
1               5                   10                  15

Ser Thr Ser Ala Ile
            20


<210> SEQ ID NO 509
<211> LENGTH: 21
<212> TYPE: PRT
<213> ORGANISM: Artificial Sequence
```

<220> FEATURE:
<223> OTHER INFORMATION: Description of Artificial Sequence: Synthetic
peptide

<400> SEQUENCE: 509

Val Ile Ile Ile Gly Leu Ser Val Val Val Ile Thr Leu Thr Gly Ile
1 5 10 15

Ser Met Ser Ala Ile
20

<210> SEQ ID NO 510
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 510

Glu Asp Phe Phe Leu Lys Cys Arg Leu Gln Lys Gln Glu Ile Gln Arg
1 5 10 15

Arg Pro Ser Val Phe
20

<210> SEQ ID NO 511
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 511

Leu Ser Ser Leu Cys Met Cys Val Ser Asn Phe His Ile Asn Glu Leu
1 5 10 15

Leu Pro Thr Thr Leu
20

<210> SEQ ID NO 512
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 512

Leu Leu Thr Trp Val Asn Cys Ser Ser Val Gln Trp Ala Thr Arg Val
1 5 10 15

Gln Asp Ile Phe Thr
20

<210> SEQ ID NO 513
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 513

Met Arg Gly Arg Met Gly Ser Ser Val Ile Asn Glu Ile Ser Val Glu
1 5 10 15

Glu Val Asn Lys Met
20

<210> SEQ ID NO 514
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 514

Asn Val Val Arg Asp Trp Leu Gly Val Gly Asp Pro Val Leu Thr Pro
1 5 10 15

Pro Gln Glu His Pro
20

<210> SEQ ID NO 515
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 515

Thr Lys Glu Glu Glu Asn Glu Met Tyr Asn Ser Thr Phe Phe Tyr Glu
1 5 10 15

Asn Leu Lys Ile Pro
20

<210> SEQ ID NO 516
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 516

Pro Phe Pro Phe Leu Met Ser Leu Arg Asp Gln Asp Phe Ile Ser Glu
1 5 10 15

Gln Lys Phe Gln Glu
20

<210> SEQ ID NO 517
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 517

Asn Ala Asn Phe Ser Ala Glu Leu Leu Pro Met Thr Cys Gly Asn Leu
1 5 10 15

Lys Gly Val Leu His
20

<210> SEQ ID NO 518
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 518

```
Phe Lys Phe Glu Leu Gln Ser Asp Phe Ala Lys Phe Ser Glu Ser Arg
1               5                   10                  15

Gly Ser Thr Ala Lys
            20


<210> SEQ ID NO 519
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Glu Gly Arg Arg Asp Ile Gly Lys Gln Val Lys Glu Glu Lys Pro Gly
1               5                   10                  15

Ala Gly Lys Lys Asp
            20


<210> SEQ ID NO 520
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 520

Tyr Cys Ala Ala Pro Glu Arg Arg Glu Thr Tyr Glu His Ser Ser Glu
1               5                   10                  15

Ala Lys Ala Phe His
            20


<210> SEQ ID NO 521
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Thr Met His Asp Lys Gln Gly Glu Val Arg Phe Lys Cys Leu Thr Ala
1               5                   10                  15

Leu Gln Gly Leu Tyr
            20


<210> SEQ ID NO 522
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Ser Leu Lys Val Ile Gly Arg Gly Ala Phe Ser Glu Val Arg Leu Val
1               5                   10                  15

Gln Lys Lys Asp Thr
            20


<210> SEQ ID NO 523
<211> LENGTH: 17
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 523

Met Lys Asp Arg Thr Gln Lys Leu Arg Ser Ala Lys Asp Ser Asp Asp
1 5 10 15

Glu

<210> SEQ ID NO 524
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 524

Arg Ile Gln Arg Gln Leu Lys Ile Thr Gly Arg Thr Thr Thr Asn Glu
1 5 10 15

Glu

<210> SEQ ID NO 525
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 525

Ala Ala Asn Tyr Leu Ile Gly Gln Lys Glu Val Lys Arg Trp Gly Thr
1 5 10 15

Ala His Gly Ser Ile
20

<210> SEQ ID NO 526
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 526

Val Leu Tyr Tyr Glu Asp Met Lys Lys Asp Thr Lys Gly Thr Ile Lys
1 5 10 15

Lys Ile Cys Asp Phe
20

<210> SEQ ID NO 527
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 527

Glu Glu Ser Gly Trp Ser Ser Ser Ser Pro Ile Cys Val Pro Ile Asp
1 5 10 15

Cys Gly Leu Pro Pro
20

<210> SEQ ID NO 528
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 528

Ile Pro Gln Asp Arg Pro Thr Ser Glu Glu Phe Leu Lys His Met Phe
1 5 10 15

Val Leu Arg Glu Arg
20

<210> SEQ ID NO 529
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 529

Thr Cys Ser Asp Met Met Ser Phe Leu Val Asn Ile Ala Ser Ile Ala
1 5 10 15

Met Leu Val Lys Ile
20

<210> SEQ ID NO 530
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 530

Thr Glu Ser Gly Arg Asn Ser Pro Glu Lys Asp Lys Gly Lys Ile Asp
1 5 10 15

Ile Gln Ala Tyr Leu
20

<210> SEQ ID NO 531
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 531

Gln Pro Asp Val Cys Phe Leu Leu Phe Gly Leu Arg
1 5 10

<210> SEQ ID NO 532
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 532

Gln Pro Glu Lys Arg Leu Lys Ala Glu Ser Leu Lys Thr Val Phe Ser
1 5 10 15

Cys Ser Asp Glu Ser
20

<210> SEQ ID NO 533
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 533

Phe Thr Ile Leu Leu Val Val Thr Asn Arg Asn Thr Gln Glu Thr Leu
1 5 10 15

Leu Cys Met Ala Cys
20

<210> SEQ ID NO 534
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 534

Tyr Leu Asp Cys Ala Gln Ala Asp Ser Val Cys Asn Leu Pro Arg Ala
1 5 10 15

Phe Ser Gly Leu Thr
20

<210> SEQ ID NO 535
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 535

Asn Tyr Asp Val Leu Ala Tyr Cys Ile Ile Lys Ala Leu Ala Asn Pro
1 5 10 15

Glu Lys Glu Arg Met
20

<210> SEQ ID NO 536
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 536

Gly Thr Ile Asp Thr Lys Arg Asn Ile Ser Val Glu Glu Gly Gly Ser
1 5 10 15

Val Ile Leu Gln Cys
20

<210> SEQ ID NO 537
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 537

Ser Leu Val Gly Ser Ser Leu Ser Ala Phe Thr Leu Leu Pro Leu Gln
1 5 10 15

Gly Asp Arg Asp Arg
20

<210> SEQ ID NO 538
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 538

Leu Asp Arg Tyr Phe Tyr His Val Asn Asn Asn Gln Pro Ile Asp Leu
1 5 10 15

Thr Lys Gly Lys Ser
20

<210> SEQ ID NO 539
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 539

Asp Glu Arg Asp Arg Gln Asn Ala Arg Leu His Glu Glu Asn Ala Arg
1 5 10 15

Leu Arg Leu Glu Asn
20

<210> SEQ ID NO 540
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 540

Ser Arg Glu Gln Phe Met Glu His Leu Tyr Ser Gln Arg Lys Pro Leu
1 5 10 15

Val Leu Glu Gly Leu
20

<210> SEQ ID NO 541
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 541

Met Glu Thr Cys Tyr Asn Leu Lys Ser Pro Ala Val Lys Arg
1 5 10

<210> SEQ ID NO 542
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 542

Trp Gly Leu Leu Ser His Cys Lys Val Arg Lys Thr Gln Glu Tyr Thr
1 5 10 15

Arg Asn Val Val Arg
20

<210> SEQ ID NO 543
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 543

Val Phe Gly Pro Ser Ala Ser His Ala Gly Lys Leu Leu Val Phe Pro
1 5 10 15

Met Asp Gly Ser His
20

<210> SEQ ID NO 544
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 544

Ala Arg Gln Ala Val Phe Thr Ala Lys Tyr Leu Glu Asp Met Lys His
1 5 10 15

Lys Thr Thr Leu Leu
20

<210> SEQ ID NO 545
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 545

Lys Glu Lys Ile Leu Gly Leu Leu Ser Ser Ser Thr Gly Asp Ala Ser
1 5 10 15

Tyr Gln Gln Leu Met
20

<210> SEQ ID NO 546
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 546

Lys Arg Ala Asn Asn Gly Lys Phe Thr Leu His Asp Leu Leu Val Val
1 5 10 15

Pro Met Gln Arg Val
20

<210> SEQ ID NO 547
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 547

Cys Ser Thr Thr Gly Phe Ser Ile Gly Met His Ile Leu Ser Phe Ala
1 5 10 15

His Asp Ala Val Phe
20

<210> SEQ ID NO 548
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 548

Thr Thr Cys Ile Leu Gln Gln Thr Thr Phe Glu Val Ala Phe Thr Met
1 5 10 15

Ala Leu Ala Thr Val
20

<210> SEQ ID NO 549
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 549

Ser Ile Leu Ala Ser Ser Ala Gly Met Leu Glu Cys Ile Phe Val Pro
1 5 10 15

Lys Cys Tyr Thr Ile
20

<210> SEQ ID NO 550
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 550

Cys Ile Leu Ile Gln Val Ile Val Cys Ala Ile Trp Leu Arg Ala Ser
1 5 10 15

Pro Pro Ser Val Asp
20

<210> SEQ ID NO 551
<211> LENGTH: 21
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 551

His Gly Gln Ile Ile Ile Val Cys His Lys Asp Ser Val Asn Ala Phe
1 5 10 15

Tyr Cys Val Leu Gly
20

<210> SEQ ID NO 552
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 552

Thr Thr Ser Gln Trp Asp Val Ser Pro Ser Ile Lys Asp Phe Thr Phe
1 5 10 15

Gly Asn Glu Tyr Gly
20

<210> SEQ ID NO 553
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 553

Asn Glu Tyr Gly Thr Phe Ala Phe Gly Gln Tyr His Ser Glu Ile Ser
1 5 10 15

Gly Phe Lys His Phe
20

<210> SEQ ID NO 554
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 554

Leu Ser Glu Pro Ser Cys Phe Trp Arg Ile Lys Asn Ser Glu Asp Ser
1 5 10 15

Asp Gly Asp Leu Gln
20

<210> SEQ ID NO 555
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 555

Asn Leu Asn Glu Ile Gln Asp Glu Tyr Leu Glu Leu Thr Cys Ala Phe
1 5 10 15

Ile Leu Ala Ala Val
20

<210> SEQ ID NO 556
<211> LENGTH: 21
<212> TYPE: PRT

<213> ORGANISM: Artificial Sequence
<220> FEATURE:
<223> OTHER INFORMATION: Description of Artificial Sequence: Synthetic peptide

<400> SEQUENCE: 556

Tyr Leu Gly Leu Thr Cys Ala Phe Ile Leu Val Ala Val Gln Lys Pro
1 5 10 15

Ile Glu Lys Asp Tyr
20

<210> SEQ ID NO 557
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 557

Pro Ala Ala Ser Leu Gln Phe Gln Gly Leu Ser Glu Gly Val Arg Ala
1 5 10 15

Gly Pro Val Pro Ser
20

<210> SEQ ID NO 558
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 558

Ala Ala Cys His Pro Thr Lys Asn Ile Ile Thr Ser Ala Ala Leu Glu
1 5 10 15

Asn Asp Lys Thr Ile
20

<210> SEQ ID NO 559
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 559

Phe Glu Asn Arg Lys Gly Leu Ser Ser His Thr Arg Ser His Leu Arg
1 5 10 15

Gln Met Gly Val Thr
20

<210> SEQ ID NO 560
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 560

Ala Pro Leu Glu Trp Leu Arg Tyr Phe Asp Lys Lys Glu Leu Glu Leu
1 5 10 15

Met Leu Cys Gly Met

20

<210> SEQ ID NO 561
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 561

Leu Gly Ile Thr Lys Thr Ser Lys Glu Ser Thr Phe Lys Ala Ala Arg
1 5 10 15

Lys Tyr Cys Pro His
20

<210> SEQ ID NO 562
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 562

Tyr Lys Asn Met Arg Glu Thr Leu Val Tyr Phe Thr His Leu Asp Tyr
1 5 10 15

Val Asp Thr Glu Ile
20

<210> SEQ ID NO 563
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 563

Glu Thr Ser Arg Asn Ala Gly Pro Ser Pro Val Ala Gln Ala Pro Ala
1 5 10 15

Asp Arg Pro Val Ser
20

<210> SEQ ID NO 564
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 564

Val Lys Gln Lys Gly Thr Gly Lys Gly Lys Asp Arg Thr Asn Thr Ile
1 5 10 15

Ser Met Thr Gly Gly
20

<210> SEQ ID NO 565
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 565

Gln Arg Ile Tyr His Gly Lys Lys Pro Tyr Lys Ser Ser Lys Ser Asp
1 5 10 15

Lys Cys Phe Thr His
20

<210> SEQ ID NO 566
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 566

Lys Ile Ile Gly Asp Ala Ser Thr Gln Thr Asn Ala Leu Lys Leu Pro
1 5 10 15

Pro Ser Gln Pro Pro
20

<210> SEQ ID NO 567
<211> LENGTH: 43
<212> TYPE: DNA
<213> ORGANISM: Artificial Sequence
<220> FEATURE:
<223> OTHER INFORMATION: Description of Artificial Sequence: Synthetic probe

<400> SEQUENCE: 567
attattatta ttcaaatgga tttatttatt tatttattta ttt 43

<210> SEQ ID NO 568
<211> LENGTH: 43
<212> TYPE: DNA
<213> ORGANISM: Artificial Sequence
<220> FEATURE:
<223> OTHER INFORMATION: Description of Artificial Sequence: Synthetic probe

<400> SEQUENCE: 568
attattatta tttaaatgga tttatttatt tatttattta ttt 43

<210> SEQ ID NO 569
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 569
aagtgaaaat caagcgcggg 20

<210> SEQ ID NO 570
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 570
caatttggcg acacagtcgg 20

<210> SEQ ID NO 571

<211> LENGTH: 1176
<212> TYPE: DNA
<213> ORGANISM: Homo sapiens

<400> SEQUENCE: 571

```
atgaaccctc aaattcgcaa tccgatggaa cggatgtaca gggacacatt ttacgacaat     60

tttgagaacg agcccatact ctacggtagg agctatacgt ggctttgtta tgaagtgaaa    120

atcaagcgcg ggcgcagtaa tctcctgtgg gacaccggag tatttcgagg gcaggtctat    180

ttcaaaccgc aataccatgc tgagatgtgc tttctgtcct ggttctgtgg aaatcagctg    240

cccgcgtaca aatgctttca gataacatgg ttcgtctcct ggaccccatg ccccgactgt    300

gtcgccaaat tggctgaatt tctttctgaa catccgaacg tgacgctcac aatcagcgca    360

gctcggctgt attactactg ggagcgggat tacaggcggg ctctttgtag attgtctcag    420

gccggagcta gggtcaagat catggactat gaggagttcg catactgttg ggagaacttt    480

gtgtataacg aagggcagca gtttatgccg tggtataagt ttgacgagaa ctatgccttc    540

ctgcatcgga ctttgaaaga gatacttcga tatttgatgg atcctgacac ctttactttt    600

aatttcaata atgacccccct tgtcctgcgg cgcagacaga catatctgtg ctatgaagta    660

gagcgccttg acaatgggac gtgggtgctg atggaccagc acatgggttt cctttgcaat    720

gaagcaaaaa acctgctttg cggtttctac ggtagacatg cggaactgcg gttcttggat    780

ctcgtgccca gtctccagct ggatcccgcg caaatctata gggtaacttg gttcatcagc    840

tggagtccat gtttctcatg ggctgtgcc ggagaggtca gggcttttct ccaagagaat    900

actcatgtta ggctccgcat ttcgccgcc agaatctatg actatgaccc tctctataaa    960

gaagcgctcc aaatgcttcg agacgccggc gcccaggtct ccattatgac ctacgacgaa   1020

ttcgagtatt gctgggacac ctttgtttat aggcagggct gccccttca gccatgggat   1080

gggctggagg agcactcaca agcactgagc ggcagactta gagctatact tcaaaatcag   1140

ggtaactacc catacgatgt tccagattac gcttga                              1176
```

<210> SEQ ID NO 572
<211> LENGTH: 1176
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 572

```
atgaaccctc aaattcgcaa tccgatggaa cggatgtaca gggacacatt ttacgacaat     60

tttgagaacg agcccatact ctacggtagg agctatacgt ggctttgtta tgaagtgaaa    120

atcaagcgcg ggcgcagtaa tctcctgtgg gacaccggag tatttcgagg gcaggtctat    180

ttcaaaccgc aataccatgc tgcgatgtgc tttctgtcct ggttctgtgg aaatcagctg    240

cccgcgtaca aatgctttca gataacatgg ttcgtctcct ggaccccatg ccccgactgt    300

gtcgccaaat tggctgaatt tctttctgaa catccgaacg tgacgctcac aatcagcgca    360

gctcggctgt attactactg ggagcgggat tacaggcggg ctctttgtag attgtctcag    420

gccggagcta gggtcaagat catggactat gaggagttcg catactgttg ggagaacttt    480

gtgtataacg aagggcagca gtttatgccg tggtataagt ttgacgagaa ctatgccttc    540

ctgcatcgga ctttgaaaga gatacttcga tatttgatgg atcctgacac ctttactttt    600

aatttcaata atgacccccct tgtcctgcgg cgcagacaga catatctgtg ctatgaagta    660
```

-continued

```
gagcgccttg acaatgggac gtgggtgctg atggaccagc acatgggttt cctttgcaat    720

gaagcaaaaa acctgctttg cggtttctac ggtagacatg cggcgctgcg gttcttggat    780

ctcgtgccca gtctccagct ggatcccgcg caaatctata gggtaacttg gttcatcagc    840

tggagtccat gtttctcatg ggctgtgcc  ggagaggtca gggcttttct ccaagagaat    900

actcatgtta ggctccgcat tttcgccgcc agaatctatg actatgaccc tctctataaa    960

gaagcgctcc aaatgcttcg agacgccggc gcccaggtct ccattatgac ctacgacgaa   1020

ttcgagtatt gctgggacac ctttgtttat aggcagggct gcccctttca gccatgggat   1080

gggctggagg agcactcaca agcactgagc ggcagactta gagctatact tcaaaatcag   1140

ggtaactacc catacgatgt tccagattac gcttga                             1176


<210> SEQ ID NO 573
<211> LENGTH: 21
<212> TYPE: PRT
<213> ORGANISM: Homo sapiens

<400> SEQUENCE: 573

Lys Phe Met Trp Ser Glu Ile Ser Tyr Leu Ala Lys Trp Trp Asp Ile
1               5                   10                  15

Ile Asp Ile Pro Lys
            20


<210> SEQ ID NO 574
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 574

Trp Met Lys Asn Ser Leu Lys Val His Ser Asn Ser Val Leu Glu Gln
1               5                   10                  15

Val Trp Asp Ile Phe
            20


<210> SEQ ID NO 575
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 575

Thr Lys Glu Glu Glu Asn Glu Met Tyr Asn Leu Thr Phe Phe Tyr Glu
1               5                   10                  15

Asn Leu Lys Ile Pro
            20
```

METHODS AND MATERIALS FOR TREATING CANCER

CROSS-REFERENCE TO RELATED APPLICATIONS

This application is a National Stage application under 35 U.S.C. § 371 of International Application No. PCT/US2019/024994, having an International Filing Date of Mar. 29, 2019, which claims priority to U.S. Application Ser. No. 62/751,334, filed on Oct. 26, 2018, and of U.S. Patent Application Ser. No. 62/650,171, filed on Mar. 29, 2018. The disclosures of the prior applications are considered part of (and are incorporated by reference in) the disclosure of this application.

SEQUENCE LISTING

The instant application contains a Sequence Listing which has been submitted electronically in ASCII format and is hereby incorporated by reference in its entirety. Said ASCII copy, created on Mar. 29, 2019, is named 07039-1786WO1_SL.txt and is 164,895 bytes in size.

BACKGROUND

1. Technical Field

This document relates to methods and materials for treating a mammal having cancer. For example, compositions (e.g., vaccines) containing cells (e.g., tumor cells) expressing APOBEC3 can be administered to a mammal (e.g., a human) having cancer to induce an immune response (e.g., an anti-tumor immune response) within the mammal.

2. Background Information

Pediatric high grade gliomas (pHGGs) including anaplastic astrocytoma, glioblastoma multiforme (GBM), and diffuse intrinsic pontine glioma (DIPG), manifest as an aggressive spectrum of diseases that represent a devastating and urgent unmet clinical need. Although relatively rare in children (1.78 per 100 000), patients are faced with a dismal prognosis with a two year median survival ranging from 30% for cerebral cortex located tumors, to less than 10% for pontine located tumors (Jones, Nat Rev Cancer 14, doi: 10.1038/nrc3811 (2014); and Mackay et al. Cancer Cell 32:520-537 (2017)).

SUMMARY

This document provides methods and materials related to treating a mammal having cancer. For example, this document provides compositions (e.g., vaccines) containing cells (e.g., tumor cells) expressing probable DNA dC→dU-editing enzyme (APOBEC3) polypeptides. The compositions (e.g., vaccines) provided herein can be administered to a mammal (e.g., a human) having cancer to induce an immune response (e.g., an anti-tumor immune response) within the mammal.

As demonstrated herein, tumor cells overexpressing an APOBEC3B polypeptide generate a library of heteroclictic epitopes which prime both CD4 and CD8 T cells that have escaped central tolerance and which recognize newly mutated antigens from the vaccine. These T cells generated against the APOBEC3B-induced somatic mutations in the tumor cell vaccine were able to cross react with unaltered self-epitopes expressed on the tumor cells. As also demonstrated herein, the acquired mutational burden on APOBEC3B overexpressing melanoma tumor cells included neoantigens (e.g., tumor-specific antigens) having epitopes with a MHC class I higher binding affinity than the wild type antigens. These results demonstrate that ex vivo production of a tumor antigen loaded autologous DC can facilitate T cell priming in situ. The ability to induce these neoantigens provides an opportunity to generate a CD8 T cell response and/or a CD4 T cell response that cross-reacts with tumor cells to mediate anti-tumor therapy (e.g., an anti-tumor T cell response).

In general, one aspect of this document features methods for treating a cancer in a mammal. The methods can include, or consist essentially of, administering to the mammal a composition comprising one or more tumor cells expressing APOBEC3 (e.g., tumor cells expressing an APOBEC3 polypeptide from exogenous nucleic acid such as nucleic acid of a viral vector). The tumor cells can be obtained from the mammal to be treated. The tumor cells can be obtained from a donor mammal. The mammal can be a human. The cancer can be a glioma, a melanoma, a prostate cancer, a lung cancer, or a colon cancer. In some cases, the cancer can be a melanoma. In some cases, the cancer can be a glioma such as a high-grade glioma (e.g., anaplastic astrocytoma, glioblastoma multiforme, and diffuse intrinsic pontine glioma). The method also can include administering one or more immune checkpoint inhibitors to the mammal. The immune checkpoint inhibitors can be an anti-PD-1 antibody, an anti-PD-L1 antibody, an anti-CLTA4 antibody, an anti-Tim3 antibody, or a combination thereof. In some cases, the one or more tumor cells expressing APOBEC3 and the one or more immune checkpoint inhibitors can be administered to the mammal at the same time. In some cases, the one or more tumor cells expressing APOBEC3 and the one or more immune checkpoint inhibitors can be administered to the mammal independently.

In another aspect, this document features methods for inducing an anti-tumor immune response in a mammal having cancer. The methods can include, or consist essentially of, administering to the mammal a composition comprising one or more tumor cells expressing APOBEC3 (e.g., tumor cells expressing an APOBEC3 polypeptide from exogenous nucleic acid such as nucleic acid of a viral vector). The tumor cells can be obtained from the mammal to be treated. The tumor cells can be obtained from a donor mammal. The mammal can be a human. The cancer can be a melanoma. The cancer can be a glioma such as a high-grade glioma (e.g., anaplastic astrocytoma, glioblastoma multiforme, and diffuse intrinsic pontine glioma). The method also can include administering one or more immune checkpoint inhibitors to the mammal. The immune checkpoint inhibitors can be an anti-PD-1 antibody, an anti-PD-L1 antibody, an anti-CLTA4 antibody, an anti-Tim3 antibody, or a combination thereof. In some cases, the one or more tumor cells expressing APOBEC3 and the one or more immune checkpoint inhibitors can be administered to the mammal at the same time. In some cases, the one or more tumor cells expressing APOBEC3 and the one or more immune checkpoint inhibitors can be administered to the mammal independently.

In another aspect, this document features a composition including one or more tumor cells having nucleic acid encoding an APOEBC3 polypeptide (e.g., exogenous nucleic acid encoding an APOBEC3 polypeptide) under conditions where the cells express APOEBC3 polypeptides and the APOEBC3 polypeptides generate a library of tumor antigens. The APOEBC3 polypeptides can be human APOEBC3 polypeptides. The APOEBC3 polypeptides can be APOEBC3B polypeptides. The tumor antigens can include one or more self antigens. The tumor antigens can include one or more non-self antigens. The tumor antigens can include one or more heteroclitic mutations. The tumor antigens can include one or more neoantigens. The nucleic acid encoding an APOEBC3 polypeptide can be a viral vector. The viral vector can be an adenoviral vector, an adeno-associated virus (AAV) vector, a lentiviral vector, or a retroviral vector. The nucleic acid encoding an APOEBC3 polypeptide can be an expression plasmid. The one or more tumor cells can be present within a dendritic cell, and the dendritic cell can present the library of tumor antigens.

In another aspect, this document features a method for identifying tumor antigens in a mammal having cancer. The methods can include, or consist essentially of, administering a composition including one or more tumor cells expressing an APOBEC3 polypeptide (e.g., tumor cells expressing an APOBEC3 polypeptide from exogenous nucleic acid such as nucleic acid of a viral vector) to cancer cells obtained from a mammal having cancer under conditions where the tumor cells expressing the APOBEC3 polypeptide can induce one or more missense mutations in a tumor antigen present in the cancer cells obtained from the mammal; and identifying said the missense mutation(s). The APOEBC3 polypeptide can be an APOEBC3B polypeptide. The mammal can be a human. The APOEBC3 polypeptide can be a human APOEBC3 polypeptide. The cancer can be a melanoma. The cancer can be a glioma. The method also can include administering one or more immune checkpoint inhibitors to the cancer cells obtained from the mammal. An immune checkpoint inhibitor can be an anti-PD-1 antibody, an anti-PD-L1 antibody, an anti-CLTA4 antibody, an anti-Tim3 antibody, or a combination thereof. The identifying step can include whole genome sequencing. The method also can include validating the missense mutation(s). The validating step can include using an in silico major histocompatibility complex (MHC) binding affinity algorithm. The tumor antigen including one or more missense mutations can be a heteroclitic peptide.

In another aspect, this document features a method for making a tumor cell capable of creating tumor antigens. The methods can include, or consist essentially of, introducing a nucleic acid encoding an APOBEC3 polypeptide into a cancer cell. The APOEBC3 polypeptide can be an APOEBC3B polypeptide. The cancer cell can be a human cancer cell. The APOEBC3 polypeptide can be a human APOEBC3 polypeptide. The cancer cell can be a melanoma cell. The cancer cell can be a glioma cell. The cancer cell can express satheid APOBEC3 polypeptide.

In another aspect, this document features a composition comprising, or consisting essentially of, a cell having a polypeptide comprising the amino acid sequence of SEQ ID NO:4, 6, 8, 10, 12, 14, 16, 18, 20, or 22. The cell can be a cancer cell. The polypeptide can comprise the amino acid sequence of SEQ ID NO:8. The cell can comprise exogenous nucleic acid encoding an APOBEC3 polypeptide.

In another aspect, this document features a method for treating a cancer in a mammal. The method comprises, or consists essentially of, administering to the mammal a composition comprising, or consisting essentially of, a cell having a polypeptide comprising the amino acid sequence of SEQ ID NO:4, 6, 8, 10, 12, 14, 16, 18, 20, or 22. The cell can be a cancer cell. The polypeptide can comprise the amino acid sequence of SEQ ID NO:8. The cell can comprise exogenous nucleic acid encoding an APOBEC3 polypeptide.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 16 (Table 1). Amino acid changes induced by APOBEC3B. Mutations that resulted in a G to A or C to T transitions and an amino acid change.

FIG. 17 (Table 2). Generation of 21mer mutant and wild type peptides. Missense mutations from Table 1 were translated into peptides with the missense mutation flanked by 10 amino acids on each side, as well as corresponding peptides with the wild type amino acid sequence. Peptides shown include SEQ ID NOs: 25-566.

FIG. 20. The APOBEC3B expressed from the lentiviral vector has catalytic function. (A) Assay principle. A fluorescent probe (SEQ ID NO:567) containing a single APOBEC3B target site (underlined) will be mutated in the presence of APOBEC3B to a mutated fluorescent probe (SEQ ID NO:568). This mutated site can be modified by UDG and cleaved by alkali treatment. Smaller cleavage products thus indicate the presence of APOBEC3B activity (see, e.g., Akre et al., *PLoS ONE* 11(5): e0155391 (2016)). (B) 293T transduced with a lentiviral vector expressing the WT or CM (catalytic mutant) human APOBEC3B. Cells were selected for 7 days in puromycin and lysed in HED buffer. Lysates were incubated for 1 hour at 37° C. with in the presence of UDG with the 43-bp 3' FITC probe. Reactions were treated with 2M NAOH, heated at 95° C. for 10 minutes and run on a 15% TBE urea gel and imaged it with a Typhoon imager. (C) SOH cells were transduced at an MOI of 2 with Lentivirus expressing the WT or CM (catalytic mutant) human APOBEC3B. 3 days post transduction, lysates were incubated with 3' FITC substrate described in panel A for the indicated periods of time.

FIG. 22. An exemplary nucleic acid expressing a wild type, human APOBEC3B polypeptide (SEQ ID NO:571).

FIG. 23. An exemplary nucleic acid expressing a catalytically inactive APOBEC3B polypeptide (SEQ ID NO:572). Nucleotides that are modified relative a nucleic acid expressing a wild type, human APOBEC3B polypeptide are shown in bold font.

DETAILED DESCRIPTION

Figure 1A:
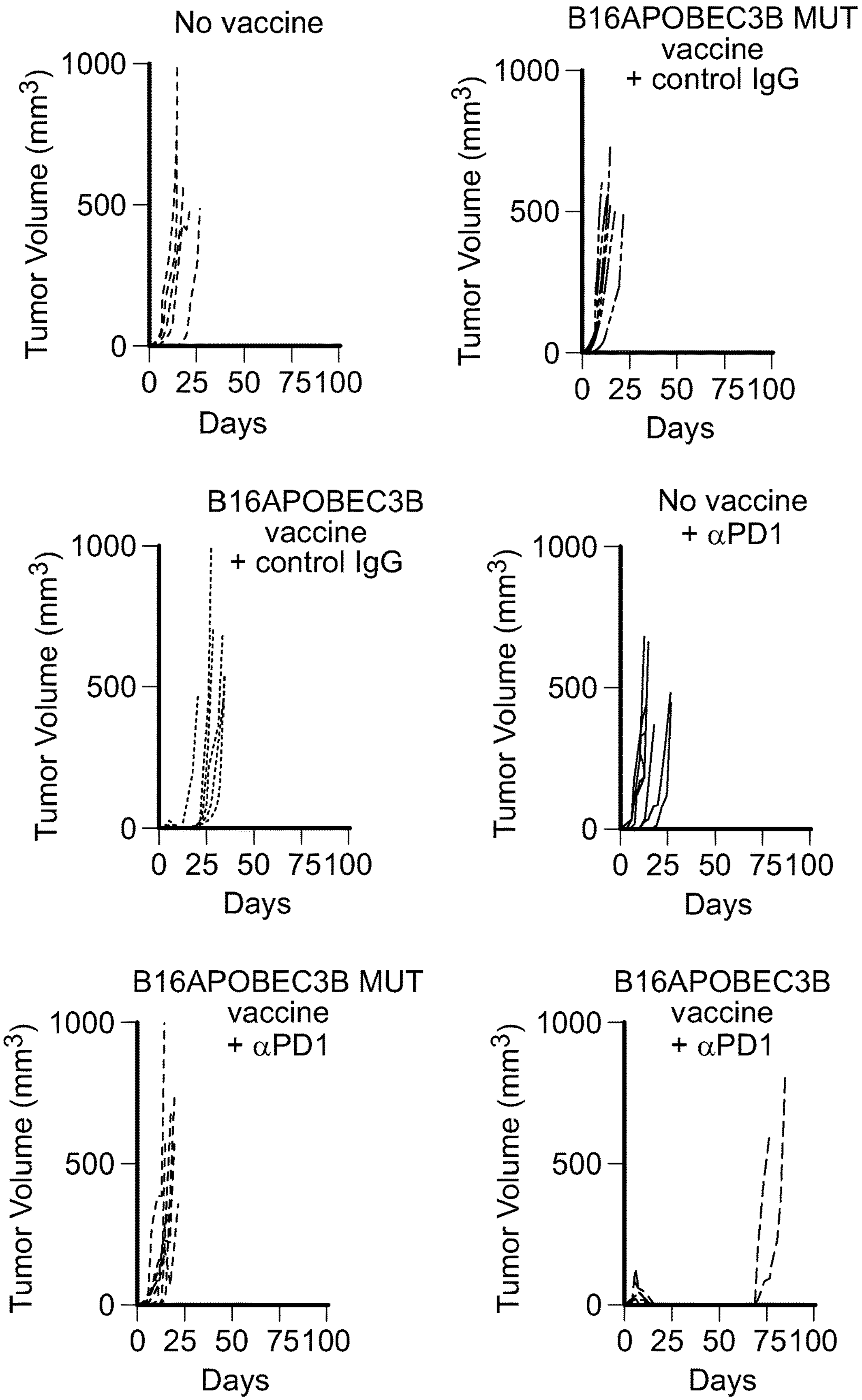
FIG. 1. (A) C57BL/6 bearing subcutaneous B16 tumors were treated with freeze-thawed B16APOBEC3B or B16APOBEC3B MUT vaccine for 5 consecutive days beginning on day 5. Anti-PD1 was administered 3 times per week for two weeks beginning on day 12. (B) As described in A with CD8, CD4 or NK depletion concurrent with anti-PD1. (C) In vitro splenocyte cytokine recall from mice treated in A and co-cultured with parental B16 cells.

This document provides methods and materials related to treating a mammal having cancer. For example, this document provides compositions (e.g., vaccines) for treating cancer. The term "vaccine" as used herein refers to immunogenic compositions that are administered to a mammal for the prevention, amelioration, or treatment of diseases (e.g., cancer). In some cases, compositions provided herein can contain cells (e.g., tumor cells) expressing APOBEC3 which can generate antigens (e.g., neoantigens) having epitopes (e.g., mutated epitopes) which are immunogenic in a mammal having cancer. This document also provides methods for treating a mammal having cancer. For example, the compositions (e.g., vaccines) provided herein can be administered to a mammal (e.g., a human) having cancer to induce an immune response (e.g., an anti-tumor immune response) within the mammal. An anti-tumor immune response can be effective to reduce the severity of the cancer, to reduce a symptom of the cancer, and/or to reduce the number of cancer cells present within the mammal. A vaccine administered to a mammal can induce a protective immune response and/or a therapeutic immune response.

Expression of APOBEC3 in a cell (e.g., a tumor cell) can induce mutations (e.g., somatic mutations) which generate a library of antigens (e.g., tumor antigens such as mutated tumor antigens) reflecting a transcriptional profile of the cell (e.g., self-antigens, self-peptides, and self-epitopes). For example, a tumor cell expressing APOBEC3B can include a library of mutated tumor-specific antigens. In some cases, the library of antigens can include altered self-antigens, altered self-peptides, and/or altered self-epitopes.

Expression of APOBEC3 in a cell (e.g., a tumor cell) can generate any appropriate antigens. In some cases, an antigen can be a tumor antigen (e.g., a mutated tumor antigen). In some cases, an antigen can be a heteroclitic antigen. In some cases, an antigen can be a neoantigen. In some cases, an antigen can include one or more mutations (e.g., pre-existing mutations and/or non-pre-existing mutations). For example, when an antigen includes a mutation, the mutation can be a heteroclitic mutation. In some cases, an antigen can be a self-antigen. In some cases, an antigen can be a non-self antigen (e.g., a xenogenic or foreign antigen such as a viral peptide).

Any appropriate cell can be used in compositions (e.g., vaccines) described herein (e.g., containing one or more cells (e.g., tumor cells) expressing APOBEC3). In some cases, a cell can be a tumor cell. In some cases, a cell expressing APOBEC3 can be an autologous cell (e.g., from the mammal to be treated as described herein). In some cases, a cell expressing APOBEC3 can be an allogeneic cell (e.g., from a mammal other than the mammal to be treated, such as cells from a donor mammal or a cells from a mammalian cell line).

Compositions (e.g., vaccines) described herein (e.g., containing one or more cells (e.g., tumor cells) expressing APOBEC3) can include one or more cells expressing any appropriate APOBEC3. In some cases, the APOBEC3 polypeptide can be from any appropriate source. For example, the APOBEC3 can be a human APOBEC3 (e.g., any one APOBEC3A though APOBEC3BH, or any combination thereof). For example, the APOBEC3 can be a murine APOBEC3. For example, the APOBEC3 polypeptide can be a recombinant (e.g., chimeric) APOBEC3 polypeptide. In some cases, an APOBEC3 polypeptide can be an APOBEC3B polypeptide.

In some cases, compositions (e.g., vaccines) described herein (e.g., containing one or more cells (e.g., tumor cells) expressing APOBEC3) can include one or more cells modified to express APOBEC3 polypeptides. APOBEC3 can be expressed using any appropriate method. In some cases, a nucleic acid expressing APOBEC3 can be introduced into a cell (e.g., a cell to be used in a composition described herein). A nucleic acid expressing APOBEC3 can be any appropriate type of nucleic acid (e.g., DNA, RNA, or a combination thereof). In some cases, nucleic acid expressing an APOBEC3B polypeptide can include the nucleic acid sequence set forth in SEQ ID NO:571 (FIG. 22). Examples of nucleic acids that can be used to express APOBEC3 polypeptides include, without limitation, expression plasmids and viral vectors (e.g., adenoviral, AAV, lentiviral such as HIV-based lentiviral, or retroviral vectors). Nucleic acids that can be used to express APOBEC3 polypeptides can be introduced into a cell using any appropriate method. Examples of methods that can be used to introduce nucleic acids into cells include, without limitation, transfection and electroporation.

Compositions (e.g., vaccines) described herein (e.g., containing one or more cells (e.g., tumor cells) expressing APOBEC3) can be administered to a mammal using any appropriate method. In some cases, compositions described herein can be administered to a mammal in the absence of any delivery vehicle. In some cases, compositions described herein can be administered to a mammal using a delivery vehicle such as one or more antigen-presenting cells (e.g., dendritic cells, macrophages, and B cells). For example, one or more cells expressing APOBEC3 polypeptides can be loaded into dendritic cells, and the dendritic cells containing the cells expressing APOBEC3 polypeptides can be administered to a mammal.

Any appropriate mammal having cancer can be treated as described herein. For example, humans and other primates such as monkeys having cancer can be treated with compositions (e.g., vaccines) described herein (e.g., containing one or more cells (e.g., tumor cells) expressing APOBEC3) induce an immune response (e.g., an anti-tumor immune response) within the mammal within the human or other primate. In some cases, dogs, cats, horses, cows, pigs, sheep, mice, and rats having cancer can be treated with a composition (e.g., vaccine) described herein.

When treating a mammal (e.g., a human) having a cancer as described herein, the cancer can be any appropriate cancer. In some cases, a cancer treated as described herein can have a low mutational burden. Examples of cancers that can be treated as described herein include, without limitation, glioma (e.g., pediatric high grade gliomas (pHGGs) including anaplastic astrocytoma, glioblastoma multiforme (GBM), and diffuse intrinsic pontine glioma (DIPG)), melanoma, prostate cancer, lung cancer (e.g., non-small cell lung cancer), and colon cancer.

Once identified as having a cancer (e.g., glioma), a mammal can be administered a composition (e.g., a vaccine) described herein (e.g., containing one or more cells (e.g., tumor cells) expressing APOBEC3). In some cases, methods described herein can include identifying a mammal as having a cancer (e.g., a glioma). Any appropriate method can be used to identify a mammal having cancer. For example, imaging techniques and biopsy techniques can be used to identify mammals (e.g., humans) having cancer.

In some cases, a composition (e.g., a vaccine) described herein (e.g., containing one or more cells (e.g., tumor cells) expressing APOBEC3) can be administered to a mammal having a cancer as a combination therapy with one or more additional agents used to treat a cancer. The one or more additional agents used to treat a cancer can include any appropriate cancer treatments. In some cases, a cancer treatment can include surgery. In some cases, a cancer treatment can include radiation therapy. In some cases, a cancer treatment can include administration of a pharmacotherapy such as a chemotherapy, hormone therapy, targeted therapy, and/or cytotoxic therapy. Examples of cancer treatments include, without limitation, administration of one or more immune checkpoint inhibitors (e.g., anti-PD-1, anti-PD-L1, anti-CLTA4, and/or anti-Tim3 antibodies). For example, a mammal having cancer can be administered a vaccine containing one or more tumor cells expressing APOBEC3 and administered one or more immune checkpoint inhibitors. In cases where a mammal having cancer is treated with a vaccine containing one or more tumor cells expressing APOBEC3 and administered and is treated with one or more immune checkpoint inhibitors, the one or more immune checkpoint inhibitors can be administered at the same time or independently. For example, the vaccine containing one or more tumor cells expressing APOBEC3 can be administered first, and the one or more immune checkpoint inhibitors administered second, or vice versa.

The invention will be further described in the following examples, which do not limit the scope of the invention described in the claims.

EXAMPLES

Example 1: Identifying a New Class of Tumor Antigens

The family of APOBEC3 cytosine deaminase enzymes catalyze cytosine to uracil deamination of single stranded DNA (ssDNA) to generate C to T transitions, and to a lesser frequency C to G transversion mutations.

Figure 1B:
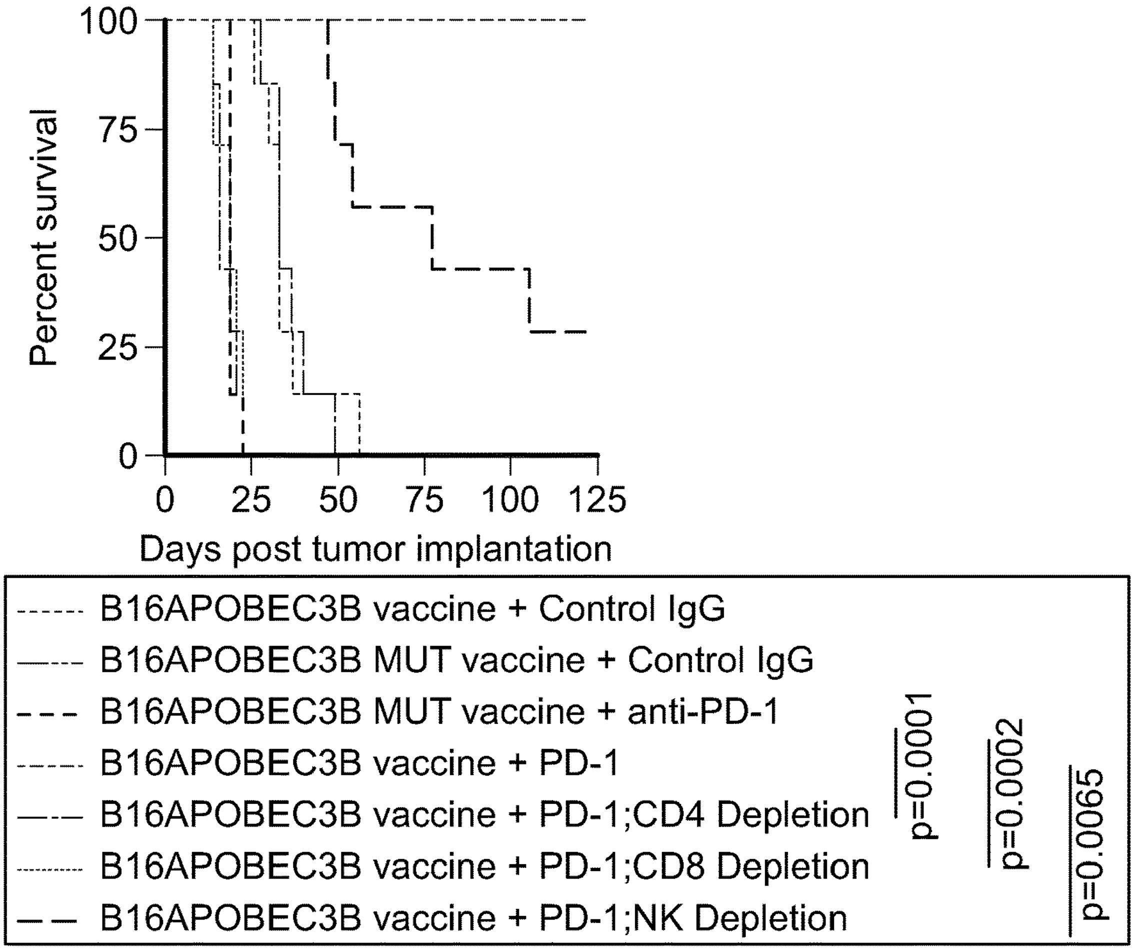
Figure 1C:
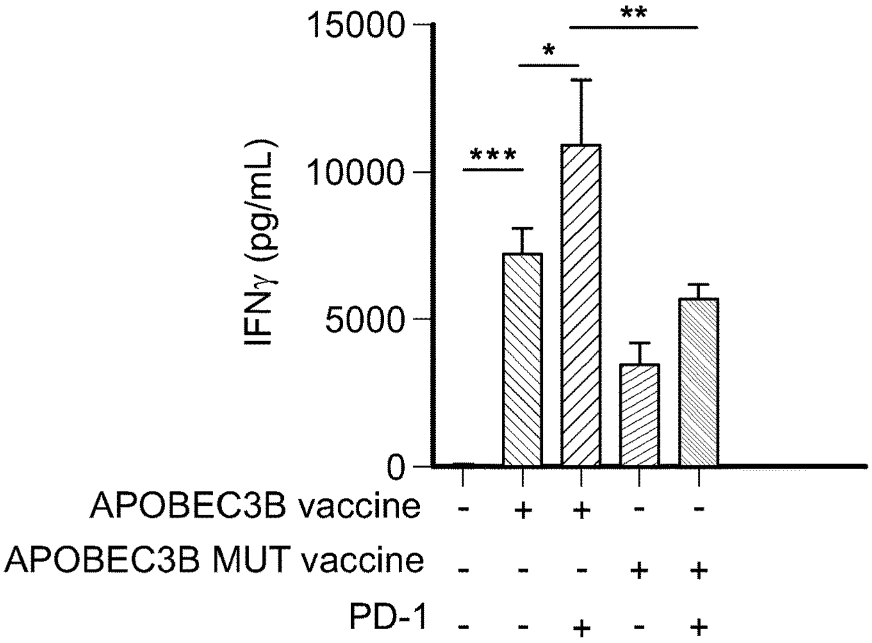

Whether a freeze-thawed whole tumor cell vaccine prepared from B16 melanoma cells stably overexpressing human APOBEC3B, or a catalytically inactive mutant (APOBEC3B MUT), could treat established subcutaneous parental B16 tumors was evaluated. While the B16APOBEC3B vaccine could modestly slow tumor growth as a single agent, a synergistic therapeutic effect was observed when combined with PD-1 checkpoint blockade and led to cures in 75-100% of mice (FIG. 1A, B). In contrast, the vaccine produced from B16 cells overexpressing the catalytically inactive APOBEC3B did not provide any tumor control even in combination with anti-PD1. These data confirmed that APOEBEC3B induced mutations were necessary over and above the endogenous neoepitope repertoire of parental B16 cells to prime an adaptive anti-tumor response. Both a CD4 and CD8 response was elicited by vaccination, as depletion of either cellular compartment abrogated therapy (FIG. 1B). Moreover, T cells isolated from mice treated with the vaccine and anti-PD1 as in FIG. 1A produced very high levels of interferon (IFN)-γ when co-cultured with parental unmodified B16 melanoma cells, the magnitude of which correlated with the observed therapeutic activity (FIG. 1C). Of particular importance, no evidence of vitiligo associated with the APOBEC3B vaccine was seen, despite the robust anti-tumor therapy.

Figure 2A:
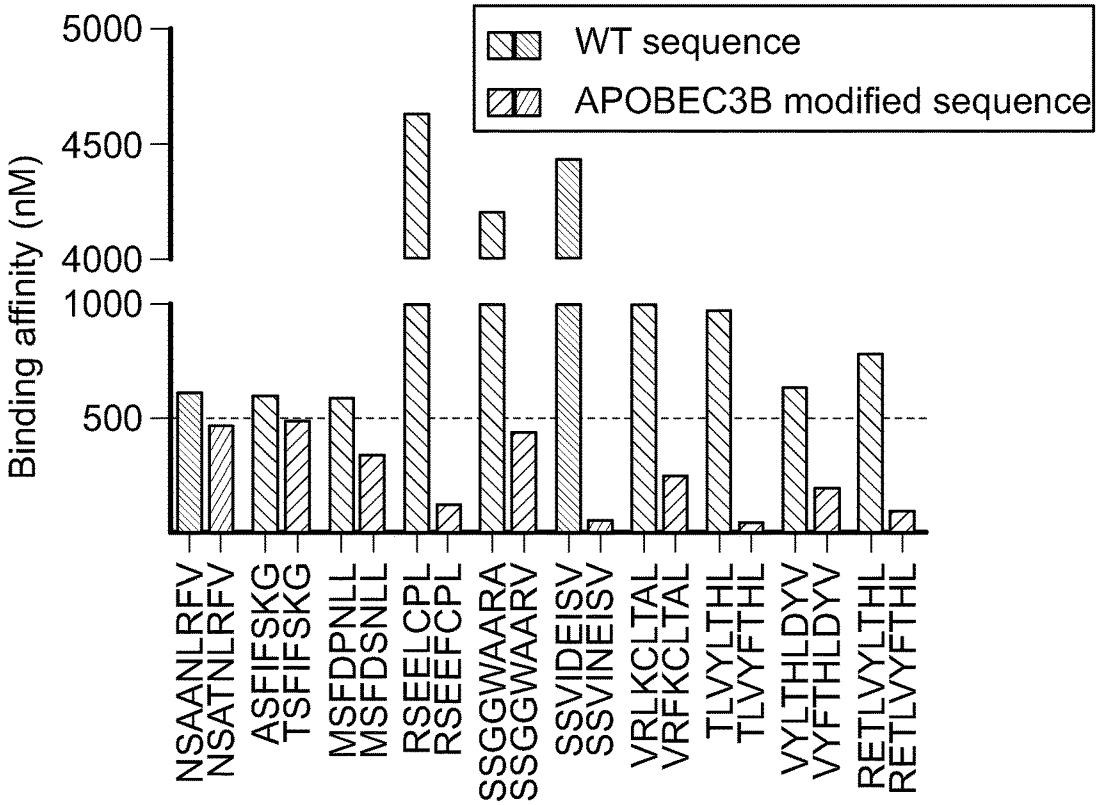
FIG. 2A discloses SEQ ID NOS 3-22, respectively, in order of appearance. (B) Splenocytes from mice vaccinated with five doses of the B16APOBEC3B or B16APOBEC3BMUT vaccine were co-cultured with B16 cells transfected with a polyepitope construct expressing the wild type or the APOBEC3B mutations identified from A.
Figure 2B:
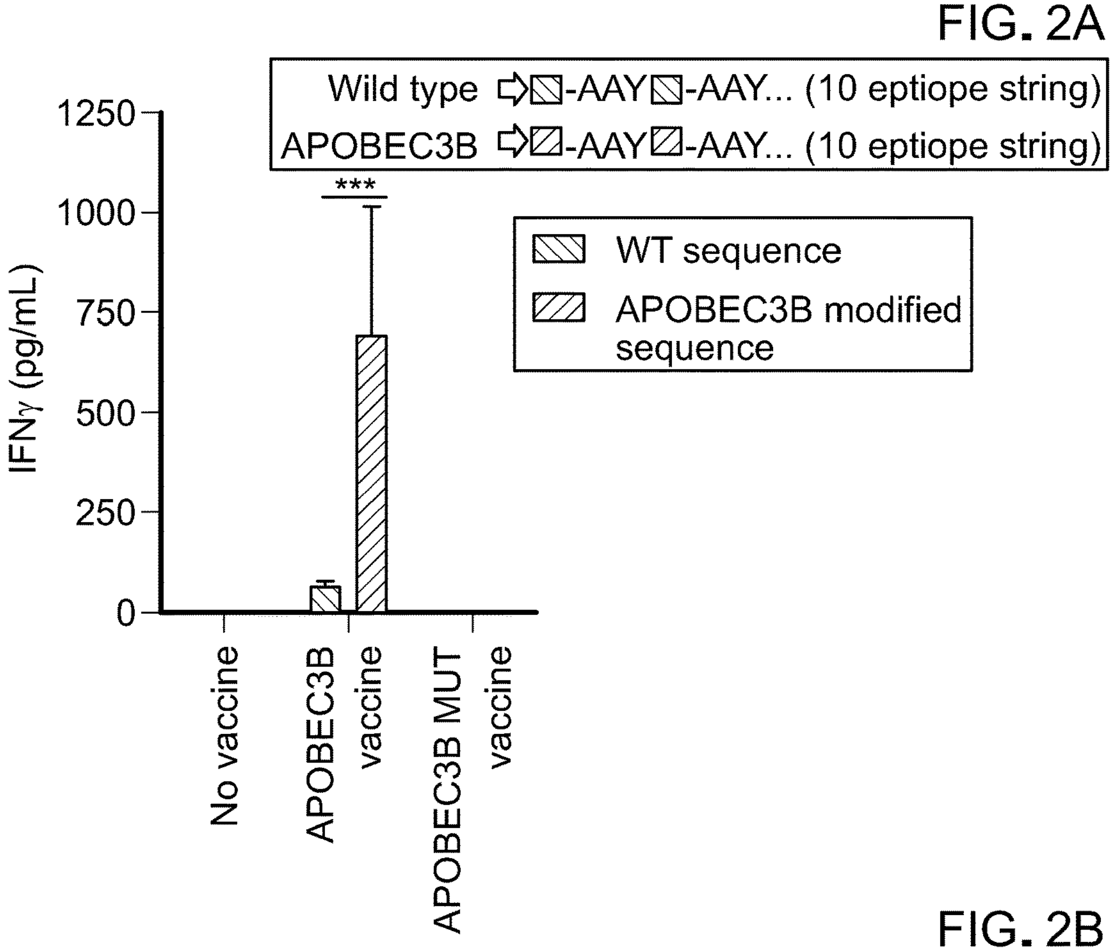
FIG. 2. (A) Predicted binding affinity to $H2K^b$ (darker shades) or $H2D^b$ (lighter shades) of peptides encoding non-synonymous mutations identified from the B16APOBEC3B overexpressing cell line using NetMHC4.0. Bolded letter indicates mutation.

Whole genome sequencing of B16 APOBEC3B and APOBEC3B MUT overexpressing cell lines revealed the presence of 301 C to T or G to A missense mutations which were unique to the APOBEC3B line. These coding variants specific to the APOBEC3B cell line were filtered through an in silico MHC binding affinity algorithm to identify octamer or nonamer peptides whose increase binding affinity for $H2K^b$ or $H2K^d$ was below a threshold of 500 nM. A list of 36 candidates was further refined using the EMBL-EBI Expression Atlas for expression in skin tissue to identify 10 high affinity APOBEC3B-induced heteroclitic peptides (FIG. 2A). Expression constructs were generated to encode a 10 polyepitope string separated by Ala-Ala-Tyr (AAY) spacers between the epitopes (see, e.g., Velders et al., J Immunol 166:5366-5373 (2001)) and tagged with an N-end degron motif (see, e.g., Varshaysky, Protein Sci 20, 1298-1345, doi:10.1002/pro.666 (2011)), and transfected into B16 melanoma cells. The ability of the B16 cells modified by APOBEC3B to prime T cells against these heteroclitic peptide candidates was experimentally validated in vitro (FIG. 2B). A specific IFNγ recall response was detected from the T cells of mice vaccinated with the APOBEC3B vaccine upon restimulation with either the APOBEC3B-modified polyepitope construct or the wild-type polyepitope construct. Although the IFNγ recall response from APOBEC3B vaccinated mice to the wild type sequences was significantly lower than to the mutated sequences, it was nonetheless clearly detectable. In contrast, no IFNγ was detected in response to the wild type or mutated constructs from APOBEC3B MUT vaccinated mice.

Figure 3A:
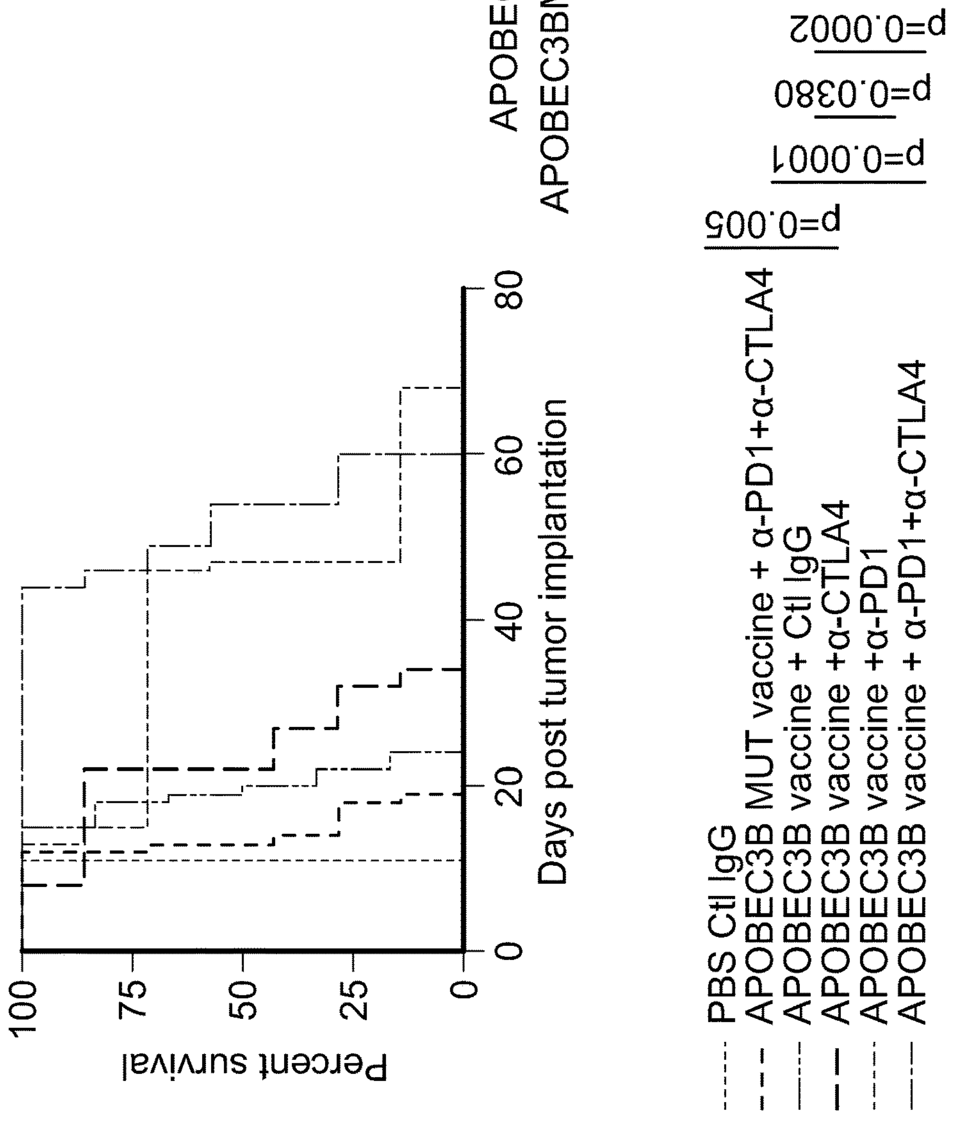
FIG. 3. (A) GL261 cells were implanted into C57BL/6 mice and treated with a freeze thawed APOEBC3B or APOBEC3B MUT modified GL261 cell vaccine for 5 consecutive days beginning on day 5. Immune checkpoint inhibitors were administered 3 times per week for 2 weeks beginning on day 5. (B) Splenocytes from mice treated as in A were co-cultured with parental GL261 cells and IFNγ was measured by ELISA. No additional checkpoint inhibitors were included in the in vitro assay.
Figure 3B:
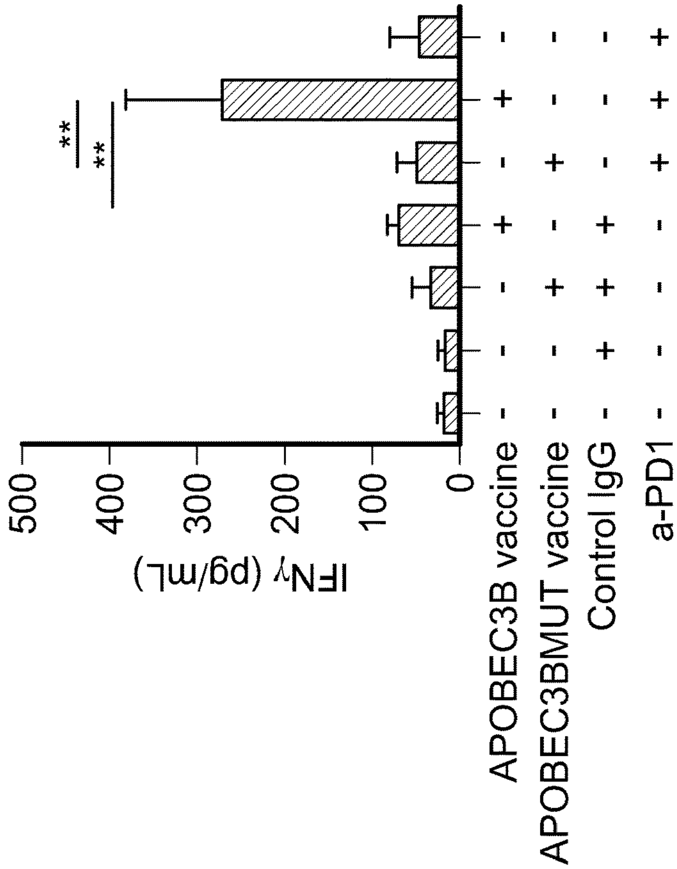

The B16 melanoma model was a useful proof of concept for the altered-self library strategy, and whether the approach could be extended to an orthotopic brainstem model of HGG was determined. The location of the tumor in the brainstem poses potential problems for therapeutic approaches for this disease, including the risk of toxicity associated with an inflammatory reaction in an anatomically important region. Nonetheless, GL261 cells stereotactically implanted into the brainstem using previously published coordinates (Caretti, Brain Pathol 21:441-451 (2011)) were significantly responsive to treatment with an APOBEC3B-modified GL261 vaccine in combination with anti-PD-1 checkpoint blockade (FIG. 3A). Importantly, neither acute nor chronic symptoms that could be associated with the therapy, or that could be indicative of neurological autoimmunity, were observed prior to sacrifice due to tumor burden. The priming of a T cell response by the APOBEC3B-modified GL261 vaccine was confirmed in vitro following co-culture of splenocytes from mice treated as in FIG. 3A with parental unmodified GL261 cells (FIG. 3B). As seen in the B16 vaccination model, the APOBEC3B-modified vaccine primed a modest T cell response that was significantly amplified through anti-PD-1 blockade.

Figure 4:
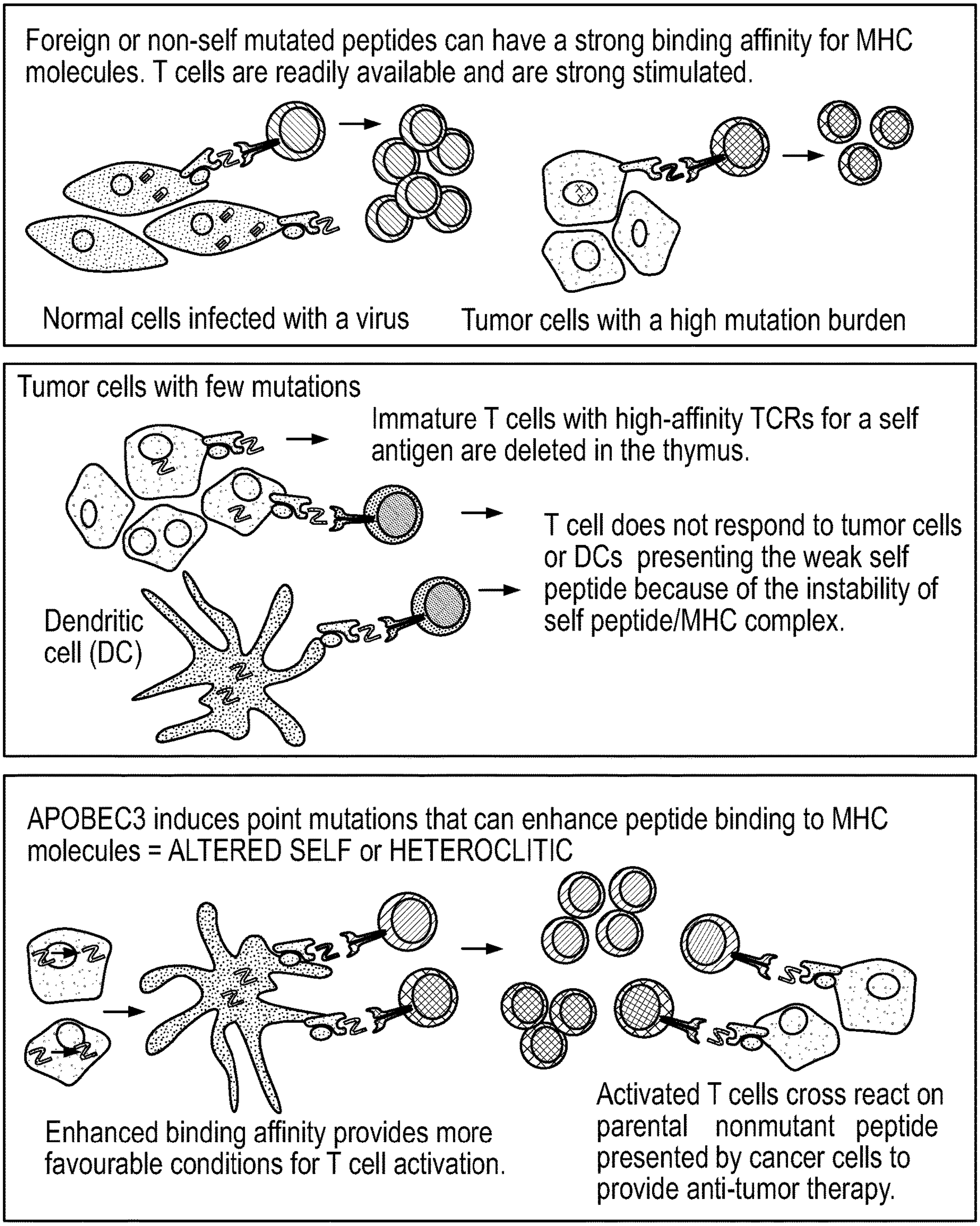
FIG. 4. Schematic representation of the APOBEC3B-modified altered self tumor cell vaccination approach.

Cumulatively, these data show that, when overexpressed in tumor cells, APOBEC3B generates a library of heteroclitic sequences which primes both CD4 and CD8 T cells that have escaped central tolerance and which recognize newly mutated antigens from the vaccine. Critically, these T cells generated against the APOBEC3B-induced somatic mutations in the cell vaccine are also able to recognize the corresponding unaltered self epitopes expressed on the tumor cells (Summarized in FIG. 4). There are three core principles that underlie the current proposal: (1) Dendritic cells are the most potent antigen presenting cell type and ex vivo differentiation, maturation, and loading of antigen, circumvents tumor microenvironmental limitations; (2) a paucity of targetable immunogenic neoepitopes in a tumor can be overcome through the introduction of mutations ex vivo which function as heteroclitic peptides in a vaccination setting; and (3) integration of immune checkpoint blockade (ICB) into the vaccination schedule amplifies the anti-tumor T cell response to provide a synergistic therapeutic effect.

Figure 5A:
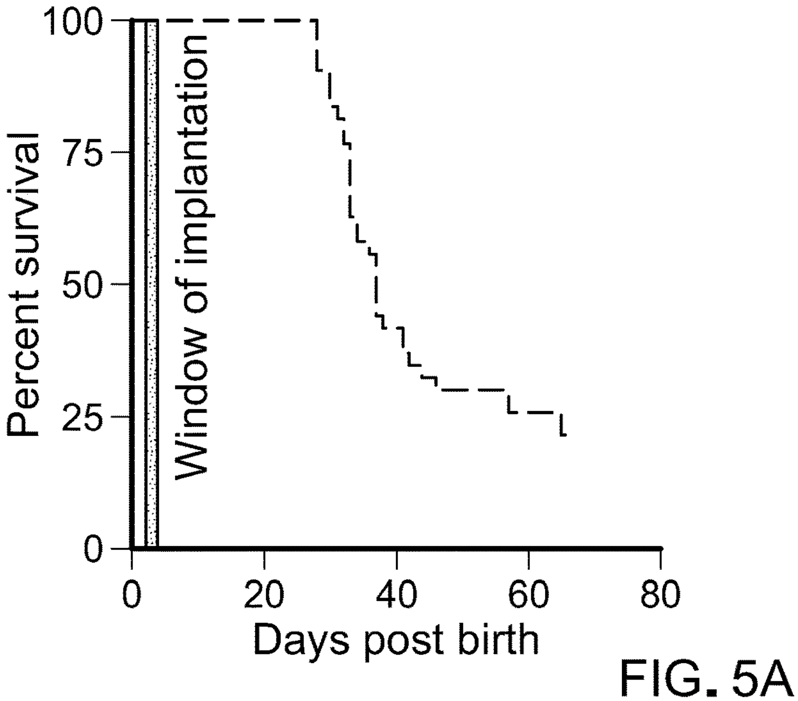
FIG. 5. RCAS DIPG genetically engineered mouse model. DF-1 producer cells are injected into the brainstem of Nestin tv-a/p53 foxed neonatal mice (Postnatal day 3-4). Viruses encoding PDGFB, Cre, and, H3.3 K27M infect Nestin expressing cells. Tumor symptoms develop within 4-6 weeks (A). H&E reveals that tumors exhibit high-grade characteristics and infiltrate adjacent brain parenchyma (B). Tumors grow out of midbrain and pons structures (C).
Figure 5B:
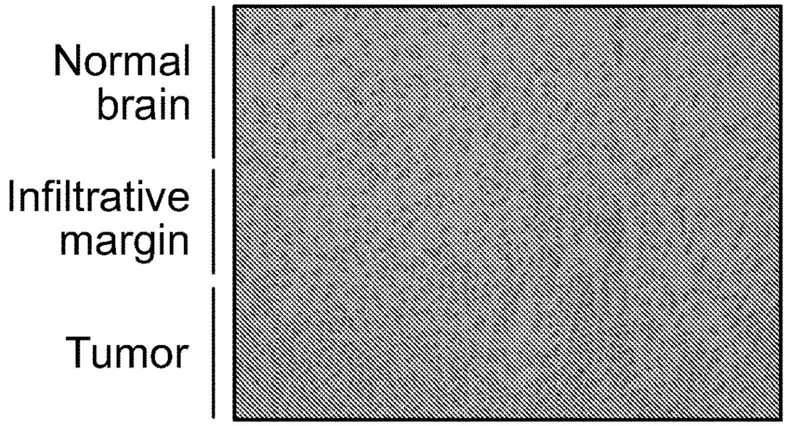
Figure 5C:
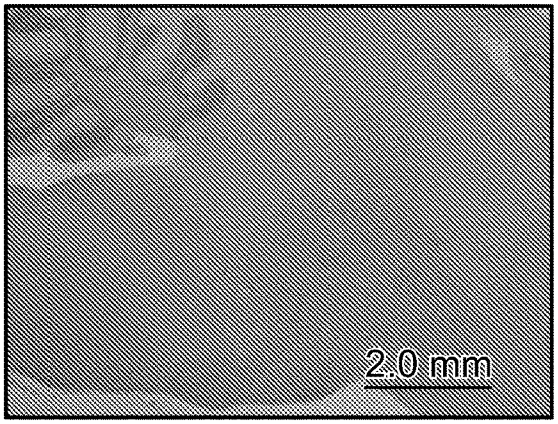

Example 2: APOBEC3B Tumor Cell Vaccine Platform in a Genetically Engineered Mouse Model of pHGG GL261 tumors are a modestly representative model of HGG and can be implanted into the brainstem. However, they do not recapitulate the molecular features that are unique to pediatric HGGs. Antigenetically engineered mouse model (GEMNI), which anatomically and molecularly captures the features of DIPG was used. The tumors arise from Nestin expressing neural progenitor cells which are thought to be the cell of origin of DIPGs (Becher et al., Cancer Res 70:2548-2557 (2010)), and progress in the context of the developing brain under the influence of immunoediting. A breeding colony was established for the Nestin tv-a/p53 floxed mice and validated that when DF-1 producer cells transfected with the RCAS plasmids are injected directly into the brainstem of neonatal mice, brainstem tumors develop within approximately 4-6 weeks post injection and necessitate euthanasia (Halvorson et al., PLoS One 10:e0118926 (2015)) (FIG. 5A). It was confirmed histologically that the tumors are located in the pons or midbrain regions of the animals and that the tumor is invasive into the adjacent brain parenchyma (FIGS. 5B and C).

APOBEC3B mutational burden induced through various vector or transfection platforms for therapeutic vaccination. Using an explanted cell line from the RCAS DIPG model, and a retroviral pBABE vector encoding APOBEC3B, it was validated the APOBEC3B modified tumor vaccines can prime an adaptive T cell response to provide therapy in this genetically engineered mouse model in an analogous manner to the B16 and GL261 models. To translate this concept to a clinical approach, it was functionally defined how the duration and expression level of APOBEC3B correlates with (1) the frequency and reproducibility of the induced mutations in tumor lines, (2) the magnitude of the CD4 and CD8 T cell response, and (3) the overall therapeutic value of the vaccine in the GL261 orthotopic model and the RCAS DIPG GEMM.

Although the retroviral expression system has worked well, alternative methods to introduce APOBEC3B were explored that provide more transient expression and which may be more amenable to meet FDA requirements for product manufacture. To this end, an E1/E3 deleted replication incompetent Adenovirus was constructed using the ViraPower Adenoviral Expression System (ThermoFisher) that expresses APOBEC3B using an inducible Cre-LoxP system and has enabled us to overcome difficulties associated with overexpression of APOBEC3B during viral rescue. A pCDNA plasmid construct expressing APOBEC3B was used. Retrovirus or adenovirus infection or plasmid transfection is conducted at various multiplicities of infection (MOIs) or concentrations of DNA, and cellular RNA is isolated following multiple population doublings for RNA sequencing using the TruSeq Stranded mRNA Library Prep Kit (Illumina). The coding transcriptome was interrogated to simultaneously identify single nucleotide variants and short indels introduced by APOBEC3B, and to provide an abundance value for both APOBEC3B and putative neoepitope peptides, as the MHC immunopeptidome is enriched in peptides derived from highly abundant transcripts (Fortier et al., J Exp Med 205: 595-610 (2008)). RNA-seq analysis is done in collaboration with the Biostatistics and Bioinformatics Core at Mayo Clinic. Briefly, reads from the parental explanted cell line, as well as those from the APOBEC3B-modified lines, is mapped to the mouse genome (GRCm38/mm10) using the STAR aligner. RNA-seq identified variants is called using the Broad Institute's Unified Genotyper and Haplotype Caller from their Genome Analysis Tool Kit, and an expression value will be quantified for each gene from Subread's featureCounts software. Variants will be filtered and annotated using multiple tools including; Ensembl's Variant Effect Predictor, Harvard's SIFT/PolyPhen, and the Wellcome Trust Centre's Clinical Annotation of Variants algorithms to identify C to T missense mutations with an adjacent 5'T to identify likely APOBEC3B induced mutations. Finally, candidate 15-mer long peptides with 7 amino acids flanking the mutated amino acid on either side will be fed into the NetMHC4.0 algorithm (as in FIG. 2) to predict their MHC class I $H2D^b$ and $H2K^b$ and MHC class II $IA^b$ binding affinity.

For each snapshot time point at which RNA is isolated, and for each APOBEC3B expression method, a freeze thawed vaccine is prepared and administered to RCAS DIPG or GL261 tumor bearing mice in combination with PD-1 checkpoint blockade as described for the GL261 and B16 models. The impact on overall survival is assessed, and a subset of mice will be sacrificed for immune monitoring. T cells is harvested from spleens and cervical lymph nodes, labeled with CFSE, and co-cultured with the parental RCAS DIPG or GL261 cells in vitro. The proliferation of these T cells, as well as their polyfunctional cytokine response (IFNγ, TNFα, IL2), is measured by intracellular staining and flow cytometry and used as a metric of the magnitude of the potency of the vaccine. These assays are performed with T cells restimulated with peptide pools containing the wild type sequence or the putative high affinity neoeiptopes predicted with NetMHC4.0. Thus, the overall mutation burden, the frequency of the mutations, and the abundance of transcripts which are predicted to contain APOBEC3B-induced mutations and to bind to MHC with high affinity, is correlated with the therapeutic value of the vaccine.

Evaluation of potential toxicity associated with the priming of T cells recognizing heteroclitic epitopes specific to pHGG. No evidence of vitiligo was observed in mice treated with the APOBEC3B-modified B16 tumor cell vaccine as a single agent or in combination with immune checkpoint blockade, nor was evidence of neurological autoimmune symptoms associated with the APOBEC3B-modified GL261 vaccine observed. Autoimmunity has neither been observed following vaccination with a VSV based altered self cDNA libraries. T cells that have escaped central tolerance and which weakly bind to self antigens, but can be primed and expanded through heteroclitic peptide vaccination, remain relatively weak as single clonal populations. Thus, the selectivity of the approach relies on the cumulative therapeutic strength of this polyclonal repertoire of T cells which recognize the neoplastic immunopeptidome signature presented on a tumor cell, but that differs from untransformed cells.

An evaluation of any potential toxicity that may be associated with the APOBEC3B induced altered-self-library vaccination approach is done. In order to monitor the potential pathological role that T cells primed with an APOBEC3B-modified vaccine may have, T cells are harvested from the cervical lymph nodes and spleens of tumor bearing mice that are vaccinated with APOBEC3B- or catalytically inactive APOBEC3B-modified tumor cells and adoptively transferred to non-tumor bearing recipient mice following a dose escalation ladder. Recipient mice are monitored for the development of neurological symptoms for at least 150 days, and serial snapshot histological analysis is performed to verify whether a T cell infiltrate and corresponding tissue destruction is present (Mayo Clinic Arizona Pathology Core). In order to push this system, adoptive T cell transfers and the above described readouts is performed for mice which receive a sham surgery to cause physical trauma and induce an inflammatory response which may additionally recruit T cells. Should autoimmunity be observed under these circumstances, it is evaluated whether current clinical protocols for the management of autoimmunity, such as the employment of corticosteroids for patients receiving immune checkpoint blockade, can mitigate the pathology.

Integrate the APOBEC3B-modified whole cell vaccine into a clinically analogous dendritic cell vaccination platform and optimize adjuvant therapy. Inactivated whole tumor cell vaccination is a relatively inefficient method of vaccination and the magnitude of the observed therapeutic response speaks to the increase in immunogenicity gained by APOBEC3B modification. This novel repertoire of heteroclitic peptide targets is leveraged by loading bone marrow derived dendritic cells (BMDCs) with tumor cells modified with APOBEC3B. Murine BMDCs are differentiated in GMCSF and matured with TNFα and PGE2. To mimic a clinical protocol for the generation of tumor cell lysate, APOBEC3B-modified cells are resuspended in a hypotonic solution and freeze thawed three times and fed to dendritic cells. Dendritic cells are administered to tumor bearing mice within 24 hours of antigen loading. The magnitude of the CD4 and CD8 T cell response are compared between mice receiving freeze thawed lysate vaccine and tumor cell loaded BMDCs by flow cytometry following restimulation of T cells in vitro with parental RCAS DIPG tumor cells or peptides identified. The overall therapeutic effect of the DC vaccine compared with freeze thawed lysate vaccine is compared in mice which additionally receive anti-PD1, anti-CTLA-4, anti-Tim3, or combinations of ICB, or control IgG. T cells from mice vaccinated in this manner is adoptively transferred to recipient sentinel mice to monitor the potential development of autoimmune toxicity, as described.

Statistical Analyses. For Aim 1, 10 mice per group are used for survival analysis. If censoring exists, survival across groups are compared using the log-rank test. If censoring does not exist, then a Student's t-statistic (2 groups) or analysis of variance (ANOVA) (>2 groups) will be utilized to compare survival times. For studies with >2 groups, the overall F-statistic will be evaluated first; if the F-statistic p-value <0.05, then contrast statements will be used to test for pairwise comparisons of interest. Importantly, the studies described in Aim 1 include multiple "control" groups that while they are important to verify that the animal study was performed correctly, are not of biological interest. For all analyses, $\alpha=0.05$ will be used. Assuming $\sigma=30$, 10 mice per group will provide 80% power to detect a difference of 40 days, with a two-sided $\alpha=0.05$. Alternatively, assuming $\sigma=6$ a difference of 10 days can be detected. As demonstrated in FIGS. 1 and 3, large effect sizes are expected and statistically-significant changes with 7-8/group can be detected, highlighting the feasibility of these studies. For in vitro analysis of T cell responses, 4-5 mice per group are compared using ANOVA models.

Figures 6A, 6B:
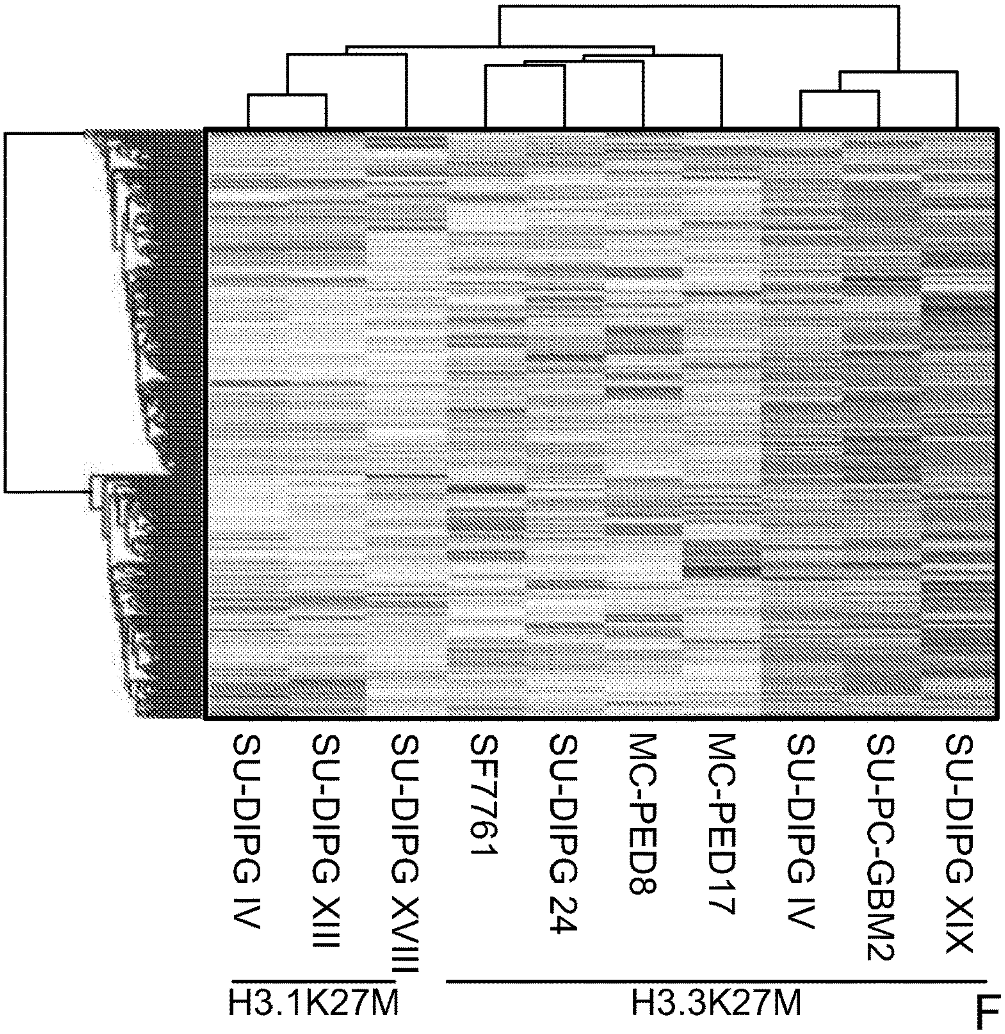
FIG. 6. (A) Mutational characterization of human DIPG cell lines. (B) Unsupervised hierarchy clustering and heat-map of genes with a differential expression between cell lines bearing an H3.1 or H3.3 K27M mutation.

Example 3: Transduction Protocol for the Preparation of APOBEC3B Mutation Induced Tumor Cell Vaccines Using a Biobank of Primary Human pHGG Cell Lines The preclinical development and testing of novel therapeutic approaches for pHGG and DIPG in particular has been limited by the scarcity of human cell lines that authentically represent the disease. Although surgical resection for DIPG tumors is not possible, biopsies are routinely performed at Mayo either with a stereotactic needle or in an open fashion depending on the tumor characteristics for each patient. This practice has enabled the procurement of sufficient tissue to generate a novel biobank over the last three years of cell lines for in vitro and xenograft testing. To date, the pediatric brain tumor biobank includes 20 novel cell lines which capture a variety of histological subtypes, including DIPG, medulloblastoma, ependymoma, meningioma, GBM, and others. The presence of mutations common to DIPG within novel cell lines and in the context of cell lines obtained from collaborators at other institutes (FIG. 6A) was evaluated. In addition to this molecular characterization, RNA-seq was performed on this subset of DIPG lines (FIG. 6B).

APOBEC3B mutational burden in human DIPG cell culture conditions. Having established a target range of APOBEC3B-induced mutations that optimally primes a T cell response that can cross react and provide therapy against a parental tumor, a protocol was developed to achieve this same mutational burden in human cell lines using human-specific cell culture reagents. B16 and GL261 cells are highly cell culture adapted and due to their rapid rate of division APOBEC3B overexpression is only tolerated for up to three weeks before the cells either transcriptionally silence the transgene or die as a result of the accumulation of mutations in key genomic loci. There is both heterogeneity in the growth characteristics within the primary cell bank of cell lines which grow as tumor neurospheres and as adherent lines, and substantial differences from the murine B16, GL261 lines, and from the explanted RCAS DIPG line. Using three DIPG lines (MC PED-17, SU-DIPG-IV, and SU-DIPG-VI) which represent distinct H3.3 and H3.1 H27M mutation classes, and transcriptional profiles (FIG. 6), APOBEC3B was introduce using the adenoviral or retroviral vectors, or through plasmid transfection, and perform an analogous profiling of APOBEC3B-induced mutations by RNA-seq as described after multiple population doublings. Together the data correlating the growth rate of the cells, method of culture, the method of APOBEC3B introduction, and the overall induced mutational load, allows us to develop an algorithm to consistently induce the target mutational burden in novel cell lines.

APOBEC3B modified tumor vaccination strategy in an in vitro priming assay using healthy human donor peripheral blood cells. The timescale required for therapy in rapidly progressing pHGG patients is not compatible with the generation of sufficient autologous tumor material to prepare a DC vaccine and therefore necessitates a pre-existing allogeneic tumor cell bank for off the shelf use. Studies described (see, e.g., FIG. 1-3) have been, or are, performed in genetically identical mice. As the allogeneic setting already presents a degree of altered self, how the target mutation burden identified overlays on a pre-existing set of non-tolerized neoepitopes is explored. Using an established in vitro T cell priming assay (Prestwich et al., Clin Cancer Res 15:4374-4381 (2009)), the ability of DCs presenting lysate from APOBEC3B-modified human DIPG cell lines bearing variable mutational burdens to prime a polyclonal T cell response which can cross react back on the parental unmodified cell immunopeptidome is evaluated.

Peripheral blood mononuclear cells (PBMCs) are collected from healthy donors, and microbead sorted $CD14^+$ monocytes will be differentiated into DCs in the presence of GMCSF and IL4, and matured with TNFα and PGE2 in serum free X-VIVO media, according to the established DC workflow. Monocyte derived DCs (moDCs) are loaded with APOBEC3B-modified DIPG cell lysate and co-cultured with autologous healthy T cells for two weeks in the presence of additional IL2 and IL7. In vitro primed T cells, as well as uncultured T cells, are labeled with CFSE and restimulated with moDCs loaded with lysate from either the parental unmodified pHGG cell line or the APOBEC3B-modified line. The proliferation of the T cells and their ability to produce IFNγ, TNFα, IL2 is measured by flow cytometry. The cytokine recall response is evaluated in the presence or absence of checkpoint blocking antibodies. The ability of fluorescently labeled moDCs loaded with no cell lysate, unmodified DIPG cell lysate, or APOBEC3B-modified cell lysate, to act as targets and be specifically killed by in vitro primed T cells in a VITAL assay (Hermans et al., J Immunol Methods 285:25-40 (2004)) is evaluated.

A second important aspect of vaccination with allogeneic tumor material is the conservation between the peptidome of the cell line lysate and the recipient patient tumor. The relative abundance of the peptides presented by the DCs can shape the priming of the novel tumor-specific T cell repertoire. The in vitro T cell priming assay is used to evaluate the importance of conservation of expression patterns on the T cell recall response to DCs loaded with tumor lysates with varying degrees of dissimilarity to the original priming lysate. The RNA-seq determined hierarchical clustering (FIG. 6B) is used to evaluate recall with dissimilar histone mutations, as well as more histologically unrelated tumor types from the biobank such as a GBM or medulloblastoma. In parallel, the DIPG RCAS and GL261 mouse models are used to investigate the magnitude of the recall response of T cells from DIPG vaccinated mice to GL261 and vice versa.

Example 4: APOBEC3B pHGG Cell Banks for Use in Clinical Trials for Pediatric High Grade Glioma The workflows established for the pHGG biobank and the adult GBM GMP cell bank used in the previous DC vaccine trial (MC1272; NCT01957956) are expanded. Biopsy or surgical specimens are pathologically confirmed and expanded using a clinical scale Good Manufacturing Practice (GMP) compliant production protocol in a proprietary culture medium that exploits the growth factors and cytokines found in human platelets that promotes in vitro growth of primary tumors. Platelets are cell bodies released from megakaryocytes and that express growth factors such as EGF, FGF, VEGF, and PDGF. The generation of the novel APOBEC3B modified GMP lines proceeds in two distinct steps: (1) the establishment, expansion, and characterization of the novel cell lines; and (2) the introduction of APOBEC3B through the gene delivery methods described herein. The expression of a variety of markers to evaluate their differentiation state (Nestin, GFAP, olig2, β-tubulin) is evaluated and the presence of additional tumor associated antigens that are commonly overexpressed in pHGG (GD2, EphA2, IL13R2α, EGFR, EGFR, ErbB2, etc) by qRT-PCR and western blots. Release criteria for the novel cell lines includes measures of sterility, endotoxin, mycoplasma, greater than 90% of cells have karyotypic abnormalities, and lack of replication competent retrovirus if this method of gene transfer is chosen. RNA-seq will be performed as described to identify specific commonly seen DIPG mutations (FIG. 6A), and to validate the introduction of the target mutational burden. The algorithm developed herein is to seamlessly generate a cell product that is functionally analogous to the mouse counterparts.

Example 5: Cancer Immunotherapy with APOBEC3B-Induced Heteroclitic Library Tumor Cell Vaccines and Immune Checkpoint Blockade A freeze-thawed whole tumor cell vaccine prepared from B16 melanoma cells stably overexpressing human APOBEC3B treated established subcutaneous parental B16 tumors and, when combined with PD-1 checkpoint blockade, cured between 75%-100% of mice. Depletion of either CD4 or CD8 cells abrogated therapy. Moreover, T cells from mice treated with the vaccine and anti-PD1 produced high levels of interferon (IFN)-γ when co-cultured with parental unmodified B16 melanoma cells, correlating with therapeutic activity. Whole genome sequencing of B16 APOBEC3B overexpressing cell lines identified 301 C to T or G to A missense mutations unique to the APOBEC3B line. Using an in silico MHC binding affinity algorithm for peptides whose binding affinity for $H2K^b$ or $H2K^d$ was below a threshold of 500 nM, 10 high affinity APOBEC3B-induced heteroclitic peptides were identified and the ability of the B16 cells modified by APOBEC3B to prime T cells against these heteroclitic peptide candidates was experimentally validated in vitro. This approach was extended to an orthotopic brainstem model of High Grade Glioma. Thus, GL261 cells stereotactically implanted into the brainstem were significantly responsive to treatment with an APOBEC3B-modified GL261 vaccine in combination with anti-PD-1 checkpoint blockade and the priming of a T cell response to the APOBEC3B-modified GL261 vaccine was confirmed in vitro.

In summary, these data show that, when overexpressed in tumor cells, APOBEC3B generates a library of heteroclictic sequences, which primes both CD4 and CD8 T cells that have escaped central tolerance and which recognize both newly mutated antigens from the vaccine, as well as the corresponding unaltered self-epitopes expressed on the tumor cells. This approach represents a potent new method to develop neo-epitope based vaccine as a strategy for the treatment of, for example, pediatric high grade glioma.

Example 6: An APOBEC3B Induced Library of Heteroclitic Neoepitopes Enhances Tumor Vaccines and Sensitizes T Cell Responses to Checkpoint Blockade This example demonstrates that vaccination with tumor cell lines expressing human APOBEC3B primed tumor reactive T cells in vivo that were reactive against parental murine melanoma or glioma tumors, and that the efficacy of these T cells was amplified by ICB therapy. Candidate heteroclitic neoepitopes were identified using whole genome sequencing of APOBEC3B-altered vaccines and an in silico MHC-I binding screen. Following ex vivo validation, an individual neoepitope vaccine in combination with ICB was shown to partially recapitulate in vivo efficacy against unaltered tumors. Therefore, APOBEC3B can be used to enhance the immunogenicity of cell lysate vaccines via the introduction of heteroclitic epitopes.

Results

Figure 7A:
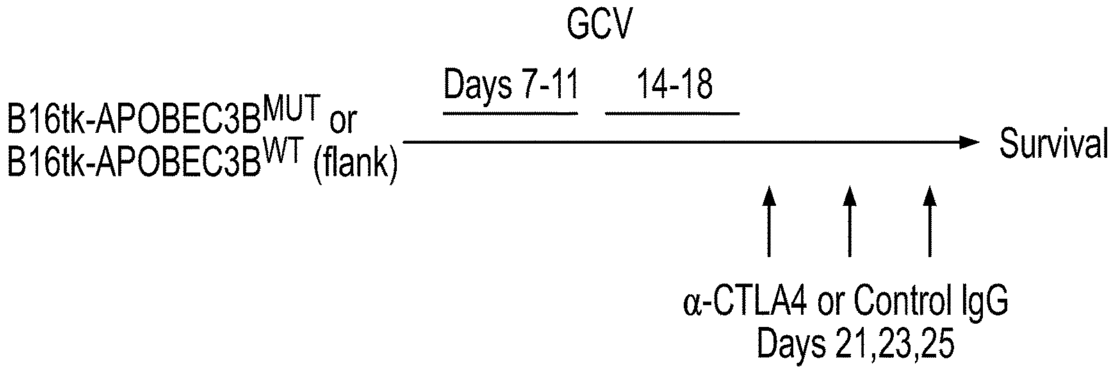
FIG. 7. APOBEC3B expression enhances tumor escape but sensitizes tumors to immune checkpoint blockade therapy. (A) On day 0, $2\times10^5$B16TK cells expressing either APOBEC3B$^{MUT}$ or APOBEC3B$^{WT}$ were subcutaneously implanted into the right flank of C57B1/6 mice. Two 5-day courses of GCV therapy (50 mg/kg i.p.) were administered from days 7-11, and 14-18, followed by anti-CTLA4 antibody or control IgG (5 mg/kg i.p.) on days 21, 23, and 25. (B, C) Mice were treated according to the regimen in (A) (n=7 mice/group) tumor volumes were measured three times per week and sacrificed when tumors grew above 1 cm in length or width.
Figure 7B:
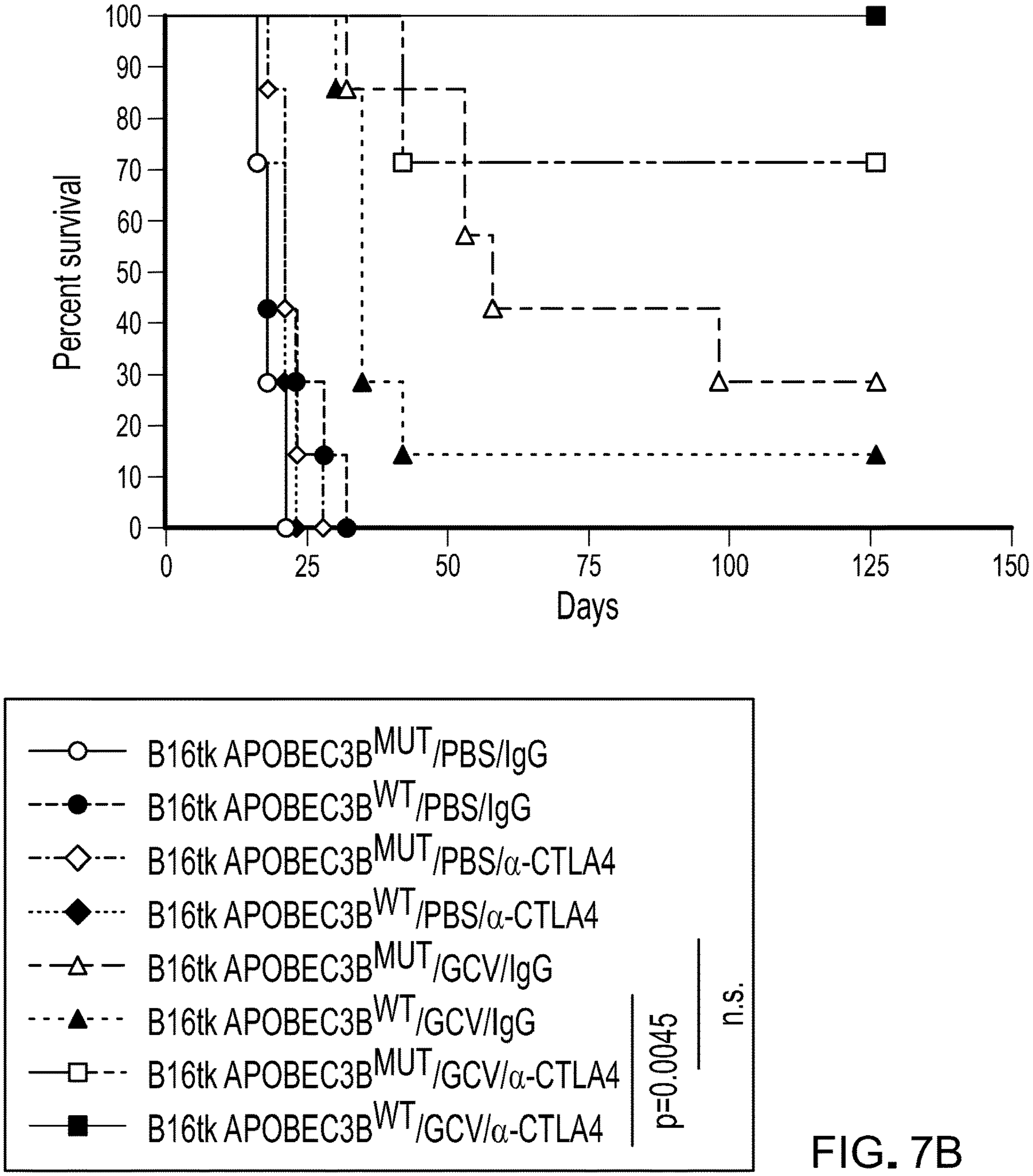
Figure 7C:
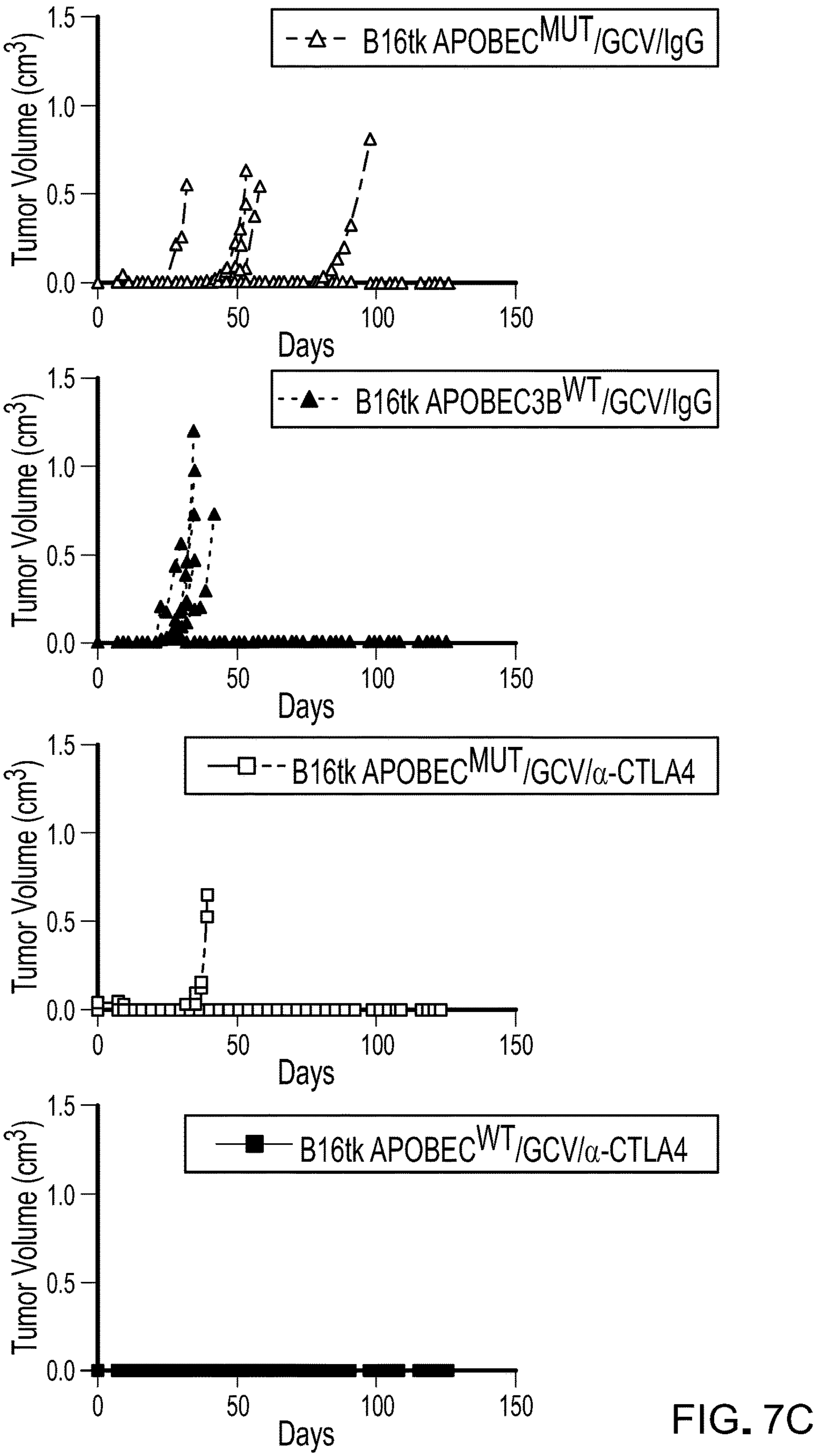

APOBEC3B Overexpression Promotes Anti-Tumor Immune Responses in the Context of Checkpoint Inhibitor Therapy To test if neoepitopes introduced by APOBEC3B mutational events could be recognized by cognate T cells, B16 murine melanomas stably expressing the HSVtk suicide gene and either wild-type APOBEC3B ($APOBEC3B^{WT}$) or the catalytically inactive APOBEC3B mutant ($APOBEC3B^{MUT}$) were treated with two 5-day courses of ganciclovir (GCV) prodrug therapy, followed by anti-CTLA4 checkpoint inhibitor therapy (FIG. 7A). GCV therapy extended survival over untreated controls (FIG. 7B), however $APOBEC3B^{WT}$ tumors escaped therapy more quickly than $APOBEC3B^{MUT}$ tumors. (FIG. 7C). Sequencing of HSVtk in the escaped tumors revealed a consistent C-to-T, APOBEC3B signature mutation at base 21, resulting in a premature stop codon. Anti-CTLA4 therapy extended the median survival of mice bearing GCV-treated APOBEC3B$^{MUT}$ tumors, confirming that HSVtk-mediated cell killing is immunogenic. However, anti-CTLA4 transformed the less-effective GCV therapy for APOBEC3B$^{WT}$ tumors into a sustained, curative treatment. These results suggested that while APOBEC3B overexpression can drive tumor escape from targeted small molecule therapy, it generated an increased mutational burden and allowed for recognition and rejection by the immune system in the context of immune checkpoint blockade.

Figure 8A:
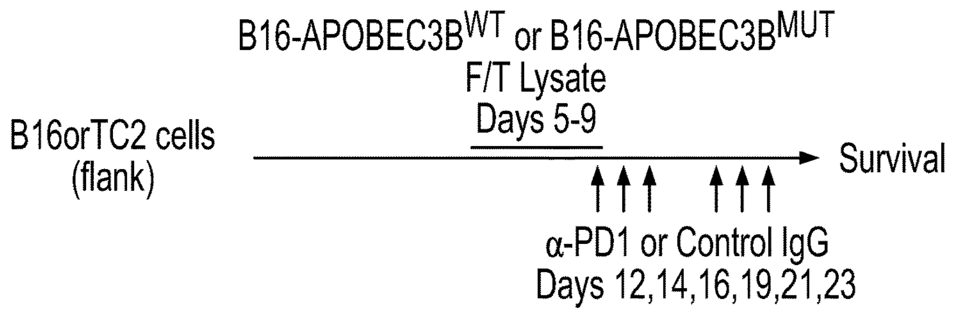
FIG. 8. APOBEC3B enhances B16 cell lysate vaccine and synergizes with immune checkpoint blockade therapy. (A) On day 0, $2\times10^5$ B16 murine melanoma or TC2 murine prostate carcinoma were implanted subcutaneously into the right flank of C57B1/6 mice. One 5-day course of APOBEC3B$^{WT}$ or APOBEC3B$^{MUT}$-modified B16 cell vaccines (freeze/thaw lysate of $10^6$ cells i.p.) was administered from days 5-9. This was followed by anti-PD1 antibody or IgG control (12.5 mg/kg i.p.) on days 12, 14, 16, 19, 21 and 23. (B) Mice (n=8/group) were treated according to the regimen in (A) and tumor volumes were measured three times per week. (C) Kaplan-Meier survival curves representing experiment described by (A) and (B). (D) Treatment of subcutaneous B16 murine melanomas as in (A), except with the addition of anti-CTLA4 antibody (5 mg/kg i.p.) as a monotherapy or in combination with anti-PD1 (n=7 mice/group). The Black triangle, red circle, and brown square symbols represent three separate groups of 7 mice treated with B16-APOBEC3B$^{WT}$ vaccine with anti-PD1, anti-CTLA4, or anti-PD1/anti-CTLA4 antibody therapy that all had 100 percent survival at 150 days.
Figure 8B:
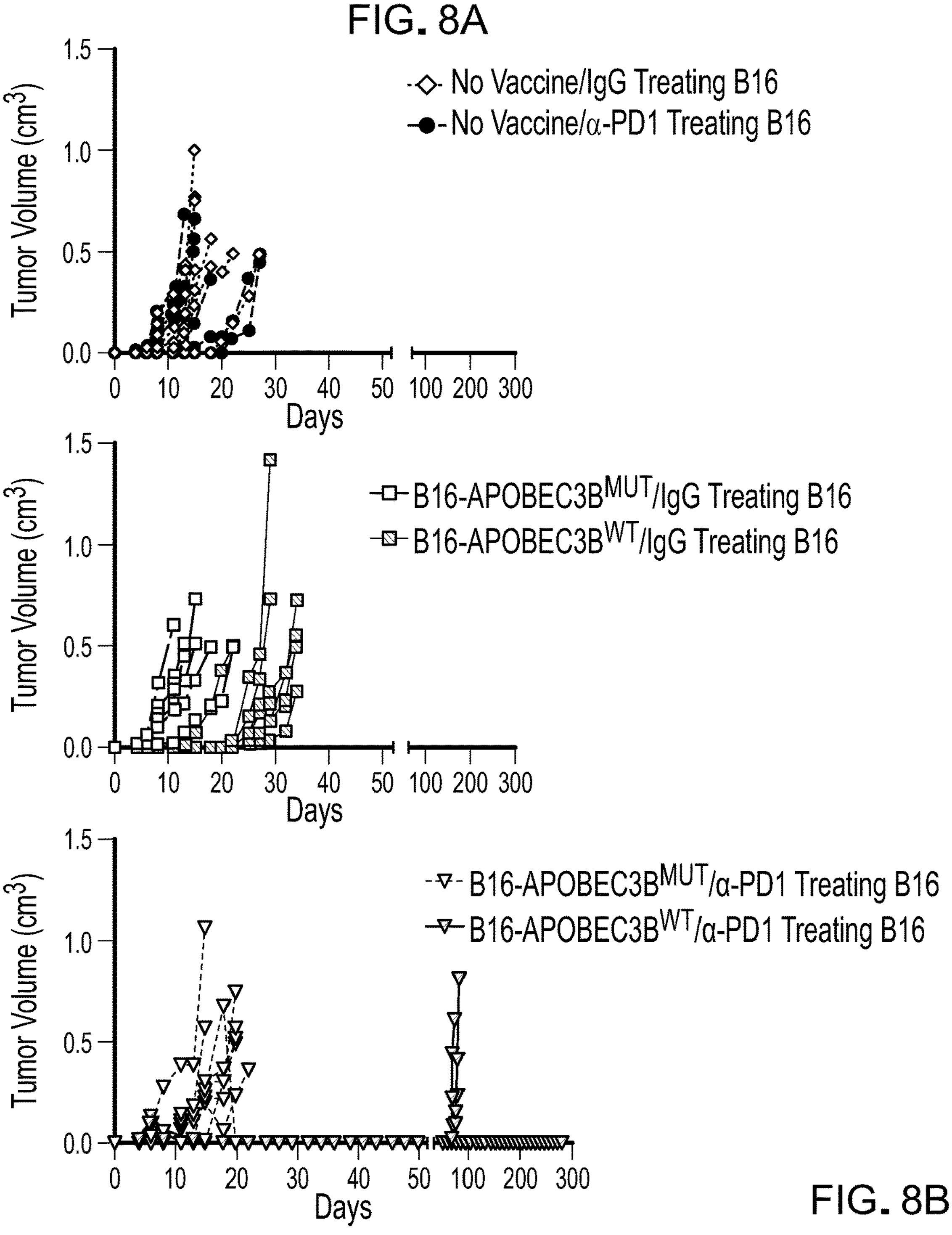
Figure 8C:
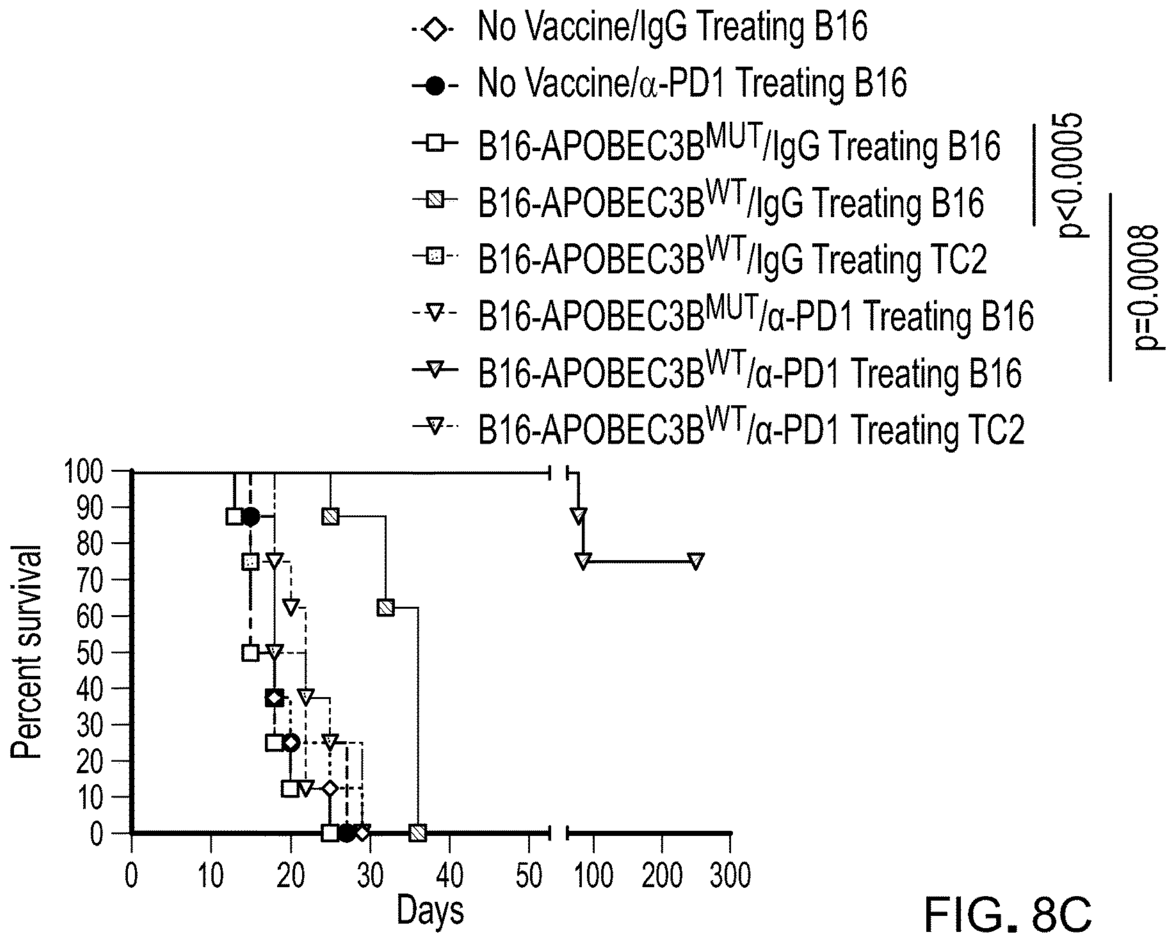
Figure 8D:
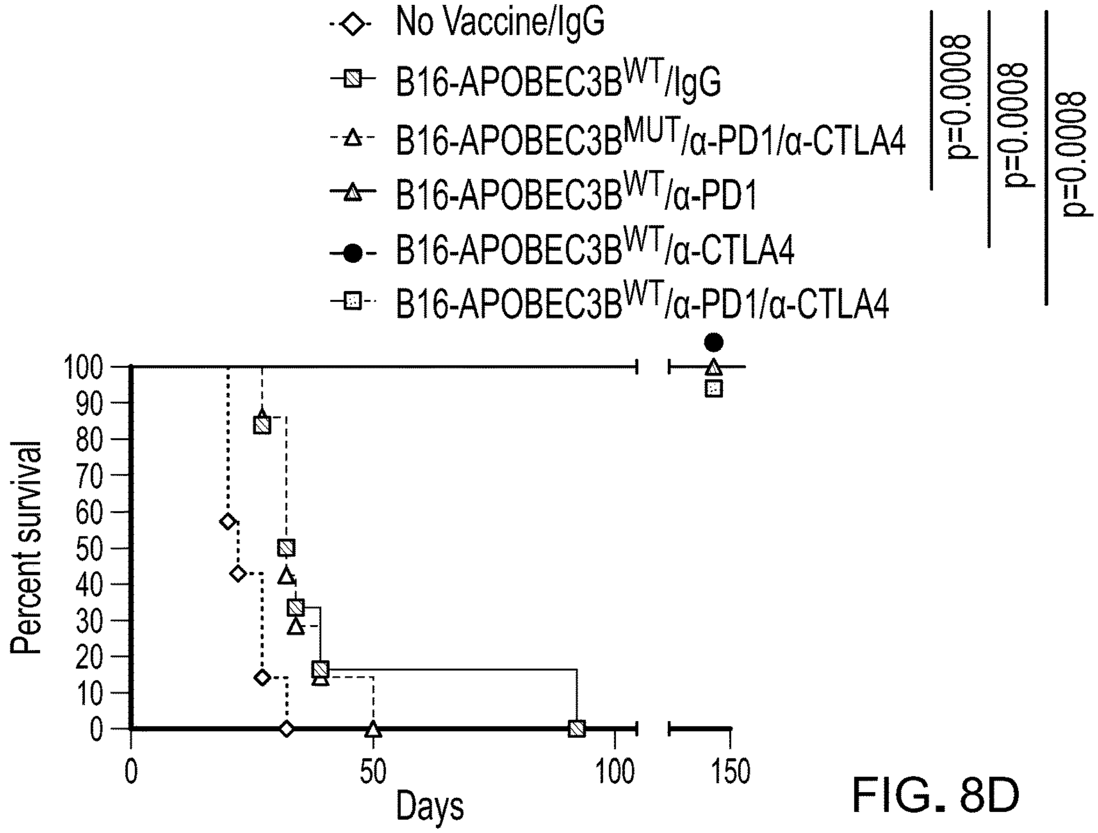

APOBEC3B Overexpression Improves Tumor Lysate Vaccine Efficacy when Combined with Immune Checkpoint Blockade In order to capitalize upon the mutational burden generated by APOBEC3B expression without contributing to tumor evolution, an APOBEC3B-modified freeze-thawed tumor lysate vaccine was generated. Mice bearing subcutaneous B16 parental tumors were treated with B16 cell lysates retrovirally transduced to express either APOBEC3B$^{WT}$ or APOBEC3B$^{MUT}$, followed by anti-PD1 or control immunoglobulin (IgG) (FIG. 8A). Mice treated with the tumor vaccine modified by overexpression of the APOBEC3B$^{WT}$ exhibited delayed tumor growth (FIG. 8B) and prolonged survival (FIG. 8C) compared to mice treated with B16-APOBEC3B$^{MUT}$ vaccines. This suggested that APOBEC3B overexpression can improve the immunogenicity of tumor cell vaccines. Only the B16-APOBEC3B$^{WT}$ vaccine sensitized treated mice to immune checkpoint inhibition, with the addition of anti-PD1 therapy causing complete and sustained tumor regression out to 250 days in 75% of mice (FIG. 8C). This study was repeated with anti-PD1, anti-CTLA4, and combination checkpoint blockade, demonstrating similar results (FIG. 8D). B16 tumor lysate vaccines administered to mice bearing subcutaneous TC2 syngeneic prostate tumors were ineffective even in the context of APOBEC3B$^{WT}$/anti-PD1 therapy (FIG. 8C), suggesting the induced T cell response reflected the specific immunopeptidome of the vaccine. Symptoms, such as vitiligo, that would be associated with autoimmunity were not observed in any of these experiments.

B16-APOBEC3B Vaccination Elicits a CD4, CD8, and NK Cell Anti-Tumor Response

Figure 9A:
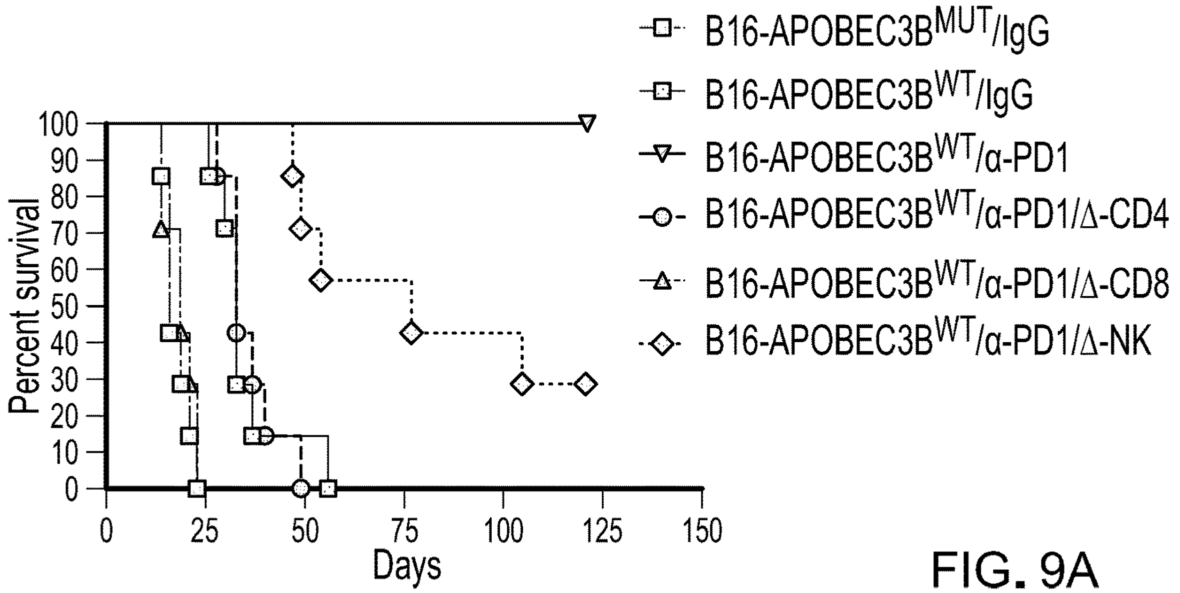
FIG. 9. CD4, CD8, and NK cells mediate APOBEC3B$^{WT}$ vaccination. (A) B16-APOBEC3B$^{WT}$ vaccination and/or antibody-mediated checkpoint inhibition was performed as in FIG. 8A, with the addition of antibodies depleting CD4 T cells, CD8 T cells, NK cells, or control IgG on day 4 after subcutaneous tumor implantation and weekly thereafter (n=7 mice/group). (B) Spleens and lymph nodes obtained from mice (n=3 per group) succumbing to their disease in (FIG. 8B, C) were made into single-cell suspensions and co-cultured with B16 target cells for 72 hours. Supernatant from the co-culture was assayed using a mouse interferon gamma ELISA. ANOVA used followed by Tukey's multiple comparison test. $*p\leq0.05$. (C) Spleens and lymph nodes obtained from mice treated with B16-APOBEC3B$^{WT}$ vaccination and/or antibody-mediated checkpoint inhibition were made into single-cell suspensions and reinfused at dose of $1.2\times10^7$ cells intravenously per B16 subcutaneous tumor-bearing mouse (n=7 mice per group).
Figure 9B:
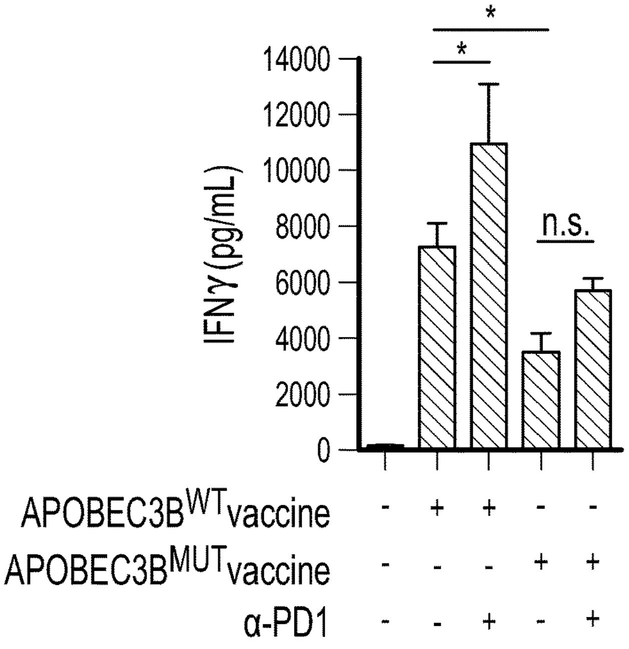
Figure 9C:
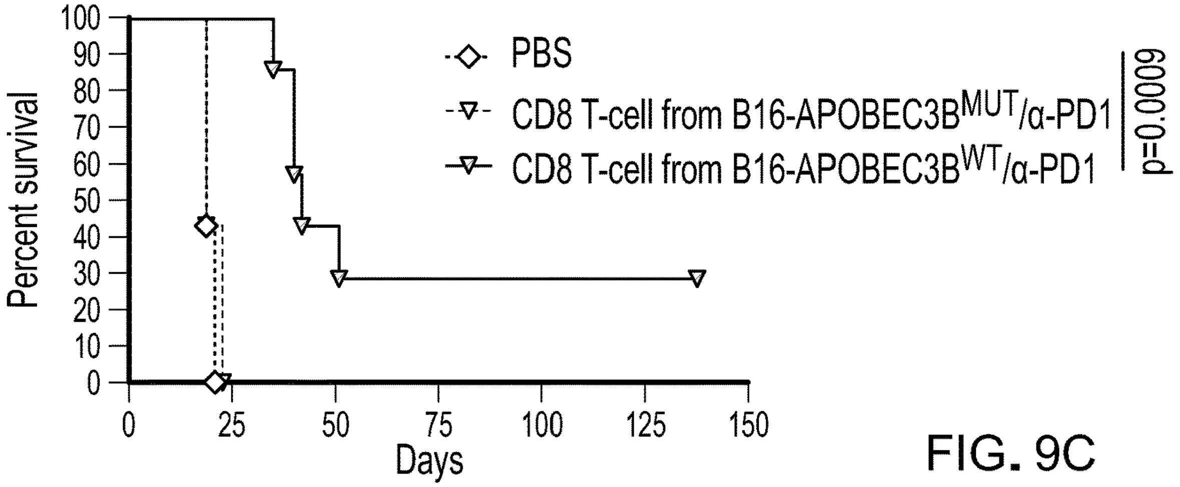

To identify the immune subsets involved in the vaccine's therapeutic efficacy, B16-APOBEC3B$^{WT}$ vaccination and checkpoint blockade studies were repeated with depletion of CD4, CD8, or NK cells. Depletion of CD4, CD8, and NK cells significantly reduced the efficacy of the B16-APOBEC3B$^{WT}$ and anti-PD1 therapy (FIG. 9A). When co-cultured in vitro with parental, unmodified tumor cells, splenocytes from mice which received B16-APOBEC3B$^{WT}$ vaccines secreted significantly more interferon gamma (IFNγ) than mice treated with B16-APOBEC3B$^{MUT}$ (FIG. 9B). This IFNγ secretion was increased even further when B16-APOBEC3B$^{WT}$ vaccination was combined with ICB. When transferred into untreated mice bearing subcutaneous parental B16 tumors, CD8 T cells from mice treated with the B16-APOBEC3B$^{WT}$ vaccine conferred partial protection against parental B16 tumors. In contrast, adoptive transfer of CD8 T cells from mice which received the control B16-APOBEC3B$^{MUT}$ vaccine did not slow tumor growth compared to adoptive transfer of CD8 T cells from naïve mice (FIG. 9C). Together, these results indicated that CD4, CD8, and NK cells were involved in B16-APOBEC3B$^{WT}$ vaccine/checkpoint inhibitor combined therapy.

Figure 10A:
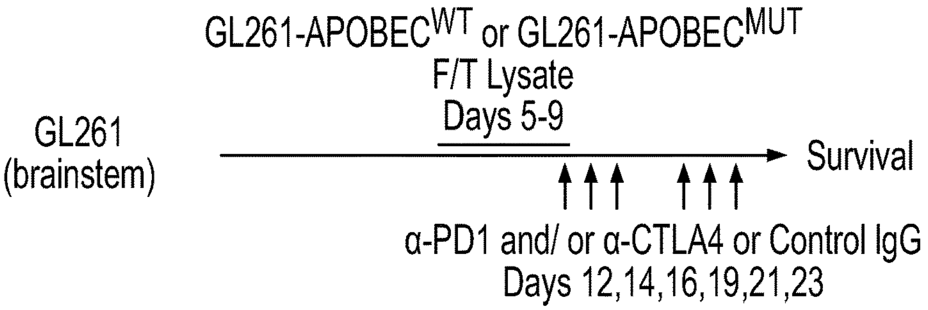
FIG. 10. APOBEC3B modified GL261 cell lysate vaccine also effective against orthotopic gliomas. (A) Treatment strategy from (FIG. 8A) was adapted to target GL261 murine gliomas. In summary, on day 0, $5\times10^4$ GL261 murine glioma cells were implanted into the brainstem of C57B1/6 mice. One 5-day course of APOBEC3B$^{WT}$ or APOBEC3B$^{MUT}$-modified GL261 cell vaccines (freeze/thaw lysate of $10^6$ cells i.p.) was administered from days 5-9. This was followed by anti-PD1 antibody, anti-CTLA4 antibody or IgG control (12.5 mg/kg i.p.) on days 12, 14, 16, 19, 21 and 23. (B) Kaplan-Meier survival curves representing experiment described by (A) (n=7 mice/group). (C) Spleens and lymph nodes obtained from mice treated with GL261-APOBEC3B$^{WT}$ vaccination and/or antibody-mediated checkpoint inhibition were made into single-cell suspensions and co-cultured with GL261 target cells for 72 hours. Supernatant from the co-culture was assayed using a mouse interferon gamma ELISA. ANOVA was used followed by Tukey's multiple comparison test. $p\leq0.01$, $*p\leq0.001$.
Figure 10B:
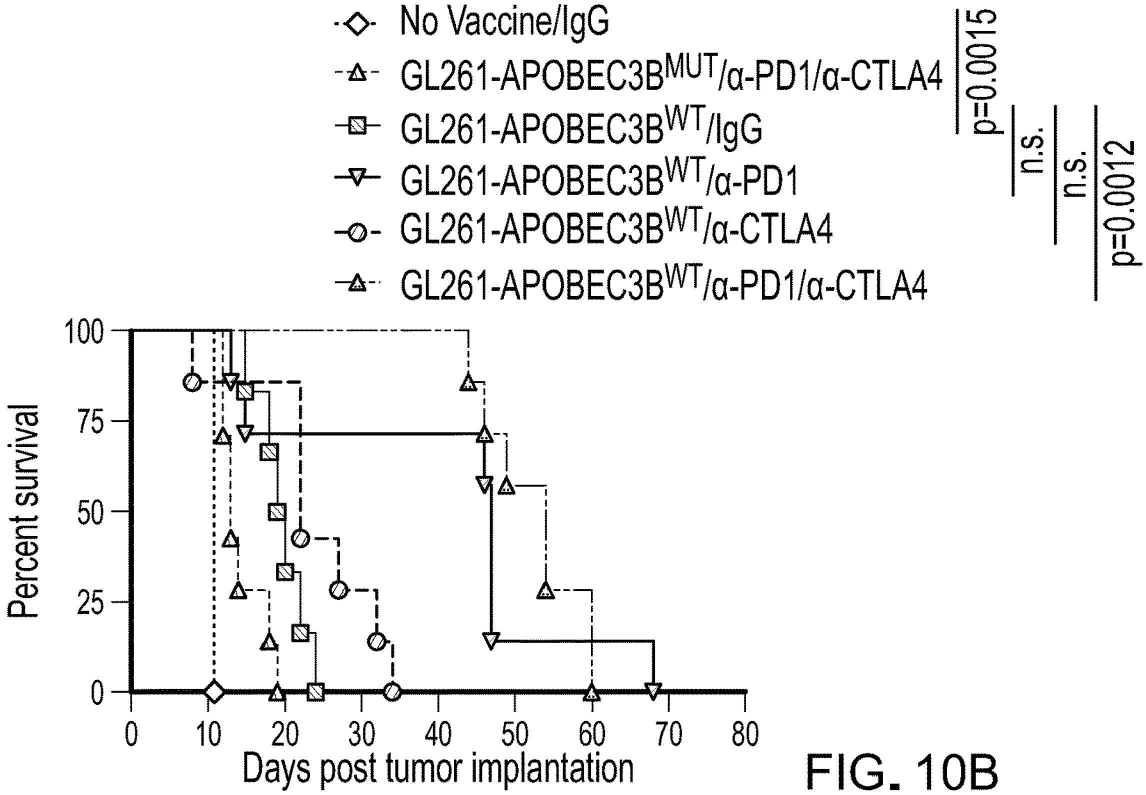

APOBEC3B Overexpressing Tumor Cell Vaccine Confers Therapeutic Efficacy in an Aggressive Brainstem Glioma Model To validate that APOBEC3B-modified vaccination efficacy is not limited to melanomas or subcutaneous tumors, the APOBEC3B-modified tumor vaccine platform was tested in an aggressive brainstem glioma model. Mice bearing brainstem-implanted GL261 tumors were treated with an APOBEC3B$^{WT}$ or APOBEC3B$^{MUT}$-modified GL261 vaccine (FIG. 10A). Mice treated with the GL261-APOBEC3B$^{WT}$-modified vaccine survived significantly longer than untreated controls (FIG. 10B). The GL261-APOBEC3B$^{WT}$-modified vaccine in combination with anti-PD1 doubled median survival, though when controlling for multiple comparisons it did not reach statistical significance when compared to untreated controls. However, the combination of anti-CTLA4 and anti-PD1 therapy with the GL261-APOBEC3B$^{WT}$ vaccine significantly improved survival compared to mice treated with control immunoglobulin, with all mice surviving past 40 days.

Figure 10C:
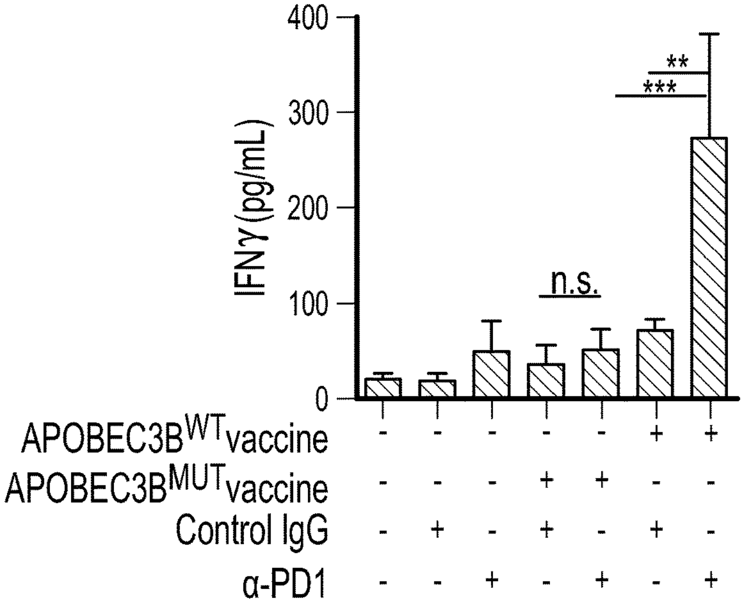

To determine if the T cell response raised by the APOBEC3B-modified vaccine cross-reacted onto unmodified parental tumor cells, splenocytes from treated mice were co-cultured with parental GL261 cell in vitro. Splenocytes isolated from mice that received the GL261-APOBEC3B$^{WT}$ vaccine and ICB secreted significantly increased levels of IFNγ after 72 hours of co-incubation with parental GL261 tumors compared to mice receiving only the GL261-APOBEC3B$^{WT}$ vaccine (FIG. 10C). These results showed that the APOBEC3B$^{WT}$-modified vaccine and ICB strategy is effective against a second tumor type and retains efficacy in an immunologically distinct site like the brainstem.

APOBEC3B Induces Neoepitopes with Predicted Heteroclitic Activity

Figure 11A:
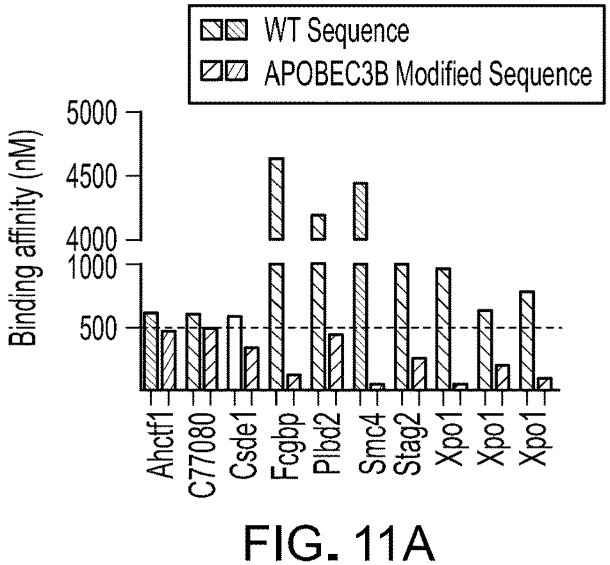
FIG. 11. Mutated peptides with differential MHC binding were identified as potential heteroclitic neoepitopes. (A) The seven genes leading to ten peptides that showed differential MHC I binding between the wildtype and mutated peptide are shown. The threshold for binding affinity was set at 500 nM with weak binding being above 500 nM and strong binding being below 500 nM. (B) Expression plasmids were constructed that encoded either all ten wild type (wild type epitope string) or all ten mutated peptide sequences (APOBEC3B epitope string) with AAY spacers between each peptide to enhance cleavage and presentation. (C) Splenocytes from naïve, B16-APOBEC3B$^{WT}$, or B16-APOBEC3B$^{MUT}$ vaccinated mice were collected and co-cultured with parental tumors that over-expressed either the wild type or APOBEC3B epitope string. ANOVA was used followed by Tukey's multiple comparison test. $***p\leq0.001$. (D) IFN-γ recall responses against (1) parental tumors, (2) wild type string, (3) APOBEC3B string, (4-11) individual wildtype epitopes, (12-19) individual mutated epitopes from T cells isolated from naïve (red), B16-APOBEC3B$^{WT}$ (grey) or B16-APOBEC3B$^{MUT}$ vaccinated mice (blue). Dashed line indicates upper limit of detection.

A screen of the B16tk-APOBEC3B$^{WT}$-modified, VSV-escaped population, compared to the B16tk parental cells using whole genomic sequencing identified 1,048,576 mutations unique to the B16-APOBEC3B$^{WT}$ overexpressing cells. (SRA Submission: SRP159367). Of those, 237 contained C to T or G to A transitions that lead to missense mutations and were consistent with APOBEC3B mutational activity (Table 1; FIG. 16). These mutational sites were converted into 21-amino acid sequences, with 10 amino acids flanking the mutational site (Table 2; FIG. 17). 8-10 mer peptides were generated from these sequences with the mutated amino acid in every position from the amino terminal to the carboxy terminal end, and these peptides were filtered through an MHC binding affinity algorithm (Table 3). To determine if a proportion of APOBEC3B-induced neoepitopes in the vaccine cells could also act as heteroclitic peptides, the potential neoepitopes were screened for differential binding to MHC Class I. Thresholds were set for binding affinity to either H2K$^{b}$ (FIG. 11A dark grey and dark blue) or H2D$^{b}$ (FIG. 11A light grey and light blue), such that wild-type peptide binding was above 500 nM, while APOBEC3B-mutated peptide binding was below 500 nM. By refining this list using the EMBL-EBI Expression Atlas eight candidate proteins were identified that were expressed in the skin: Ahctfl, C77080, Csde1, Fcgbp, Plbd2, Smc4, Stagg, and Xpo1 (which contained three candidate peptide sequence variants) (FIG. 11A).

TABLE 3

MHC binding affinities for heteroclitic neoepitope candidates. Binding affinities for the top ten heteroclitic neoepitope candidates with differential binding affinity to either H-2-Db or H-2-Kb and also expressed in the skin.

| Gene | variant no | HLA | peptide (SEQ ID NO) | pep ID | Affinity (nM) | peptide_MT (SEQ ID NO) | Affinity (nM) MT | differentialMT subtractWT | logFCMT WT |
|---|---|---|---|---|---|---|---|---|---|
| Ahctf1 | 14 | H-2-Db | NSAANLRFV (SEQ ID NO: 3) | WT_A578T_ Ahctf1 | 615.66 | NSATNLRFV (SEQ ID NO: 4) | 469.31 | -146.35 | 0.762287626 |
| C77080 | 31 | H-2-Kb | ASFIFSKG (SEQ ID NO: 5) | WT_A903T_ C77080 | 602.55 | TSFIFSKG (SEQ ID NO: 6) | 491.96 | -110.59 | 0.816463364 |
| Csdel | 86 | H-2-Kb | MSFDPNLL (SEQ ID NO: 7) | WT_P5S_ Csde1-00 | 587.81 | MSFDSNLL (SEQ ID NO: 8) | 345.25 | -242.56 | 0.587349654 |
| Fcgbp | 111 | H-2-Kb | RSEELCPL (SEQ ID NO: 9) | WT_L715F_ Fcgbp- | 4640.94 | RSEEFCPL (SEQ ID NO: 10) | 129.99 | -4510.95 | 0.028009412 |
| Plbd2 | 299 | H-2-Kb | SSGGWAARA (SEQ ID NO: 11) | WT_AI6V_ Plbd2-0 | 4202.63 | SSGGWAARV (SbQ ID NO: 12) | 440.6 | -3762.03 | 0.104839II3 |
| Smc4 | 338 | H-2-Db | SSV1DEISV (SEQ ID NO: 13) | WT_D767N_ Smc4-0 | 4439.13 | SSVINEISV (SEQ ID NO: 14) | 56.05 | -4383.08 | 0.012626348 |
| Stag2 | 356 | H-2-Kb | VRLKCLTAL (SEQ ID NO: 15) | WT_L345F_ Stag2- | 1084.75 | VRFKCLTAL (SEQ ID NO: 16) | 256.26 | -828.49 | 0.236238765 |
| Xpol | 404 | H-2-Kb | TLVYLTHL (SEQ ID NO: 17) | WT_L464F_ Xpo1-2 | 969.17 | TLVYFTHL (SEQ ID NO: 18) | 47.79 | -921.38 | 0.049310235 |
| Xpol | 404 | H-2-Kb | VYLTHLDYV (SEQ ID NO: 19) | WT_L464F_ Xpo1-2 | 638.67 | VYFTHLDYV (SEQ ID NO: 20) | 198.86 | -439.81 | 0.311365807 |
| Xpol | 404 | H-2-Kb | RETLVYLTHL (SEQ ID NO: 21) | WT_L464F_ Xpo1-2 | 782.12 | RETLVYFTHL (SEQ ID NO: 22) | 99.65 | -682.47 | 0.127410116 |

In Vitro Validation of APOBEC3B-Induced Neoepitopes

Figure 11C:
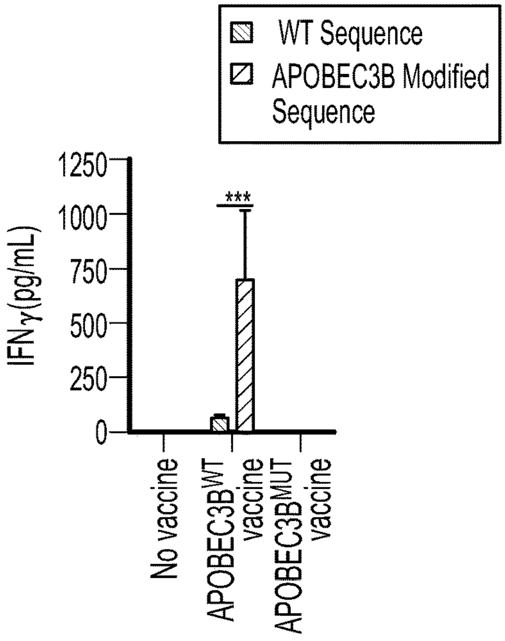
Figure 11B:
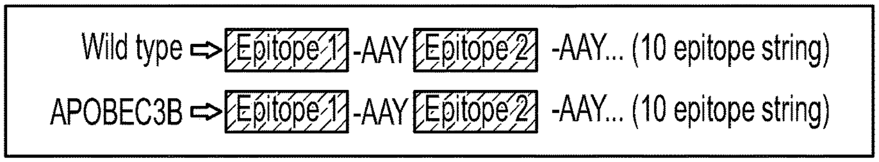
Figure 11D:
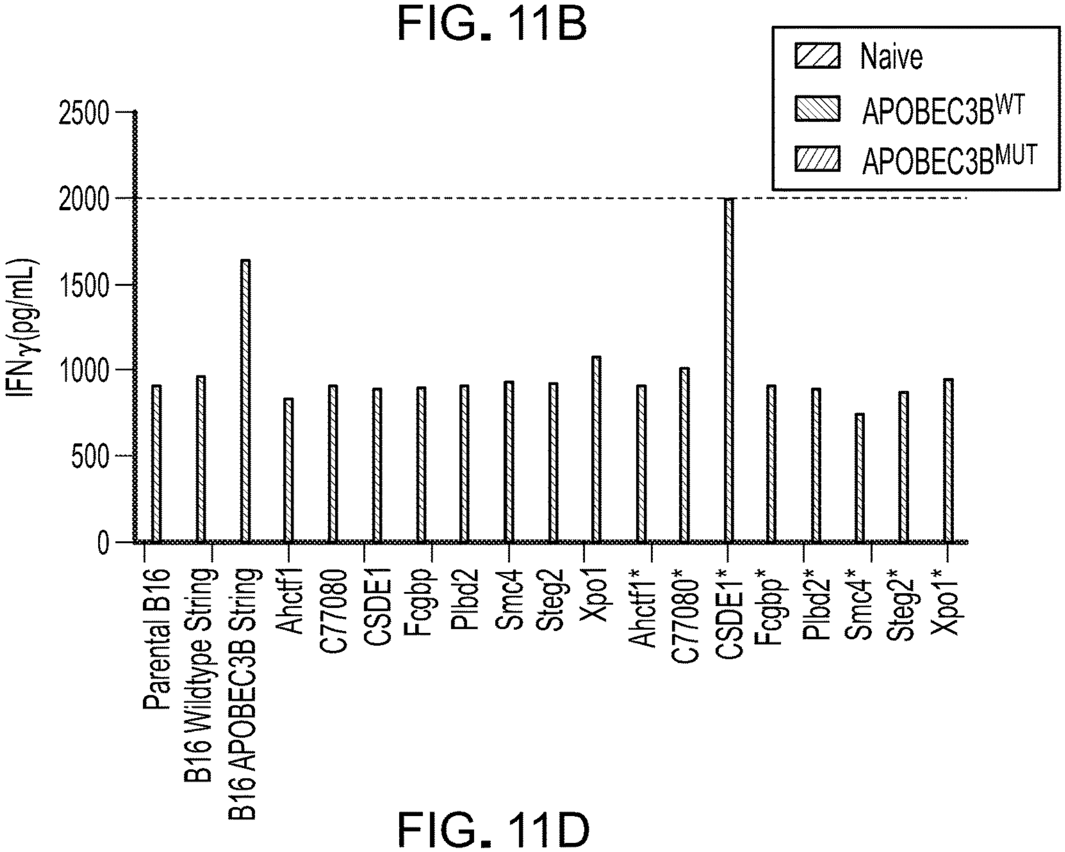

To evaluate experimentally whether the B16-APOBEC3B$^{WT}$ vaccine was able to prime T cells against the in silico-predicted neoepitope candidates, B16 cell lines were generated that transiently overexpressed the 10 wild type (B16-WT sequence) peptides or the mutant neoepitope peptides (B16-APOBEC3B modified sequence). Expression constructs contained the ten wild type or neoepitope peptides separated by Ala-Ala-Tyr (AAY) spacers between each peptide and tagged with an N-end degron motif to increase MHC Class I presentation (FIG. 11B). Splenocytes from unvaccinated or B16-APOBEC3B$^{MUT}$ vaccine treated mice showed no IFNγ recall response to cells overexpressing B16-WT peptides or B16-APOBEC3B modified peptides (FIG. 11C). However, splenocytes from mice treated with the B16-APOBEC3B$^{WT}$ vaccine and ICB showed a strong recall response against cells expressing the B16-APOBEC3B modified peptides. They also showed a recall response against B16-WT sequence cells. This suggested that one or more of the 10 candidate epitopes were also heteroclitic epitopes generated within the B16-APOBEC3B$^{WT}$ vaccine, such that it was able to activate T cells to cross react against wild type epitopes expressed on parental B16 cells. To identify which of these predicted neoepitopes may be targets for T cell responses in the C57B1/6 mice, expression constructs were created for each of the individual neoepitopes. Splenocytes from naïve mice or from mice vaccinated with the B16-APOBEC3B$^{MUT}$ vaccine did not generate a recall response against parental B16 tumor cells in vitro (FIG. 11D). In contrast, as before, splenocytes from mice vaccinated with B16-APOBEC3B$^{WT}$ cells showed a significant recall response against parental B16 cells (FIG. 11D), suggesting that T cell responses against those neoepitopes in the vaccine, which also serve as heteroclitic epitopes, could cross react against wild type epitopes expressed on the parental, unmodified cells. In particular, splenocytes from mice vaccinated with B16-APOBEC3B$^{WT}$ cells also showed a significant enhancement of the recall response against parental B16 cells overexpressing the mutated cold shock domain-containing protein E1 (CSDE1) peptide (FIG. 11D: CSDE1*). Over-expression of none of the remaining 9 potential predicted APOBEC3B-modified neoepitopes enhanced the recall response above that seen in response to parental B16 cells themselves (FIG. 11D). These results confirmed that vaccination with B16-APOBEC3B$^{WT}$ cells induced T cell responses against parental B16 tumors and suggest that an APOBEC3B-mutated neoepitope within CSDE1 may function as a heteroclitic epitope.

Figure 12A:
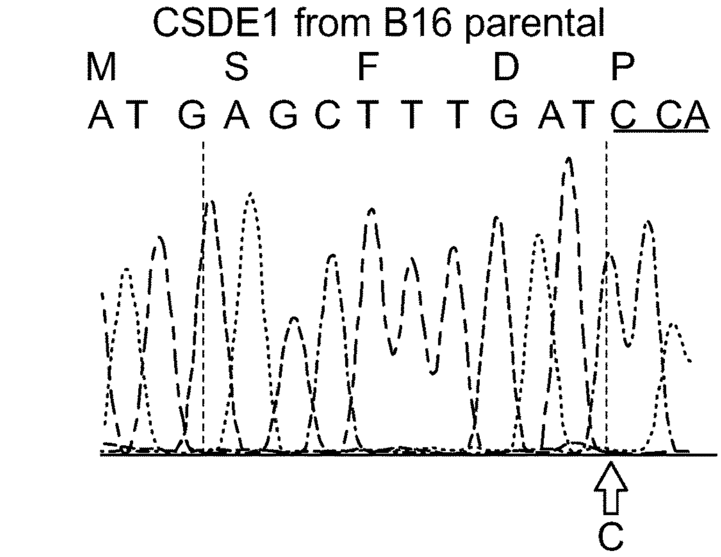
FIG. 12. Sequencing of APOBEC3B$^{WT}$ modified vaccines generates reproducible mutations in CSDE1. Sanger sequencing of CSDE1 from parental B16 cells (A), B16 cells treated with APOBEC3B$^{MUT}$ modified vaccine (B), and B16 cells treated with APOBEC3B$^{WT}$ vaccine (C) was performed. CSDE1 from parental B16 cells contained a wild type ATGAGCTTTGATCCA (SEQ ID NO:1) nucleic acid sequence encoding a wild type MSFDP (SEQ ID NO:23) polypeptide sequence (A), CSDE1 from B16 cells treated with APOBEC3B$^{MUT}$ modified vaccine contained a wild type ATGAGCTTTGATCCA (SEQ ID NO:1) nucleic acid sequence encoding a wild type MSFDP (SEQ ID NO:23) polypeptide sequence (B), and CSDE1 from B16 cells treated with APOBEC3B$^{WT}$ vaccine converted the wild type ATGAGCTTTGATCCA (SEQ ID NO:1) nucleic acid sequence encoding a wild type MSFDP (SEQ ID NO:23) polypeptide sequence to a mutated ATGAGCTTTGATTCA (SEQ ID NO:2) nucleic acid sequence encoding a mutated MSFDS (SEQ ID NO:24) polypeptide sequence (C). Figures are representative of three independent experiments. Each preparation of the APOBEC3B$^{WT}$ modified vaccine had proportions of cells containing a C or a T at the thirteenth base pair, corresponding to the P5S amino acid change seen in FIG. 11 and FIG. 13.
Figure 12B:
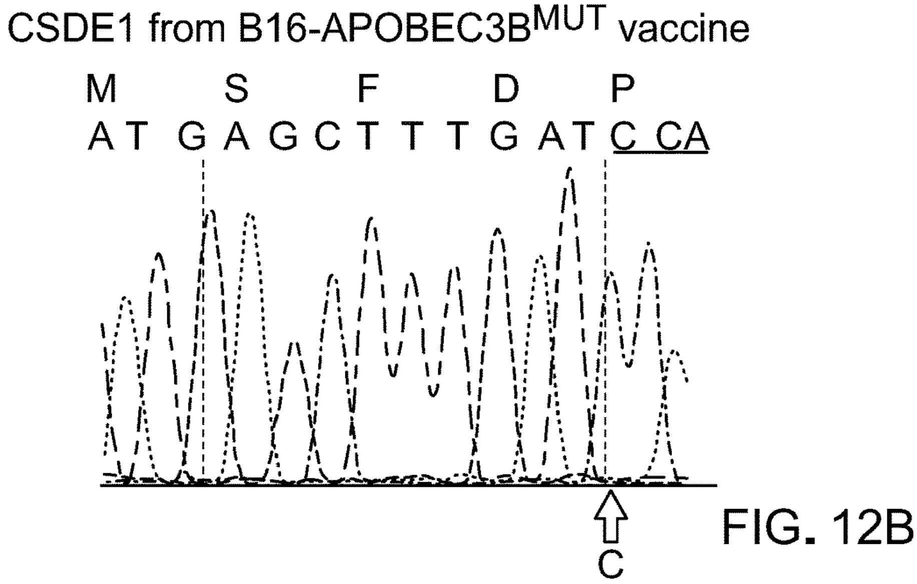
Figure 12C:
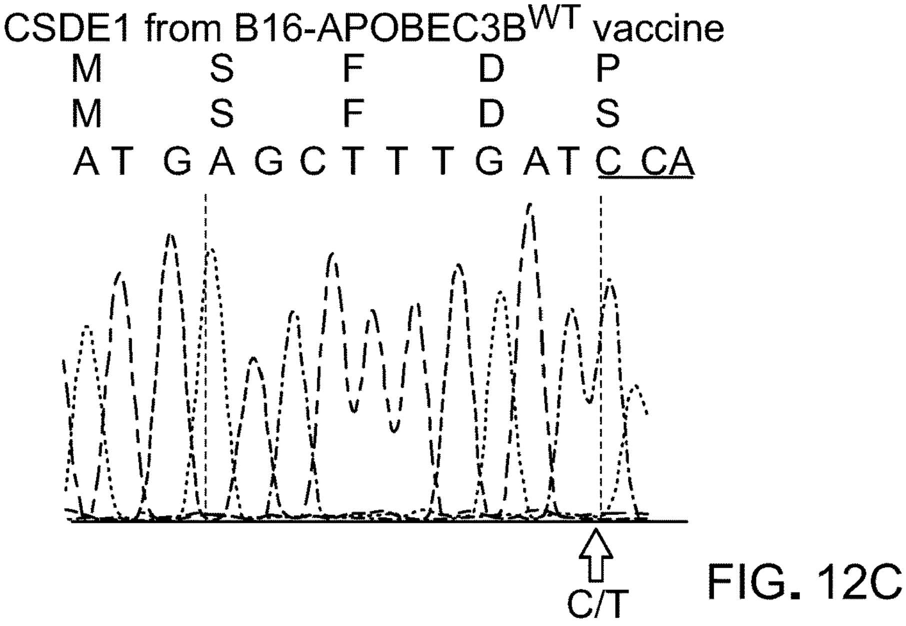
Figure 13:
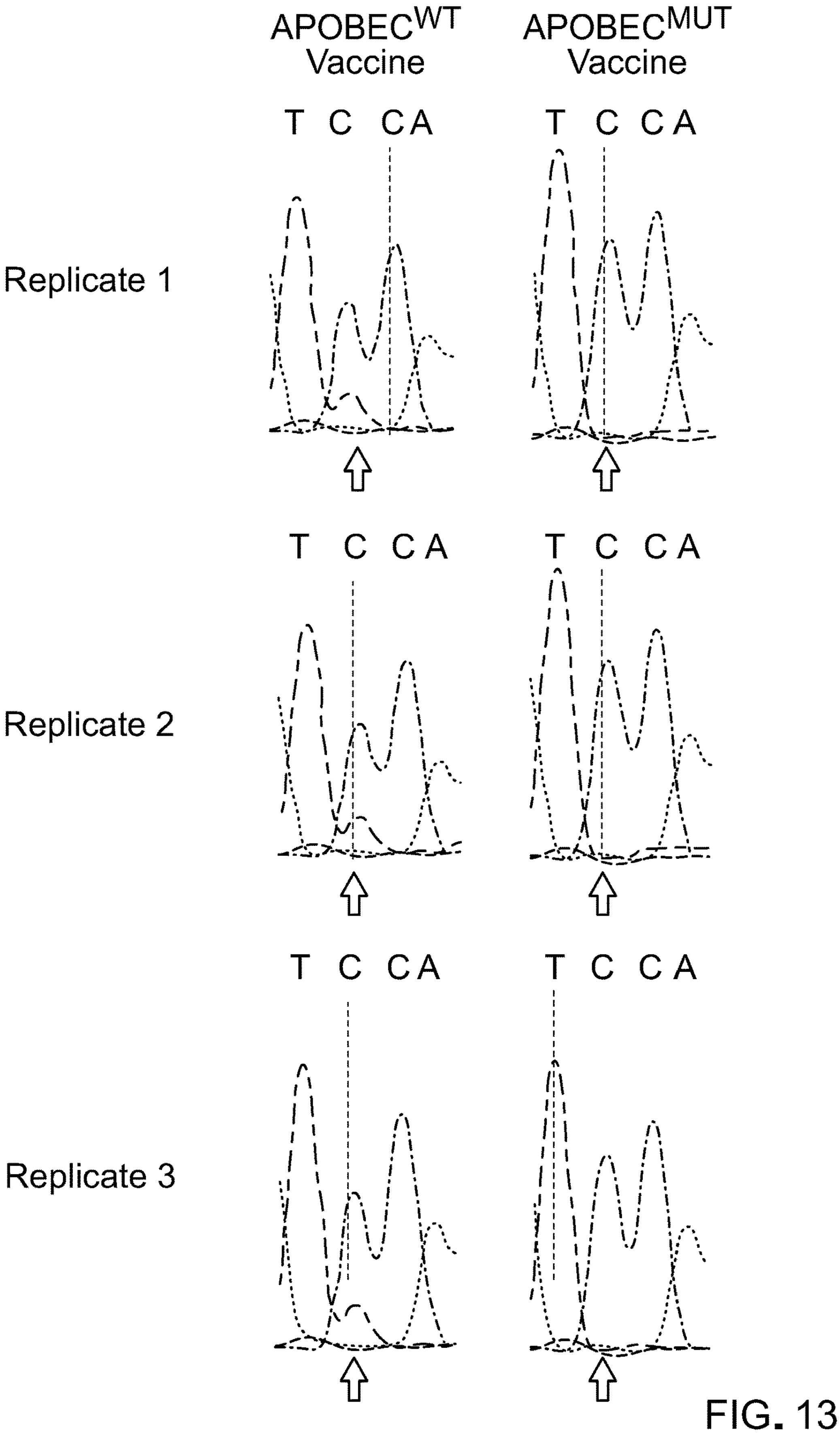
FIG. 13. Detection of CSDE1 mutation in vaccine preparations. Sanger sequencing of CSDE1 from B16-APOBEC3B$^{WT}$ or B16-APOBEC3B$^{MUT}$ vaccine preparations was performed in three independent experiments. Each preparation of the B16-APOBEC3B$^{WT}$ vaccine had a proportion of the cells containing a C with another containing a T at the thirteenth base pair, corresponding to the P5S amino acid change.

In order to validate that the putative CSDE1 heteroclitic epitope was indeed present in the vaccine preparation, the CSDE1 gene was sequenced in B16-APOBEC3B$^{WT}$ vaccine cells used in FIGS. 8-10. Consistent with the lack of APOBEC3B deaminase activity of the APOBEC3B$^{MUT}$ construct, B16 parental and B16 APOBEC3B$^{MUT}$ cell vaccines contained only the wild type ATGAGCTTTGATCCA (SEQ ID NO:1) sequence (FIG. 12A, 12B). However, the vaccine preparation contained a mixed population of cells carrying either the wild type ATGAGCTTTGATCCA (SEQ ID NO:1) sequence, as found homogeneously in the parental B16 and B16-APOBEC3B$^{MUT}$ vaccine populations or the mutated ATGAGCTTTGATTCA (SEQ ID NO:2) sequence (FIG. 12C), which encodes the heteroclitic CSDE1 neoepitope (FIG. 11D). It was further validated that the CSDE1 mutation is a reproducible and consistent target of APOBEC3B activity in B16 cells in two additional vaccine preparations (FIG. 13).

Figure 14A:
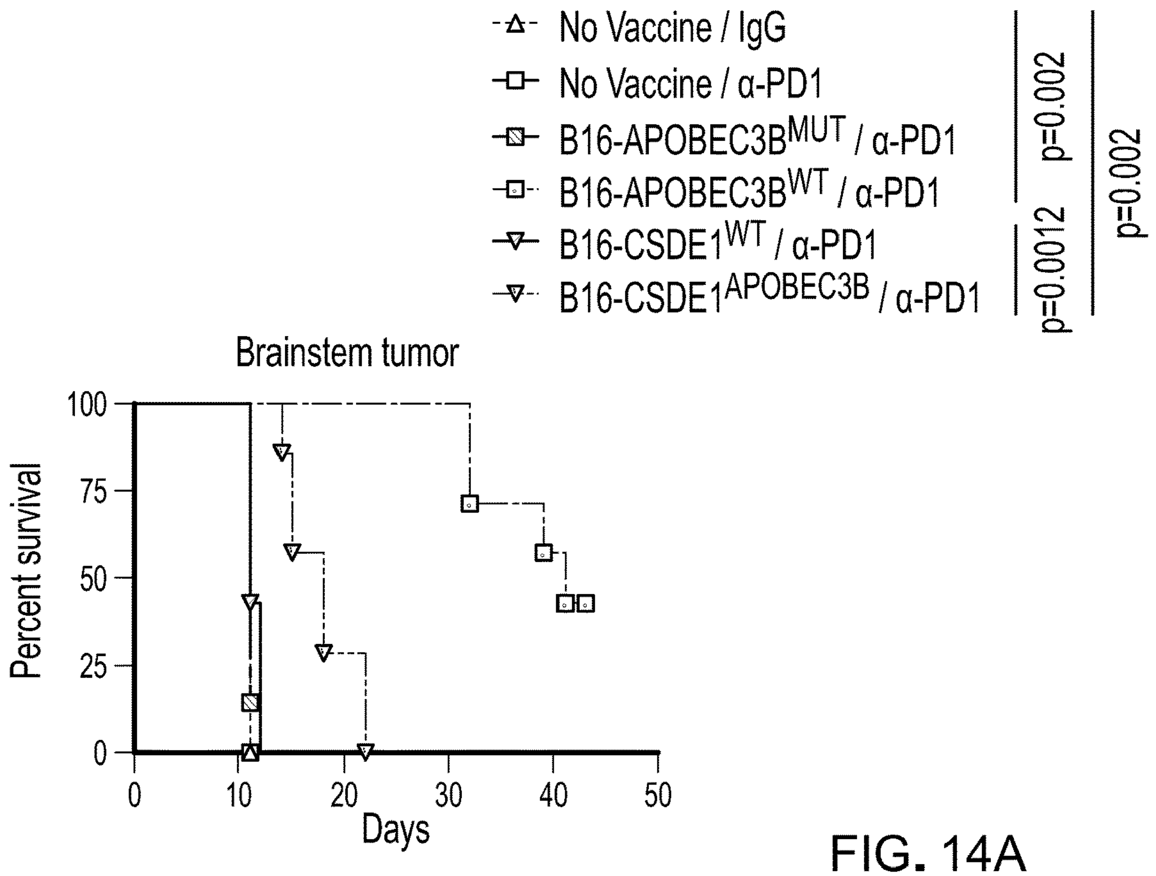
FIG. 14. Vaccination with a cold shock domain-containing protein E1 (CSDE1) mutant peptide increases survival. (A) On day 0, $2\times10^5$ B16 murine melanoma cells were implanted subcutaneously into the right flank of C57B1/6 mice. Two 5-day courses of B16-APOBEC3B$^{WT}$, B16-APOBEC3B$^{MUT}$, B16-CSDE1$^{WT}$, or B16-CSDE1$^{MUT}$ vaccines (freeze/thaw lysate of $1\times10^6$ cells i.p.) were administered from days 5-9 and 12-16. This was followed by anti-PD1 antibody or IgG control (12.5 mg/kg i.p.) on days 12-16, 19, 21, and 23. Kaplan-Meier survival curves representing experiment described. (B) On day 0, $5\times10^4$ B16 murine melanoma cells were implanted into the brainstem of C57B1/6 mice. One 5-day course of APOBEC3B$^{WT}$ or APOBEC3B$^{MUT}$-modified B16 cell vaccines (freeze/thaw lysate of $10^6$ cells i.p.) was administered from days 5-9. This was followed by anti-PD1 antibody or IgG control (12.5 mg/kg i.p.) on days 12, 14, 16, 19, 21 and 23. Kaplan-Meier survival curves representing experiment described (n=7 mice/group). (C) Spleens and lymph nodes obtained from mice treated with B16-CSDE1$^{APOBEC3B}$ vaccination and antibody-mediated checkpoint inhibition in (B) were made into single-cell suspensions and co-cultured with B16 or TC2 target cells expressing WT-CSDE1 or Mut-CSDE1 for 72 hours. Supernatant from the co-culture was assayed using a mouse interferon gamma ELISA. ANOVA was used followed by Tukey's multiple comparison test. $^{}p\leq 0.01$, $^{*}p\leq 0.001$.
Figure 14B:
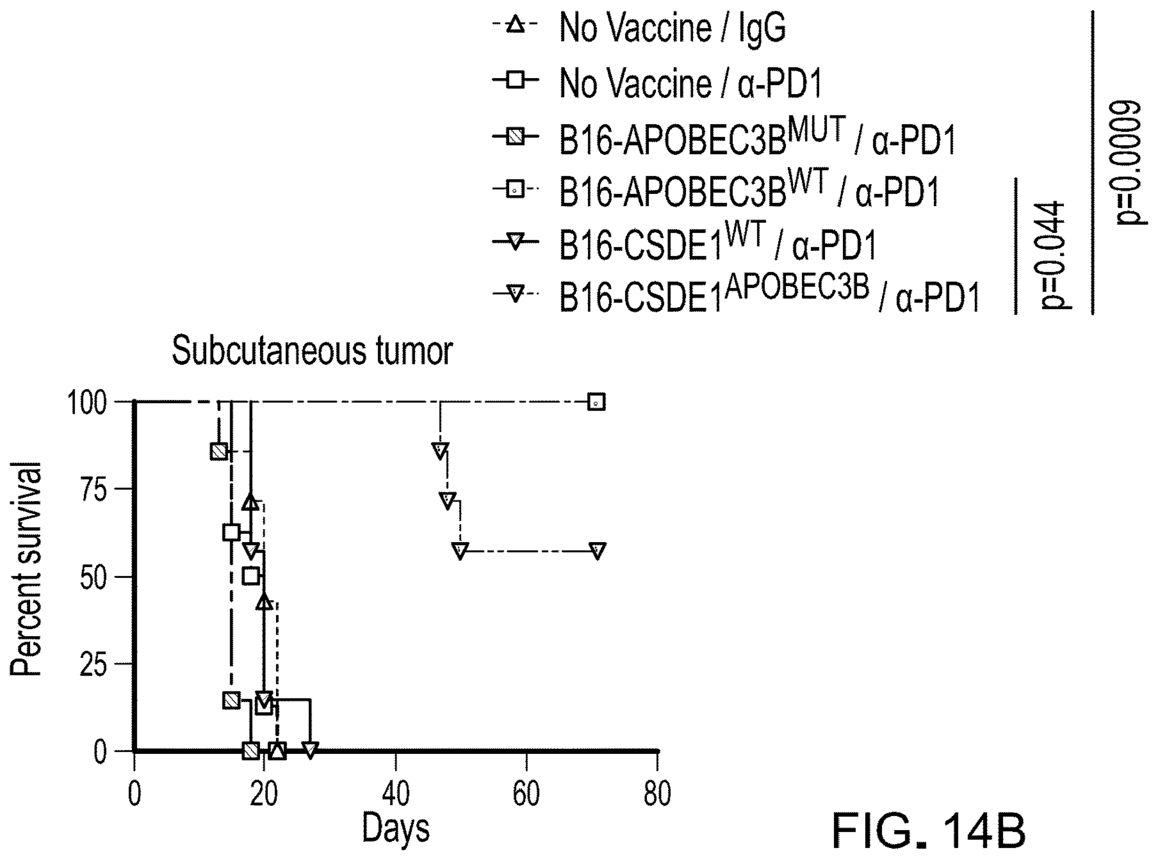
Figure 14C:
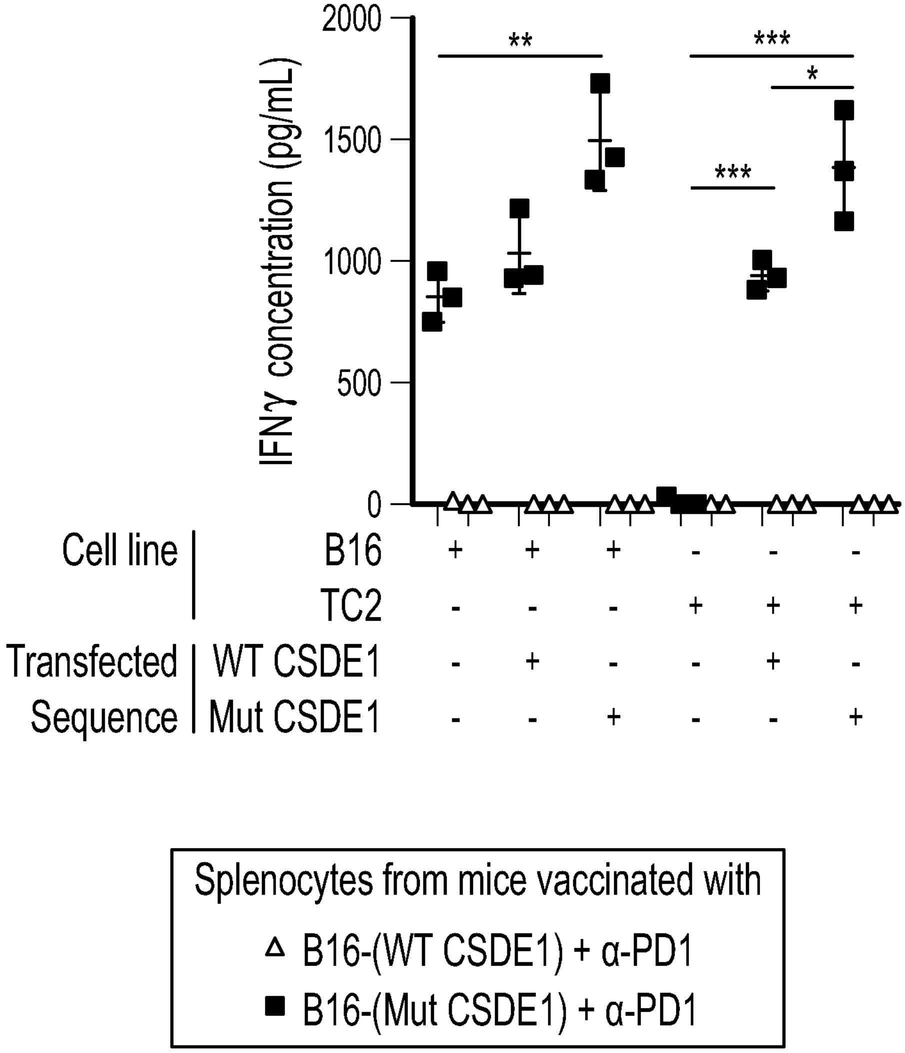
Figure 15A:
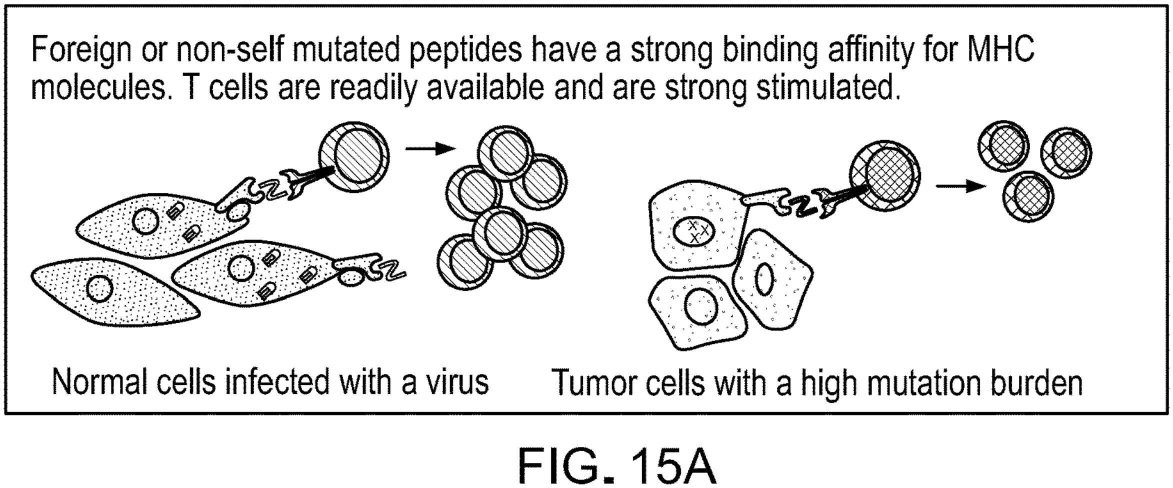
FIG. 15. Model for mechanism of action of APOBEC3B modified vaccines. (A) Strong T cell responses occur when T cells recognize foreign antigen presented in MHC. If a tumor has a high mutational burden, self peptides can be recognized as non-self and the tumor will be cleared through normal immunosurveillance. (B) T cells that react strongly against self-peptides are deleted within the thymus while T cells with weak affinity are able to escape deletion. (C) Modifying tumor cell vaccines with overexpression of APOBEC3B can generate single amino acid changes throughout the genome. When these mutated peptides are presented they have the ability to activate weakly reactive T cells. These activated T cells can react against and clear non-mutated tumor.
Figure 15B:
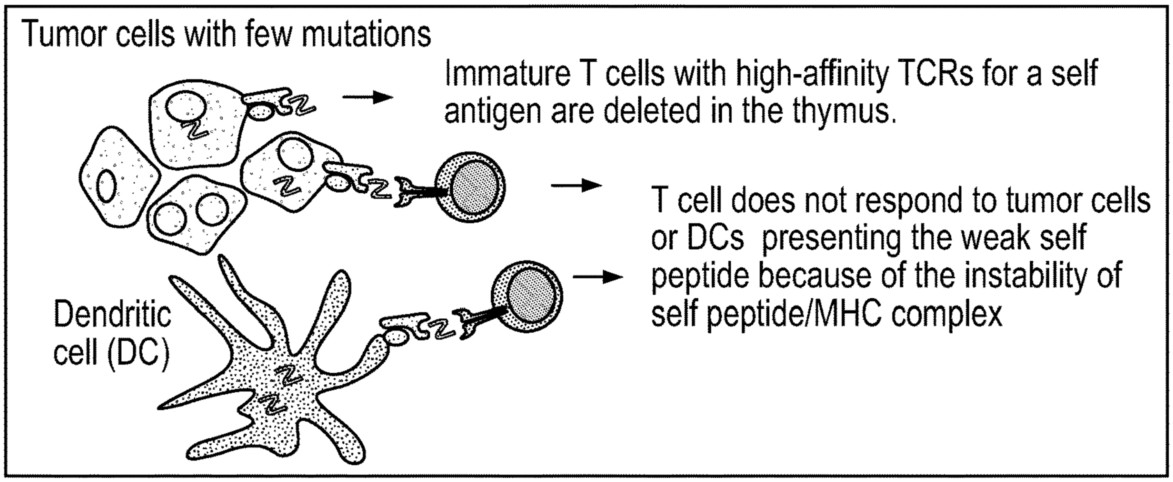
Figure 15C:
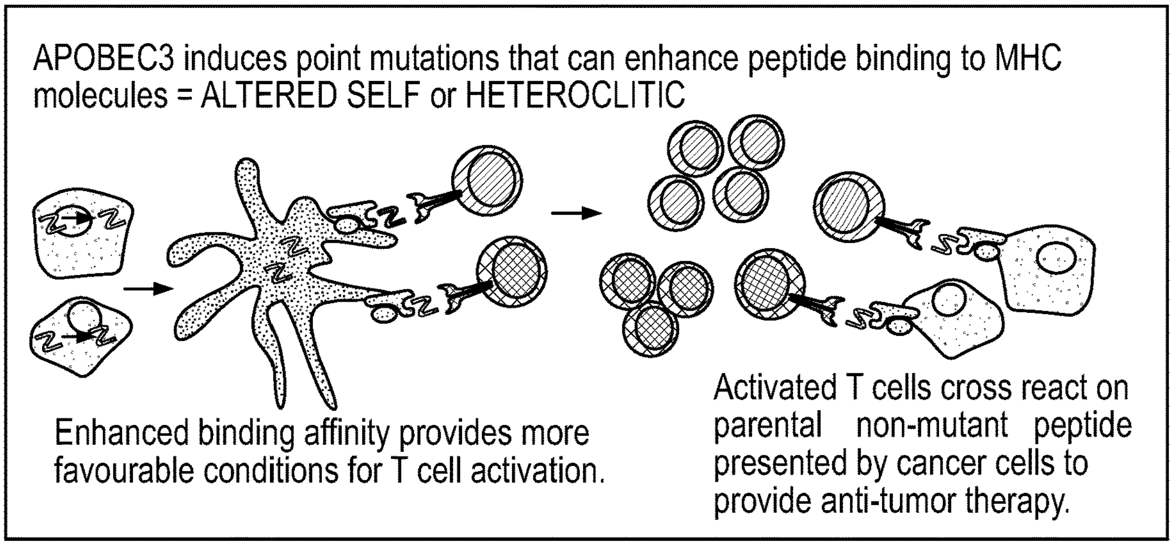
Figure 18A:
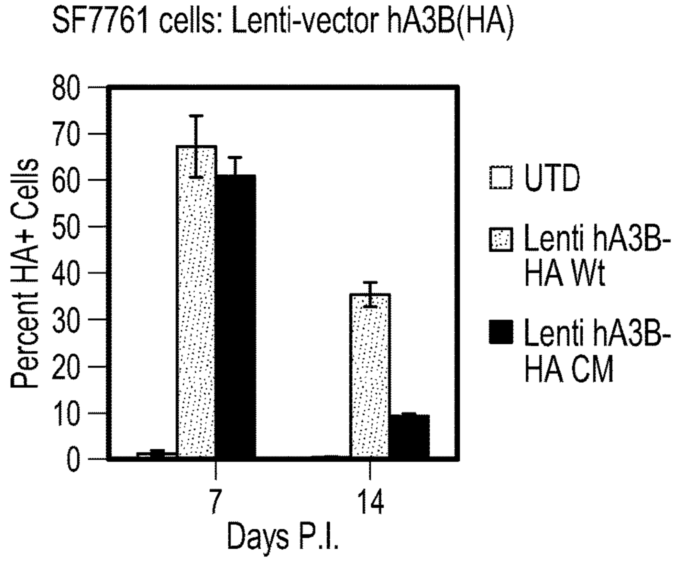
FIG. 18. Protein expression of APOBEC3B from lentivirus and AAV vectors. (A,C) SF7761 DIPG cells were transduced with a lentivirus (MOI 3) or an AAV6 (5e3 genome copies/cell) vector, respectively, expressing the HA-tagged WT or catalytically inactive mutant human APOBEC3B. (B,D) SOH DIPG cells were transduced with a lentivirus (MOI 1) or an AAV6 (1e4 genome copies/cell) vector, respectively, expressing the HA-tagged WT or catalytically inactive mutant human APOBEC3B. Cells were harvested at the indicated timepoints and HA expression analyzed by flow cytometry. N=3/sample.
Figure 18B:
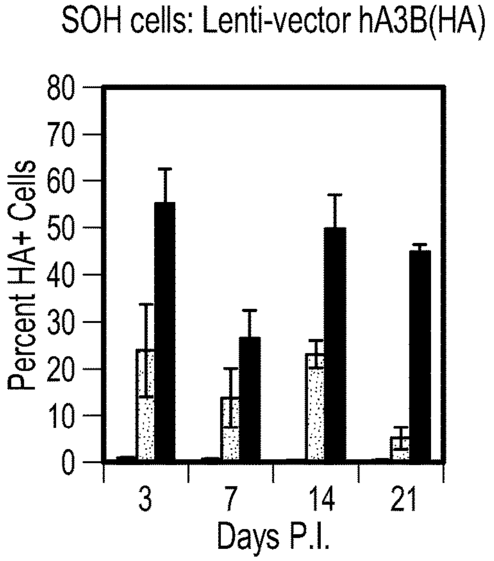
Figure 18C:
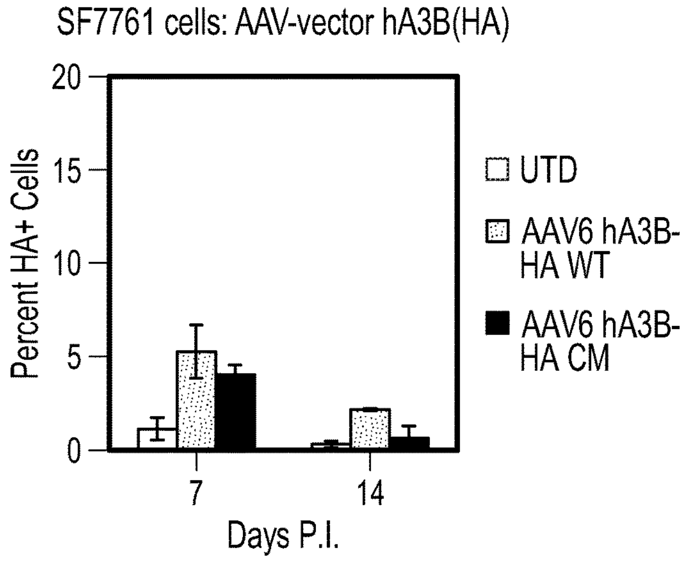
Figure 18D:
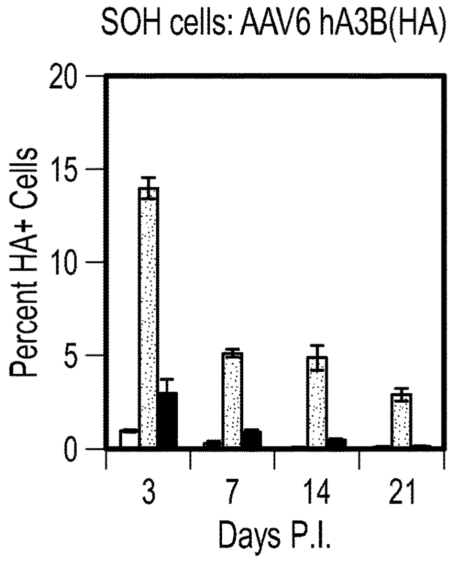
Figure 19A:
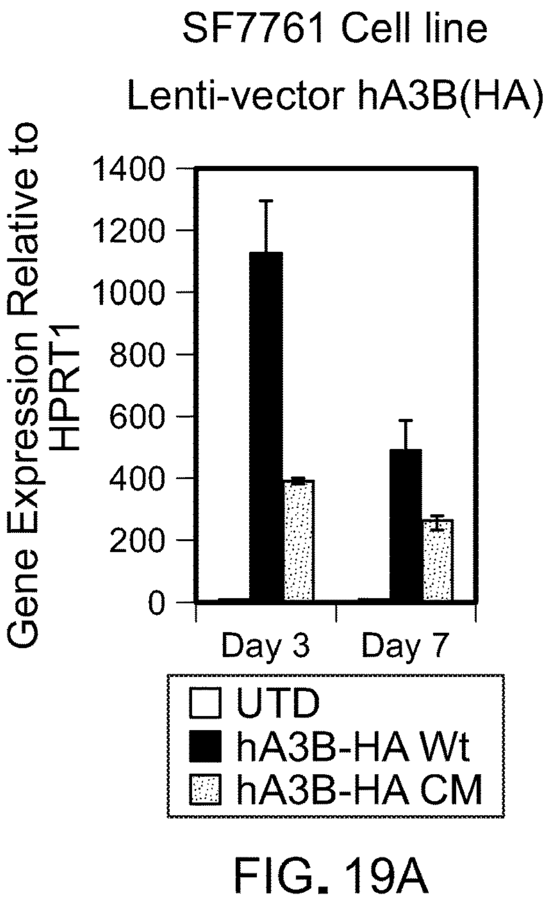
FIG. 19. mRNA expression of APOBEC3B from lentivirus and AAV vectors. (A,C) SF7761 DIPG cells were transduced with a lentivirus (MOI 3) or an AAV6 (5e3 genome copies/cell) vector, respectively, expressing the HA-tagged WT or catalytically inactive mutant human APOBEC3B. (B,D) SOH DIPG cells were transduced with a lentivirus (MOI 1) or an AAV6 (1e4 genome copies/cell) vector, respectively, expressing the HA-tagged WT or catalytically inactive mutant human APOBEC3B. RNA from cells was harvested at the indicated time points, and qRT PCR was performed to determine the expression of APOBEC3B relative to the housekeeping gene HPRT1. N=3/sample.
Figure 19B:
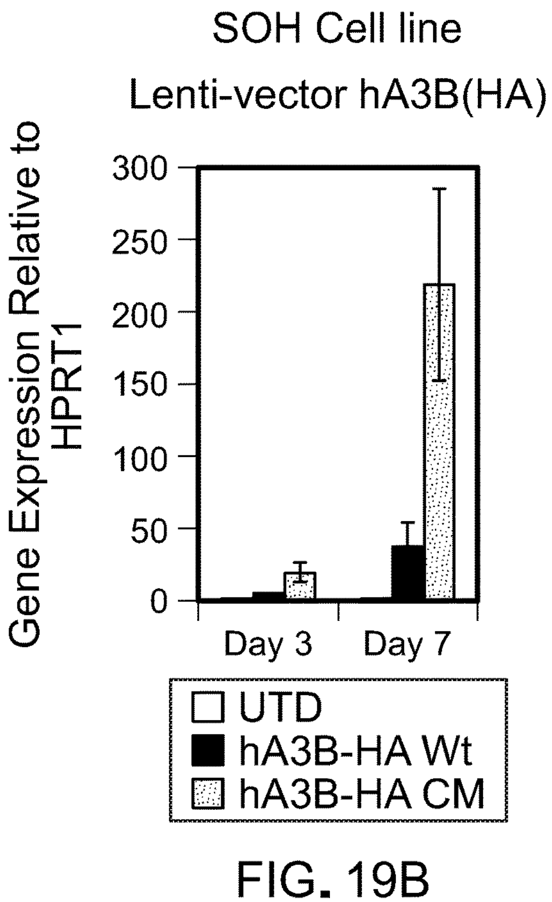
Figure 19C:
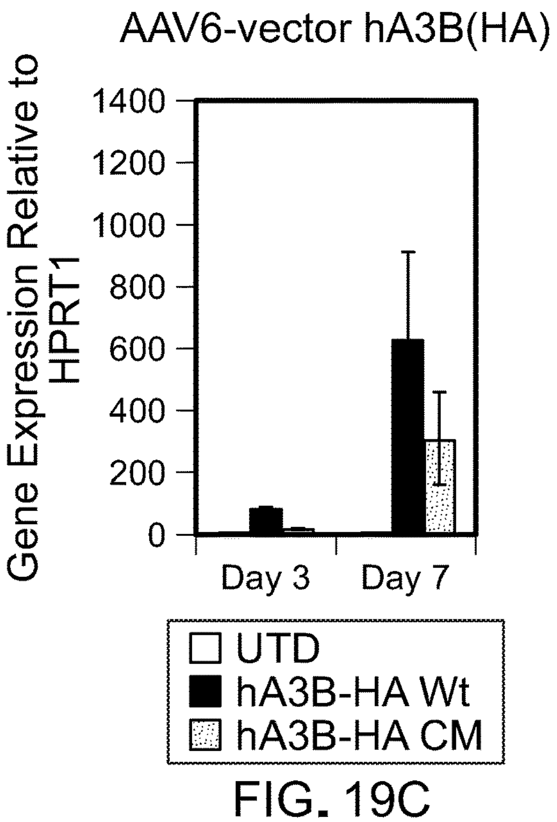
Figure 19D:
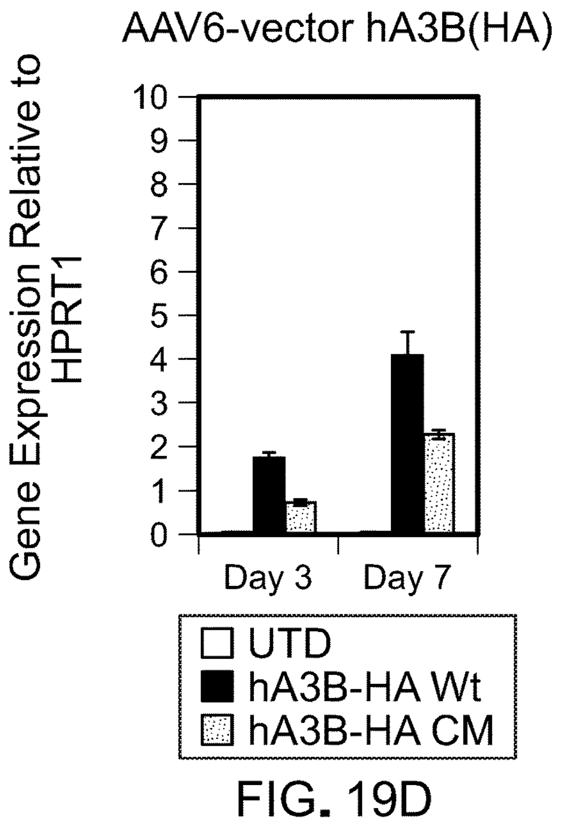

The CSDE1 Heteroclitic Epitope Primes T Cells which Provide Therapy Against B16 Tumors It was then sought to evaluate the strength of the CSDE1 epitope and its relative contribution to the in vivo vaccine efficacy. B16 cells transfected with the mutant CSDE1 epitope (CSDE1*) or the wild-type parental epitope (CSDE1) were used as a vaccine in combination with anti-PD1 to treat parental B16 tumors in the flank or brainstem. Mice vaccinated with B16 cells expressing CSDE1 succumbed to disease at the same time as untreated controls (FIG. 14A, FIG. 14B). The single CSDE1* epitope achieved a partial response, whereas the B16-APOBEC3B$^{WT}$ vaccine was significantly more effective, highlighting the value of vaccination with a wide range of antigens to prevent tumor escape. When splenocytes from these mice were cocultured with either parental B16 or TC2 prostate tumor cells expressing either CSDE1 or CSDE1* epitopes, only mice vaccinated with B16-CSDE1* and treated with ICB showed an IFNγ recall response against parental B16 cells (FIG. 14C). In the context of an irrelevant TC2 tumor, mice vaccinated with B16-CSDE1* reacted against both CSDE1* and CSDE1 epitopes, thereby confirming that the mutant CSDE1 acts as a heteroclitic peptide.

Materials and Methods

Study Design

This study was designed to evaluate the use of an APOBEC3B modified vaccine to prolong survival of tumor bearing mice and investigate its synergy with immune checkpoint blockade. Seven mice per group were used for each experiment to achieve statistical power to make multiple comparisons. Mice were randomized at time of tumor implantation and tumors were measured by a single blinded individual.

Cell Lines

B16.F1 murine melanoma cells were obtained from the ATCC. B16TK cells were derived from a B16.F1 clone transfected with a plasmid expressing the Herpes Simplex Virus thymidine kinase (HSV-1 TK) gene in 1997/1998. Following stable selection in 1.25 μg/mL puromycin, these cells were shown to be sensitive to Ganciclovir (Cymevene) at 5 μg/mL (see, e.g., Le et al., 2010 *Cancer J* 16:304; Lipson et al., 2015 *J Transl Med* 13:214; Dyall et al., 1998 *J Exp Med* 188:1553). B16TK cells were grown in DMEM (HyClone, Logan, Utah, USA)+10% FBS (Life Technologies)+1.25 μg/mL puromycin (Sigma) until challenge. TRAMP-C2 (TC2) cells are derived from a prostate tumor that arose in a TRAMP mouse and were characterized as described elsewhere (see, e.g., Foster et al., 1997 *Cancer Res* 57:3325; Gingrich et al., 1996 *Cancer Res* 56:4096). Cell lines were authenticated by morphology, growth characteristics, PCR for melanoma specific gene expression (gp100, TYRP-1 and TYRP-2) and biologic behavior, tested mycoplasma-free, and frozen. Cells were cultured less than 3 months after thawing. Cells were tested for mycoplasma using the MycoAlert Mycoplasma Detection Kit (Lonza Rockland, Inc. ME, USA).

Immune Cell Activation

Spleens and lymph nodes were immediately excised from euthanized C57B1/6 or OT-I mice and dissociated in vitro to achieve single-cell suspensions. Red blood cells were lysed with ACK lysis buffer (Sigma-Aldrich) for 2 minutes. Cells were resuspended at $1\times10^6$ cells/mL in Iscove's Modified Dulbecco's Medium (IMDM; Gibco) supplemented with 5% FBS, 1% penicillin-streptomycin, 40 μmol/L 2-Mercaptoethanol. Cells were co-cultured with target cells as described in the text. Cell-free supernatants were then collected 72 hours later and tested for IFNγ (Mouse IFNγ ELISA Kit; OptEIA, BD Biosciences) production by ELISA as directed in the manufacturer's instructions.

APOBEC3 Overexpression and Vaccine Preparation

B16TK cells were transduced with a retroviral vector encoding either full length functional APOBEC3B (APOBEC3B$^{WT}$) or a mutated, catalytically inactive form of APOBEC3B (APOBEC3B$^{MUT}$) as a negative control (see, e.g., Pak et al., 2011 *J Virol* 85:8538). 48 hours post transduction with either pBABE-Hygro APOBEC3B$^{WT}$ or pBABE-Hygro APOBEC3B$^{MUT}$ viruses, bulk populations of cells were selected in hygromycin for 2 weeks and used for experiments. Overexpression of APOBEC3B was confirmed by both Western Blot (using a rabbit monoclonal anti-human APOBEC3B (184990, Abcam, San Francisco, CA)) and qrtPCR as previously described elsewhere (see, e.g., Huff et al., 2018 *Mol Ther Oncolytics* 11: 1-13). It was observed that over-expression of APOBEC3B is toxic in that elevated levels of APOBEC3B are seen within 72 hours post-transfection/transduction and return to similar levels to that seen in parental unmodified cells. Without being bound by theory, this may be because mutagenesis by APOBEC3B is tolerable to the cell up to a certain threshold, and then in cells where critical mutations are induced, this can be lethal. In other cells, overexpression of APOBEC3B may not reach the threshold, or mutations may not be induced in critical genes, allowing those cells to survive carrying the APOBEC3B-induced mutations.

B16 or GL261 cells either left untreated, or modified to over-express either functional APOBEC3B (B16-APOBEC$^{WT}$) or the non-functional APOBEC3B MUT protein (B16-APOBEC3B$^{MUT}$) were expanded in T175 flasks. At 80-90% confluency, cells were trypsinized and washed three times in PBS (HyClone). Aliquots of $5\times10^7$ cells were re-suspended in a volume of 1 mL PBS and then freeze-thawed for three cycles in liquid nitrogen. 100 μl of these freeze-thawed vaccine preparations were administered intraperitoneally (i.p.) to mice (the equivalent of $10^6$ cells per injection).

In Vivo Experiments

All in vivo studies were approved by the Institutional Animal Care and Use Committee at Mayo Clinic. 6-8 week old female C57BL/6 mice were purchased from Jackson Laboratories (Bar Harbor, Maine). Mice were challenged subcutaneously with $2\times10^5$B16TK murine melanoma cells, their APOBEC3B$^{WT}$ or APOBEC3B$^{MUT}$ derivatives, parental B16 murine melanoma cells, or TC2 murine prostate carcinoma cells in 100 μL PBS. Alternatively, $5\times10^4$ GL261 cells or 1×10$^4$ B16 cells were implanted in 2 μL intracranially into the brainstem. Subcutaneous tumors were treated with a two week course of GCV (50 mg/kg) administered i.p. daily; or with a 5 day course of B16-APOBEC3B$^{WT}$ or B16-APOBEC3B$^{MUT}$ cell vaccines as described in the text. Subcutaneous tumors were measured 3 times per week, and mice were euthanized when tumors reached 1.0 cm in diameter. GL261 tumor cells were stereotactically implanted into the brainstems of C57B1/6 mice as described elsewhere (see, e.g., Caretti et al., 2011 *Brain Pathol* 21:441). Intracranial tumors were treated with a 5 day course of GL261- or B16-APOBEC3B$^{WT}$ or APOBEC3B$^{MUT}$ cell vaccines as described in the text. Mice were sacrificed upon emergence of neurological symptoms or weight loss.

Immune Cell Depletions and Checkpoint Inhibition

To deplete specific immune subsets, mice were treated with intraperitoneal (i.p.) injections (0.1 mg per mouse) of anti-CD8 (Lyt 2.43, BioXCell), anti-CD4 (GK1.5, BioXCell), anti-NK (anti-asialo-GM-1, Cedarlane) and IgG control (ChromPure Rat IgG Jackson ImmunoResearch) at day 4 after tumor implantation and then weekly thereafter. FACS analysis of spleens and lymph nodes confirmed subset specific depletions. For immune checkpoint blockade, mice were treated intravenously with anti-PD1 (0.25 mg; catalog no. BE0146; Bio X Cell), anti-CTLA-4 (0.1 mg; catalog no. BE0164; Bio X Cell), anti-asialo GM1 (0.1 mg; catalog no. CL8955; Cedarlane), or isotype control rat IgG (catalog no. 012-000-003; Jackson ImmunoResearch) antibody at times described in each experiment.

Next Generation Sequencing

DNA for whole genome sequencing was prepared from B16tk cells that overexpressed either APOBEC3B$^{WT}$ or parental, unmodified cells. These cells were initially generated from an experiment investigating the role of APOBEC3B overexpression on the generation of resistance to Vesicular Stomatitis Virus (VSV) oncolysis (see, e.g., Huff et al., 2018 *Mol Ther Oncolytics* 11: 1-13). Following three rounds of infection with VSV, genomic DNA was isolated from APOBEC3B expressing cells resistant to infection or parental, mock-infected cells. Five hundred nanograms of each sample was prepared using an Ultra kit (New England Bio) and underwent paired end 150 bp sequencing on the Illumina HiSeq 4000 by Mayo's Genome Analysis Core. Sequences were aligned to the mm10 C57B1/6 genome by the Mayo's Bioinformatics Core Facility and mutational changes were detected between the two samples. These mutations contained 301 C to T or G to A missense mutations which were unique to the APOBEC3B$^{WT}$ line. These coding variants were filtered through NET MHC 2.0 binding affinity algorithm to identify octamer or nonamer peptides whose binding affinity for H2K$^b$ or H2K$^d$ was below a threshold of 500 nM, and whose their corresponding wild-type peptides had a binding affinity to the same molecules above 500 nM. A list of 36 candidates was further refined using the EMBL-EBI Expression Atlas for expression in skin tissue to identify 10 high affinity APOBEC3B-induced heteroclitic peptides.

APOBEC3B-Modified Epitope Expression cDNAs encoding either wild type (un-mutated) or APOBEC3B-mutated 9 mer peptides derived from the screen described above were synthesized and cloned into the plasmid pcDNA3.1+P2A-eGFP (Genescript), where the cDNA is expressed from a CMV promoter and co-expressed with an eGFP protein. pcDNA3.1-EPITOPE+P2A-eGFP plasmids were transfected into B16 cells using Lipofectamine. Cultures in which transfection of over 50% of cells was confirmed by GFP analysis 48-72 hours post transfection were used either as targets in immune activation assays (above) or were expanded in T175 flasks. At 80-90% confluency, cells were trypsinized and washed three times in PBS. Aliquots of 5×10$^7$ cells were re-suspended in a volume of 1 mL PBS and then freeze-thawed for three cycles in liquid nitrogen. 100 μl of these freeze-thawed vaccine preparations were administered intra-peritoneally to mice (the equivalent of 10$^6$ cells per injection).

Statistics

Survival curves were analyzed by the Log-Rank test with Holm-Bonferroni correction for multiple comparisons. Student's T tests, one way ANOVA and two way ANOVA were applied for in vitro assays as appropriate. Statistical significance was set at $p<0.05$ for all experiments. In summary, when overexpressed in tumor cells, APOBEC3B generated a library of heteroclitic sequences which primed both CD4 and CD8 T cells that had escaped central tolerance and which recognized both newly mutated antigens from the vaccine, and the corresponding unaltered self epitopes expressed on the tumor cells. These results validate the methodology to identify new candidate tumor antigens which may be targeted by vaccination.

Example 7: APOBEC3 Overexpression

Materials and Methods

Plasmid Construction

Both wild-type (WT) human APOBEC3B (NM_004900.4) and an APOBEC3B catalytic mutant (CM) which contains the E68A/E255A mutations were synthesized as codon-optimized Gene Blocks (Integrated DNA Technologies) with a C-terminal HA-tags.

Both constructs were then cloned into a lentiviral vector, pSIN-CSGW-PGKpuro by way of Bcl1/BamH1-hybrid and Xho1/Sal1 hybrid sites. Additionally, both WT and CM APOBEC3B were cloned into pAAV-MCS (Stratagene) by way of Bcl1/BamH1 and Xho1 sites. All sequences were validated by Sanger sequencing (GeneWiz) using primers that flank the coding region.

Vector Productions

Human embryonic kidney 293T cells maintained in Dulbecco's modified Eagle's medium with 10% fetal bovine serum. All plasmid transfections were done using Fugene6 (Promega). The AAV vector stocks were produced in 293T cells using the helper-free transfection method according to the manufacturer's protocol (Stratagene). AAV6 capsid-expressing plasmid pRep2Cap6 (Stratagene) were used for AAV6 vector production. Briefly, 293T cells were transfected with three plasmids, including pHelper (Stratagene), Rep2Cap6, and a transfer vector plasmid (pAAV-CMV-EmGFP, pAAV-CMV-hA3B-WT, pAAV-CMV-hA3B-CM). Three days after transfection, AAV6 vector-producing 293T cells were harvested for vector purification. The cells were lysed by three rounds of freeze-and-thaw, followed by ultracentrifuge concentration (62,500 rpm for 2 hours) through Optiprep Density Gradient Medium (Sigma). The resulting AAV6 vectors were desalted and further concentrated using Amicon Ultra-15 100k filtration (Amicon). The titers (genomic copy numbers/mL) of concentrated AAV6 vector stocks were determined by Q-PCR using plasmid DNA standards and AAV genomic sequence-specific primers and fluorescent probe.

HIV-based lentiviral vectors were generated by three plasmid transfection (p8.91QV, VSV-G and pHR SIN expression plasmid) in 293T cells. Cells were cultured for three days, the culture media was then collected, passed through a 0.45 μm filter and concentrated down by ultra-centrifugation at 25,000 rpms for 1.5 hours. The resulting viral pellets were resuspended in PBS and titered in 293T cells by FACS either GFP or HA expressions (refer to flow cytometry section for more details).

Cell-Lines

The human DIPG neurosphere cell-lines, SOH and SF7761 (Millipore Cat #SCC126), were cultured in tumor stem medium (TSM) containing Neurobasal-A Media (Invitrogen, Cat #10888-22) and D-MEM/F-12 media (Invitrogen, Cat #11330-032) at a 1:1 ratio. This was further supplemented with 1 M HEPES, 100 mM MEM Sodium Pyruvate, 10 mM MEM Non-Essential Amino Acids, GlutaMax-I supplement (1×), and Antibiotic-Antimycotic (1×). Working TSM was prepared freshly, by further supplementing in B-27 supplement Minus Vitamin A (Invitrogen, Cat #12587-010), 20 ng/ml H-EGF (Shenandoah Biotech, Cat #100-26), 20 ng/ml H-FGF (Shenandoah Biotech, Cat #100-146), 10 ng/ml H-PDGF-AA (Shenandoah Biotech, Cat #100-16), 10 ng/ml H-PDGF-BB (Shenandoah Biotech, Cat #100-18) and 2 μg/ml Heparin solution (StemCell Tech, Cat #07980). Cells were maintained at 37° C. in a 5% $CO_2$ humidified incubator.

DIPG Transductions

SOH or SF7761 cells were dissociated in TrypLE Express (Invitrogen, Cat #12605010), counted and seeded in working TSM at 1e5 cells/well of a 48-well plate. Within 4-hours post-dissociation, cells were transduced with either AAV6 vectors at MOI of 10,000 genome copies/cell or lentiviral vectors at a MOI of 1 or 3. Cells were harvested at indicated times for subsequent analysis.

Flow Cytometry

Cells were collected, dissociated into single-cell suspensions by incubation in TrypLE Express for 10 minutes at 37° C. Following incubation, cells were briefly pelleted, washed in PBS, pelleted and re-suspended PBS containing Zombie NIR solution (Biolegend, Cat #423105). Cells were protected from light and incubated at room temperature for 15 minutes. Cells were then washed in PBS, fixed and permeabilized with BD Cytofix/Cytoperm kit (BD Biosciences, Cat #554714) at room temperature for 20 minutes. Cells were maintained in 1× perm/wash buffer (BD Biosciences), blocked with 5% fetal bovine serum for at least 1 hour before applying primary antibodies. All antibodies were diluted in 1× perm/wash buffer and incubated overnight at 4° C. with PE anti-HA.11 Epitope Tag Antibody (Biolegend, Cat #901518) at 1:200 dilution. Following incubation, cells were washed 2× in PBS and analyzed on CantoX flow cytometer (BD Biosciences). Analysis of the results was performed using FlowJo software.

RT-qPCR

Roughly 1e5-2e5 cells were directly lysed in RLT buffer (Qiagen RNeasy Plus Kit, Cat #74134) supplemented with beta-mercaptoethanol. RNA was purified based on manufactures protocol. 100 ng of total RNA was converted into cDNA by SuperScript III Reverse Transcriptase (Invitrogen, Cat #18080044), dNTP solutions (Thermo Fisher Scientific, #18427013), RNaseOUT (Thermo Fisher Scientific, #10777019) and Random Hexamer (Thermo Fisher Scientific, #48190011).

SYBR-green quantitative PCR was conducted using qPCR Master mix kit (MIDSCI, Cat #BEQPCR-IC). Primer sequences used to detect the codon-optimized hA3B transcripts were generated by primer-blast software (NIH):

```
hA3B Codon Opt Forward:
                                   (SEQ ID NO: 569)
AAGTGAAAATCAAGCGCGGG

hA3B Codon Opt Reverse:
                                   (SEQ ID NO: 570)
CAATTTGGCGACACAGTCGG
```

PrimeTime primer assays were purchased from IDT for the detection of endogenous hA3B transcripts and for housekeeping reference gene detection, Hs.PT.58.45417356 and Hs.PT.58v.45621572, respectively.

The PCR conditions were 95° C. for 10 minutes enzyme activation, 95° C. for 15 seconds denaturation, 60° C. for 60 seconds annealing and extension, and overall 40 cycles were performed.

DNA Cytosine Deaminase Oligo Cleavage Assay.

293T cells were seeded at 1e5 cells/well and transduced with Lenti-hA3B-Wt or CM 4 hours later. The cells were allowed to grow for 72-hours before passage and puromycin selection (3.33 μg/ml). At day 7 post-infection, the APOBEC3B expressing 293Ts were dissociated in Trypsin and counted. Whole-cell extracts were prepared from 1e6 cells in 200 μl of HED buffer (25 mM HEPES, 5 mM EDTA, 10% Glycerol, 1 mM DTT and 1× EDTA-free Protease inhibitor (Roche)). Lysates were kept on ice, sonicated and centrifuged at 4° C. for 30 minutes. The resulting supernatant was collected and used immediately for deamination reactions. The 20 μl deamination reaction contained 1 μl 4 pM 3'FITC labeled 43-mer oligo, 0.25 μl UDG (NEB), 0.25 μl RNAse A, 2 μl 10× UDG buffer (NEB) and 16.5 μl whole-cell lysates. This was mixed and incubated at 37° C. for 1 hour. 2 μl of 1M NaOH was added, and the mixture was heated at 95° C. for 10 minutes, cooled briefly, and then 22 μl of 2× Formamide loading buffer was added. 5 μl of each reaction were loaded on to a 15% TBE Urea gel. Electrophoresis at 100 volts for roughly one hour was performed. Gels were imaged on a Typhoon gel imager (GE Healthcare).

Human T Cell Activation Assays

Human donor PBMC were sorted into CD3+ cells and CD14+ monocytes. Monocytes were differentiated into immature DC with GM-CSF (800 U/ml) and IL-4 (1000 U/ml) for 7 days. DC were then loaded with cell lysates (from PG1 human paediatric DIPG cells, human Me1888 or PG-1-APOBEC3B transduced PG-1 cells) at an equivalent of ~$2\times10^5$ tumour cells per $10^4$ DC on days 7, 8, and 9 and grown in GM-CSF, IL-4, TNF-α (1100 U/ml), IL-1β (1870 U/ml), and IL-6 (1000 U/ml), to generate mature DC actively presenting tumor associated antigens of PG1 cells. On day 10, autologous donor CD3+ T cells were thawed and co-cultured with mature, loaded DC at an E:T ratio of 10:1. 10 days later, CD3+ T cells were purified from the culture by magnetic beads and labelled with Cell Tracker Violet. These expanded CD3+ T cells were then co-cultured with autologous 10 day mature DC loaded three times with PG1 lysates (as above) as targets at a ratio of 10 (T):1 (DC). 72 hours later, proliferation of the CD3+ T cells was measured using flow cytometry for dilution of Cell trace violet and levels of IFN-g released into the supernatants were measured by ELISA.

Immunostaining

PC3, SW80 and H226 cells were transduced with a lentiviral vector (MOI 1) or AAV6 (1e4 gc/cell) expressing the HA-tagged WT or catalytically inactive mutant human APOBEC3B. 48 hours post transduction, cells were reseeded in chamber slides and 24 h later fixed with 4% paraformaldehyde, permeabilized in BD Cytofix Cytoperm and blocked with 5% FBS in PBS. Cells were stained with anti-rat HA and donkey anti-rat AF594; rabbit anti-H2AX and donkey anti-rabbit FITC. Nuclei were counterstained by 4',6-diamidino-2-phenylindole (DAPI). Stained cells were observed through a Zeiss LSM 780 confocal laser scanning microscope, and the images were analyzed by using the Zeiss imaging software.

Results

Lentiviral vectors and AAV vectors were used to express either a wild type (WT) or catalytically inactive mutant (CM) human APOBEC3B. The APOBEC3B was tagged with HA in order to track the expression of the protein. The expression of the transgene was confirmed by flow cytometry using an anti-HA antibody (FIG. 18) and by qRT-PCR (FIG. 19) in two different DIPG cell lines.

The cytidine deaminase function of the transgene expressed from the lentivirus was demonstrated using a deaminase assay (FIG. 20). A fluorescently labeled probe which contained an APOBEC3B site was incubated with lysate from transduced cells. Mutation of the probe by APOBEC3B in the presence of Uracil DNA Glycosylase (UDG) allows for alkali cleavage and the detection of the smaller cleavage fragment. Transduction of 293T cells or a DIPG cell line with the hA3B-WT, but not the catalytically inactive mutant, resulted in the detection of the cleavage product.

Figure 21:
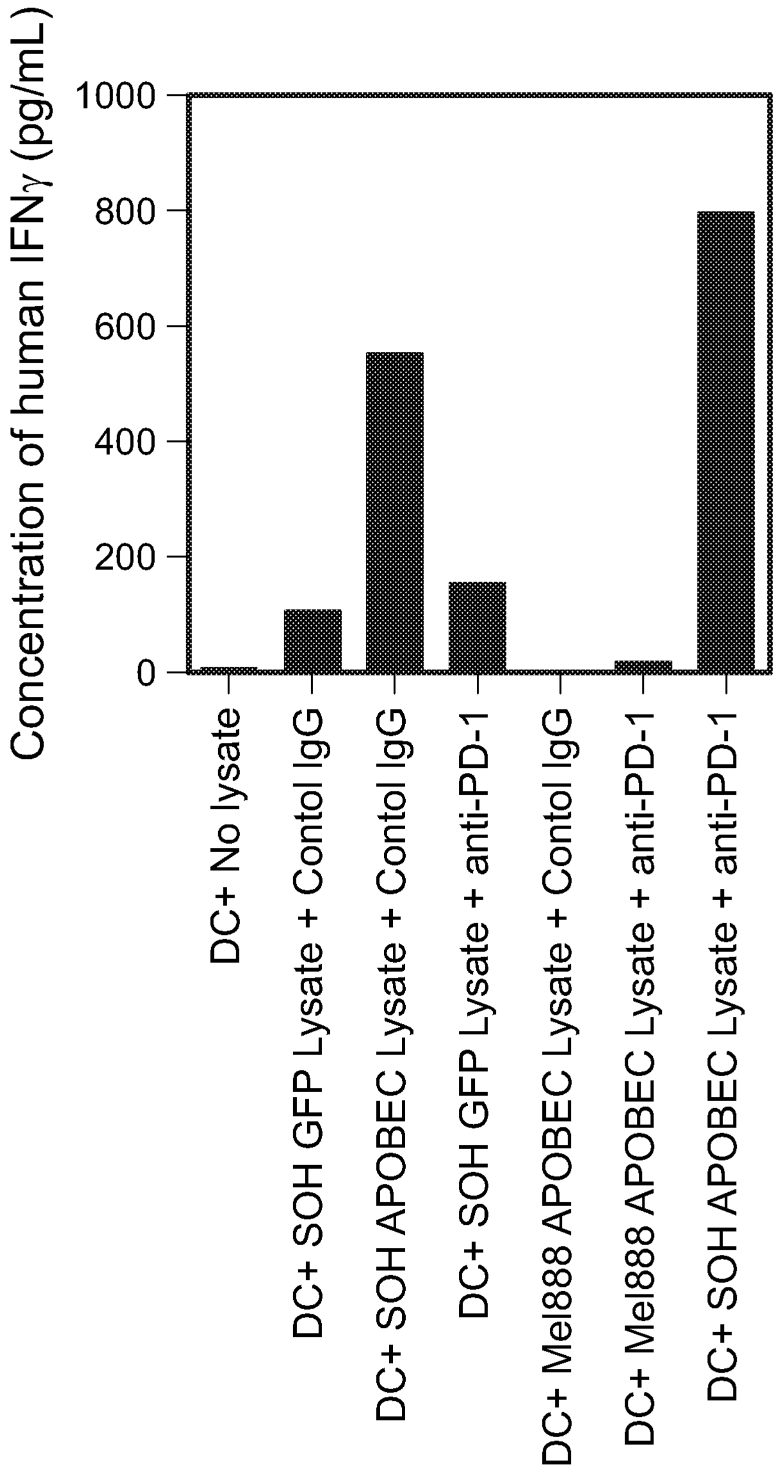
FIG. 21. In vitro priming and recall response of human T cells with DC loaded APOBEC modified cell lysate. CD14+ monocytes and CD3+ T cells were harvested from the PBMCs of a healthy donor. Monocytes were differentiated into dendritic cells using GMCSF and IL4 and matured with TNFα, IL1b, IL6 and PGE2. Mature DCs were loaded with lysates of SOH cells transduced with lentivirus expressing GFP or APOBEC3B (equivalent of $10^5$ cells per $10^4$ DC). DC pulsed targets were cocultured with T cells at E:T of 10:1 for 5 days. CD3 cells were then purified, and co-cultured with fresh autologous DC loaded with SOH lysate for 72 hours. Interferon gamma (IFNg) was measured in the supernatant.

To demonstrate the functionality of the vector to increase the immunogenicity of a cell substrate in a DC vaccine, a lentiviral vector was used in an in vitro priming and recall assay (FIG. 21). Dendritic cells were isolated from a healthy donor and differentiated in vitro from monocytes and loaded with lysate from the SOH cell line, or lysate from lentivirus APOBEC3B transduced cells. DCs were used to prime autologous T cells for 5 days, and then fresh DCs loaded with the parental SOH cell line were used to restimulate the in vitro primed T cells. Consistent with the results from the murine studies, the recall response against the parental SOH line was amplified if the T cells were primed with APOBEC3B modified lysate rather than the lysate transduced with the control GFP expressing virus. Furthermore, the recall response was enhanced in the presence of anti-PD1 antibodies.

Figure 24:
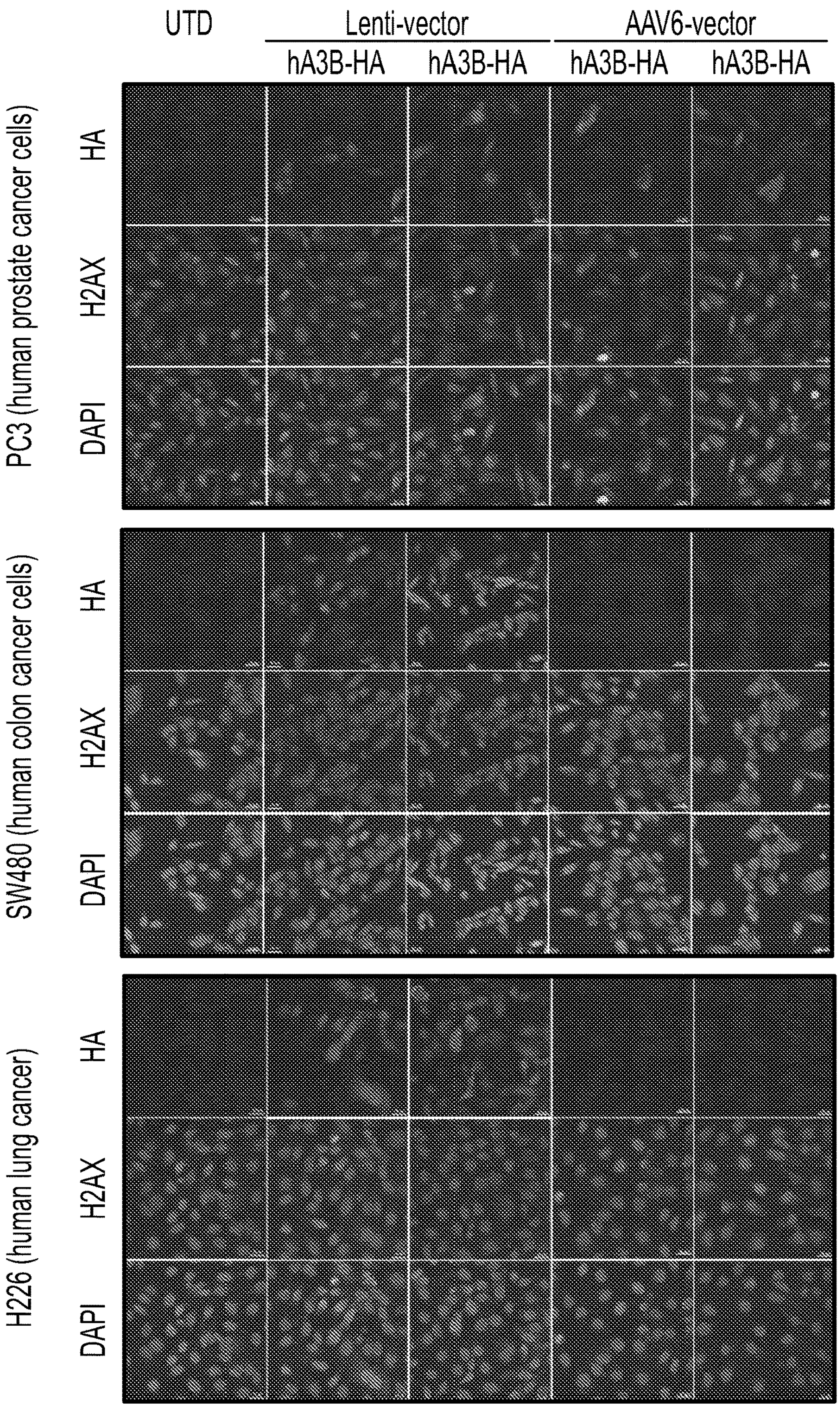
FIG. 24. Representative fluorescent confocal microscopy images of three human cancer cell lines (PC3, SW480, H226) transduced with a lentiviral vector (MOI 1) or AAV6 (1e4 gc/cell) expressing the HA-tagged WT or catalytically inactive mutant human APOBEC3B. 48 hours post transduction, cells were reseeded in chamber slides and 24 hours later fixed and permeabilized. Cells were stained with rat-anti HA and rabbit anti-H2AX. Nuclei were counterstained with DAPI.

APOBEC3B expressing lentivirus and AAV vectors can be used to transduce a variety of other cancer cell types, including prostate cancer, colon cancer, and lung cancer (FIG. 24).

Together these results demonstrate that APOBEC3B modified cancer cell vaccines can be used for a broad array of cancer etiologies.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a cancer in a mammal, said method comprising administering to said mammal a composition comprising one or more tumor cells comprising exogenous nucleic acid encoding an APOBEC3 polypeptide, wherein said cells express said APOBEC3 polypeptide, and wherein said composition induces an anti-tumor immune response within the mammal.

2. The method of claim 1, wherein said one or more tumor cells are obtained from a mammal to be treated.

3. The method of claim 1, wherein said one or more tumor cells are obtained from a donor mammal.

4. The method of claim 1, wherein said mammal is a human.

5. The method of claim 1, said method further comprising administering one or more immune checkpoint inhibitors to said mammal.

6. The method of claim 5, wherein said one or more tumor cells expressing APOBEC3 and said one or more immune checkpoint inhibitors are administered to said mammal at the same time.

7. The method of claim 5, wherein said one or more tumor cells expressing APOBEC3 and said one or more immune checkpoint inhibitors are administered to said mammal independently.

8. A vaccine composition comprising one or more tumor cells comprising exogenous nucleic acid encoding an APOBEC3 polypeptide, wherein said cells were obtained from a mammal to be treated with said composition, wherein said exogenous nucleic acid was introduced into said cells such that said cells express said APOBEC3 polypeptide, and wherein said cells comprise a library of mutated tumor antigens generated by said APOBEC3 polypeptide.

9. The composition of claim 8, wherein said APOBEC3 polypeptide is a human APOBEC3 polypeptide.

10. The composition of claim 8, wherein said APOBEC3 polypeptide is a APOBEC3B polypeptide.

11. The composition of claim 8, wherein said tumor antigens comprise one or more self antigens.

12. The composition of claim 8, wherein said tumor antigens comprise one or more non-self antigens generated from a viral peptide present in said tumor cells.

13. The composition of claim 8, wherein said nucleic acid encoding said APOBEC3 polypeptide is a viral vector.

14. The composition of claim 13, wherein said viral vector is an adenoviral vector, an adeno-associated viral vector, a lentiviral vector, or a retroviral vector.

* * * * *